US009724668B2

(12) United States Patent
Zhou et al.

(10) Patent No.: US 9,724,668 B2
(45) Date of Patent: Aug. 8, 2017

(54) IRON METAL ORGANIC FRAMEWORK MATERIALS

(71) Applicant: The Texas A&M University System, College Station, TX (US)

(72) Inventors: Hong-Cai Zhou, College Station, TX (US); Dawei Feng, College Station, TX (US); Kecheng Wang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/165,247

(22) Filed: May 26, 2016

(65) Prior Publication Data

US 2016/0346759 A1 Dec. 1, 2016

Related U.S. Application Data

(63) Continuation of application No. PCT/GB2014/053506, filed on Nov. 26, 2014.

(60) Provisional application No. 61/909,149, filed on Nov. 26, 2013.

(30) Foreign Application Priority Data

Aug. 8, 2014 (GB) .................................. 1414113.9
Aug. 8, 2014 (GB) .................................. 1414114.7
Aug. 8, 2014 (GB) .................................. 1414115.4
Aug. 8, 2014 (GB) .................................. 1414117.0

(51) Int. Cl.

| | |
|---|---|
| *C07C 29/147* | (2006.01) |
| *B01J 20/22* | (2006.01) |
| *C07F 15/02* | (2006.01) |
| *C07F 15/04* | (2006.01) |
| *C07F 15/06* | (2006.01) |
| *C07F 5/06* | (2006.01) |
| *C07F 7/00* | (2006.01) |
| *B01J 20/28* | (2006.01) |
| *C01B 3/00* | (2006.01) |
| *C01B 3/50* | (2006.01) |
| *C01B 21/04* | (2006.01) |
| *C01B 31/20* | (2006.01) |
| *C07C 7/13* | (2006.01) |
| *C07F 7/28* | (2006.01) |

(52) U.S. Cl.
CPC ....... *B01J 20/226* (2013.01); *B01J 20/28057* (2013.01); *B01J 20/28061* (2013.01); *B01J 20/28066* (2013.01); *B01J 20/28069* (2013.01); *B01J 20/28071* (2013.01); *B01J 20/28073* (2013.01); *B01J 20/28076* (2013.01); *C01B 3/0015* (2013.01); *C01B 3/508* (2013.01); *C01B 21/0455* (2013.01); *C01B 31/20* (2013.01); *C07C 7/13* (2013.01); *C07F 5/06* (2013.01); *C07F 5/069* (2013.01); *C07F 7/006* (2013.01); *C07F 7/28* (2013.01); *C07F 15/02* (2013.01); *C07F 15/025* (2013.01); *C07F 15/04* (2013.01); *C07F 15/045* (2013.01); *C07F 15/06* (2013.01); *C07F 15/065* (2013.01); *C01B 2210/0015* (2013.01); *Y02E 60/324* (2013.01)

(58) Field of Classification Search
USPC .......................... 556/45, 81, 110, 118, 133
See application file for complete search history.

(56) References Cited

U.S. PATENT DOCUMENTS

| | | | |
|---|---|---|---|
| 5,648,508 A | 7/1997 | Yaghi | |
| 6,930,193 B2 | 8/2005 | Yaghi et al. | |
| 7,196,210 B2 | 3/2007 | Yaghi et al. | |
| 7,879,221 B2 | 2/2011 | Putter et al. | |
| 8,173,827 B2 | 5/2012 | Chang et al. | |
| 8,222,179 B2 | 7/2012 | Matzger et al. | |
| 8,337,591 B2 | 12/2012 | Zhou et al. | |
| 8,648,002 B2 | 2/2014 | Schubert et al. | |
| 8,658,562 B2 | 2/2014 | Loiseau et al. | |
| 9,102,691 B2 | 8/2015 | Zhou et al. | |
| 2008/0214806 A1 | 9/2008 | Schubert et al. | |
| 2009/0092818 A1 | 4/2009 | Kiener et al. | |
| 2010/0154635 A1 | 6/2010 | Schubert et al. | |
| 2011/0319604 A1 | 12/2011 | Loiseau et al. | |
| 2012/0055880 A1 | 3/2012 | Loiseau et al. | |
| 2012/0121904 A1 | 5/2012 | Serre et al. | |
| 2012/0167761 A1 | 7/2012 | Kiener et al. | |
| 2013/0129608 A1 | 5/2013 | Watanabe et al. | |

(Continued)

FOREIGN PATENT DOCUMENTS

| | | |
|---|---|---|
| EP | 2291384 B1 | 4/2013 |
| EP | 2876112 A1 | 5/2015 |

(Continued)

OTHER PUBLICATIONS

Ma; Crystal Growth and Design, 2013, 2286-2291.*
Search Report and Written Opinion of the European Patent Office for EP2876112A1 dated Feb. 10, 2015 (3 pages).
Search Report and Written Opinion of the International Searching Authority (EPO) for PCT/GB2014/053506 dated Jun. 2, 2015 (7 pages).
Search Report of the UK Patent Office for Application No. GB1414114.7 dated Oct. 7, 2014 (4 pages).

(Continued)

*Primary Examiner* — Pancham Bakshi
(74) *Attorney, Agent, or Firm* — Reising Ethington P.C.

(57) ABSTRACT

The invention relates to an improved process for preparing metal-organic framework materials, metal-organic frameworks obtainable by such processes, methods using the same, and the use thereof. The process of the invention provides an improved process for preparing metal-organic frameworks in particular monocrystalline metal-organic frameworks having large crystal sizes. The invention also relates to metal organic frameworks comprising iron or titanium, and their uses.

14 Claims, 51 Drawing Sheets

(56) References Cited

U.S. PATENT DOCUMENTS

| | | |
|---|---|---|
| 2013/0204025 A1 | 8/2013 | Buso et al. |
| 2014/0212944 A1 | 7/2014 | Tian et al. |
| 2015/0047505 A1 | 2/2015 | Schroder et al. |

FOREIGN PATENT DOCUMENTS

| | | |
|---|---|---|
| FR | 2942229 A1 | 8/2010 |
| WO | 2007118888 A1 | 10/2007 |
| WO | 2008142059 A1 | 11/2008 |
| WO | 2009133366 A2 | 11/2009 |

OTHER PUBLICATIONS

Volkringer et al., "Synthesis, Single-Crystal X-ray Microdiffraction, and NMR Characterizations of the Giant Pore Metal-Organic Framework Aluminum Trimesate MIL-100" (2009) Chem. Mater. 21, 5695-5697.

Volkringer et al., "Occurrence of Uncommon Infinite Chains Consisting of Edge-Sharing Octahedra in a Porous Metal Organic Framework-Type Aluminum Pyromellitate Al4(OH)8[C10O8H2] (MIL-120): Synthesis, Structure, and Gas Sorption Properties" (2009) Chem. Mater. 21, 5783-5791.

Volkringer et al., "High-Throughput Aided Synthesis of the Porous Metal-Organic Framework-Type Aluminum Pyromellitate, MIL-121, with Extra Carboxylic Acid Functionalization" (2010) Inorg. Chem. 49, 9852-9862.

Serra-Crespo et al., "Synthesis and Characterization of an Amino Functionalized MIL-101 (Al): Separation and Catalytic Properties" (2011) Chem. Mater. 23, 2565-2572.

Schoedel et al., "[M3(m3-O)(O2CR)6] and related trigonal prisms: versatile molecular building blocks for crystal engineering of metal-organic material platforms" (2014) Chem. Sci. 5, 1269-1282.

Search Report and Written Opinion of the International Searching Authority (EPO) for PCT/GB2014/053507 dated Feb. 6, 2015 (7 pages).

Search and Examination Report of the UK Patent Office for Application No. GB1414113.9 dated Oct. 8, 2014 (4 pages).

Search and Examination Report of the UK Patent Office for Application No. GB1414115.4 dated Oct. 8, 2014 (4 pages).

Serre et al., "A Route to the Synthesis of Tirvalent Transition-Metal Porous Carboxylates with Trimeric Secondary Building Units," (2004) Angew. Chem. Int. Ed. 43, 6286-6289.

Bloch et al., "Hydrocarbon Separations in a Metal-Organic Framework with Open Iron(II) Coordination Sites," (2012) Science 335, 1606-1610.

Cavka et al., "A New Zirconium Inorganic Building Brick Forming Metal Organic Frameworks with Exceptional Stability," (2008) J. Am. Chem. Soc 130 13850-13851.

Devic et al., "High valence 3p and transition metal based MOFs," (2014) Chem. Soc. Rev. 43, 6097-6115.

Surble et al., "A new isoreticular class of metal-organic-frameworks with the MIL-88 topology," (2006) Chem. Commun. 284-286.

Falaise et al., "Capture of iodine in highly stable metal-organic frameworks: a systematic study," (2013) Chem. Commun. 49, 10320-10322.

Feng et al. "Zirconium-Metalloporphyrin PCN-222: Mesoporous Metal-Organic Frameworks with Ultrahigh Stability as Biomimetic Catalysts," (2012) Angew. Chem. Int. Ed. 51, 10307-10310.

Volkringer et al., "Synthesis, Single-Crystal X-ray Microdiffraction, and NMR Characterizations of the Giant Pore Metal-Organic Framework Aluminum Trimesate MIL-100," (2009) Chem. Mater. 21, 5695-5697.

Ferey et al., "Large breathing effects in three-dimensional porous hybrid matter: facts, analyses, rules and consequences," (2009) Chem. Soc. Rev. 38, 1380-1399.

Fournier et al., "Derivatives of tetraphenylmethane and tetraphenylsilane: Synthesis of new tetrahedral building blocks for molecular construction," (2003) Can. J. Chem. 81, 376-380.

Horcajada et al., "Porous metal-organic-framework nanoscale carriers as a potential platform for drug delivery and imaging," (2010) Nature Materials 9, 172-178.

Horike et al., "Soft porous crystals," (2009) Nature Chemistry 1, 695-704.

Bauer et al., "High-Throughput Assisted Rationalization of the Formation of Metal Organic Frameworks in the Iron(III) Aminoterephthalate Solvothermal System," (2008) Inorganic Chemistry 47, 7568-7576.

Jiang et al., "Au@ZIF-8: CO Oxidation over Gold Nanoparticles Deposited to Metal-Organic Framework," (2009) J. Am. Chem. Soc. 131, 11302-11303.

Jiang et al., "Pore Surface Engineering with Controlled Loadings of Functional Groups via Click Chemistry in Highly Stable Metal-Organic Frameworks," (2012) J. Am. Chem. Soc. 134, 14690-14693.

Kreno et al., "Metal-Organic Framework Materials as Chemical Sensors," (2012) Chem. Rev. 112, 1105-1125.

Pham et al., "Novel Route to Size-Controlled Fe-MIL-88B-NH2 Metal-Organic Framework Nanocrystals," (2011) Langmuir, 27 15261-15267.

Murray et al., "Highly-Selective and Reversible O2 Binding in Cr3(1,3,5-benzenetricarboxylate)2," (2010) J. Am. Chem. Soc. 132, 7856-7857.

Pearson, "Physical and Inorganic Chemistry," (1963) J. Am. Chem. Soc. 85, 3533-3539.

Phan et al., "Synthesis, Structure, and Carbon Dioxide Capture Properties of Zeolitic Imidazolate Frameworks," (2010) Accounts Chemical Research 43, 58-67.

Ol'Khovik et al., "Synthesis and Properties of 4,4'-Bis[5-alkyl(aryl)benzoxazol-2-yl]-2-hydroxy(alkoxy) biphenyls," (2006) Russian Journal of Organic Chemistry 42, 1164-1168.

Seo et al., "A homochiral metal-organic porous material for enantioselective separation and catalysis," (2000) Nature 404, 982-986.

Zhou et al., "Ultraviolet resistance of azo-containing poly(1,3,4-oxadiazole) fibers," (2013) Polymer Degradation and Stability 98, 691-696.

Wang et al., "Metal-Organic Frameworks Based on Double-Bond-Coupled Di-Isophthalate Linkers with High Hydrogen and Methane Uptakes," (2008) Chem. Mater. 20, 3145-3152.

Wang et al., "Postsynthetic modification of metal-organic frameworks," (2009) Chem. Soc. Rev. 38, 1315-1329.

Yaghi et al., "Reticular Synthesis and the design of new materials," (2003) Nature 423, 705-714.

Yang et al., "Irreversible Network Transformation in a Dynamic Porous Host Catalyzed by Sulfur Dioxide," (2013) J. Am. Chem. Soc. 135, 4954-4957.

\* cited by examiner

PCN-250

IRON METAL ORGANIC FRAMEWORK MATERIALS

CROSS-REFERENCE TO RELATED APPLICATIONS

This application is a continuation of International Application PCT/GB2014/053506, having an international filing date of Nov. 26, 2014 and published as WO2015/079229A1, which in turn claims priority to GB 1414113.9 (filed Aug. 8, 2014), GB1414114.7 (filed Aug. 8, 2014), GB1414115.4 (filed Aug. 8, 2014), GB1414117.0 (filed Aug. 8, 2014), and US Provisional Application No. 61/909,149 (filed Nov. 26, 2013). The contents of each of the aforementioned applications are incorporated herein by reference in their entirety.

TECHNICAL FIELD

The present invention relates to processes for preparing metal-organic framework materials and the use thereof. In particular, the invention relates to a process for preparing large crystal metal organic frameworks such as monocrystalline metal organic frameworks and to large crystals metal organic frameworks obtained by said process. More specifically, it relates to the preparation of massive single crystal Fe/Al/Ti/Cr etc. metal organic frameworks.

BACKGROUND

Metal-Organic Frameworks (MOFs) have garnered significant interests in the last two decades due to their promising potential in many applications such as gas adsorption, separation, catalysis and sensing. For example, see Yaghi, O. M.; O'Keeffe, M.; Ockwig, N. W.; Chae, H. K.; Eddaoudi, M.; Kim, J. Nature 2003, 423, 705. (b) Ferey, G.; Mellot-Draznieks, C.; Serre, C.; Millange, F. Acc. Chem. Res. 2005, 38, 217. (c) Horike, S.; Shimomura, S.; Kitagawa, S. Nat. Chem. 2009, 1, 695. (d) Seo, J. S.; Whang, D.; Lee, H.; Jun, S. I.; Oh, J.; Jeon, Y. J.; Kim, K. Nature 2000, 404, 982. (e) Jiang, H.-L.; Liu, B.; Akita, T.; Haruta, M; Sakurai, H.; Xu, Q. J. Am. Chem. Soc. 2009, 131, 11302. (f) Kreno, L. E.; Leong, K.; Farha, O. K.; Allendorf, M.; Van Duyne, R. P.; Hupp, J. T. Chem. Rev. 2012, 112, 1105. (g) Yang, S.; Liu, L.; Sun, J.; Thomas, K. M.; Davies, A. J.; George, M. W.; Blake, A. J.; Hill, A. H.; Fitch, A. N.; Tang, C. C.; Schröder, M. J. Am. Chem. Soc. 2013, 135, 4954. (h) Bloch, E. D.; Queen, W. L.; Krishna, R.; Zadrozny, J. M.; Brown, C. M.; Long, J. R. Science 2012, 335, 1606. (i) Wang, Z.; Cohen, S. M. Chem. Soc. Rev. 2009, 38, 1315.

Compared with other porous materials such as zeolite and mesoporous silica, MOFs are based on crystalline porous structures tunable on the atomic scale, which can be designed and functionalized by judicious choice of metal nodes and modification of the organic linkers. However, one of the limitations of most MOFs is their low chemical stability, which undoubtedly hampers their application in industry. A rule of thumb for the construction of stable MOFs comes from the simple Hard and Soft Acid and Base Theory, which guides the selection of the metal-ligand combination for a MOF. For example, see Pearson, R. G. J. Am. Chem. Soc. 1963, 85, 3533. Because the carboxylate group is a hard Lewis base, hard Lewis acids such as $Fe^{3+}$, $Cr^{3+}$, $Zr^{4+}$ and $Ti^{4+}$ are usually considered good candidates for the construction of robust MOFs. This method has become the focus of some recent research efforts but very few stable MOFs have been obtained, especially in single crystal form. For example, see (a) Cavka, J. H.; Jakobsen, S.; Olsbye, U.; Guillou, N.; Lamberti, C.; Bordiga, S.; Lillerud, K. P. J. Am. Chem. Soc. 2008, 130, 13850. (b) Ferey, G.; Serre, C. Chem. Soc. Rev. 2009, 38, 1380. (c) Phan, A.; Doonan, C. J.; Uribe-Romo, F. J.; Knobler, C. B.; O'Keeffe, M.; Yaghi, O. M. Acc. Chem. Res. 2010, 43, 58. (d). Murray, L. J.; Dinca, M.; Yano, J.; Chavan, S.; Bordiga, S.; Brown, C. M.; Long. J. R. J. Am. Chem. Soc. 2010, 132, 7856. (e) Feng, D.; Gu, Z.-Y.; Li, J.-R.; Jiang, H.-L.; Wei, Z.; Zhou, H.-C. Angew. Chem. Int. Ed. 2012, 51, 10307. (f) Jiang, H.-L.; Feng, D.; Liu, T.-F.; Li, J.-R.; Zhou, H.-C. J. Am. Chem. Soc. 2012, 134, 14690. The main reason is that MOFs based on these metal ions of high valence are difficult to crystallize. Occasionally, MOFs in the form of crystalline powder were obtained, but structure solution and refinement based on Powder X-Ray Diffraction (PXRD) data is not straightforward. Furthermore, the incorporation of rarely reported metal nodes into MOFs is less predictable and controllable.

There is also a need to provide MOFs in monocrystalline and polycrystalline form. A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. They are different from monocrystalline materials. Large single crystals are very rare in nature and can be difficult to produce in the laboratory.

Metal-organic frameworks are coordination polymers having an inorganic-organic hybrid framework that comprises metal ions and organic ligands coordinated to the metal ions. These materials may be three-dimensional, i.e. have three-dimensional lattices in which the metallic species are joined together periodically by spacer ligands.

Metal-organic frameworks have many applications including, for example, in the field of adsorption, storage, separation or controlled release of chemical substances, such as, for example gases, or in the field of catalysis. Metal-organic frameworks may also be useful in the field of pharmaceuticals (controlled release of medicaments) and in the field of cosmetics.

There are in fact a growing number of applications for metal-organic frameworks and as such there is an ever growing need for new such materials with a variety of properties and a need for new metal-organic frameworks having improved properties.

In addition, there is a need to develop new processes for preparing metal-organic frameworks that allow for the preparation of a wide variety of metal-organic frameworks and/or improve the quality of the metal-organic frameworks obtained.

However, metal organic (framework) powder material has been prepared by various methods but prior to the present invention large single crystals of metal organic frameworks containing a number of different metal ions have not been prepared.

For example, a number of iron metal organic frameworks have been synthesised but there remains a need to develop a synthesis that is robust and can be used to prepare a wide range of metal organic frameworks. In particular, there remains a need to provide monocrystalline iron metal organic frameworks having large crystal size. Furthermore, monocrystalline aluminium and titanium metal organic frameworks have not been prepared prior to the present invention. In fact, serious difficulties have been experienced preparing crystalline metal organic frameworks containing iron, aluminium or titanium.

As evidenced in the literature, it is still not possible to provide MOFs containing a wide range of metal ions that have large crystal sizes. In fact, a number of difficulties still exist that prevent successful synthesis of large crystal MOFs. These difficulties are also put into context when the size of crystals achieved in the literature is reviewed.

Firstly, the zinc based molecular organic framework MOF-5 ($ZN_4O(BDC)_3$) is one of the first and most successful MOFs reported to date. It is reported, e.g. see Nanomaterials in Catalysis edited by Phillipe Serp, Karine Philippot, that single and polycrystalline cubic crystals of MOF-5 have been prepared with crystal size ranging from 50 to 200 µm. MOF-5 could be viewed as the standard bearer of MOFs against which all subsequent MOFs are compared. In reality, since details of MOF-5 were first made available, no-one has been able to achieve similar crystal sizes to those achieved by MOF-5. In particular, there are no reports of any MOFs containing other metal ions (e.g. iron, aluminium, and titanium) having crystals sizes anywhere near that reported for MOF-5.

For iron MOFs, U.S. Pat. No. 8,173,827 B2 exemplifies the preparation of a couple of MOFs (namely Fe-BTC-1 and Fe-BTC-2). However, the MOFs described in this patent have been prepared only on the nanoscale. For example, Fe-BTC-1 is reported to have a particle size ranging from 0.2 µm to 0.5 µm; and Fe-BTC-2 is reported to have a particle size ranging from 2 µm to 5 µm. These crystal sizes are a factor of 10 smaller than those reported for MOF-5. Furthermore, these MOFs appear to be amorphous materials; the processes described therein fail to provide crystalline materials, let alone monocrystalline materials.

In addition, Horcajada et al in Nature Materials, Vol. 9, February 2010, 172-178 describes the preparation of a number of iron MOFs but the authors have not been successful in preparing large crystals of iron MOFs. In contrast, they have only bee able to prepare iron-MOFs on the nanoscale. For example, MOFs labelled MIL-53, MIL-88, MIL-100 and MIL-101 have been prepared and particle sizes ranging from 50 nm to 350 nm are reported. The authors have therefore failed to prepare a MOF having a particle size greater than 0.35 µm.

In addition, Langmuir 2011, 27, 15261-15267 reports the preparation of an iron MOF labelled Fe-MIL-88B—$NH_2$. However, again the authors have only been able to prepare the iron-MOF with small crystal sizes (e.g. 3.5 µm by 1.2 µm).

For titanium MOFs, the realization of polycrystalline structures remains elusive. In the literature, Kaskel et al (J. Mater. Chem., 2006, 16, 2354-2357) appear to be the first to describe a titanium porous inorganic-organic hybrid material (labelled in the prior art as TT-1). However, the titanium based MOF prepared by Kaskel et al is amorphous; it is not crystalline. The Kaskel et al document itself acknowledges that only a few titania-based MOFs have been prepared because of the difficulties experienced. None of them are crystalline, let alone monocrystalline having a large crystal size. In 2009, Ferey et al (J. Am. Chem. Soc. 2009, 131, 10857-10859) described a "well-crystallised white hybrid solid" (labelled in the prior art MIL-125) which was also the subject of US patent application US2012/0121904 A1. However, the crystals of MIL-125 which have been prepared are relatively small. For example, particle sizes for MIL-125 are reported by Kim et al in Catalysis Today 204 (2013) 85-89 to range from 0.004 mm to 0.005 mm.

For aluminium MOFs, there is very little literature associated with the preparation of aluminium-based MOFs. In the literature, Ferey et al (Chem. Mater. 2009, 21, 5695-5697 & Chem. Mater. 2009, 21, 5783-5791) describe the preparation of aluminium MOFs (labelled as MIL-100, MIL-120, and MIL-121) using hydrothermal synthesis, which were also the subject of US patent application US2012/0055880 A1. The sizes of the crystals obtained were however relatively small. For example, US2012/0055880 reports crystal sizes ranging from 1 micron up to only 30 microns (0.001 mm to 0.03 mm).

There is therefore a need to provide crystalline MOFs that exhibit a greater crystal size. As well as providing crystalline products, there is also a need to provide MOFs in monocrystalline and polycrystalline form. A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. They are different from amorphous materials. Large single crystals are very rare in nature and can be difficult to produce in the laboratory.

Metal-organic frameworks are coordination polymers having an inorganic-organic hybrid framework that comprises metal ions and organic ligands coordinated to the metal ions. These materials may have three-dimensional lattices in which the metallic species are joined together periodically by spacer ligands.

As discussed above, to date it has not been possible to prepare MOFs having large crystal sizes and excellent stability using a process that is robust and suitable for preparing MOFs involving a wide range of metal ions and a wide range of carboxylate ligands.

SUMMARY OF THE DISCLOSURE

According to one aspect, the invention provides process of preparing a metal-organic framework comprising a metal ion cluster of formula $M_aO$, the process comprising reacting a starting compound of formula $M_aO_y(OR_1)_b(R_2COO)_c$ with a ligand precursor having at least two carboxylic acid groups in the presence of an acid having one carboxylic acid or carboxylate group to provide a metal-organic framework comprising a $M_aO$ cluster where at least one ($R_2COO$) ligand is replaced by at least one ligand having at least two carboxylate groups; wherein each M is independently a metal ion selected from the group consisting of Group 2 through Group 16 metals; $R_1$ is alkyl or aryl; $R_2$ is alkyl or aryl; a is an integer from 1 to 8; b is an integer from 0 to 6; c is an integer from 6 to 20; and y is an integer from 1 to 10.

In one embodiment, the process comprises reacting a starting compound of formula $M_3O(CH_3COO)_6$ with a ligand precursor having at least two carboxylic acid groups in the presence of acetic acid to provide a metal-organic framework comprising a $M_3O$ cluster where at least one ($CH_3COO$) ligand is replaced by at least one ligand having at least two carboxylate groups;

wherein each M is independently a metal ion selected from the group consisting of Group 2 through Group 16 metals.

In one embodiment, at least one M is Fe(II,III), Al(III), or Ti(IV).

In one embodiment, the starting compound has a formula $Fe_2XO(CH_3COO)_6$ or $Fe_3O(CH_3COO)_6$, wherein X is a metal ion selected from the group consisting of Group 2 through Group 16 metals. For example, X may be Co(II), Ni(II), Mn(II), or Zn(II), or X may be Co(II) or Ni(II).

In one embodiment, the starting compound has a formula Al$_2$XO(CH$_3$COO)$_6$ or Al$_3$O(CH$_3$COO)$_6$, wherein X is a metal ion selected from the group consisting of Group 2 through Group 16 metals. For example, X may be Fe(III), Cr(III), V(III), Sc(III) or In(III).

In one embodiment, the process provides a metal-organic framework which comprises one or more metal-ligand clusters, each metal-ligand cluster comprising (i) two or more metal ions, wherein at least one metal ion is selected from iron, aluminium, chromium, titanium, vanadium, scandium, indium and gallium, and (ii) one or more ligands having two or more carboxylate groups.

In one embodiment, the the metal-organic framework comprises two or more, three or more, or four or more metal-ligand clusters.

In one embodiment, the at least one metal ion is selected from Fe(II), Fe(III), Al(III), Cr(III), Ti(IV), V(III), V(IV), V(V), Sc(III), In(III), Ga(III), and mixtures thereof.

In one embodiment, the metal-ligand cluster contains at least two metal ions which are different to each other.

In one embodiment, the metal-ligand cluster comprises a second metal ion selected from Al(III), Fe(II,III), Co(II), Ni(II), Mn(II), Zn(II), Mg(II), Cr(III), V(III), Sc(III), Ca(II), Ba(II) or In(III), preferably Fe(II,III), Co(II), Ni(II), Mn(II), Zn(II), or Mg(II).

In one embodiment, the metal-ligand cluster comprises three metal ions, wherein at least one metal ion is selected from iron, aluminium, chromium, titanium, vanadium, scandium, indium and gallium.

In one embodiment, the the metal-ligand cluster comprises three metal ions, wherein at least two metal ions are selected from iron, aluminium, chromium, titanium, vanadium, scandium, indium and gallium.

In one embodiment, the metal-ligand cluster has the formula M$_2$XO, wherein each M is independently a metal ion selected from iron, aluminium, chromium, titanium, vanadium, scandium, indium and gallium, and X is a metal ion selected from the group consisting of Group 2 through Group 16 metals.

In one embodiment, M is a metal ion selected from iron and aluminium, and X is a metal ion selected from Fe(II,III), Al(III), Co(II), Ni(II), Mn(II), Zn(II), Mg(II), Cr(III), V(III), Sc(III), and In(III).

In one embodiment, the metal-ligand cluster has formula Fe$_2$XO, wherein X is Fe(II,III), Co(II), Ni(II), Mn(II), Zn(II), or Mg(II).

In one embodiment, the metal-ligand cluster has formula Fe$_2$CoO or Fe$_3$O.

In one embodiment, the metal-ligand cluster has formula Al$_2$XO, wherein X is a metal ion selected from Al(III), Fe(III), Cr(III), V(III), Sc(III) or In(III).

In one embodiment, the metal cluster has a formula Al$_3$O.

In one embodiment, the one or more ligands are derived from a dicarboxylic acid, a tricarboxylic acid, a tetracarboxylic acid, a hexacarboxylic acid, or a octacarboxylic acid.

In one embodiment, the one or more ligands are derived from a carboxylic acid selected from L1 to L30 or a combination of ligands selected from L31 and L32:

L1

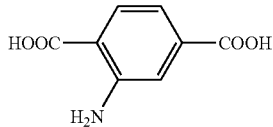
L2

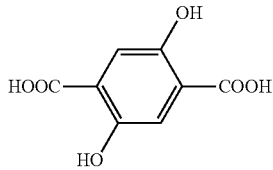
L3

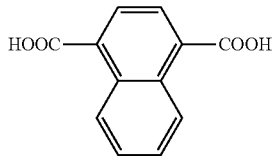
L4

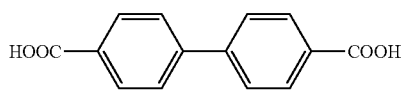
L5

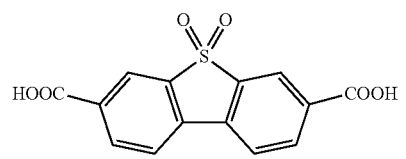
L6

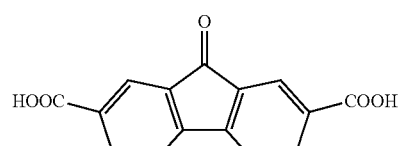
L7

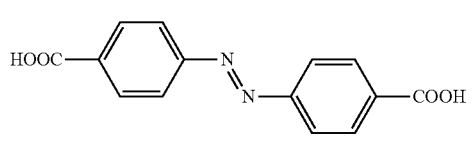
L8

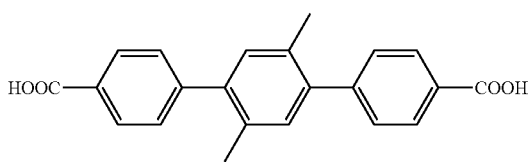
L9

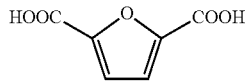
L10

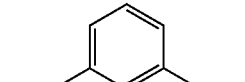
L11

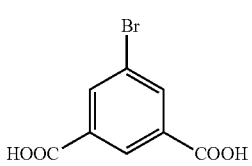
L12

L13
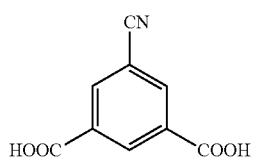
L14
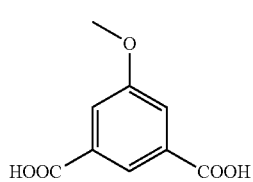
L15
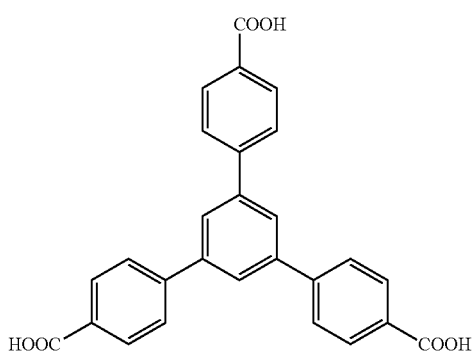
L16
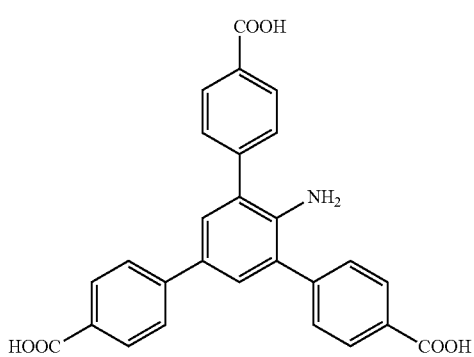
L17
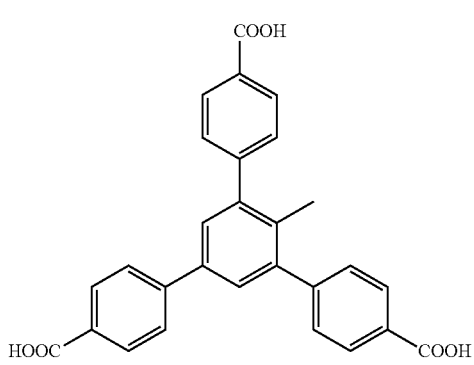
L18
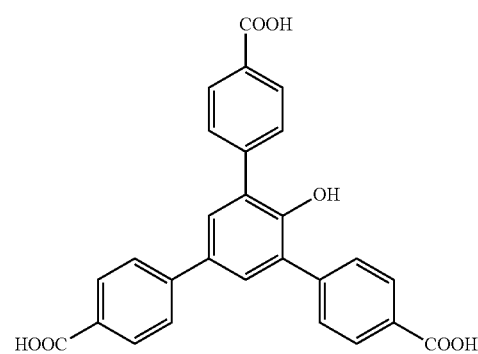
L19
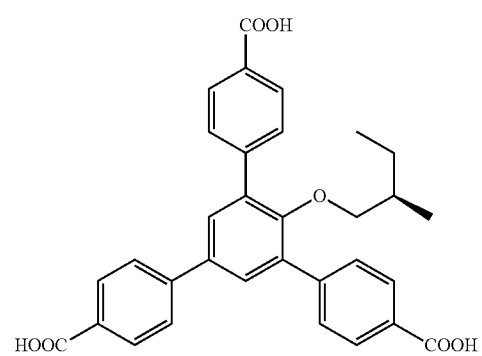
L20
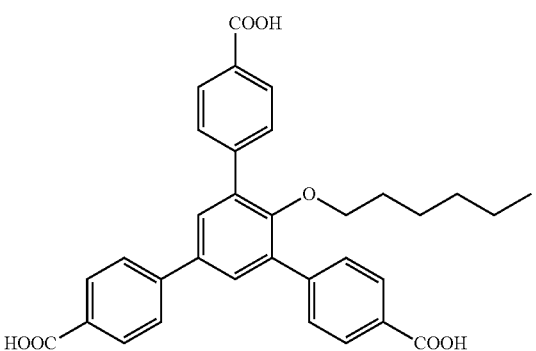
L21

-continued
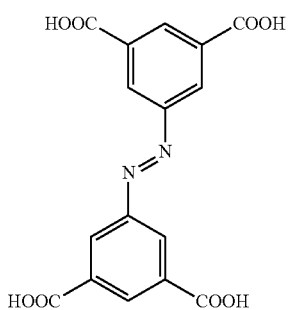
L22
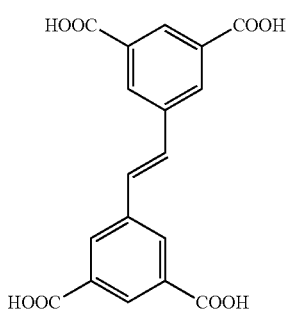
L23
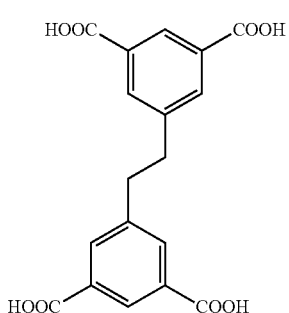
L24
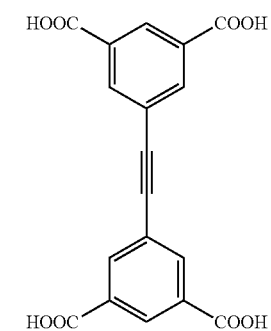
L25
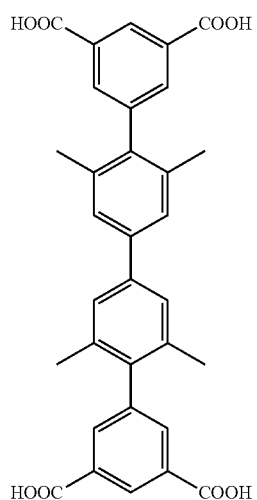
L26
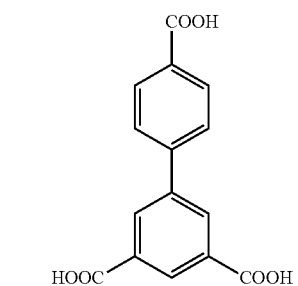
L27
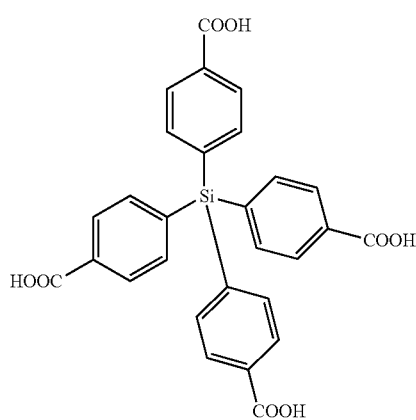
L28

L29
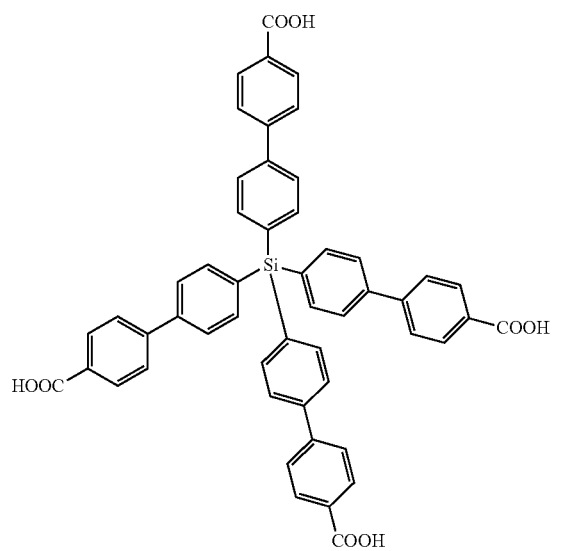
L30
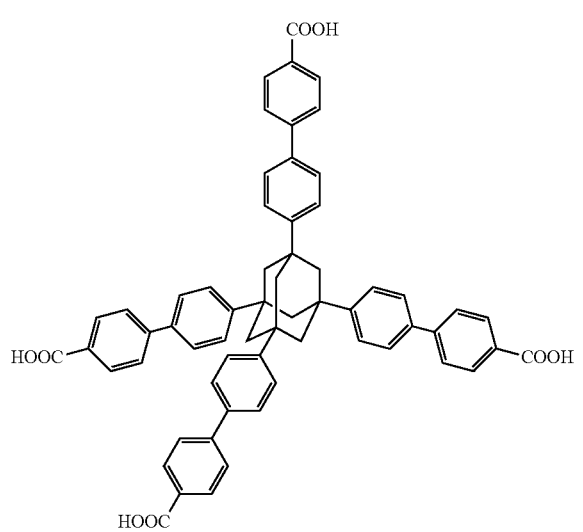
L31
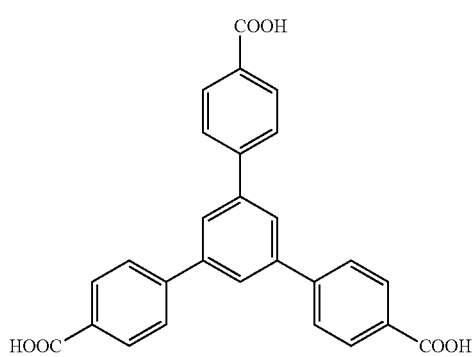
L32
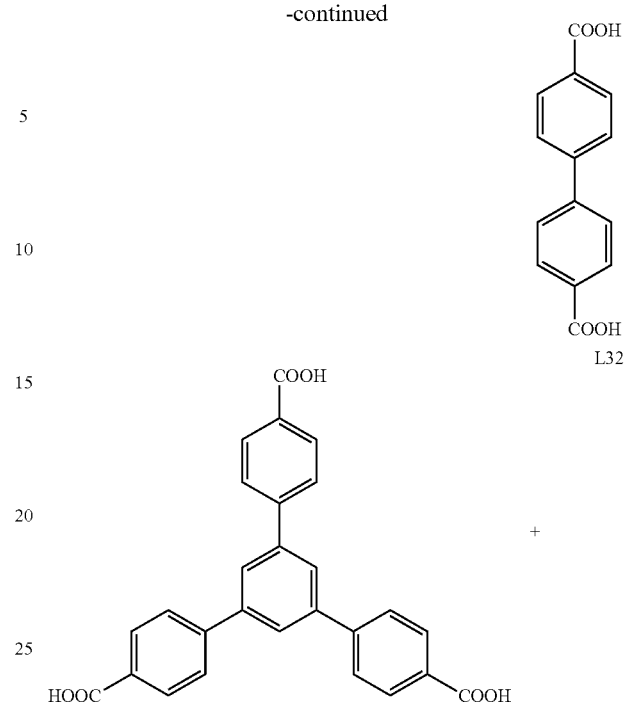
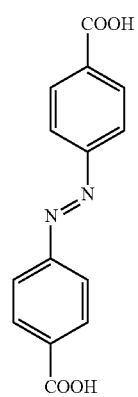
In one embodiment, the one or more ligands are derived from a carboxylic acid:
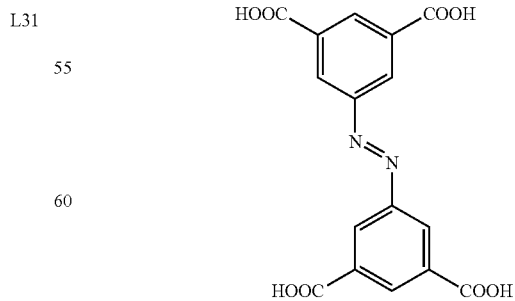
In one embodiment, the organic ligand is derived from a carboxylic acid selected from:

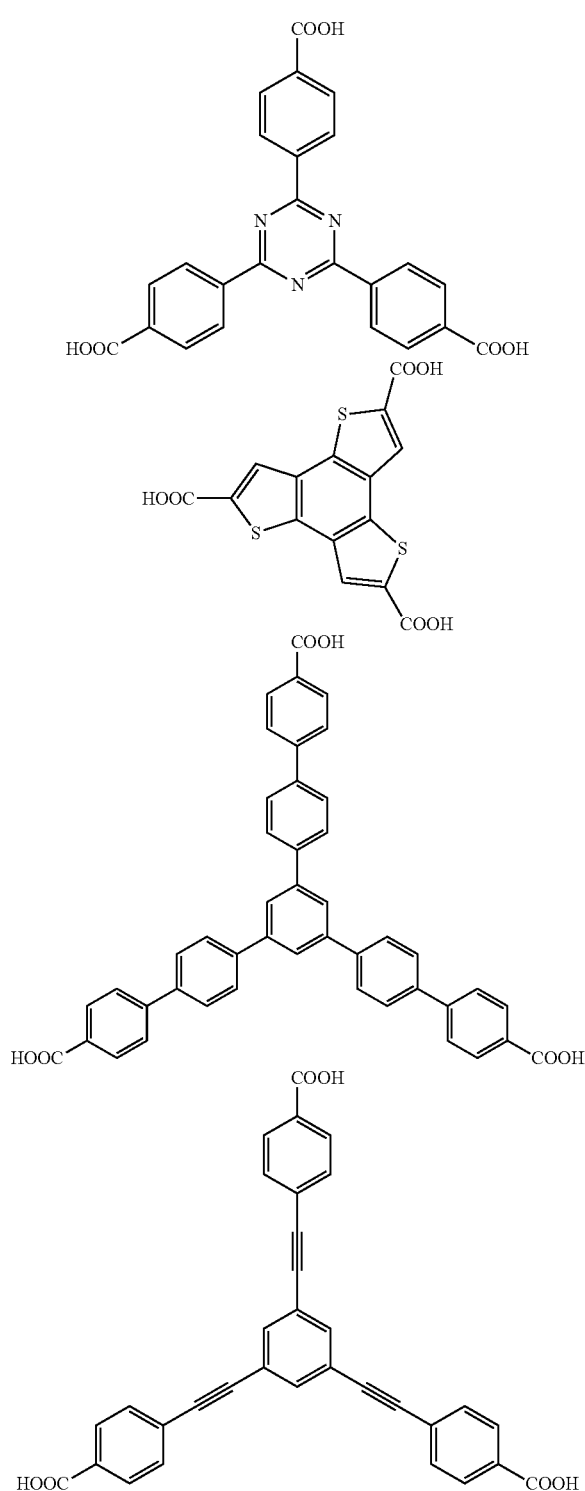

In one embodiment, each metal cluster is coordinated with 4, 5, or 6 ligands.

In one embodiment, the metal-organic framework is in crystalline form.

In one embodiment, the resulting metal-organic framework is in the form of a single crystal, the single crystal having a size of greater than or equal to 2 µm, greater than or equal to 5 µm, 10 µm, 20 µm, 30 µm, 40 µm, 5 µm, 100 µm, 150 µm, 200 µm, 300 µm, 500 µm, 750 µm, or 1000 µm.

In one embodiment, the process is a solvothermal process.

In one embodiment, the reaction is heated at elevated pressure.

The process described herein provides the first way of obtaining a large crystal metal organic frameworks, especially iron, aluminium, and titanium metal organic frameworks. Previous attempts suffered from getting amorphous products or powder instead of a single crystal. Without wishing to be bound by theory, it is thought that as a Lewis acid, the hardness of $Al^{3+}$ is very similar to or even higher than $Fe^{3+}$, so the rate of reverse reaction of crystal growing, which is essential to defect repair of crystal, is very slow. The accumulation of defects in crystals obtained via prior art methods will lead to an amorphous structure. Previously, when people tried to improve the crystallinity of Al-MOFs, the methods they tended to employ were: (1): add strong Brønsted acid, like $HNO_3$, to inhibit the deprotonation of ligand, which was thought to be a necessary step of crystal growing; (2): grow MOFs at higher temperature, this was thought to facilitate reverse reaction (ligand disassociation process).

In one embodiment, the invention provides a process for preparing a metal-organic framework comprising a metal-ligand cluster having a metal ion cluster of formula $M_aO$ and one or more ligands having two or more carboxylate groups, the process comprising reacting a starting compound having a metal ion cluster of formula $M_aO$ and one or more ligands of formula $(R_2COOO)$ with a ligand precursor compound having two or more carboxylate or carboxylic acid groups in the presence of an acid having one carboxylic group or one carboxylate group where at least one $(R_2COO)$ ligand is replaced by a ligand derived from the ligand precursor compound; wherein M is independently a metal ion selected from the group consisting of Group 2 through Group 16 metals; a is an integer from 1 to 8; and $R_2$ is alkyl or aryl.

Preferably, $R_2$ is $CH_3$.

Preferably $a=3$.

Preferably, the acid having one carboxylic acid group or one carboxylate group is selected from trifluoroacetic acid, benzoic acid, formic acid, propionic acid, sodium acetate, and acetic acid. Most preferred is acetic acid.

In one embodiment, R2 is $CH_3$, and the acid is acetic acid ($CH_3COOH$).

In one embodiment, the invention provides a process for preparing a metal-organic framework comprising a metal-ligand cluster having a metal ion cluster of formula $M_aO$ and one or more ligands having two or more carboxylate groups, the process comprising reacting a starting compound having formula $M_aO_y(OR_1)_b(R_2COO)_c$ with a ligand precursor having at least two carboxylic acid groups in the presence of an acid having one carboxylic acid or carboxylate group to provide a metal-organic framework comprising a $M_aO$ cluster where at least one $(R_2COO)$ ligand is replaced by at least one ligand having at least two carboxylate groups; wherein each M is independently a metal ion selected from the group consisting of Group 2 through Group 16 metals; $R_1$ is H, alkyl or aryl; $R_2$ is alkyl or aryl; a is an integer from 1 to 8; b is an integer from 0 to 6; c is an integer from 6 to 20; and y is an integer from 1 to 10.

Preferably, $R_1$ is H.

Preferably, $R_2$ is $CH_3$.

Preferably, $a=3$.

The starting compound may adopt a number of different combinations of M, a, b, c, and y.

For example, in one embodiment, one or more M=Fe, $a=3$, b=0, c=6, and y=1.

Alternatively, one or more M=Al, a=3, b=0, c=6, and y=1.

Alternatively, one or more M=Ti, a=6, b=6, c=6, and y=6; or one or more M=Ti, a=8, b=0, c=12, and y=10; or one or more M=Ti, a=8, b=0, c=18, and y=8.

Alternatively, one or more M=$Cr^{3+}$, a=3, b=0, c=6, and y=1.

In a preferred embodiment is provided a process for preparing a metal-organic framework comprising a metal ion cluster of formula $M_3O$, the process comprising reacting a starting compound of formula $M_3O(CH_3COO)_6$ with a ligand precursor having at least two carboxylic acid groups in the presence of an acid having one carboxylic acid group or one carboxylate group to provide a metal-organic framework comprising a $M_3O$ cluster where at least one ($CH_3COO$) ligand is replaced by at least one ligand having at least two carboxylate groups; wherein each M is independently a metal ion selected from the group consisting of Group 2 through Group 16 metals.

In some embodiments, the acid having a carboxylic acid group is selected from trifluoroacetic acid, benzoic acid, formic acid, propionic acid, sodium acetate, and acetic acid. Most preferred is acetic acid.

In preferred embodiments, the starting compound has formula $M_2XO(CH_3COO)_6$, wherein each M is independently a metal ion selected from iron, aluminium, chromium, titanium, vanadium, scandium, indium and gallium, and X is a metal ion selected from the group consisting of Group 2 through Group 16 metals. For example, X may be a metal ion selected from Al(III), Fe(II,III), Co(II), Ni(II), Mn(II), Zn(II), Mg(II), Cr(III), V(III), Sc(III), Ca(II), Ba(II) or In(III), preferably X is a metal ion selected from Fe(II, III), Co(II), Ni(II), Mn(II), Zn(II), and Mg(II).

In preferred embodiments, the starting compound has a formula $Fe_2XO(CH_3COO)_6$ or $Al_2XO(CH_3COO)_6$, wherein X is Fe(II,III), Al(III), Co(II), Ni(II), Mn(II), Zn(II), or Mg(II). For example, the starting compound may have a formula $Fe_3O(CH_3COO)_6$, $Fe_2Co(CH_3COO)_6$, or $Al_3O(CH_3COO)_6$.

Where, the starting material and the resulting MOF comprise three Fe(III) ions, an additional substituent is required in order to balance the charge of the starting compound and the resulting metal-ligand cluster. Accordingly, the invention also provides a process for preparing a metal-organic framework comprising three Fe(III) metal ions, the process comprising reacting a starting compound of formula $Fe_3O(CH_3COO)_6OH$ with a ligand precursor compound having at least two carboxylic acid groups in the presence of an acid having one carboxylic acid group or one carboxylate group to provide a metal-organic framework comprising a $Fe_3O$ cluster where at least one ($CH_3COO$) ligand is replaced by at least one ligand deriving from the ligand precursor compound.

The inventors have discovered that the use of starting compounds of formula $M_3O(CH_3COO)_6$ in the synthesis of metal-organic frameworks, in particular iron, aluminium, and titanium containing metal-organic frameworks enable the synthesis of large single crystals of these materials.

The process of the invention may be carried out using any suitable solvent. However, the following solvents are appropriate: acetic acid, water, DMF, DEF, NMP, DMSO and DMA. Acetic acid is preferred.

In one embodiment, the single crystal size is greater than or equal to 2 μm, greater than or equal to 5 μm, 10 μm, 20 μm, 30 μm, 40 μm, 50 μm, 100 μm, 150 μm, 200 μm, 300 μm, 500 μm, 750 μm, or 1000 μm.

In one embodiment, the single crystal size is from about 25 μm to about 500 μm, preferably from about 50 μm to about 200 μm.

In one embodiment, the metal-organic framework is an aluminium metal-organic framework.

In one embodiment, the metal-organic framework is an iron metal-organic framework.

In one embodiment, the metal-organic framework is a titanium metal-organic framework.

According to the process of the invention, a mixture of starting material ($M_aO_y(OR_1)_b(R_2COO)_c$; $M_3O(CH_3COO)_6$ etc.), a ligand precursor and a carboxylic acid are provided, the starting material and the ligand precursor and then reacted In the process, the amount of acid may vary depending on the ligands involved. However, an appropriate concentration of acid (such as pure glacier acetic acid) is from about 0.001 mmol/l to about 17.4 mol/l. Alternatively, an acid:solvent volume ratio of from about 0.05:2.0 to about 1.2:2.0 may be employed. Preferably, the acid:solvent ratio is from about 0.1:2.0 to about 1:2, from 0.1:2 to about 0.8:2, from about 0.1:2 to about 0.5:2, or an acid:solvent ratio of 0.1:2, 0.2:2, 0.22:2, 0.25:2, 0.3:2, 0.35:2, 0.4:2, 0.45:2, 0.5:2, 0.6:2, 0.8:2, or 1:2. It is also clear from the examples which of these ratios are preferred for the synthesis of each metal-ligand cluster.

An appropriate acid:solvent ratio for each of the exemplified metal-organic frameworks is tabulated below. Preferably, the acid is acetic acid.

| Metal-Organic Framework | Acid:Solvent Ratio |
|---|---|
| PCN-233 | 0.3-0.5:2 (ideally 0.4:2) |
| PCN-234 | 0.3-0.5:2 (0.4:2) |
| PCN-235 | 0.1-0.3:2 (0.2:2) |
| PCN-236 | 0.05-0.2:2 (0.1:2) |
| PCN-237 | 0.1-0.3:2 (0.2:2) |
| PCN-238 | 0.05-0.2:2 (0.1:2) |
| PCN-239 | 0.05-0.2:2 (0.1:2) |
| PCN-240 | 0.15-0.35:2 (0.25:2) |
| PCN-241 | 0.7-0.9:2 (0.8:2) |
| PCN-242 | 0.35-0.55:2 (0.45:2) |
| PCN-243 | 0.35-0.55:2 (0.45:2) |
| PCN-245 | 0.05-0.25:2 (0.15:2) |
| PCN-246 | 0.1-0.3:2 (0.2:2) |
| PCN-247 | 0.25-0.45:2 (0.35:2) |
| PCN-248 | 0.15-0.35:2 (0.25:2) |
| PCN-250 | 0.9-1.1:2 (1:2) |
| PCN-251 | 0.9-1.1:2 (1:2) |
| PCN-252 | 0.7-0.9:2 (0.8:2) |
| PCN-253 | 0.9-1.1:2 (1:2) |
| PCN-254 | 0.9-1.1:2 (1:2) |
| PCN-255 | 0.4-0.6:2 (0.5:2) |
| PCN-256 | 0.3-0.5:2 (0.4:2) |
| PCN-258 | 0.3-0.5:2 (0.4:2) |
| PCN-260 | 0.15-0.35:2 (0.25:2) |
| PCN-261-NH2 | 0.12-0.32:2 (0.22:2) |
| PCN-261-CH3 | 0.1-0.3:2 (0.2:2) |
| PCN-261-Chiral | 0.1-0.3:2 (0.2:2) |
| PCN-262 | 0.15-0.35:2 (0.25:2) |
| PCN-263 | 0.2-0.4:2 (0.3:2) |
| PCN-264 | 0.5-0.7:2 (0.6:2) |
| PCN-266 | 0.2-0.4:2 (0.3:2) |
| PCN-280 | 0.1-0.3:2 (0.2:2) |
| PCN-285 | 0.1-0.3:2 (0.2:2) |
| Al-ABTC MOF | 0.4-0.6:2 (0.5:2) |

Previously, MOFs were synthesized through one pot reactions, in which their inorganic building blocks assemble in situ without adequate control. Therefore, the overall design of MOFs was challenging and significantly limited. As a result, the overall design of MOFs has been dominated by changes to the organic synthesis of these materials. In contrast, the structure of MOFs can be made more predictable using the process of the invention with control of the inorganic building blocks used. Constructed with desired inorganic building blocks, the structure of MOFs becomes more designable and predictable. Meanwhile, stability and functionality can be better controlled for targeted applications, such as gas storage, separations, and catalysis.

In previous MOF one pot reactions, the inorganic building block forms in situ. Without accurate control of the inorganic building blocks, design of MOFs has mainly been dominated by organic synthesis techniques such as ligand extension and functionalization. As a result, several problems existed. For example: (i) the overall design of novel MOFs with expected structures or even simple functionalization of existing MOFs for targeted applications becomes very challenging because of the unpredictable configuration of in situ formed inorganic building blocks; (ii) mixed phases often come out together especially in metals with diverse inorganic building blocks such as $Fe^{3+}$; and (iii) the abundant and interesting inorganic cluster chemistry is almost neglected and mainly acts in a supporting role, which severely limits the potential of inorganic chemistry for MOFs' development. The process of the present invention addresses these problems by employing pre-assembled inorganic building blocks, i.e. having formula $M_3O(CH_3COO)_6$.

All previous synthesis processes are essentially based on the labile coordination bond and have never been generalized. In contrast, the process of the present invention involves building MOFs with preformed inorganic building blocks (PIBBs) through simple substitution reactions. This is possible because: (1) the inorganic building block is isolatable and soluble; (2) the inorganic building block is robust enough that the constructing moieties can be perfectly maintained while it undergoes substitution under solvothermal conditions; and (3) it should have high symmetry to allow the facile formation of infinite frameworks with many ligand types. The present invention employs a preassembled $M_3XO(CH_3COO)_6$ starting compound, such as a $Fe_2XO(CH_3COO)_6$ starting compound to construct metal-organic frameworks such as Fe-MOFs through a simple carboxylate substitution reaction.

In particular, $Fe_2XO(CH_3COO)_6$ (X=Fe(II,III), Co(II), Ni(II), Mn(II), Zn(II) etc) exhibit excellent solubility and as a result have been found to be excellent starting materials for the purpose of the present invention. Meanwhile, due to the strong electrostatic interaction between metal ion, e.g. $Fe^{3+}$, and $\mu_3$-$O_2$— and the strong coordination bond between metal ion, e.g. $Fe^{3+}$, and carboxylate, such basic carboxylate is inherently robust enough to protect the integrity of the inorganic organic building block under solvothermal conditions. Moreover, the cluster itself exhibits pseudo-$D_{3h}$ symmetry (Fe and X are indistinguishable in crystallographic refinement, indicating a disordered X position), which makes it easier to form repeating units.

Metal ions with high valency, in particular metal ions such as $Fe^{3+}$, $Ti^{3+}$, and $Al^{3+}$, as a hard Lewis acidic species, bond strongly to carboxylate, and therefore the ligand dissociation process is slow. This results in a rate of insufficient structural reorganization and defect repair that is insufficient to form a long range ordered crystalline structure. Even using $M_3O(CH_3COO)_6$ type starting materials, such as $Fe_2XO(CH_3COO)_6$, direct synthesis of metal-organic frameworks, such as Fe-MOFs, still gives rise to gel or amorphous products. In contrast, the process of the present invention uses a ligand substitution process.

Unlike soft Lewis acidic species, metal ions, e.g. $Fe^{3+}$, bonds strongly with carboxylate which results in a higher $E_a$ for the ligand dissociation process and thus a much slower reaction rate. Since intermediate species keep constant concentration, and temperature variation simultaneously changes both the forward and the reverse reaction rate, the only way to produce a balanced substitution-dissociation process is to slow down the substitution reaction rate. Without wishing to be bound by theory, this is accomplished in the process of the present invention by maintaining an optimal concentration of ligand or cluster by replacing some portion of the solvent with acetic acid, which bonds competitively to the 5-coordinated intermediate. Because it is actually the carboxylate and not the acid doing the substitution, when the deprotonation process is taken into account, extra acetic acid could simultaneously inhibit the deprotonation of ligand, which further slows down the substitution reaction and aids the crystallization process.

Consequently, with the assistance of acetic acid as a competing reagent, large crystals of metal-organic frameworks may be obtained using the process of the present invention. The process of the present invention is useful in obtaining crystalline forms of, among others, iron-containing MOFs, titanium-containing MOFs, and aluminium-containing MOFs.

In a further aspect, the present invention provides a metal-organic framework obtainable by any process of the invention described herein. In particular, the invention provides a metal-organic framework of the present invention described herein obtainable by any process of the present invention described herein.

The process of the invention can provide metal organic frameworks as described below. The invention also however is directed to the metal organic frameworks as products.

According to a further aspect, the invention provides a monocrystalline metal-organic framework comprising one or more metal-ligand clusters, each metal-ligand cluster comprising (i) a metal cluster having two or more metal ions, wherein at least one metal ion is selected from iron, aluminium, chromium, titanium, vanadium, scandium, indium and gallium, and (ii) one or more ligands having two or more carboxylate groups.

In an embodiment, the metal-organic framework comprises two or more, three or more, or four or more metal-ligand clusters. That is, the metal-organic framework comprises two, three, four or more different metal-ligand clusters having different metal ions and/or different ligands.

Each metal-ligand cluster comprises two or more metal ions wherein at least one is selected from the list above. For example, the at least one metal ion may be selected from Fe(II), Fe(III), Al(III), Cr(III), Ti(IV), V(III), V(IV), V(V), Sc(III), In(III), Ga(III), and mixtures thereof.

In some embodiments, the metal-ligand cluster contains at least two metal ions which are different to each other. One may be selected from iron, aluminium, chromium, titanium, vanadium, scandium, indium and gallium. The other may be selected from the group consisting of Group 2 through Group 16 metals; for example selected from Al(III), Fe(II,III), Co(II), Ni(II), Mn(II), Zn(II), Mg(II), Cr(III), V(III), Sc(III), Ca(II), Ba(II) or In(III), preferably Fe(II,III), Co(II), Ni(II), Mn(II), Zn(II), or Mg(II).

In one embodiment, the metal-organic framework comprises one or more metal-ligand clusters, each metal-ligand cluster comprising (i) three metal ions, wherein at least one metal ion, preferably at least two metal ions, is/are selected from iron, aluminium, chromium, titanium, vanadium, scandium, indium and gallium; and (ii) one or more ligands having two or more carboxylate groups.

The metal-ligand cluster may a metal cluster comprising the formula $M_3O$, wherein each M is independently a metal ion selected from iron, aluminium, chromium, titanium, vanadium, scandium, indium and gallium, and X is a metal ion selected from the group consisting of Group 2 through Group 16 metals. For example, X may be a metal ion selected from Al(III), Fe(II,III), Co(II), Ni(II), Mn(II), Zn(II), Mg(II), Cr(III), V(III), Sc(III), Ca(II), Ba(II) or In(III), preferably X is a metal ion selected from Fe(II,III), Co(II), Ni(II), Mn(II), Zn(II), and Mg(II).

Accordingly, in some embodiments the metal-ligand cluster contains at least one iron metal ion, preferably two iron metal ions; for example the metal core cluster may have a formula $Fe_2XO$ or $Fe_3O$ where X is as defined above. For example, X may be Co(II), Ni(II), Mn(II), Zn(II), or Mg(II), preferably X is Co(II) or Ni(II). A metal core cluster having a formula $Fe_2XO$ is preferred.

In embodiments in which it is necessary to balance the charge of the metal-ligand cluster, additional substituents/ligands may be included. For example, additional hydroxyl groups may be present in the metal-ligand cluster. In particular, in an $Fe_3$ based MOF where all three Fe ions are Fe(III) ions, the metal-ligand cluster may have a formula of $Fe_3O(ligand)_6OH$. In contrast, when one Fe ion is Fe(II), the formula is $Fe_3O(ligand)_6$.

In some embodiments, the metal-ligand cluster contains at least one aluminium metal ion, preferably two aluminium ions; for example the metal cluster may have a formula $Al_2XO$ or $Al_3O$ where X is as defined above. For example, X may be Fe(III), Cr(III), V(III), Sc(III) or In(III).

These metal-organic frameworks exhibit high gravimetric and volumetric CO, $N_2$, $H_2$ and $CH_4$ uptake. Additionally, these metal-organic frameworks exhibit extraordinary stability in water and aqueous solutions at a range of pHs.

The metal-organic framework according to the invention may be in crystalline form. Specifically, the present invention may provide a single crystal of a metal-organic framework according to the invention having a largest dimension, for example as measured/observed under a microscope, of greater than or equal to 2 μm, greater than or equal to 5 μm, 10 μm, 20 μm, 30 μm, 40 μm, 50 μm, 100 μm, 200 μm, 500 μm, 1000 μm, or 1500 μm. Generally, single crystals of a metal-organic framework according to the invention possess a largest dimension of between about 50 μm and 2000 μm.

Alternatively, the single crystals of the metal-organic framework may have a CE (circular equivalent) diameter of greater than or equal to about 50 μm, 80 μm, 100 μm, or 150 μm. For example, the CE diameter may range from about 50 μm to about 200 μm.

According to a further aspect of the invention is provided a single crystal of a metal-organic framework comprising at least one metal ion selected from iron, aluminium, chromium, titanium, vanadium, scandium, indium, and gallium, wherein the single crystal has a largest dimension of greater than or equal to 2 μm. Preferably, the single crystal has a size of greater than or equal to 5 μm, 10 μm, 20 μm, 30 μm, 40 μm, 50 μm, 100 μm, 150 μm, 200 μm, 500 μm, 1000 μm, 1500 μm, 1750 μm, or 1900 μm. Generally, the largest dimension is between about 50 μm and about 2000 μm.

The invention is also directed to iron, aluminium, and titanium metal organic frameworks. In particular, the invention is directed to iron, aluminium, and titanium metal organic frameworks having large crystal size. The invention is also directed to monocrystalline iron, aluminium, or titanium metal organic frameworks.

Iron Metal Organic Frameworks

In one aspect, the invention provides an iron metal-organic framework comprises at least one metal-ligand cluster, each metal-ligand cluster comprising at least one iron metal ion; or wherein the at least one metal-ligand cluster comprises at least two iron metal ions; or wherein the at least one metal-ligand cluster comprises three iron metal ions.

In one embodiment, the iron metal organic framework is monocrystalline. For example, the iron metal-organic framework is a single crystal of a metal organic framework comprising at least one iron metal ion.

The iron metal-organic framework may be functionalised or non-functionalised, preferably non-functionalised. For example, the metal-organic framework may be functionalised with an amine functional group.

In one embodiment, the iron metal-organic framework comprises metal-ligand clusters comprising (i) two or more metal ions, wherein at least one metal ion is iron, and (ii) one or more ligands having two or more carboxylate groups.

In one embodiment, the at least one metal ion is Fe(II) or Fe(III). The metal-ligand cluster may also comprise a second metal ion selected from Al(III), Co(II), Ni(II), Mn(II), Zn(II), Mg(II), Cr(III), V(III), Sc(III), Ca(II), Ba(II) or In(III), preferably Co(II), Ni(II), Mn(II), Zn(II), or Mg(II).

In one embodiment, the metal-ligand cluster comprises three metal ions, wherein at least one metal ion is iron. Preferably, the metal-ligand cluster comprises three metal ions, wherein at least two metal ions are iron. For example, the metal-ligand cluster may have the formula $Fe_2XO$, where X is a metal ion selected from the group consisting of Group 2 through Group 16 metals. Preferably, X is a metal ion selected from Fe, Co, Mn, Zn, Ni, Mg, Cu, or Ca, more preferably Fe, Co, Mn, Zn, or Ni, even more preferably Fe or Co. In an alternative embodiment, the metal cluster may have the formula $Fe_3O$.

In one embodiment, each metal cluster of the iron metal organic framework is coordinated with 4, 5, or 6 ligands.

In one embodiment, the iron metal-organic framework may comprise inorganic cornerstones having at least 4 coordination sites, preferably having at least 6 coordination sites, having from 6 to 12 coordination sites.

In one embodiment, the iron metal-organic framework may comprise a molar ratio of metal ions to organic linker of from about 1:0.2 to about 1:0.7, from about 1:0.45 to about 1:0.55, or about 1:0.5.

In one embodiment, the iron metal-organic framework may have a BET specific surface area of at least 100 $m^2/g$, at least 200 $m^2/g$, at least 500 $m^2/g$, at least 1000 $m^2/g$, at least 1000 $m^2/g$, at least 1100 $m^2/g$, or greater than or equal to 1200 $m^2/g$. The metal-organic framework may also have a surface area of less than or equal to 8000 $m^2/g$, less than or equal to 6000 $m^2/g$, less than or equal to 4000 $m^2/g$, or less than or equal to 3000 $m^2/g$.

In one embodiment, the iron metal-organic framework comprises cavities having a free diameter of about 4 Å to about 50 Å, about 4 Å to about 40 Å, or about 5 Å to about 25 Å.

In one embodiment, the iron metal-organic framework comprises pores having a pore volume from about 0.1 $cm^3/g$ to about 4 $cm^3/g$, from about 0.1 $cm^3/g$ to about 3 $cm^3/g$, or from about 0.2 $cm^3/g$ to about 3 $cm^3/g$.

In one embodiment, the metal-organic framework is a single crystal. For example, the single crystal may have a size greater than or equal to 2 μm, 5 μm, 10 μm, 20 μm, 30 μm, 40 μm, 50 μm, 100 μm, 150 μm, 200 μm, 300 μm, 500 μm, 750 μm, or 1000 μm. For example, the crystal may have a size ranging from about 25 μm to about 2500 μm, or from about 50 μm to about 2000 μm, or from about 500 μm to about 1500 μm.

In one embodiment, the crystal has a circular equivalent (CE) diameter of greater than equal to about 50 μm, 100 μm, 200 µm, 300 µm, 400 µm, 500 µm, 750 µm, 1000 µm, or 1250 µm. The CE diameter of the crystal may be less than or equal to 2500 µm, 2000 µm, or 1500 µm.

In one embodiment, the invention provides a single crystal of a metal-organic framework comprising at least one iron metal ion having a largest dimension, for example as observed under a microscope, of greater than or equal to about 2 µm, greater than or equal to 5 µm, 10 µm, 20 µm, 30 µm, 40 µm, 50 µm, 100 µm, 200 µm, 500 µm, 100 µm, or 1500 µm. Generally, single crystals of a metal-organic framework comprising at least one iron metal ion (e.g. comprising a metal cluster having formula $Fe_3O$ or $Fe_2CoO$) having a largest dimension of between about 50 µm and 2000 µm have been achieved.

In one embodiment, the present invention provides a single crystal of a metal-organic framework comprising at least one metal-ligand cluster, each metal-ligand cluster comprising at least one iron metal ion, preferably at least two iron metal ions, more preferably three iron metal ions, wherein the single crystal has a size greater than or equal to about 2 µm, greater than or equal to 5 µm, 10 µm, 20 µm, 30 µm, 40 µm, 50 µm, 100 µm, 200 µm, 500 µm, 1000 µm, or 1500 µm. Generally, single crystals of a metal-organic framework comprising at least one iron metal ion (e.g. comprising a metal cluster having formula $Fe_3O$ or $Fe_2CoO$) having a largest dimension of between about 50 µm and 2000 µm have been achieved.

In one embodiment, the present invention provides a single crystal of a metal-organic framework comprising at least one metal-ligand cluster, each metal-ligand cluster comprising at least one iron metal ion, preferably at least two iron metal ions, more preferably three iron metal ions, wherein the single crystal has a size greater than or equal to about 2 µm.

In one embodiment, the invention provides a single crystal of a metal-organic framework comprising at least one iron metal ion (e.g. comprising a metal cluster having formula $Fe_3O$ or $Fe_2CoO$) having a largest dimension, for example as observed under a microscope, of greater than or equal to about 2 µm, greater than or equal to 5 µm, 10 µm, 20 µm, 30 µm, 40 µm, 50 µm, 100 µm, 200 µm, 500 µm, 1000 µm, or 1500 µm. Generally, single crystals of a metal-organic framework comprising at least one iron metal ion (e.g. comprising a metal cluster having formula $Fe_3O$ or $Fe_2CoO$) having a largest dimension of between about 50 µm and 2000 µm have been achieved.

Aluminium Metal Organic Frameworks

In one aspect, the invention provides a metal-organic framework comprising at least one metal-ligand cluster, each metal-ligand cluster comprising at least one aluminium metal ion. For example, the at least one metal-ligand cluster comprises at least two aluminium metal ions, or the at least one metal-ligand cluster comprises three aluminium metal ions.

In one embodiment, the metal-organic framework is a monocrystalline metal-organic framework comprising at least one aluminium ion.

In one embodiment, the aluminium metal organic framework is a single crystal.

The aluminium metal organic framework may be functionalised or not functionalised.

In one embodiment, the aluminium metal-organic framework does not comprise an amine functional groups.

In one embodiment, the aluminium metal-organic framework comprises metal-ligand clusters comprising (i) two or more metal ions, wherein at least one metal ion is aluminium, and (ii) one or more ligands having two or more carboxylate groups.

In one embodiment, the metal-ligand cluster comprises a second metal ion selected from Fe(II,III), Co(II), Ni(II), Mn(II), Zn(II), Mg(II), Cr(III), V(III), Sc(III), Ca(II), Ba(II) or In(III), preferably Fe(II,III), Co(II), Ni(II), Mn(II), Zn(II), or Mg(II).

In one embodiment, the metal-organic framework comprises metal-ligand clusters that comprise three metal ions, wherein at least one metal ion is aluminium, or at least two metal ions are aluminium. For example, the metal-ligand cluster may have the formula $Al_2XO$, where X is a metal ion selected from the group consisting of Group 2 through Group 16 metals. For example, X may be a metal ion selected from Al(III), Fe(III), Cr(III), V(III), Sc(III) or In(III). Alternatively, the metal cluster has a formula $Al_3O$.

In one embodiment, the aluminium metal organic framework comprises metal clusters coordinated with 4, 5, or 6 ligands.

In one embodiment, the aluminium metal-organic framework comprises inorganic cornerstones having at least 8 coordination sites, or at least 10 coordination sites, or having 12 coordination sites.

In one embodiment, the aluminium metal-organic framework has a molar ratio of metal ions to organic linker of from about 1:0.2 to about 1:0.7 from about 1:0.45 to about 1:0.55, preferably about 1:0.5.

In one embodiment, the aluminium metal-organic framework has a surface area of at 200 m$^2$/g, at least 300 m$^2$/g, at least 600 m$^2$/g, at least 800 m$^2$/g, at least 1000 m$^2$/g, at least 1100 m$^2$/g, or at least 1200 m$^2$/g. Likewise, the metal-organic framework may have a surface area of less than or equal to 8000 m$^2$/g, less than or equal to 6000 m$^2$/g, less than or equal to 4000 m$^2$/g, or less than or equal to 3000 m$^2$/g.

In one embodiment, the aluminium metal-organic framework comprises cavities having a free diameter of about 4 Å to about 50 Å, or about 4 Å to about 40 Å, or about 10 Å.

In one embodiment, the aluminium metal-organic framework comprises pores having a pore volume from about 0.1 cm$^3$/g to about 4 cm$^3$/g, or from about 0.1 cm$^3$/g to about 3 cm$^3$/g, or from about 0.2 cm$^3$/g to about 3 cm$^3$/g.

In one embodiment, the aluminium metal organic framework is a single crystal.

For example, the single crystal may have a size greater than or equal to 2 µm, 5 µm, µm, 20 µm, 30 µm, 40 µm, 50 µm, 100 µm, 150 µm, 200 µm, 300 µm, 500 µm, 750 µm, or 1000 µm.

The crystal may have a crystal size from about 25 µm to about 500 µm, preferably from about 50 µm to about 200 µm.

In one embodiment, the invention provides a single crystal of a metal-organic framework comprising at least one aluminium metal ion having a largest dimension, for example as observed under a microscope, of greater than or equal to about 2 µm, greater than or equal to 5 µm, 10 µm, 20 µm, 30 µm, 40 µm, 50 µm, 100 µm, or 150 µm. Generally, single crystals of a metal-organic framework comprising at least one aluminium metal ion (e.g. comprising a metal cluster having formula $Al_3O$) having a largest dimension of between about 50 µm and 200 µm have been achieved.

In one embodiment, the present invention provides a single crystal of a metal-organic framework comprising at least one metal-ligand cluster, each metal-ligand cluster comprising at least one aluminium metal ion, preferably at least two aluminium metal ions, more preferably three aluminium metal ions, wherein the single crystal has a size greater than or equal to about 2 µm, greater than or equal to 5 µm, 10 µm, 20 µm, 30 µm, 40 µm, 50 µm, 100 µm, or 150 µm. Generally, single crystals of a metal-organic framework comprising at least one aluminium metal ion (e.g. comprising a metal cluster having formula $Al_3O$) having a largest dimension of between about 50 µm and 200 µm have been achieved.

In one embodiment, the invention provides a single crystal of a metal-organic framework comprising at least one aluminium metal ion (e.g. comprising a metal cluster having formula $Al_3O$) having a largest dimension, for example as observed under a microscope, of greater than or equal to about 2 µm, greater than or equal to 5 µm, 10 µm, 20 µm, 30 µm, 40 µm, 50 µm, 100 µm, or 150 µm. Generally, single crystals of a metal-organic framework comprising at least one aluminium metal ion (e.g. comprising a metal cluster having formula $Al_3O$) having a largest dimension of between about 50 µm and 200 µm have been achieved.

In preferred embodiments, the size of the single crystal (containing an aluminium metal ion or an iron metal ion) is greater than or equal to about 5 µm, more preferably greater or equal to than about 10 µm, greater than or equal to about 20 µm, greater than or equal to about 30 µm, greater than or equal to about 40 µm, greater than or equal to about 50 µm.

Aluminium metal-organic frameworks (Al-MOFs) have aroused great interest for a number of reasons such as aluminium is a very cheap and rich element in our planet; aluminium's atomic mass is very light (at least compared to other metal elements, especially the transition metals) which means for the MOFs with iso-structure, Al-MOFs have lower weight and therefore higher specific area, which provides improved gas adsorption; there is a very strong interaction between $Al^{3+}$ and carboxylate groups; and Al-MOFs can exhibit very high moisture, mechanical and chemical stability.

However, a great deal of effort has been put into preparing crystals of Al-MOFs without success. In fact, the inventors are not aware of any one preparing a single crystal of an Al-MOF with a single crystal size greater than about 1 µm. The same is true for iron-MOFs.

Titanium Metal Organic Frameworks

In one aspect, the invention provides a titanium metal-organic framework comprising at least one metal-ligand cluster, each metal-ligand cluster comprising at least one titanium metal ion. For example, the metal-ligand cluster may comprise at least two titanium metal ions; or may comprise three titanium metal ions.

In one embodiment, the metal-organic framework is a monocrystalline metal organic framework comprising at least one titanium ion.

In one embodiment, the metal organic framework is a single crystal.

In one embodiment, the metal-organic framework comprises metal-ligand clusters that comprise three metal ions, wherein at least one metal ion is titanium, or at least two metal ions are titanium.

In one embodiment, the titanium metal-organic framework may not comprise any amine functional groups.

In one embodiment, the single crystal of a titanium metal-organic framework is either functionalised or not functionalised, preferably not functionalised.

In one embodiment, the titanium metal-organic framework comprises a titanium(IV) oxo cluster.

In one embodiment, the metal cluster of titanium metal-organic framework comprises a $Ti_7O_6$ cornerstone.

In one embodiment, the titanium metal-organic framework comprises ligands which are porphyrinic ligands.

For example, the ligands may be derived from TCPP:

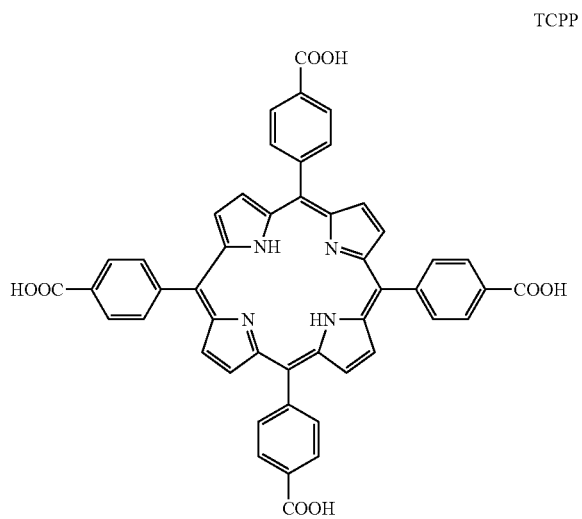 [SMILES: O=C(O)c1ccc(-c2c3nc(c(-c4ccc(C(=O)O)cc4)c4ccc([nH]4)c(-c4ccc(C(=O)O)cc4)c4nc(c(-c5ccc(C(=O)O)cc5)c5ccc2[nH]5)C=C4)C=C3)cc1]

TCPP

In one embodiment, the titanium metal-organic framework comprises metal-ligand clusters comprising (i) two or more metal ions, wherein at least one metal ion is titanium, and (ii) one or more ligands having two or more carboxylate groups.

In one embodiment, the metal-ligand cluster may comprise a second metal ion selected from Fe(II,III), Co(II), Ni(II), Mn(II), Zn(II), Mg(II), Cr(III), V(III), Sc(III), Ca(II), Ba(II) or In(III), preferably Fe(II,III), Co(II), Ni(II), Mn(II), Zn(II), or Mg(II).

In one embodiment, the titanium metal-organic framework comprises a metal cluster which is coordinated with 4, 5, or 6 ligands.

In one embodiment, the titanium metal-organic framework comprises inorganic cornerstones having at least 10 coordination sites, having at least 12 coordination sites, having at least 20 coordination sites, or at least 24 coordination sites.

In one embodiment, the titanium metal-organic framework may have a molar ratio of metal ions to organic linker of from about 1:0.2 to about 1:0.7, of from about 1:0.2 to about 1:0.55, from about 1:0.3 to about 1:0.4, or about 1:0.5.

In one embodiment, the titanium metal-organic framework may have a surface area of at least 200 $m^2/g$, at least 300 $m^2/g$, at least 600 $m^2/g$, at least 800 $m^2/g$, at least 1000 $m^2/g$, at least 1500 $m^2/g$, at least 2000 $m^2/g$, at least 2500 $m^2/g$, or at least 3000 $m^2/g$.

In one embodiment, the titanium metal-organic framework may have a surface area of less than or equal to 8000 $m^2/g$, less than or equal to 6000 $m^2/g$, preferably less than or equal to 4000 $m^2/g$, more preferably less than or equal to 3500 $m^2/g$.

In one embodiment, the titanium metal-organic framework may comprise cavities having a free diameter of about 4 Å to about 50 Å, about 4 Å to about 40 Å, about 5 Å to about 25 Å, or about 10 Å to about 20 Å.

In one embodiment, the titanium metal-organic framework may comprise pores having a pore volume from about 0.1 $cm^3/g$ to about 4 $cm^3/g$, or from about 0.4 $cm^3/g$ to about 0.9 $cm^3/g$, or from about 0.5 $cm^3/g$ to about 0.8 $cm^3/g$, or about 0.6 $cm^3/g$.

In one embodiment, the titanium metal organic framework is a single crystal. For example, the single crystal may have a size greater than or equal to 10 µm, 20 µm, 30 µm, 40 µm, 50 µm, 100 µm, 150 µm, 200 µm, 300 µm, 500 µm, 750 µm, or 1000 µm. For example, the single crystal may have a crystal size from about 10 µm to about 600 µm, preferably from about 25 µm to about 500 µm, preferably from about 50 µm to about 200 µm.

In one aspect, the invention provides a single crystal of a metal-organic framework comprising at least one titanium ion, wherein the single crystal has a size greater than or equal to 10 µm; or having a size greater than or equal to 20 µm, 30 µm, 40 µm, or 50 µm; or having a size greater than or equal to 100 µm, 150 µm, 200 µm, 300 µm, 500 µm, 750 µm, or 1000 µm.

In one embodiment, the metal-organic framework comprises at least one metal-ligand cluster, each metal-ligand cluster comprising at least one titanium metal ion; or at least two titanium metal ions; or at least three titanium metal ions.

In one embodiment, the metal-organic framework comprises a titanium(IV) oxo cluster. For example, the metal-organic framework may comprise a $Ti_7O_6$ cornerstone.

In one embodiment, the metal-organic framework further comprises carboxylate ligands. For example, the ligands may be porphyrinic ligands.

In one embodiment, the ligands may be derived from TCPP:

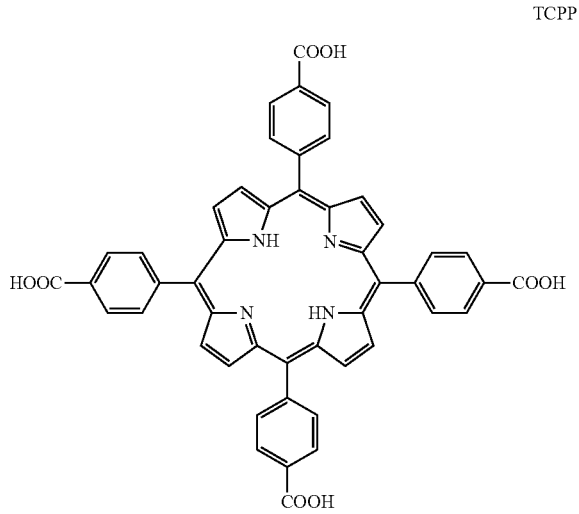 [SMILES: O=C(O)c1ccc(-c2c3nc(c(-c4ccc(C(=O)O)cc4)c4ccc([nH]4)c(-c4ccc(C(=O)O)cc4)c4nc(c(-c5ccc(C(=O)O)cc5)c5ccc2[nH]5)C=C4)C=C3)cc1]

TCPP

Alternatively, the ligands may be derived from a carboxylic acid as described in the "General" section of this specification.

In one embodiment, each metal cluster is coordinated with 4, 5, or 6 ligands.

In one embodiment, the metal-organic framework comprises inorganic cornerstones having at least 10 coordination sites, having at least 12 coordination sites, having at least 20 coordination sites, or at least 24 coordination sites.

In one embodiment, the metal-organic framework has a molar ratio of metal ions to organic linker of from about 1:0.2 to about 1:0.55, from about 1:0.3 to about 1:0.4, or about 1:0.5.

In one embodiment, the metal-organic framework has a surface area of at least 1000 $m^2/g$, at least 1500 $m^2/g$, at least 2000 $m^2/g$, at least 2500 $m^2/g$, or at least 3000 $m^2/g$.

In one embodiment, the metal-organic framework has a surface area of less than or equal to 6000 $m^2/g$, preferably less than or equal to 4000 $m^2/g$, more preferably less than or equal to 3500 $m^2/g$.

In one embodiment, the metal-organic framework comprises cavities having a free diameter of about 4 Å to about 50 Å, or about 5 Å to about 25 Å, or about 10 Å to about 20 Å.

In one embodiment, the metal-organic framework has a pore volume from about 0.1 $cm^3/g$ to about 4 $cm^3/g$, or from about 0.4 $cm^3/g$ to about 0.9 $cm^3/g$, or from about 0.5 $cm^3/g$ to about 0.8 $cm^3/g$, or about 0.6 $cm^3/g$.

In one embodiment, the metal-organic framework has a crystal size from about 25 µm to about 500 µm, preferably from about 50 µm to about 200 µm.

General

All aspects and embodiments of the invention employ carboxylate ligands. In all aspects and embodiments, these ligands may be derived from a dicarboxylic acid, a tricarboxylic acid, a tetracarboxylic acid, a hexcarboxylic acid or an octacarboxylic acid.

For the purposes of the present invention, the term "derived" means that the carboxylic acid compounds are present in partly deprotonated or fully deprotonated form.

For example, a ligand may be derived from a dicarboxylic acid, such as, for instance, oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzene-dicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzene-dicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclo-hexadiene-1,2-dicarboxylic acid, octanedicarboxylic acid, pentane-3,3-dicarboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-binaphthyidicarboxylic acid, 7-chloro-8-methylquinoline-2,3-dicarboxylic acid, 1-anilinoanthraquinone-2,4'-dicarboxylic acid, poly-tetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazine-dicarboxylic acid, 4,4'-diamino(diphenyl ether)diimidedicarboxylic acid, 4,4'-diaminodiphenylmethanediimidedicarboxylic acid, 4,4'-diamino(diphenyl sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4"-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptane-dicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbomane-2,3-dicarboxylic acid, 5-ethyl-2,3-pyridinedicarboxylic acid or camphordicarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tetracarboxylic acid, such as, for instance, 1,1-dioxidoperylo[1,12-BCD]thiophene-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

The ligands may also be derived from a carboxylic acid selected from compounds of formula L1 to L30 and combinations thereof:

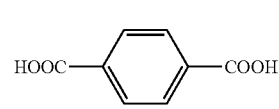

L1

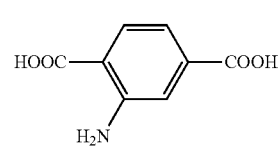

L2

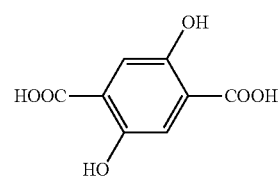

L3

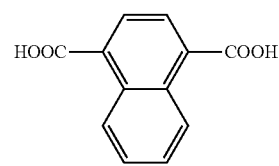

L4

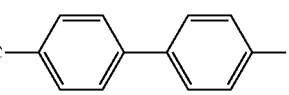

L5

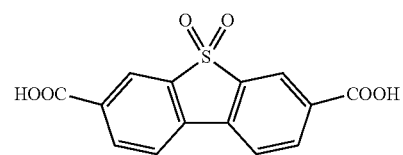

L6

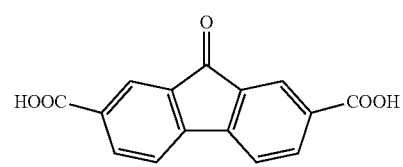

L7

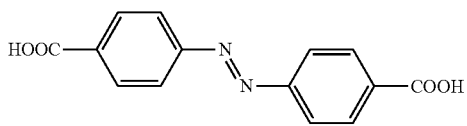

L8

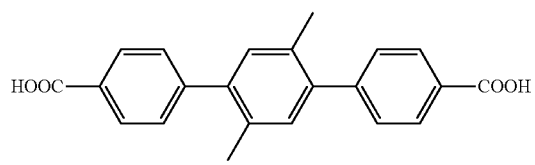

L9

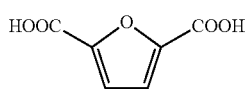
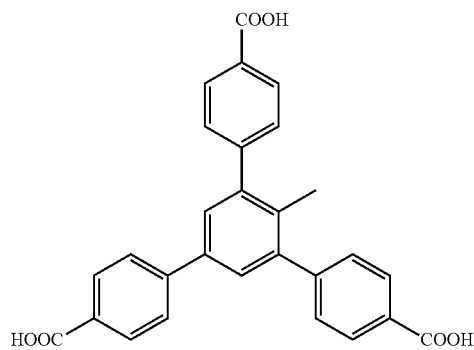
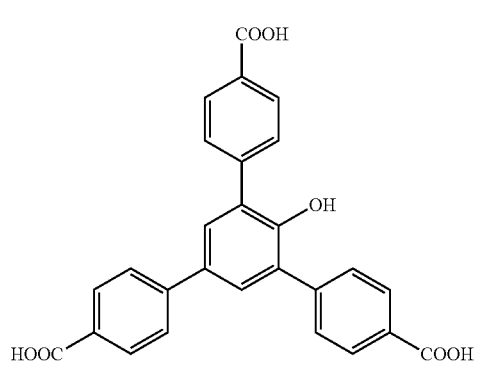
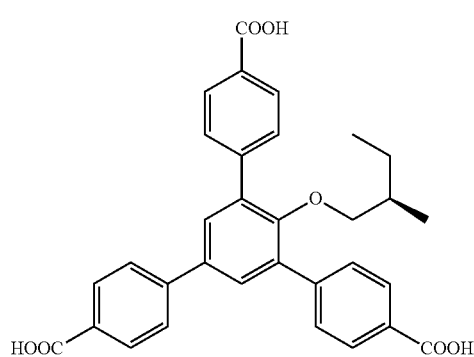
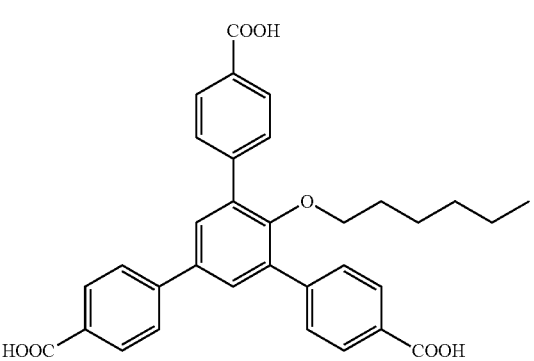

L21 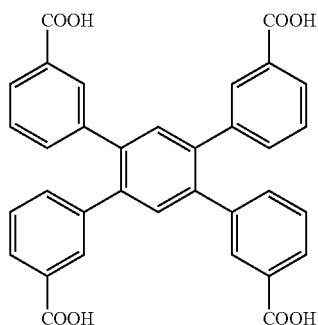
L25 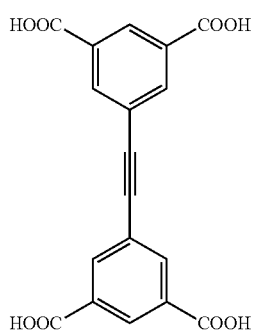
L22 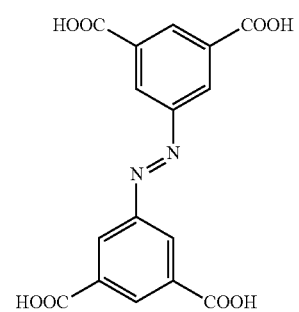
L26 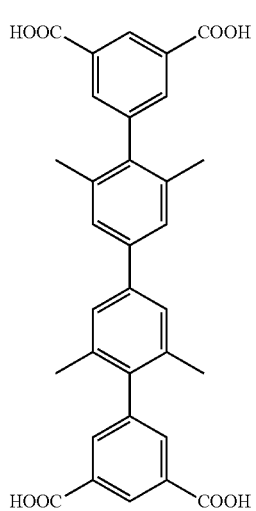
L23 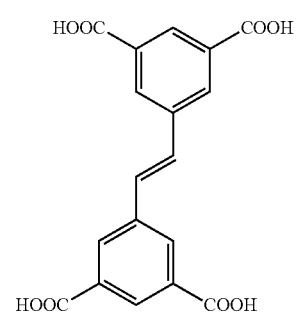
L27 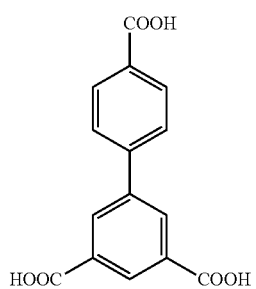
L24 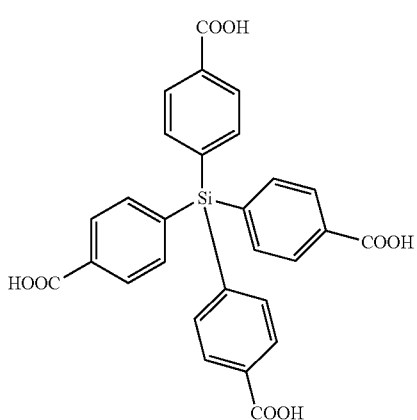

L29
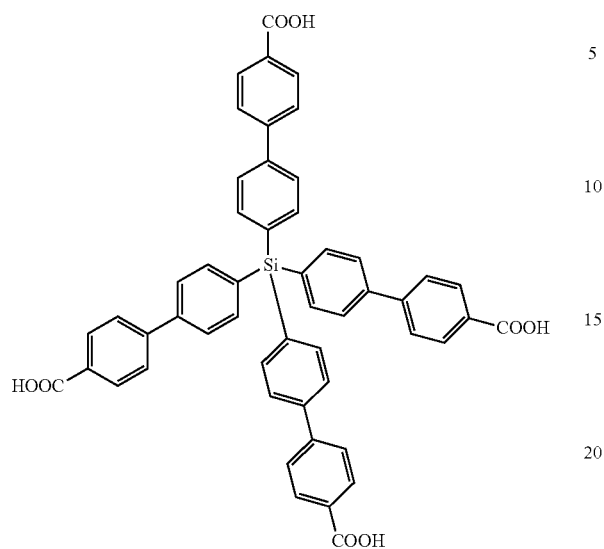
L30
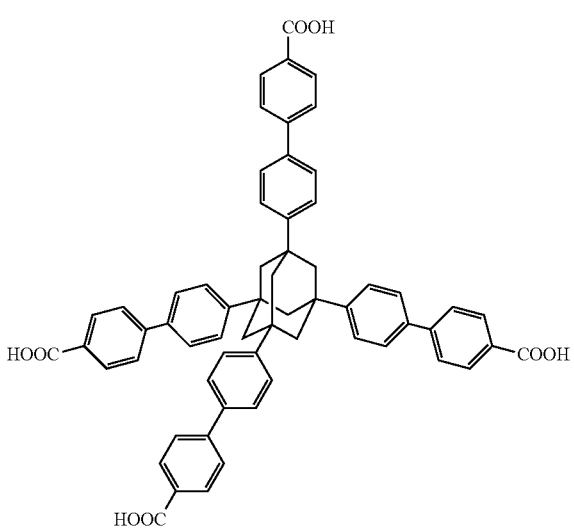
Specific combinations of ligands include (L31 and L32):
L31
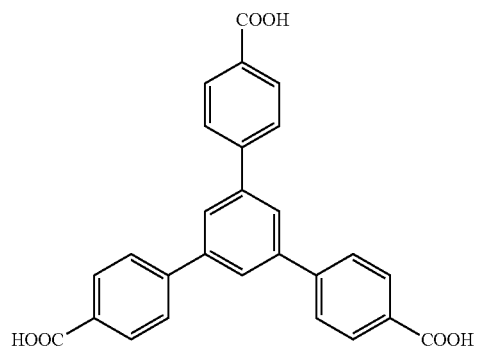
+
-continued
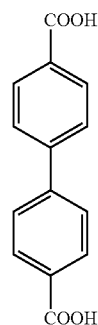
L32
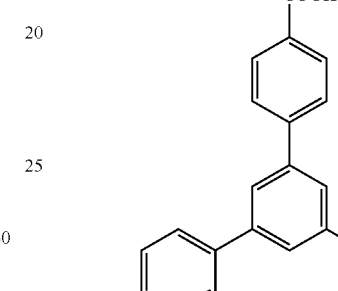
+
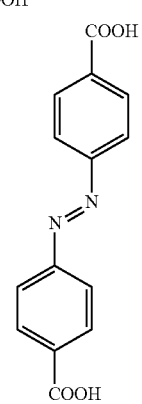
Alternatively, the ligand may be derived from a carboxylic acid selected from the following compounds or combinations thereof:
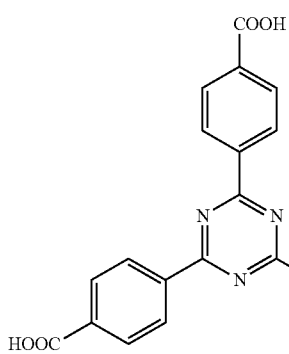

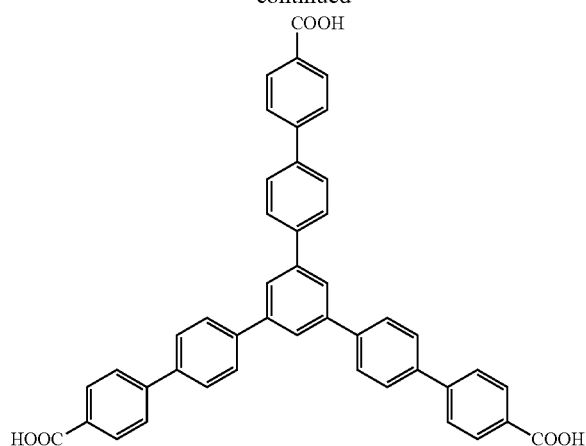
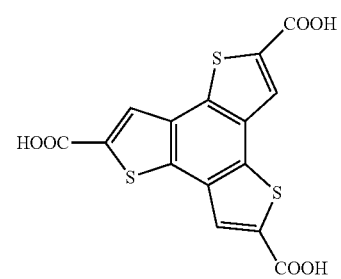
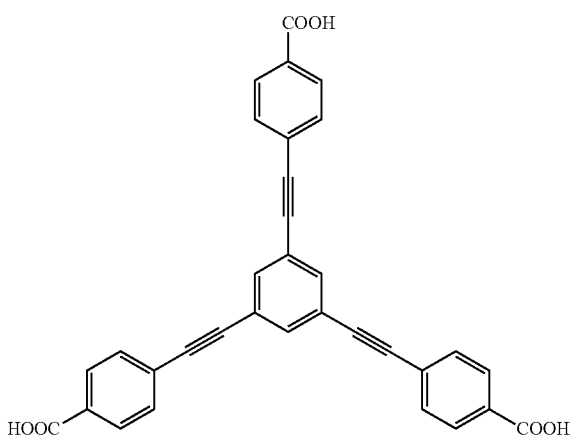
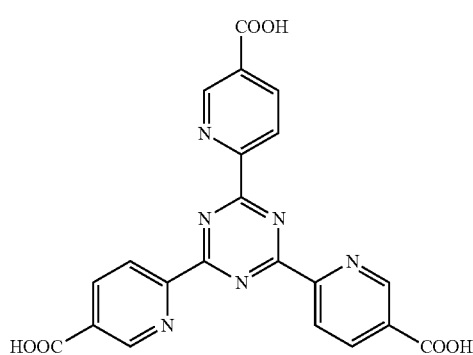
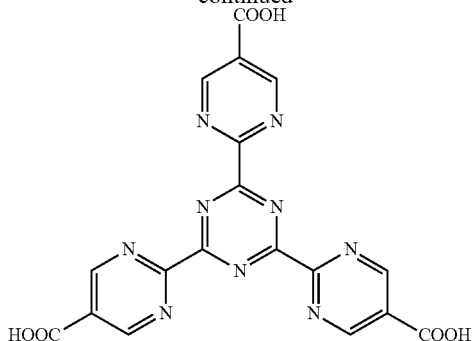
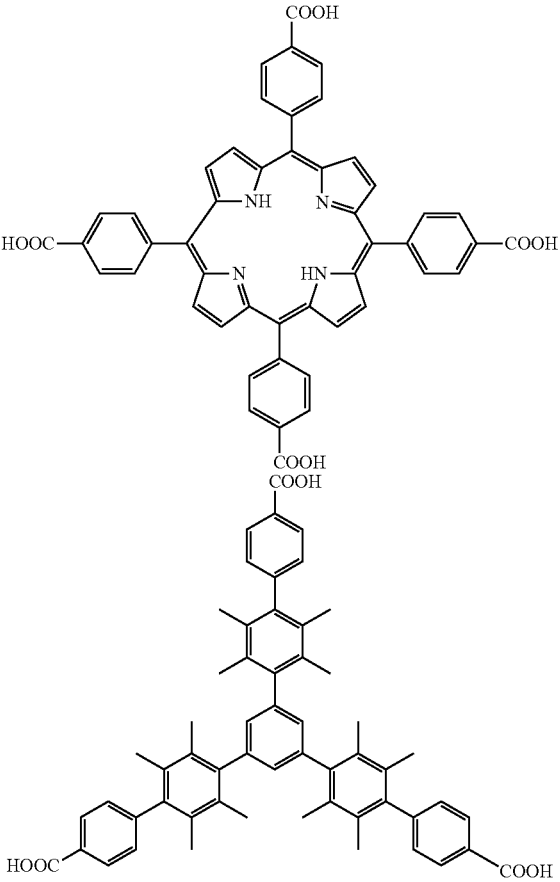
In particular, a metal-organic framework comprising a metal-ligand cluster having formula $Fe_2XO$ preferably further comprises a ligand selected from L1-L32.
In a particular embodiment, the metal-organic framework comprises a metal cluster having formula $Fe_2XO$ and one or more ligands of formula L8:
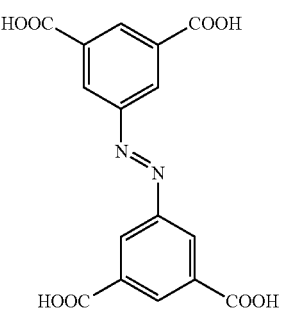
L8

For example, the metal-organic framework may have a metal cluster of formula Fe$_2$CoO and comprise six ligands of formula L8.

Alternatively, a metal-organic framework comprising a metal cluster having formula Al$_3$O preferably further comprises a ligand selected from:

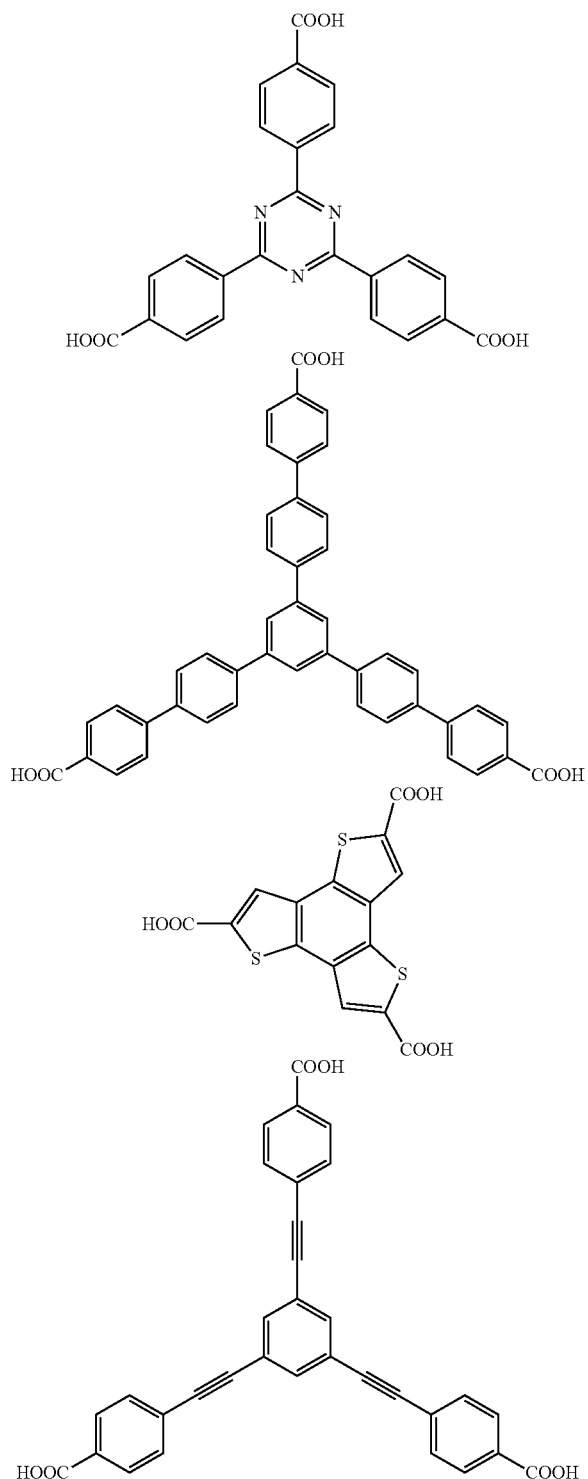

Unless otherwise specified, the crystal size may be measured as the largest dimension of the single crystal. For example, the length of the largest dimension of a crystal can be determined from a two-dimensional optical microscope image of a crystal.

Alternatively, the size may be measured as the circular equivalent (CE) diameter. For example, using a two-dimensional optical microscope image of a crystal (of any shape), the diameter of a circle with equivalent projected area can be calculated.

The specific surface area measurements were carried out by nitrogen adsorption-desorption techniques using a machine sold under the name Micrometrics ASAP 2010, on around 50 mg of material previously activated under a primary vacuum ($10^{-3}$ Torr) for 15 hours at 200° C.; the analysis being carried out by BET calculation methods.

The metal-organic frameworks according to the invention have a wide range of applications.

According to one aspect, the invention provides a method comprising uptaking at least one substance by a metal-organic framework of the present invention.

For example, the substance may be hydrogen, methane, carbon dioxide or nitrogen.

According to one aspect, the invention provides a method of storing a gas in a metal-organic framework according to the present invention. Alternatively, the invention provides the use of a metal-organic framework according to any embodiment of the present invention for storing a gas. This may be achieved by binding the gas in a plurality of linker channel sites present in the metal-organic framework, for example using van der Waals forces.

The use/method of storing gases in this way may optimise gas storage density and volumetric gas storage.

For example, the gas may be hydrogen, methane, carbon dioxide or nitrogen.

In the above embodiments of the invention, the metal-organic framework may be configured to store methane or hydrogen, for example for fuelling vehicles.

In a further aspect, the present invention provides the use of any metal-organic framework according to the invention for adsorbing a guest molecule, for example a gas molecule such as hydrogen, methane, carbon dioxide or nitrogen. In this respect, the invention also provides a method of adsorbing a guest molecule, for example a gas molecule such as hydrogen, methane, carbon dioxide or nitrogen, comprising contacting a metal-organic framework of the invention with a guest molecule source.

Accordingly, the invention also provides a metal-organic framework according to any embodiment of the present invention, further comprising one or more than one type of guest molecule.

The guest molecule may be a gas molecule such as hydrogen, methane, carbon dioxide or nitrogen.

In fact, in the context of any of the embodiments described herein, the substance, gas molecule, or gas may be selected from:

(a) H$_2$, N$_2$, Ar, O$_2$, CO$_2$, NO, NO$_2$ or CO; or (b) an alkane (C1-6), alkene (C2-4), alkyne (C2-6), alcohol (C1-6), arene (C6-8) or a substituted version of any of these;

wherein the alkane may be selected from CH$_4$, C$_2$H$_6$, C$_3$H$_8$, C$_4$H$_{10}$, C$_5$H$_{12}$ or C$_6$H$_{14}$; or a cycloalkane (C3-6) selected from the group consisting of C$_3$H$_6$, C$_4$H$_8$, C$_5$H$_{10}$ and C$_6$H$_{14}$;

wherein the alkene may be C$_2$H$_4$, C$_3$H$_6$, C$_4$H$_8$, C$_5$H$_{10}$ or C$_6$H$_{12}$;

wherein the alkyne may be C$_2$H$_2$;

wherein the alcohol may be methanol, ethanol, n-propanol, isopropanol, n-butanol or isobutanol; or wherein the arene may be a substituted arene (C6-8) such as is nitrobenzene, 1,2-dinitrobenzene, 1,3-dinitrobenzene, 1,4-dinitrobenzene, 1,2,4-trinitrobenzene or 1,3,5-trinitrobenzene.

BRIEF DESCRIPTION OF THE DRAWINGS

The invention will now be described further with reference to the following non-limiting examples and the accompanying Figures, in which:

FIG. 3o shows an optical microscope image of PCN-261-$CH_3$ (Example 26).

DETAILED DESCRIPTION

Figure 1:
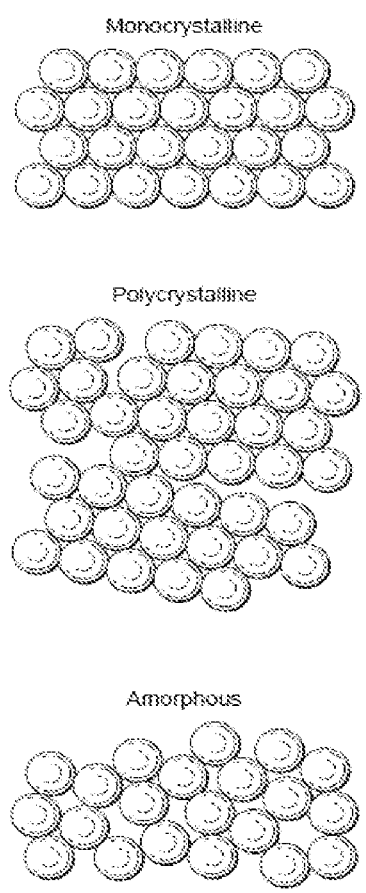
FIG. 1 illustrates the differences between amorphous, polycrystalline, and monocrystalline materials.

A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. A polycrystalline solid or polycrystal is comprised of many individual grains or crystallites. There is no relationship between the grains. Therefore, on a large enough length scale, there is no periodicity across a polycrystalline sample. They are different from monocrystalline materials. Large single crystals are very rare in nature and can be difficult to produce in the laboratory. It is desired that metal organic framework materials should be free from objectionable or incompatible impurities which detrimentally affect the crystal structure or the physical properties of the crystal. The material should be finely divided and uniform in size. Due to the absence of the defects associated with grain boundaries, monocrystalline metal organic frameworks have high surface areas and provide control over the crystallization process. The differences between amorphous, polycrystalline and (mono)crystalline are illustrated in FIG. 1.

A single crystal, as achieved by the present invention, is a monocrystalline product. A single crystal or monocrystalline solid is a material in which the crystal lattice of the entire sample is continuous and unbroken to the edges of the sample, with no grain boundaries. The symmetry exhibited by real single crystals is determined by the crystal structure of the material, normally by single-crystal X-Ray diffraction (SCRD) studies. SCRD is quite accessible in normal chemistry labs and become a routine way to obtain structures of single crystals. In contrast, a polycrystalline solid or polycrystal is comprised of many individual grains or crystallites. In polycrystalline solids, there is no relationship between neighbouring grains. Therefore, there is no periodicity across a polycrystalline sample. In the absence of single crystals, the structure of polycrystals can be determined by high-resolution powder X-Ray diffraction (PXRD), such as synchrotron resources. However, synchrontron resources are very limited all over the world.

In preferred embodiments of the invention, the monocrystalline metal organic frameworks comprise a low occurrence of twinning. For example, the monocrystalline metal organic frameworks may comprise less than about 5% twinning crystals. Most preferred, the monocrystalline metal organic frameworks comprise no twinning crystals.

In a preferred embodiment, the inorganic cornerstones of the metal organic frameworks of the invention have between 6 and 12 coordination sites. For example, a MOF (preferably monocrystalline) comprising a $Al_3O$ cluster may have 12 coordination sites. Alternatively, a MOF (preferably monocrystalline) comprising a $Fe_3O$ or $Fe_2O$ cluster may have between 6 and 12 coordination sites.

Suitable cornerstones that can be employed in the MOFs of the invention include $Fe_3O$, $Fe_2O$, $Al_3O$, $Ti_7O_8$, $Cr_3O$, $M_3O$, and $Ti_8Zr_2O_8$.

EXAMPLES

Chemicals and Instrumentation

Unless otherwise mentioned, all the reagents were purchased and used without further purification. NMR spectra were recorded on MERCURY 300 ($^1H$ 300 MHz). The following abbreviations were used to explain the multiplicities: s=singlet, d=doublet, t=triplet, q=quartet, m=multiplet, b=broad. The abbreviation for some solvent and reagent were listed here: p-Toluenesulfonate (Tos). 1,2-Dimethoxyethane (DME). tris-o-tolylphosphine (P(o-Tolyl)$_3$). N-Methyl-2-pyrrolidone (NMP). The ligands listed in Scheme S1 were purchased from Sigma Aldrich or VWR and used without further purification.

Scheme S1. Commercially available ligands.

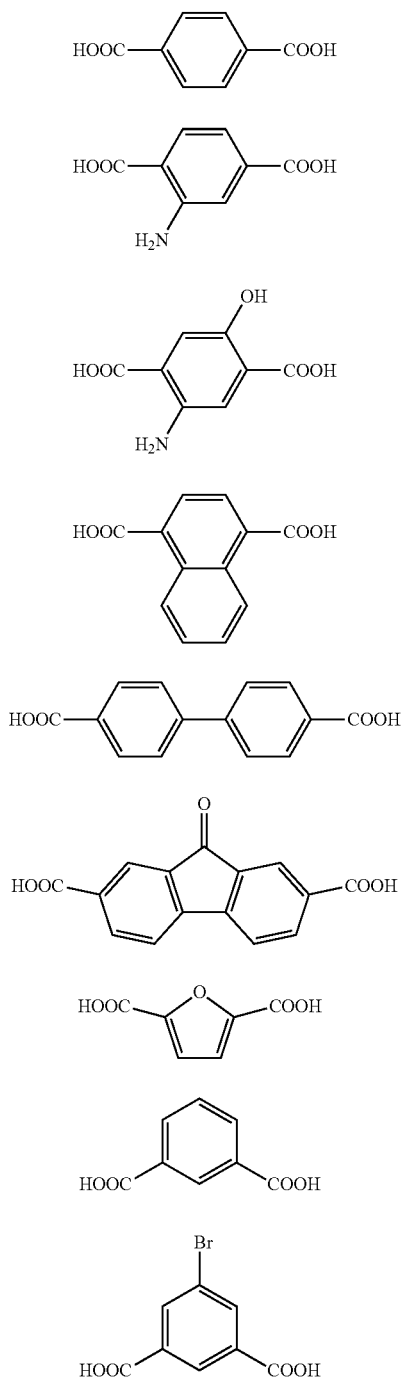

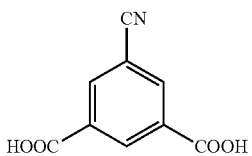

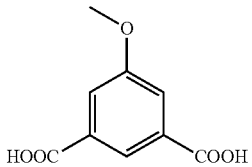

To obtain the TGA data, a TGA-50 (SHIMADZU) thermogravimetric analyzer was used with a heating rate of 5° C. min-1 under N$_2$ flow. For a single crystal analysis, a pink block crystal was taken directly from the mother liquor, transferred to oil and mounted into loop. The diffraction data set was collected at no K on a Bruker APEX CCD diffractometer with MoKα radiation ($\lambda$=0.71609 Å). The powder X-ray diffraction patterns (PXRD) were collected on a BRUKER D8-Focus Bragg-Brentano X-ray Powder diffractometer equipped with a Cu sealed tube ($\lambda$=1.54178 Å) at a scan rate of 0.5 s deg-1. Low pressure gas adsorption measurements were performed by an ASAP 2020 with the extra-pure quality gases. High pressure excess adsorption of H$_2$ and CH$_4$ were measured using an automated controlled Sieverts' apparatus (PCT-Pro 2000 from Setaram) at 77 K (liquid nitrogen bath) or 298 K (room temperature).

Regarding X-ray crystallography, the data frames were collected using the program APEX2 and processed using the program SAINT routine within APEX2. The data were corrected for absorption and beam corrections based on the multi-scan technique as implemented in SADABS (G. M. Sheldrick, *SHELXTL*, Version 6.14, Structure Determination Software Suite, Bruker AXS, Madison, Wis., 2003). The structure was solved by direct methods using the SHELXS program of the SHELXTL package and refined by full-matrix least-squares methods with SHELXL (A. L. Spek, *PLATON*, A Multipurpose Crystallographic Tool, Utrecht University, Utrecht, The Netherlands, 1998). Metal atoms were located from the E-maps and other non-hydrogen atoms were refined with anisotropic displacement parameters during the final cycles. Hydrogen atoms were placed in calculated positions with isotropic displacement parameters set to 1.2×Ueq of the attached atom. The solvent molecules are highly disordered, and attempts to locate and refine the solvent peaks were unsuccessful. Contributions to scattering due to these solvent molecules were removed using the SQUEEZE routine of PLATON (A. L. Spek, *PLATON*, A Multipurpose Crystallographic Tool, Utrecht University, Utrecht, The Netherlands, 1998) structures were then refined again using the data generated. The contents of the solvent region are not represented in the unit cell contents in the crystal data. CCDC numbers (975771-975791 and 975820-975828) contain the supplementary crystallographic data for this paper. These data can be obtained free of charge from The Cambridge Crystallographic Data Centre via www.ccdc.cam.ac.uk/data_request/cif.

Synthesis of Ligands

Synthesis of L6 was carried out in accordance with V. K, Ol'khovik, Yu. V. Matveenko, G. V. Kalechits, A. A. Pap, and A. A. Zenyuk. Synthesis and properties of 4,4'-bis[5-alkyl(aryl)benzoxazol-2-yl]-2-hydroxy (alkoxy) biphenyls. Russian Journal of Organic Chemistry, 2006, 42, 1164-1168.

New Tetrahedral Building Blocks for Molecular Construction. J. Chem. 2003, 81, 376-380.

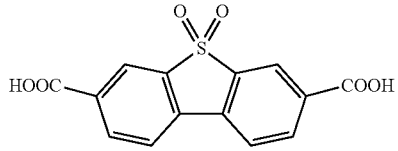

L6

Synthesis of L8 was carried out in accordance with W. Zhou, X. Yang, E. Jia, X. Wang, J. Xua, G. Ye. Ultraviolet resistance of azo-containing poly(1,3,4-oxadiazole) fibres. Polymer Degradation and Stability, 2013, 98, 691-696.

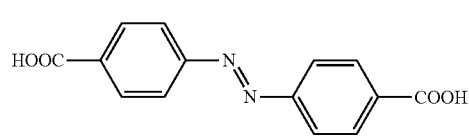

L8

Synthesis of L9 was carried out in accordance with Jiang, H.-L.; Feng, D.; Liu, T.-F.; Li, J.-R.; Zhou, H.-C., Pore Surface Engineering with Controlled Loadings of Functional Groups via Click Chemistry in Highly Stable Metal-Organic Frameworks, J. Am. Chem. Soc., 2012, 134, 14690-14693.

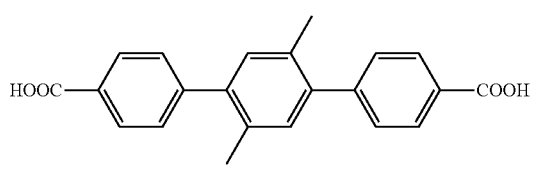

L9

Synthesis of L22 was carried out in accordance with Wang, X.-S.; Ma, S.; Rauch, K.; Simmons, J. M.; Yuan, D.; Wang, X.; Yildirim, T.; Cole, W. C.; Lopez, J. J.; de Meijere, A.; Zhou, H.-C. Metal-organic frameworks based on double-bond-coupled di-isophthalate linkers with high hydrogen and methane uptakes, Chemistry of Materials 2008, 20, 3145.

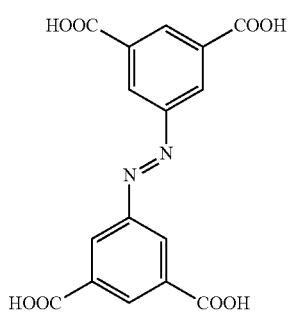

L22

Synthesis of L28 was carried out in accordance with Fournier, J.-H.; Wang, X.; Wuest, J. D. Can. Derivatives of Tetraphenylmethane and Tetraphenylsilane. Synthesis of

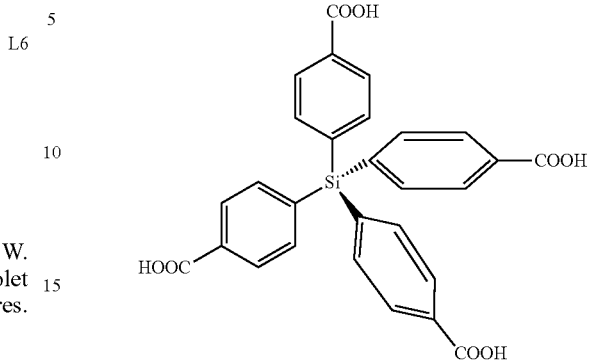

Synthesis of L15

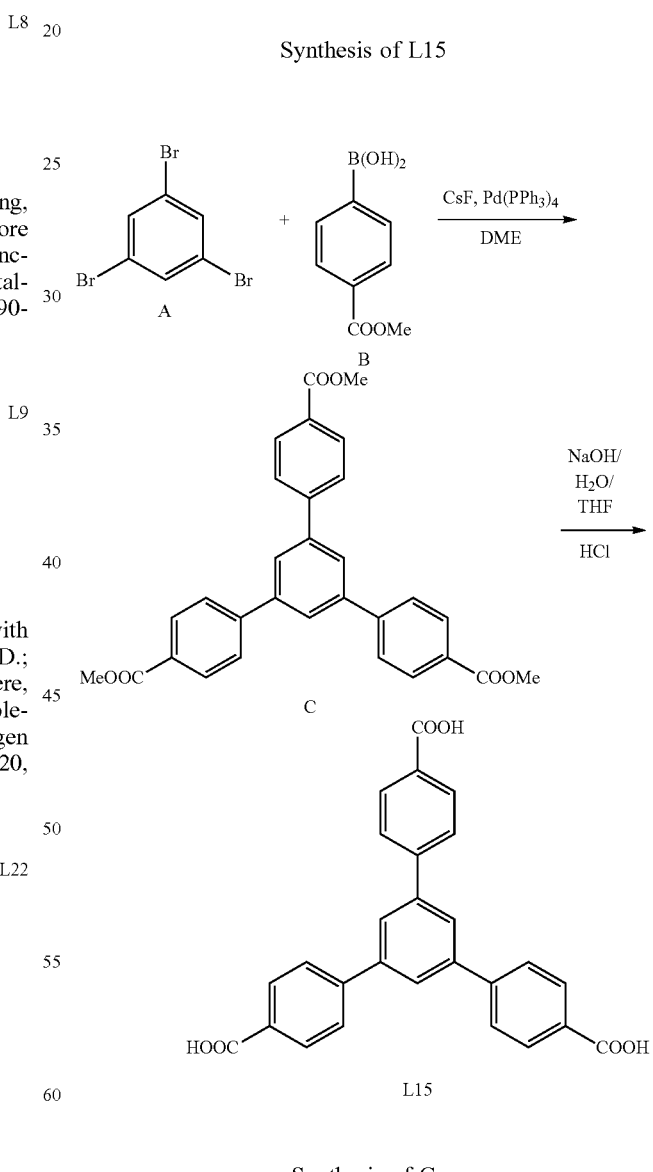

Synthesis of C

A (2 g, 6.4 mmol), B (3.78 g, 21 mmol), CsF (3 g, 20 mmol) and Pd(PPh$_3$)$_4$ (0.2 g, 0.17 mmol) was added to a 250 mL flask, and the flask was connected to Schlenk line. 200 mL DME was degassed and added through a canula. The mixture was refluxed under the nitrogen for 48 hours. The solution was dried on rotary evaporator. 100 mL H₂O was added and then extract with CHCl₃. The residue was subjected to column chromatography on silica gel (Ethyl acetate:Hexane=20:80) to yield the title compound C as white solid 2.0 g. (Yield: 65%).

Synthesis of L15

Compound C (2.0 g, 4.2 mmol) was suspended in 60 mL THF/MeOH (v:v=1:1), and 30 mL 10% NaOH solution was added. The mixture was stirred overnight. The pH value was adjusted to approximately 2 using hydrochloric acid. The resulting white precipitate was collected by filtration, washed with water, and dried under vacuum to give L15 (1.7 g, 92%). ¹H NMR (CDCl₃): δ=3.97 (s, 9H), 7.90 (d, 2H), 8.06 (d, 2H), 8.44 (d, 2H) 8.49 (t, 1H).

Synthesis of L16, L17 and L18

L16, L17 and L18 were synthesis as the same procedure for L15 except that the starting material of 1,3,5-Tribromobenzene were replaced by 2,4,6-Tribromoaniline (for L16), 2,4,6-Tribromotoluene (for L17) and 2,4,6-Tribromophenol (for L18) respectively. ¹H NMR (300 MHz, DMSO-d6) for L6. δ=4.74 (s, 2H), 7.52 (s, 2H), 7.74 (d, 4H), 7.85 (d, 2H), 7.98 (d, 2H), 8.10 (d, 4H). ¹H NMR (300 MHz, yDMSO-d6) for L17. δ=2.13 (s, 3H), 7.64 (t, 6H), 7.92 (d, 2H), 8.01 (d, 2H), 8.06 (d, 4H). ¹H NMR (300 MHz, DMSO-d6) for L18: δ=3.97 (s, 9H), 7.90 (d, 2H), 8.06 (d, 2H), 8.44 (d, 2H) 8.49 (t, 1H).

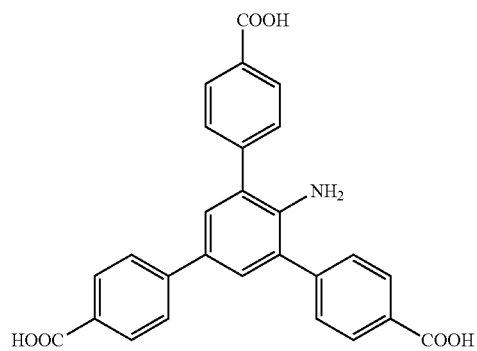

L16

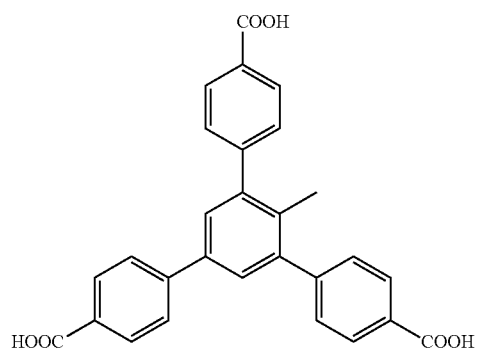

L17

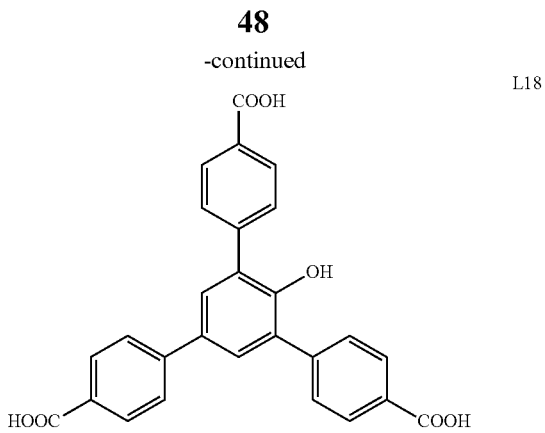

L18

Synthesis of L19

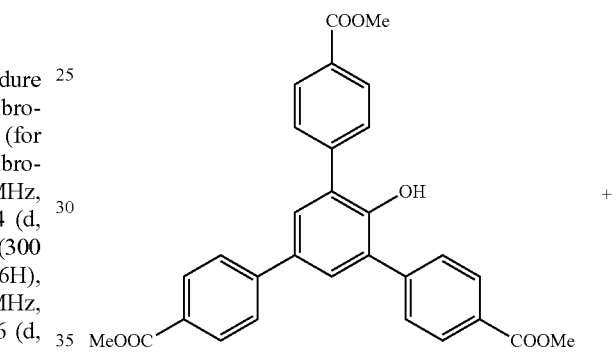

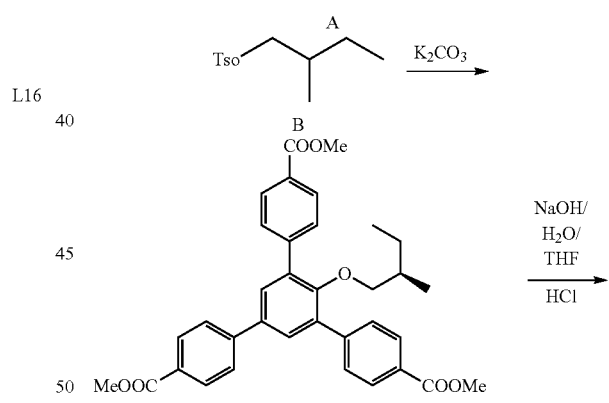

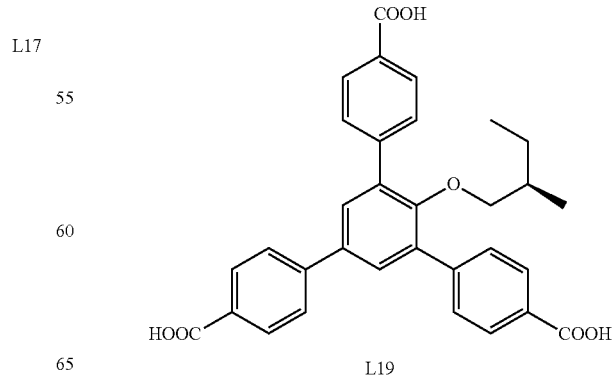

L19

Synthesis of C

To a round bottomed flask add A (2.0 g, 4.0 mmol), B (1.2 g, 5 mmol), K$_2$CO$_3$ (0.7 g), and DMF (30 mL). The resulting mixture was heated up to 60° C. for 12 h. After cooling to RT, ice water was added. The precipitate was collected, washed thoroughly with water, and dried to produce (2.4, 93%) of C. $^1$H NMR (CDCl$_3$) for: δ=0.49 (m, 6H), 0.78 (m, 1H), 1.01 (m, 1H), 1.24 (m, 1H), 3.05 (m, 2H), 3.95 (m, 9H), 7.61 (s, 2H), 7.72 (m, 6H), 8.11 (m, 2H).

Synthesis of L19

C (2.4, 3.7 mmol) was dissolved in 100 mL mixture of THF and MeOH (v/v=1/1), 50 mL 2N KOH aqueous solution was added. The mixture was stirred and refluxed overnight. The organic phase was removed. The aqueous phase was diluted to 100 mL and acidified with concentrated HCl. The precipitate was collected, washed thoroughly with water and dried to produce 1.6 g (Yield. 82.5%) of L19.

Synthesis of L20

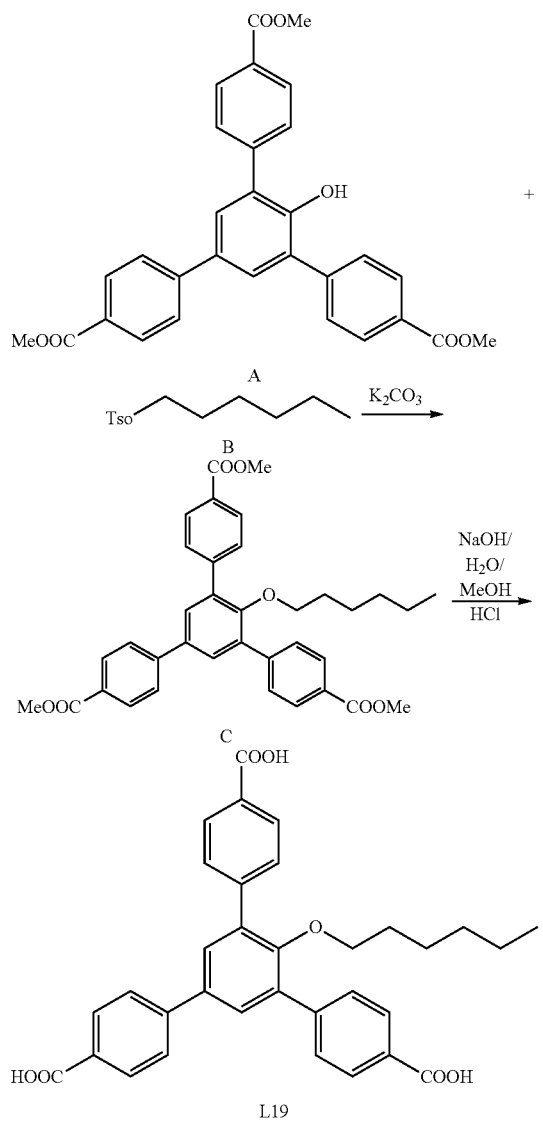

L20 was synthesized as the same procedure for L19 except the starting material B ((S)-2-Methylbutyl p-Toluenesulfonate) was replace by Hexyl p-Toluenesulfonate.

Synthesis of L21

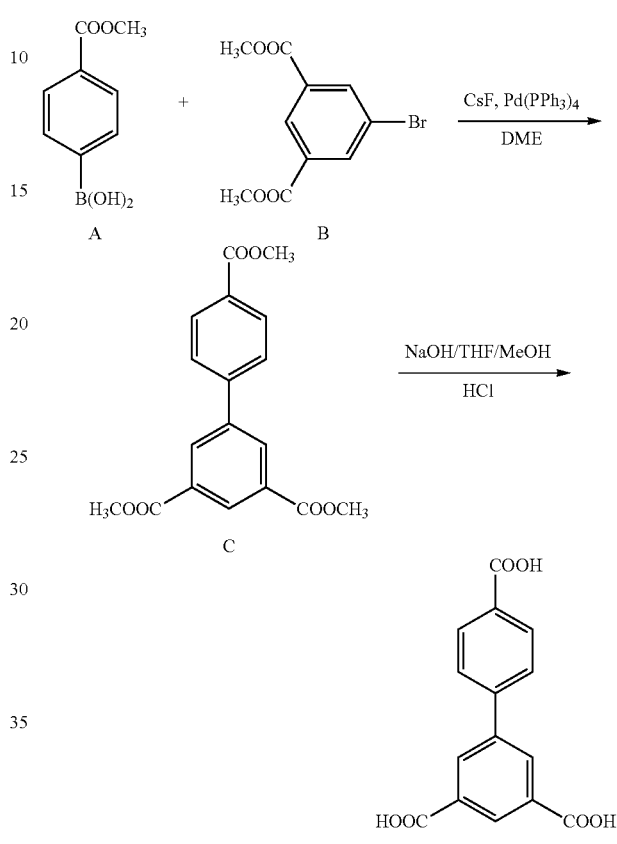

Synthesis of C

A (2 g, 11 mmol), B (2 g, 7.4 mmol), CsF (3 g, 15 mmol) and Pd(PPh$_3$)$_4$ (0.2 g, 0.17 mmol) was added to a 250 mL flask. The flask was connected to Schlenk line. 200 mL 1, 2-Dimethoxyethane was degassed and added through a canula. The flask was equipped with a water condenser and refluxed under the nitrogen for 48 hours. The solution was dried on rotary evaporator. 100 mL H$_2$O was added and then extract with CHCl$_3$. The organic phase was evaporated to dryness and purified with chloroform through a short silica gel column to yield a light yellow powder 1.56 g. (Yield: 62%). $^1$H NMR (CDCl$_3$): δ=3.97 (s, 9H), 7.90 (d, 2H), 8.06 (d, 2H), 8.44 (d, 2H) 8.49 (t, 1H).

Synthesis of L21

Compound C (1.6 g, 4.6 mmol) was suspended in 50 mL THF/MeOH (v:v=1:1), and 30 mL 10% NaOH solution was added. The mixture was stirred overnight. The pH value was adjusted to approximately 2 using hydrochloric acid. The resulting white precipitate was collected by filtration, washed with water, and dried under vacuum to give L21 (1.2 g, 91%).

Synthesis of L23

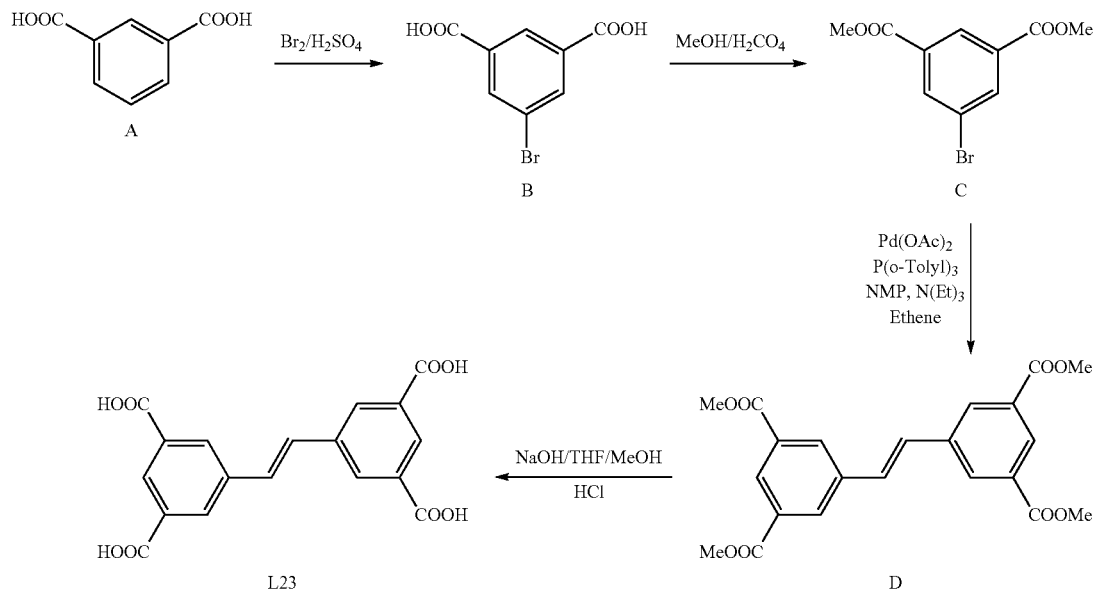

Synthesis of B

A mixture of A (12.2 g, 73.5 mmol), $Ag_2SO_4$ (13.3 g, 43 mmol) and $Br_2$ (5 ml, 97 mmol) in conc. sulphuric acid was stirred at 60° C. for 32 h. The excess of $Br_2$ was removed by addition of saturated $Na_2S_2O_3$ solution very slowly. The residue was poured into ice-water. The solids were isolated by filtration and given into a $NaHCO_3$ solution. The AgBr was then removed by filtration. The solution was acidified with concentrated hydrochloric acid to give white precipitates. The solid was filtered and washed with water several times to give the product as white solid 20.5 g (Yield. 86.7%). $^1$H-NMR (DMSO-$d_6$): δ=8.23 (d, 2H), 8.40 (t, 1H).

Synthesis of C

A solution of conc. sulphuric acid (8 ml) in methanol (30 ml) was added dropwise to a solution of B (13.2 g, 0.054 mol) in methanol (150 ml). The reaction mixture was refluxed for 20 h. After cooling to room temperature, the product was obtained as colourless crystals. After filtration, the product was washed with cold methanol to give C, 11.3 g (Yield. 76.6%). $^1$H-NMR ($CDCl_3$): δ=3.96 (s, 6H), 8.35 (d, 2H), 8.6 (t, 1H).

Synthesis of D

A 300 mL glass autoclave was charged with B (2.00 g, 7.3 mmol), $Pd(OAc)_2$ (16.4 mg, 0.0732 mmol), and $P(o\text{-}Tolyl)_3$ (44.5 mg, 0.146 mmol). The autoclave was evacuated and filled with nitrogen alternately for several times. Anhydrous triethylamine (2.2 mL, 15.8 mmol) and anhydrous NMP (2.2 mL) were added under nitrogen. The autoclave was evacuated, filled with 1.5 bar of ethane. The pressure was released, and then built up again, and this release and repressurization was repeated three more times in order to saturate the solvent with ethene. The contents of the autoclave were then kept under a pressure of 1.5 bar of ethene and stirred at 100° C. for 25.5 h. After having been cooled down to ambient temperature, the autoclave valve was opened to release excess ethene, and the mixture was taken up in methylene chloride (100 mL). The solution was washed with water (3×50 mL), dried $MgSO_4$, and concentrated under reduced pressure. The residue was subjected to column chromatography on silica gel to yield 1.181 g (78%) of the title compound as a light yellow solid. $^1$H NMR (250 MHz, $CDCl_3$): δ=3.98 (s, 12H), 7.31 (s, 2H), 8.38 (d, 4H), 8.59 (t, 2H).

Synthesis of L23

D (3 g, 7.3 mmol) was suspended in 100 mL THF/MeOH (v:v=1:1), and 20 mL 10% NaOH solution was added. The mixture was stirred overnight. The pH value was adjusted to approximately 2 using hydrochloric acid. The resulting white precipitate was collected by filtration, washed with water, and dried under vacuum to give L23 2.46 g (Yield. 95%).

Synthesis of L24

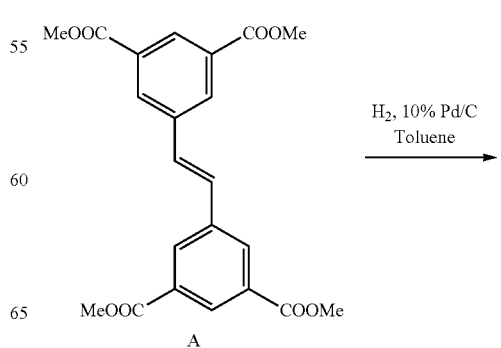

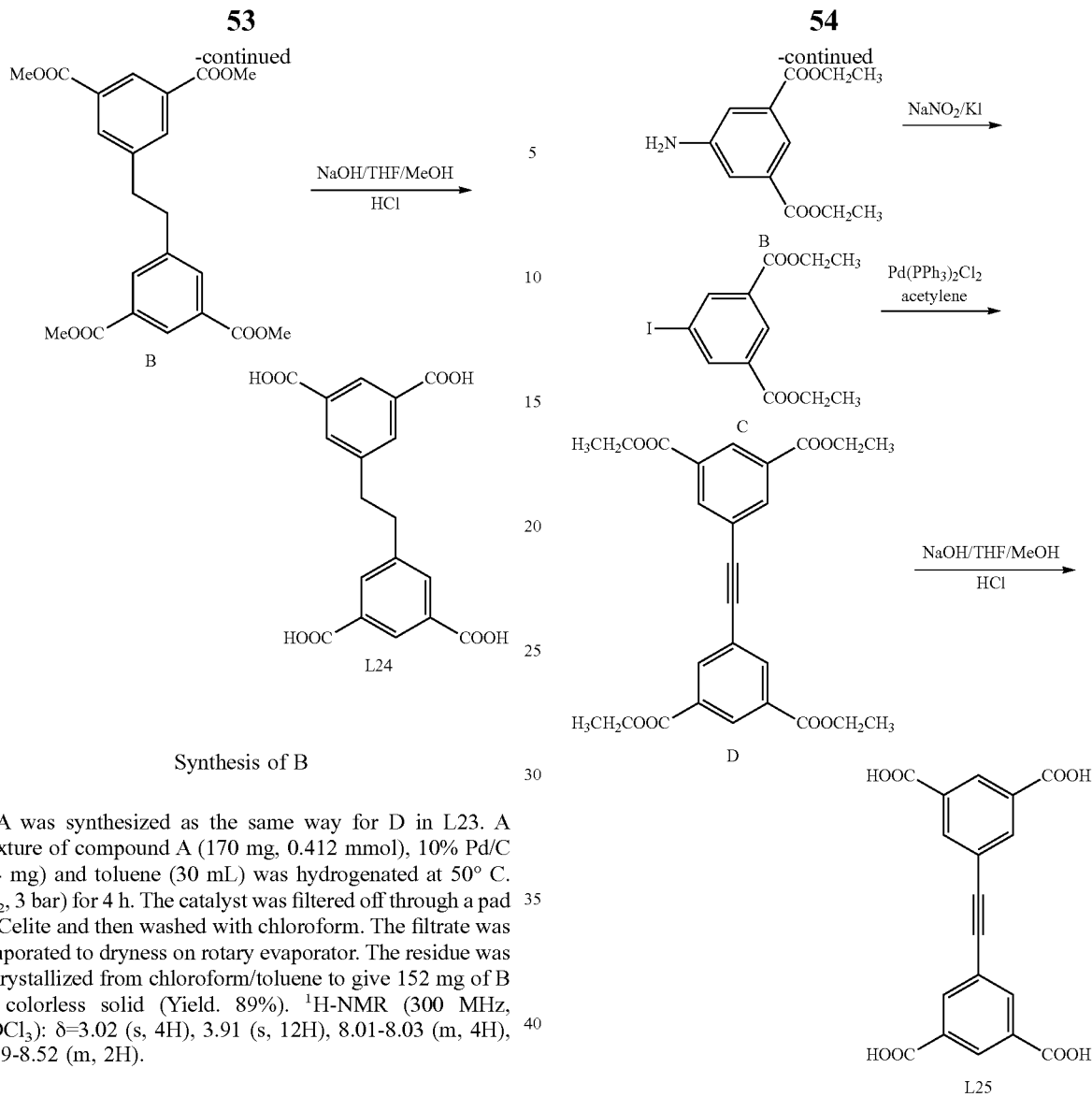

Synthesis of B

A was synthesized as the same way for D in L23. A mixture of compound A (170 mg, 0.412 mmol), 10% Pd/C (54 mg) and toluene (30 mL) was hydrogenated at 50° C. (H$_2$, 3 bar) for 4 h. The catalyst was filtered off through a pad of Celite and then washed with chloroform. The filtrate was evaporated to dryness on rotary evaporator. The residue was recrystallized from chloroform/toluene to give 152 mg of B as colorless solid (Yield. 89%). $^1$H-NMR (300 MHz, CDCl$_3$): δ=3.02 (s, 4H), 3.91 (s, 12H), 8.01-8.03 (m, 4H), 8.49-8.52 (m, 2H).

Synthesis of L24

Compound C (130 mg) was suspended in 50 mL THF/MeOH (v:v=1:1), and 3 mL 10% NaOH solution was added. The mixture was stirred overnight. The pH value was adjusted to approximately 2 using hydrochloric acid. The resulting white precipitate was collected by centrifuge, washed with water, and dried under vacuum to give L24 (100 mg, 92%). $^1$H-NMR (DMSO-d$_6$): δ=13.10 (s, br, 4H), 8.29 (s, 2H), 8.04 (s, 4H), 3.02 (s, 2H).

Synthesis of L25

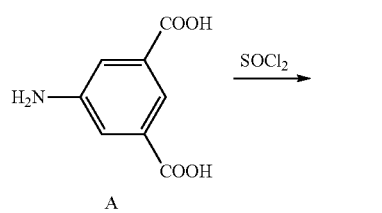

Synthesis of B 12 mL SOCl$_2$ (165 mmol) was slowly added to a stirred solution of A (10 g, 60 mmol) in 100 mL of absolute EtOH. After stirring under reflux for 5 hours, there are a lot of precipitates formed. The solvent was removed and the crude product was washed with a saturated aqueous solution of Na$_2$CO$_3$. After filtered, the solid was dried at 60° C. overnight to give B as white solid of 12.8 g (Yield. 90%). $^1$H NMR (CDCl$_3$): δ=1.4 (t, 3H), 4.3 (q, 2H), 7.5 (s, 2H), 8.1 (s, 1H).

Synthesis of C

A solution of NaNO$_2$ (2.32 g) in 20 mL water was added to a cloudy mixture of B (6.6 g, 27.8 mmol) in 30 mL 2M hydrochloric acid at 0° C. The mixture changed to clear solution slowly. After stirred at 0° C. for 45 minutes, an ice-cold KI aqueous solution was added. Then mixture changed to dark red and sticky. After 100 mL CH$_2$Cl$_2$ was added, the mixture was allowed to stir at RT for 4 hours. The aqueous phase was washed with CH$_2$Cl$_2$ three times. The combined organic phases were dried with MgSO$_4$. After the solvent was removed, the crude product was purified by column chromatography with CH$_2$Cl$_2$ as the eluent. $^1$H NMR (Acetone): δ=1.4 (t, 3H), 4.4 (q, 2H), 8.2 (s, 2H), 8.6 (s, 1H).

Synthesis of D

C (7.3 g, 20.9 mmol), Pd(PPh$_3$)$_2$Cl$_2$ (0.2 g). CuI (0.1 g) were dissolved in 200 mL Et$_2$NH under nitrogen atmosphere. The mixture was bubbled with acetylene for 8 hours at RT, and then stirred overnight. The solvent was removed and the residual powder was dissolved in CH$_2$Cl$_2$ (300 mL) and 200 mL hydrochloric acid (2M). The aqueous phase was extracted with CH$_2$Cl$_2$ twice. The mixed organic phase was washed with water twice and dried with Na$_2$SO$_4$. After the solvent was removed, the crude product was purified by column chromatography with CH$_2$Cl$_2$ as eluent to give the product as pale-yellow powder. $^1$H NMR (CHCl$_3$): δ=1.5 (t, 3H), 4.4 (q, 2H), 8.4 (s, 2H), 8.7 (s, 1H).

Synthesis of L25

D was suspended in 100 mL THF, to which was added 20 mL 2 M KOH aqueous solution. The mixture was refluxed under N$_2$ overnight. THF was removed on rotary evaporator and diluted hydrochloric acid was added into the aqueous solution until the solution became acidic. The solid was collected by filtration, washed with water several times and dried in the air.

Synthesis of L26

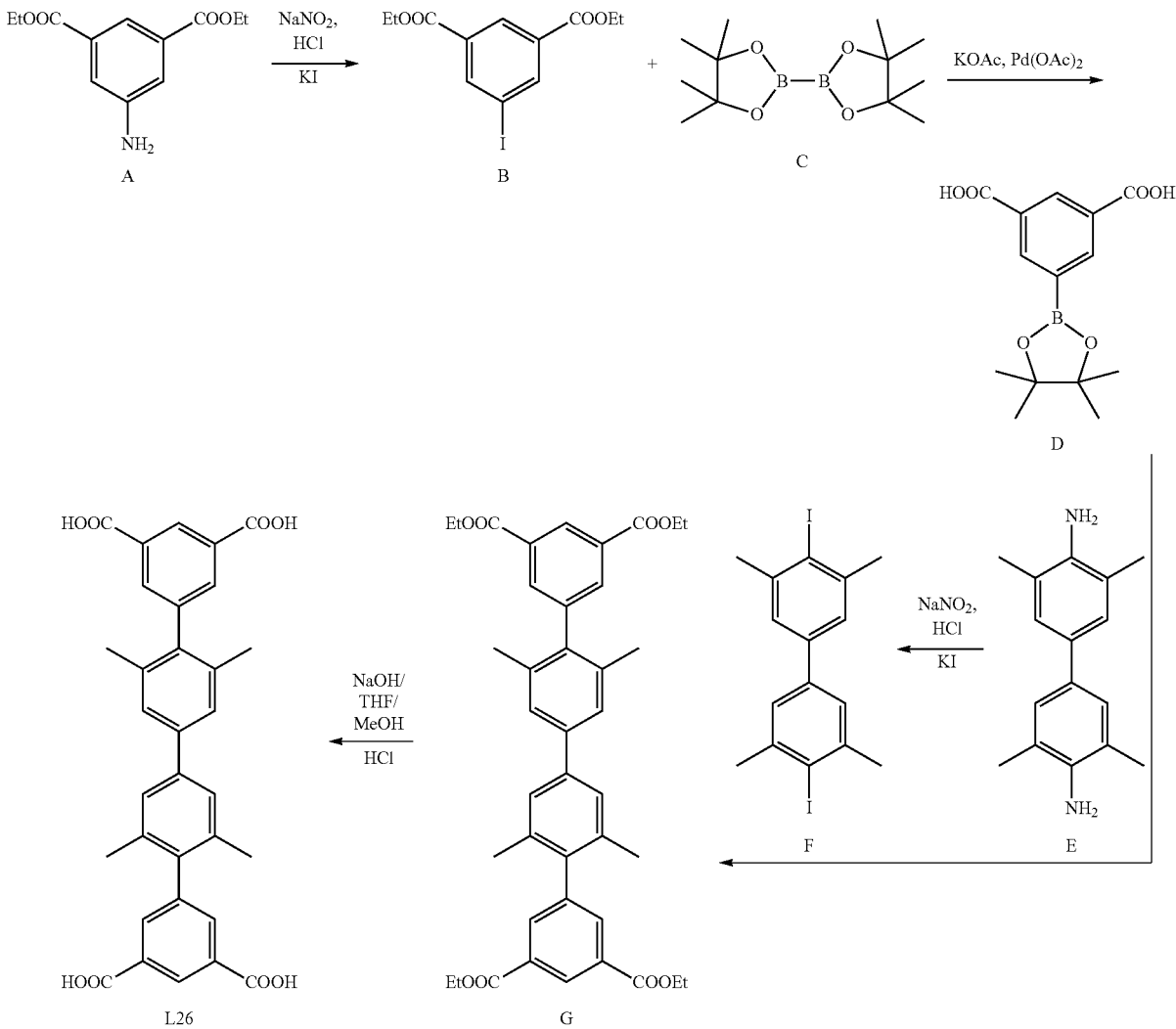

Synthesis of B

A solution of NaNO$_2$ (2.32 g) in 20 mL water was added to a cloudy mixture of A (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH₂Cl₂ was added, the mixture was allowed to stir at RT for 4 hours. The aqueous phase was washed with CH₂Cl₂ three times. The combined organic phases were dried with MgSO₄. After the solvent was removed, the crude product was purified by column chromatography with Ethyl acetate: Hexans=4:1 as the elute. (8.8 g, Yield. 91%) ¹H NMR (Acetone): δ =1.4 (t, 3H), 4.4 (q, 2H), 8.2 (s, 2H), 8.6 (s, 1H).

Synthesis of D

Degassed dry DMF (18 mL) was added to a mixture of B (3.48 g, 10 mmol), C (3.1 g, 12 mmol), potassium acetate (2.2 g, 24 mmol), and Pd(OAc)₂ (49 mg, 0.22 mmol). The mixture was heated to 90° C. (oil bath) for 24 h. After cooling to room temperature, the solution was added dropwise to water (90 mL) and stirred vigorously for 10 min. The solid was collected by filtration and purified through column chromatography on silica gel (hexane/ethyl acetate, 80:20, second point) to afford product as a white solid (2.01 g, 86%). ¹H NMR (CDCl₃): δ=1.346 (s, 12H), 1.396 (t, 6H), 4.392 (q, 4H), 8.600 (d, 2H), 8.739 (t, 1H).

Synthesis of F

A solution of NaNO₂ (2.32 g) in 20 mL water was added to a cloudy mixture of E (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH₂Cl₂ was added, the mixture was allowed to stir at RT for 4 hours. The aqueous phase was washed with CH₂Cl₂ three times. The combined organic phases were dried with MgSO₄. After the solvent was removed, the crude product was purified by column chromatography with Ethyl acetate: Hexane=4:1 as the eluent. ¹H NMR (CDCl₃): δ=2.538 (s, 12H), 7.261 (s, 4H).

Synthesis of L26

A 250-mL Schlenk flask was charged with of D (0.8 g, 3.05 mmol), F (3.7 g 8 mmol), CsF (4 g, 26.4 mmol), and 0.2 g of Pd(P(Ph)₃)₄. 120 ml of DME was degassed and transferred. A water condenser was then equipped and the flask was heated to reflux under the nitrogen for 72 hours. The solvent was dried on rotary evaporator. The residue was dissolved by CH₂Cl₂ and purified by column chromatography to white crystal. The white crystal was dissolved in a 500-mL Schlenk flask with 200 mL mixture of THF and MeOH (v/v=1:1). 100 mL of 0.3M NaOH aqueous solution was added. The flask was heated to reflux overnight. The solution is then acidified by diluted hydrochloric acid to give white precipitate, which was filtered and washed with water several times to get L26 1.2 g (Yield. 68%). ¹H NMR (DMSO): δ=2.051 (s, 12H), 7.516 (s, 4H), 7.925 (d, 4H), 8.490 (t, 2H).

Synthesis of L27

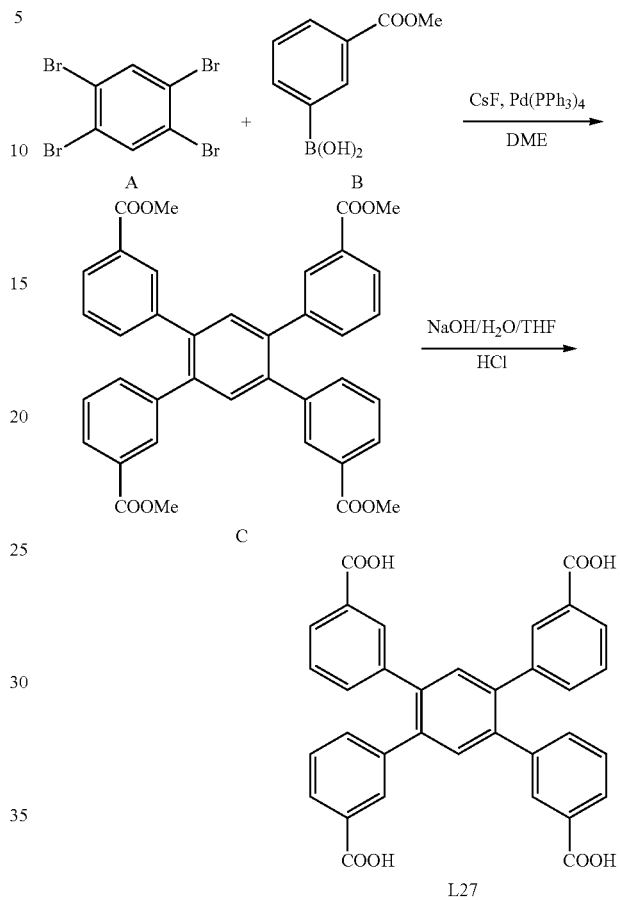

Synthesis of C

A 250-mL Schlenk flask was charged with of A (1.2 g, 3.05 mmol), B (3.28 g 18.3 mmol), CsF (4 g, 26.4 mmol), and 0.2 g of Pd(P(Ph)₃)₄. 120 ml DME was degassed and transferred. A water condenser was then equipped and the flask was heated to reflux under the nitrogen for 72 hours. The solvent was dried on rotary evaporator. The residue was dissolved by CH₂Cl₂ and purified by column chromatography to white crystal.

Synthesis of L27

The white crystal was dissolved in a 500 mL Schlenk flask with 200 mL mixture of THF and MeOH (v/v=1:1). 100 mL of 0.3M NaOH aqueous solution was added. The flask was heated to reflux overnight. The solution is then acidified by diluted hydrochloric acid to give white precipitate of C, which was filtered and washed with water several times to get L27 1.2 g (Yield. 68%). ¹H NMR (DMSO): δ=12.9 (s, 4H), 7.83 (t, 4H), 7.80 (s, 4H), 7.55 (s, 2H), 7.45 (d, 4H), 7.40 (d, 4H).

Synthesis of L29
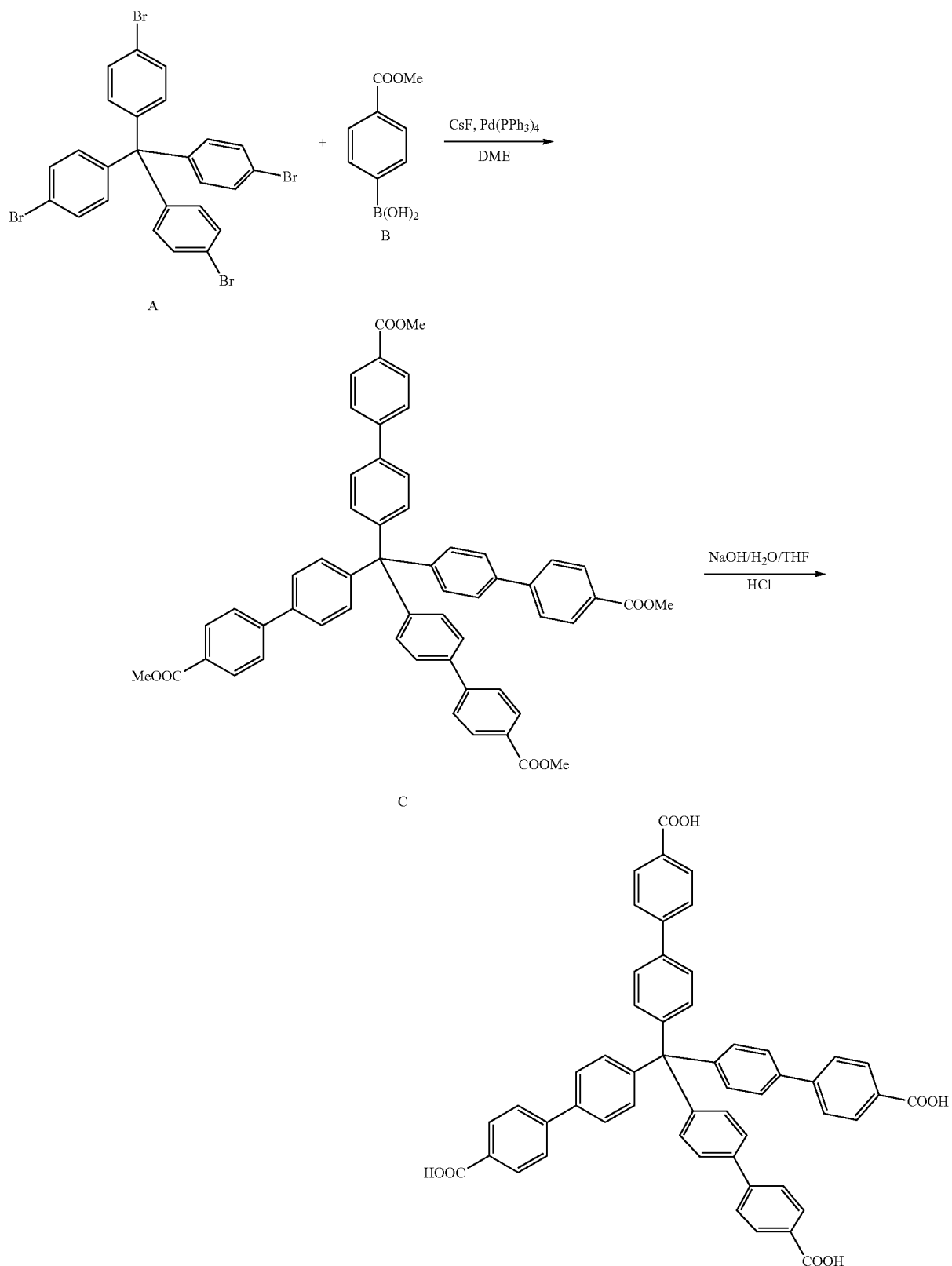

Synthesis of C

B is prepared according to the procedure described in reference 5.

A 250 mL Schlenk flask was charged with A (4 g, 6.3 mmol), B (6.79 g, 37.7 mmol), CsF (9.5 g, 63.9 mmol), and Pd(P(Ph)$_3$)$_4$ 0.3 g. 120 ml DME was degassed and transferred. A water condenser was then equipped. The flask was heated to reflux under the nitrogen for 48 hours. The solvent was dried on rotary evaporator. The residue was dissolved by CH$_2$Cl$_2$, and purified by column chromatography to get C, 4.1 g (Yield. 76%).

Synthesis of L29

C (4.1 g, 4.8 mmol) was dissolved in a 500 mL Schlenk flask with 200 mL mixture of THF and MeOH (v/v=1:1). 100 mL of 1.25M NaOH aqueous solution was added. The flask was heated to reflux overnight. The solution is then acidified by diluted hydrochloric acid to give white precipitate, which was filtered and washed with water and acetone several times. $^1$HNMR (DMSO): δ=12.93 (s, 4H), 7.99 (d, 8H), 7.81 (d, 8H), 7.76 (d, 8H), 7.41 (d, 8H).

Synthesis of L30

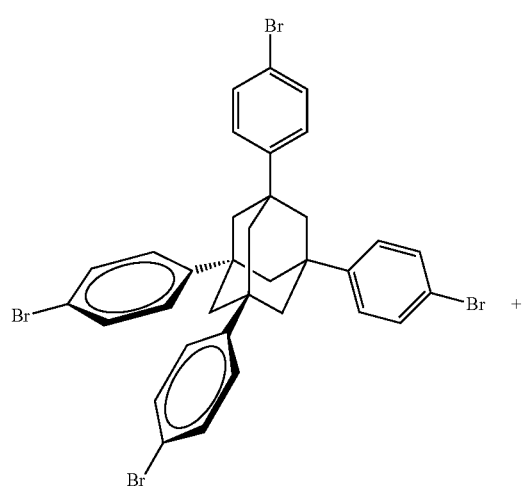

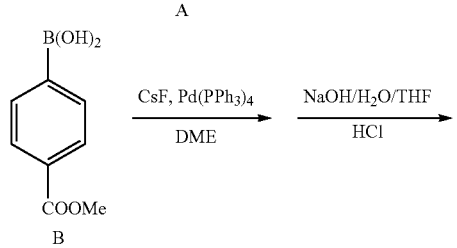

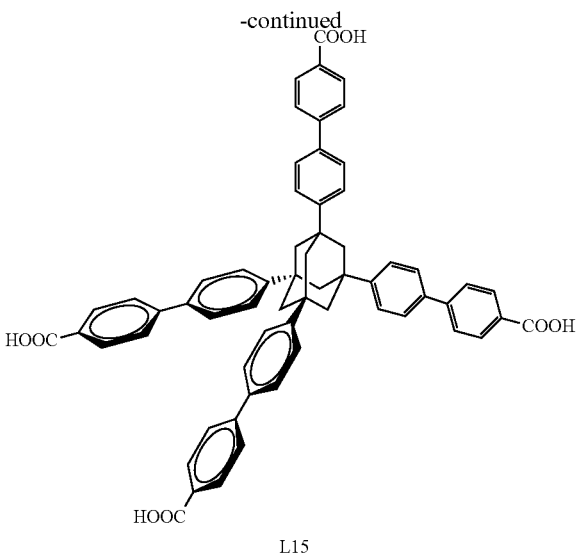

L15

Synthesis of C

B is prepared according to the procedure described in reference 1. A 250-mL Schlenk flask was charged with A (3 g, 4.0 mmol), B (4.2 g, 24 mmol), CsF (9.5 g, 63.9 mmol), and Pd(P(Ph)$_3$)$_4$ 0.3 g. 120 ml of DME was degassed and transferred. A water condenser was then equipped. The flask was heated to reflux under the nitrogen for 48 hours. The solvent was dried on rotary evaporator. The residue was dissolved by CH$_2$Cl$_2$, and purified by column chromatography to get C, 2.9 g (Yield. 76%).

Synthesis of L30

C (2.9 g, 3.0 mmol) was dissolved in a 500 mL Schlenk flask with 200 mL mixture of THF and MeOH (v/v=1:1). 100 mL of 1.25 M NaOH aqueous solution was added. The flask was heated to reflux overnight. The solution is then acidified by diluted hydrochloric acid to give white precipitate, which was filtered and washed with water and acetone several times. $^1$H NMR (CDCl$_3$): δ=2.29 (s, 8H), 3.92 (s, 12H) 7.64 (m, 6H) 8.08 (d, 2H).

The structures shown in the examples below represent the ligands employed which replace the (CH$_3$COO) ligands seen in the starting material whilst retaining the same metal ion cluster.

Example 1: Synthesis of PCN-233

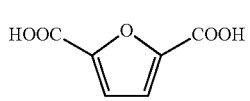 (L10)

L10 (15 mg), Fe$_2$CoO(CH$_3$COO)$_6$ (15 mg) and acetic acid (0.4 ml) in 2 mL of DMF were ultrasonically dissolved in a Pyrex vial. The mixture was heated in 120° C. oven for 12 h. After cooling down to room temperature, dark brown crystals were harvested by filtration (Yield. 80%).

Figure 2A:
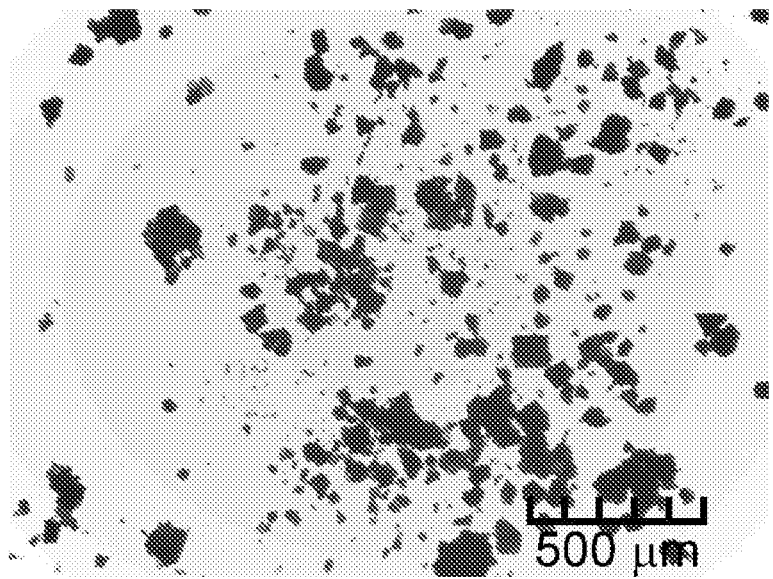
FIG. 2A shows an optical microscope image of PCN-233 (Example 1).
Figure 2B:
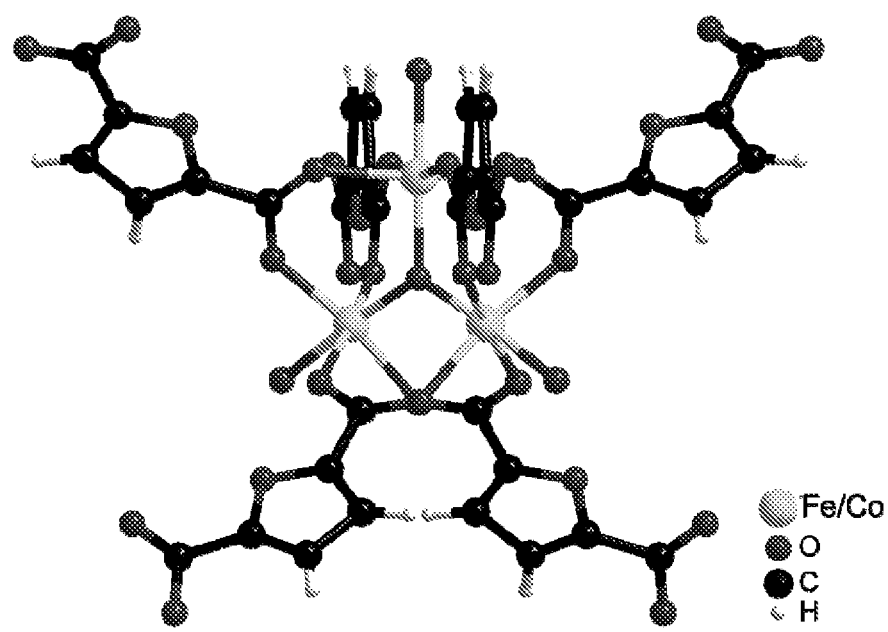
FIG. 2B illustrates a fragment structure of PCN-233 (Example 1).

An optical microscope image of PCN-233 is shown in FIG. 2a. FIG. 2b illustrates a fragment structure of PCN-233.

The crystal data and structure refinements for a single crystal of PCN-233 (Example 1) are shown in Table 1.

TABLE 1

| Compound PCN-233 Absolute structure parameter: 0.24(3) | | | |
|---|---|---|---|
| Formula | $Fe_2Co_1C_{18}H_6O_{19}$ | $\mu$ (mm$^{-1}$) | 0.960 |
| Fw | 696.86 | F(000) | 690 |
| Color/Shape | Brown Square | $\theta_{max}$ [deg] | 26.73 |
| Crystal system | Monoclinic | Completeness | 98.2% |
| Space group | C2 | Collected reflections | 9633 |
| a (Å) | 16.697(9) | | |
| b (Å) | 13.848(9) | Unique reflections | 4977 |
| c (Å) | 10.873(5) | Parameters | 182 |
| α (°) | 90.00 | Restraints | 8 |
| β (°) | 101.62(5) | $R_{int}$ | 0.0802 |
| γ (°) | 90.00 | R1 [I > 2σ(I)] | 0.0615 |
| V (Å$^3$) | 2463(2) | wR2 [I > 2σ(I)] | 0.1083 |
| Z | 2 | R1 (all data) | 0.1031 |
| T (K) | 110(2) | wR2 (all data) | 0.1147 |
| $d_{calcd.}$ (g/cm$^3$) | 0.940 | GOF on F$^2$ | 0.958 |
| | | $\Delta\rho_{max}/\Delta\rho_{min}$ [e · Å$^3$] | 0.762/−0.480 |

Note*APEX2 v2012.2.0 and SAINT v7.68A data collection and data processing programs, respectively. Bruker Analytical X-ray Instruments, Inc., Madison, WI; SADABS v2008/1 semi-empirical absorption and beam correction program. G. M. Sheldrick, University of Göttingen, Germany.

**G. M. Sheldrick, SHELXTL, Version 6.14, Structure Determination Software Suite, Bruker AXS, Madison, Wis., 2003.

Example 2: Synthesis of PCN-234

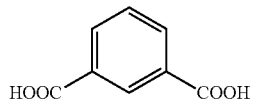

L11 (8 mg), Fe$_3$O(CH$_3$COO)$_6$OH (15 mg) and acetic acid (0.4 ml) in 2 mL of H$_2$O were ultrasonically dissolved in a Pyrex vial. The mixture was heated in 120° C. oven for 12 h. After cooling down to room temperature, dark brown crystals were harvested by filtration (Yield. 80%).

Figure 3A:
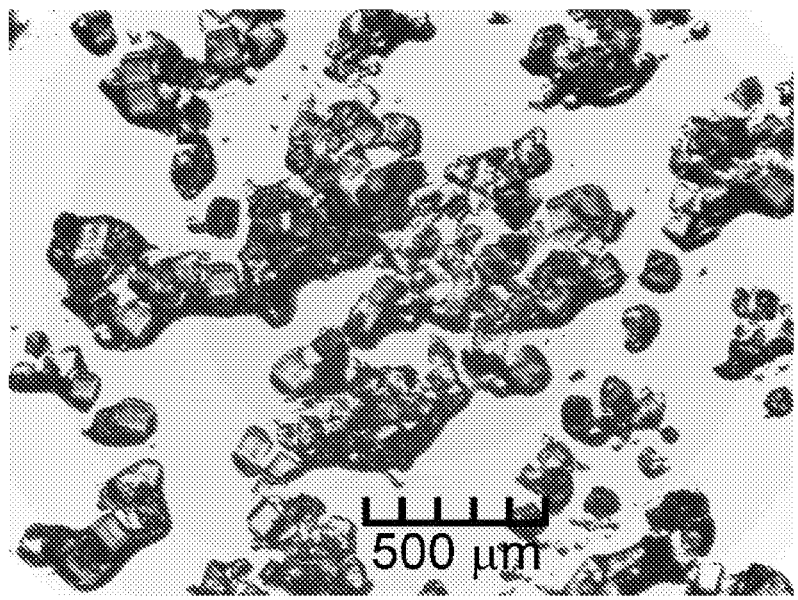
FIG. 3A shows an optical microscope image of PCN-234 (Example 2).
Figure 3B:
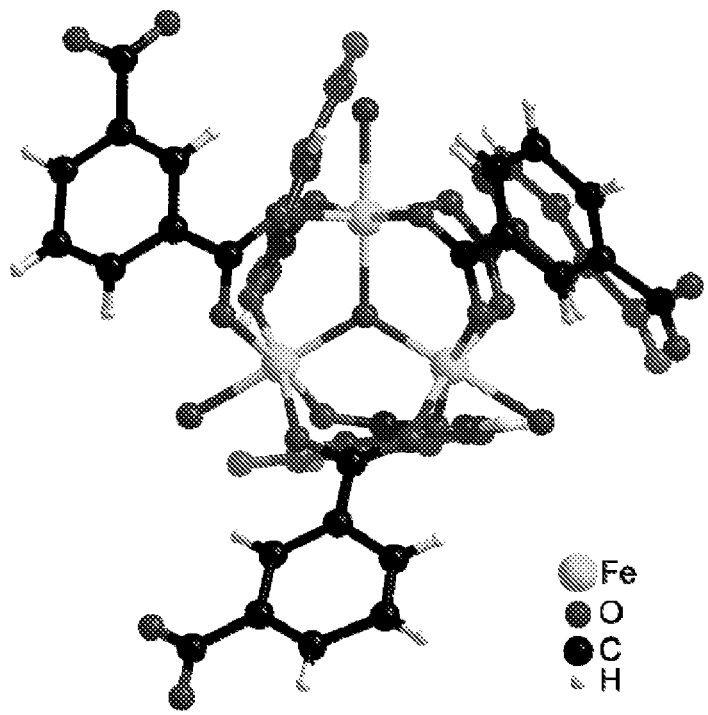
FIG. 3B illustrates a fragment structure of PCN-234 (Example 2).

An optical microscope image of PCN-234 is shown in FIG. 3a. FIG. 3b illustrates a fragment structure of PCN-234.

The crystal data and structure refinements for a single crystal of PCN-234 (Example 2) are shown in Table 2.

TABLE 2

| Compound PCN-234 | | | |
|---|---|---|---|
| Formula | $Fe_3C_{24}H_{13}O_{16}$ | $\mu$ (mm$^{-1}$) | 1.284 |
| Fw | 724.89 | F(000) | 2904 |
| Color/Shape | Orange Cube | $\theta_{max}$ [deg] | 23.98 |
| Crystal system | Cubic | Completeness | 99.4% |
| Space group | Pa$\bar{3}$ | Collected reflections | 58247 |
| a (Å) | 19.153(3) | Unique reflections | 1824 |
| b (Å) | 19.153(3) | Parameters | 82 |
| c (Å) | 19.153(3) | Restraints | 12 |
| α (°) | 90.00 | $R_{int}$ | 0.1253 |
| β (°) | 90.00 | R1 [I > 2σ(I)] | 0.1687 |
| γ (°) | 90.00 | wR2 [I > 2σ(I)] | 0.3399 |
| V (Å$^3$) | 7026.6(19) | R1 (all data) | 0.1968 |
| Z | 8 | wR2 (all data) | 0.3534 |
| T (K) | 110(2) | GOF on F$^2$ | 1.008 |
| $d_{calcd.}$ (g/cm$^3$) | 1.370 | $\Delta\rho_{max}/\Delta\rho_{min}$ [e · Å$^3$] | 0.952/−1.243 |

Example 3: Synthesis of PCN-235

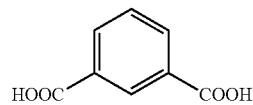

L11 (15 mg), Fe$_2$CoO(CH$_3$COO)$_6$ (15 mg) and acetic acid (0.2 ml) in 2 mL of DMF were ultrasonically dissolved in a Pyrex vial. The mixture was heated in 150° C. oven for 24 h. After cooling down to room temperature, dark brown crystals were harvested by filtration (Yield. 80%).

Figure 4A:
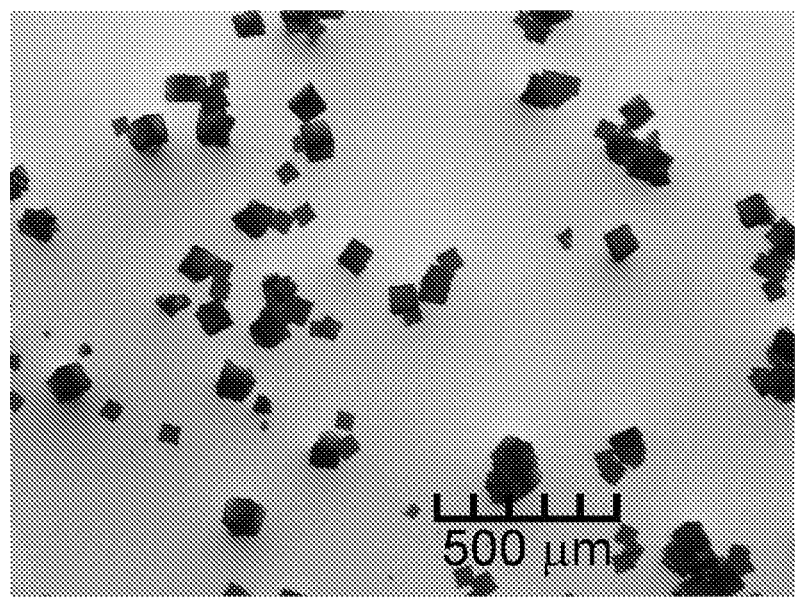
FIG. 4A shows an optical microscope image of PCN-235 (Example 3).
Figure 4B:
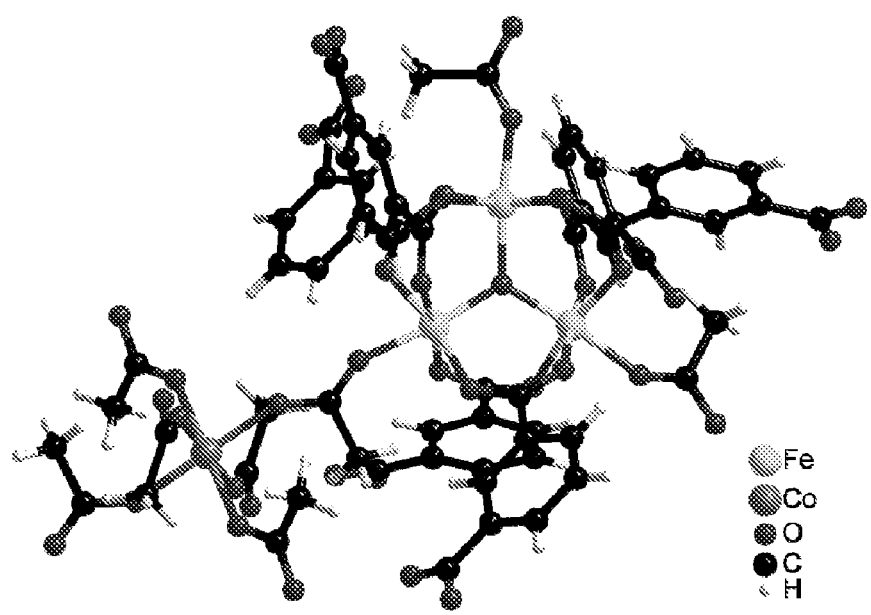
FIG. 4B illustrates a fragment structure of PCN-235 (Example 3).

An optical microscope image of PCN-235 is shown in FIG. 4a. FIG. 4b illustrates a fragment structure of PCN-235.

The crystal data and structure refinements for a single crystal of PCN-235 (CCDC 975773) are shown in Table 3.

TABLE 3

| Compound PCN-235 | | | |
|---|---|---|---|
| Formula | $Fe_6CoC_{60}H_{44}O_{38}$ | $\mu$ (mm$^{-1}$) | 1.423 |
| Fw | 1766.98 | F(000) | 3564 |
| Color/Shape | Brown Cube | $\theta_{max}$ [deg] | 25.88 |
| Crystal system | Cubic | Completeness | 99.9% |
| Space group | Pa$\bar{3}$ | Collected reflections | 54302 |
| a (Å) | 19.627(7) | Unique reflections | 2451 |
| b (Å) | 19.627(7) | Parameters | 155 |
| c (Å) | 19.627(7) | Restraints | 1 |
| α (°) | 90.00 | $R_{int}$ | 0.1276 |
| β (°) | 90.00 | R1 [I > 2σ(I)] | 0.0671 |
| γ (°) | 90.00 | wR2 [I > 2σ(I)] | 0.1668 |
| V (Å$^3$) | 7561(5) | R1 (all data) | 0.0899 |
| Z | 4 | wR2 (all data) | 0.1817 |
| T (K) | 110(2) | GOF on F$^2$ | 1.002 |
| $d_{calcd.}$ (g/cm$^3$) | 1.552 | $\Delta\rho_{max}/\Delta\rho_{min}$ [e · Å$^3$] | 0.828/−2.060 |

Example 4: Synthesis of PCN-236

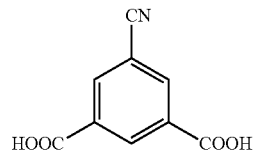 [SMILES: N#Cc1cc(C(=O)O)cc(C(=O)O)c1]

L13 (15 mg), Fe$_2$CoO(CH$_3$COO)$_6$ (15 mg) and acetic acid (0.1 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 5A:
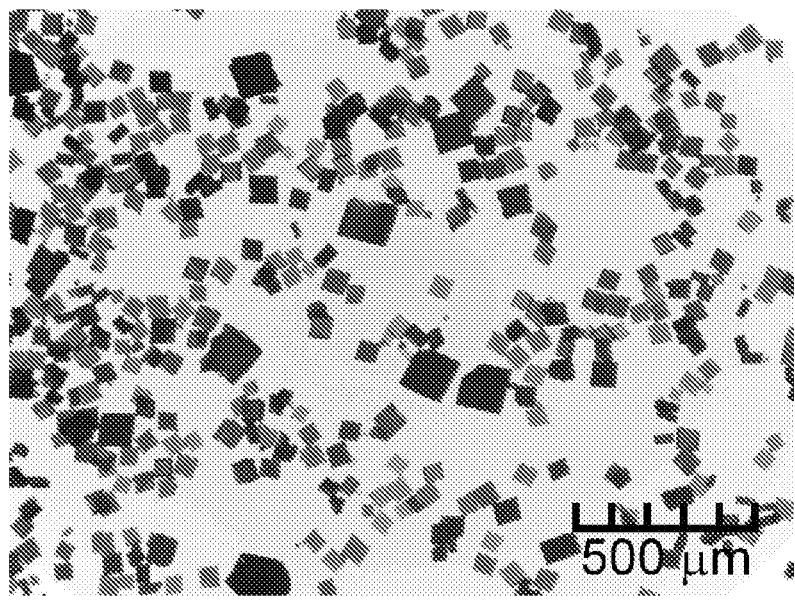
FIG. 5A shows an optical microscope image of PCN-236 (Example 4).
Figure 5B:
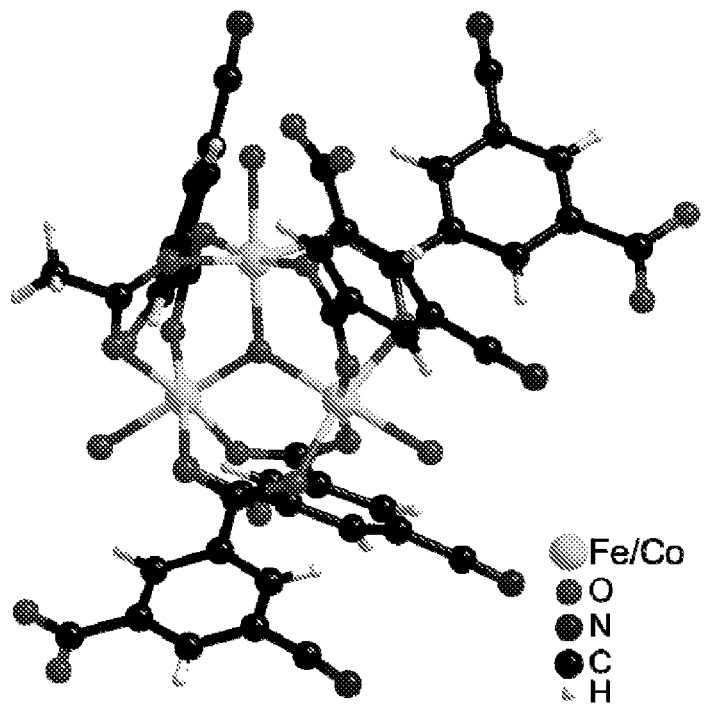
FIG. 5B illustrates a fragment structure of PCN-236 (Example 4).

An optical microscope image of PCN-236 is shown in FIG. 5a. FIG. 5b illustrates a fragment structure of PCN-236.

The crystal data and structure refinements for a single crystal of PCN-236 (CCDC 975774) are shown in Table 4.

TABLE 4

| Compound PCN-236 | | | |
|---|---|---|---|
| Formula | $Fe_4Co_2C_{49}H_{21}N_5O_{32}$ | $\mu$ (mm$^{-1}$) | 0.748 |
| Fw | 1532.97 | F(000) | 3056 |
| Color/Shape | Brown Square | $\theta_{max}$ [deg] | 26.59 |

TABLE 4-continued

Compound PCN-236

| Crystal system | Orthorhombic | Completeness | 99.5% |
|---|---|---|---|
| Space group | Pnna | Collected reflections | 132886 |
| a (Å) | 19.635(3) | Unique reflections | 13207 |
| b (Å) | 36.750(6) | Parameters | 320 |
| c (Å) | 17.556(3) | Restraints | 48 |
| α (°) | 90.00 | $R_{int}$ | 0.1102 |
| β (°) | 90.00 | R1 [I > 2σ(I)] | 0.0699 |
| γ (°) | 90.00 | wR2 [I > 2σ(I)] | 0.1822 |
| V (Å³) | 12668(3) | R1 (all data) | 0.1699 |
| Z | 4 | wR2 (all data) | 0.2057 |
| T (K) | 110(2) | GOF on F² | 1.001 |
| $d_{calcd.}$ (g/cm³) | 0.804 | $\Delta\rho_{max}/\Delta\rho_{min}$ [e · Å³] | 0.638/−0.576 |

Example 5: Synthesis of PCN-237

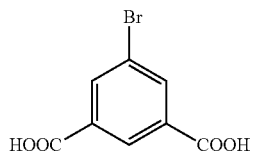

L12 (15 mg), Fe₂CoO(CH₃COO)₆ (15 mg) and acetic acid (0.2 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 6A:
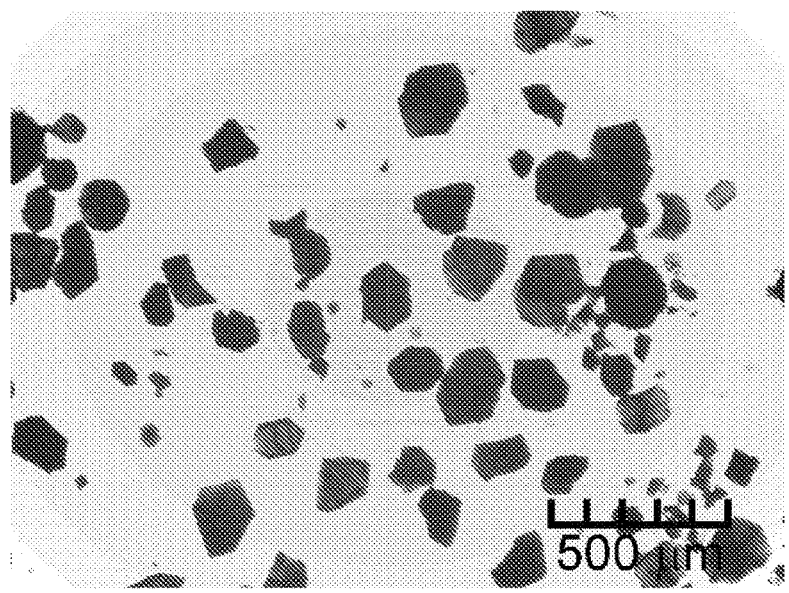
FIG. 6A shows an optical microscope image of PCN-237 (Example 5).
Figure 6B:
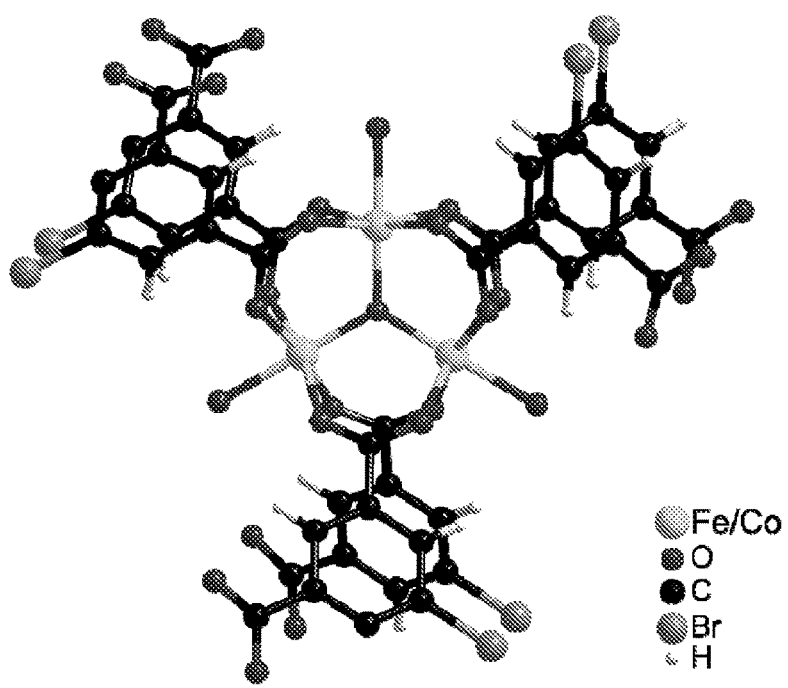
FIG. 6B illustrates a fragment structure of PCN-237 (Example 5).

An optical microscope image of PCN-237 is shown in FIG. 6a. FIG. 6b illustrates a fragment structure of PCN-237.

The crystal data and structure refinements for a single crystal of PCN-237 (CCDC 975775) are shown in Table 5.

TABLE 5

Compound PCN-237
Absolute structure parameter: 0.02(5)

| Formula | Fe₂Co₁C₂₄H₉Br₃O₁₆ | μ (mm⁻¹) | 3.279 |
|---|---|---|---|
| Fw | 963.67 | F(000) | 930 |
| Color/Shape | Brown Hexagon | $\theta_{max}$ [deg] | 27.14 |
| Crystal system | Hexagonal | Completeness | 99.5% |
| Space group | P 6̄ 2c | Collected reflections | 15835 |
| a (Å) | 15.392(4) | Unique reflections | 1974 |
| b (Å) | 15.392(4) | Parameters | 96 |
| c (Å) | 12.425(3) | Restraints | 31 |
| α (°) | 90.00 | $R_{int}$ | 0.0674 |
| β (°) | 90.00 | R1 [I > 2σ(I)] | 0.0741 |
| γ (°) | 120.00 | wR2 [I > 2σ(I)] | 0.1530 |
| V (Å³) | 2549.4(12) | R1 (all data) | 0.1032 |
| Z | 2 | wR2 (all data) | 0.1635 |
| T (K) | 110(2) | GOF on F² | 1.010 |
| $d_{calcd.}$ (g/cm³) | 1.255 | $\Delta\rho_{max}/\Delta\rho_{min}$ [e · Å³] | 1.144/−0.504 |

Example 6: Synthesis of PCN-238

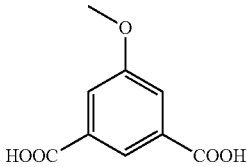

L14 (15 mg), Fe₂CoO(CH₃COO)₆ (15 mg) and acetic acid (0.1 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 7A:
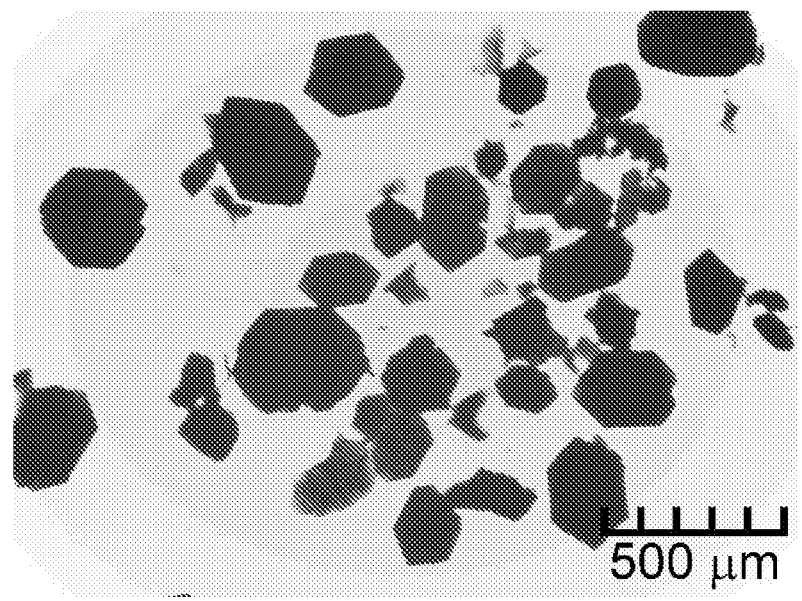
FIG. 7A shows an optical microscope image of PCN-238 (Example 6).
Figure 7B:
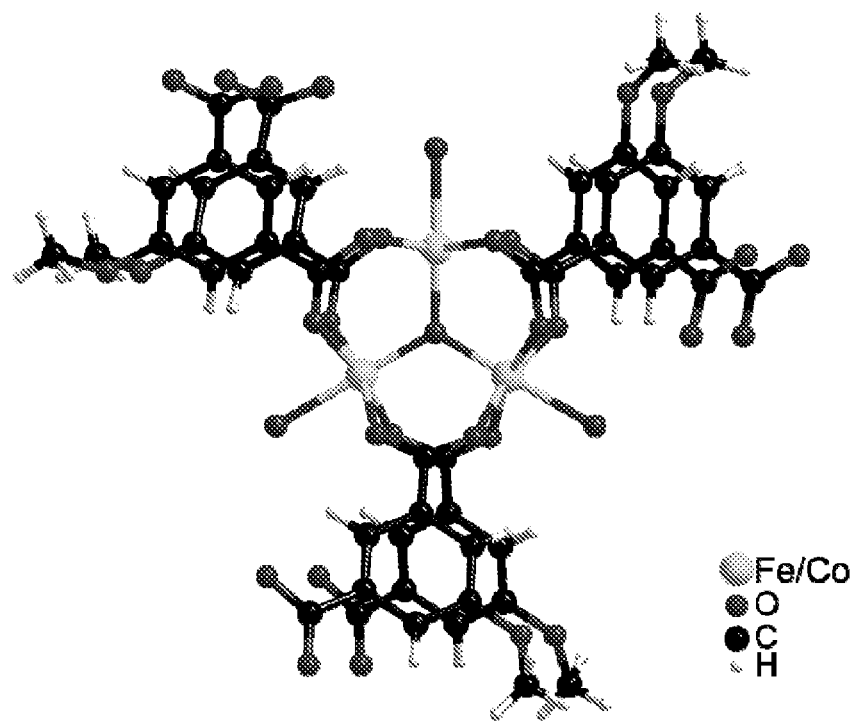
FIG. 7B illustrates a fragment structure of PCN-238 (Example 6).

An optical microscope image of PCN-238 is shown in FIG. 7a. FIG. 7b illustrates a fragment structure of PCN-238.

The crystal data and structure refinements for a single crystal of PCN-238 (CCDC 975776) are shown in Table 6.

TABLE 6

Compound PCN-238
Absolute structure parameter: 0.05(11)

| Formula | Fe₂Co₁C₂₇H₁₈O₁₉ | μ (mm⁻¹) | 0.924 |
|---|---|---|---|
| Fw | 817.04 | F(000) | 822 |
| Color/Shape | Brown Hexagon | $\theta_{max}$ [deg] | 24.65 |
| Crystal system | Hexagonal | Completeness | 99.3% |
| Space group | P 6̄ 2c | Collected reflections | 21511 |
| a (Å) | 15.460(4) | Unique reflections | 1524 |
| b (Å) | 15.460(4) | Parameters | 75 |
| c (Å) | 12.475(14) | Restraints | 29 |
| α (°) | 90.00 | $R_{int}$ | 0.1164 |
| β (°) | 90.00 | R1 [I > 2σ(I)] | 0.1213 |
| γ (°) | 120.00 | wR2 [I > 2σ(I)] | 0.2296 |
| V (Å³) | 2582(3) | R1 (all data) | 0.1591 |
| Z | 2 | wR2 (all data) | 0.2475 |
| T (K) | 110(2) | GOF on F² | 1.013 |
| $d_{calcd.}$ (g/cm³) | 1.051 | $\Delta\rho_{max}/\Delta\rho_{min}$ [e · Å³] | 0.832/−0.398 |

Example 7: Synthesis of PCN-240

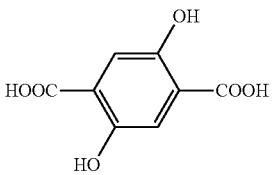

L3 (10 mg), Fe₂CoO(CH₃COO)₆ (10 mg) and acetic acid (0.25 ml) in 2 mL of DEF and H₂O (v/v=1/1) were ultrasonically dissolved in a Pyrex vial. The mixture was heated in 150° C. oven for 24 h. After cooling down to room temperature, dark brown crystals were harvested by filtration (Yield. 80%).

Figure 8A:
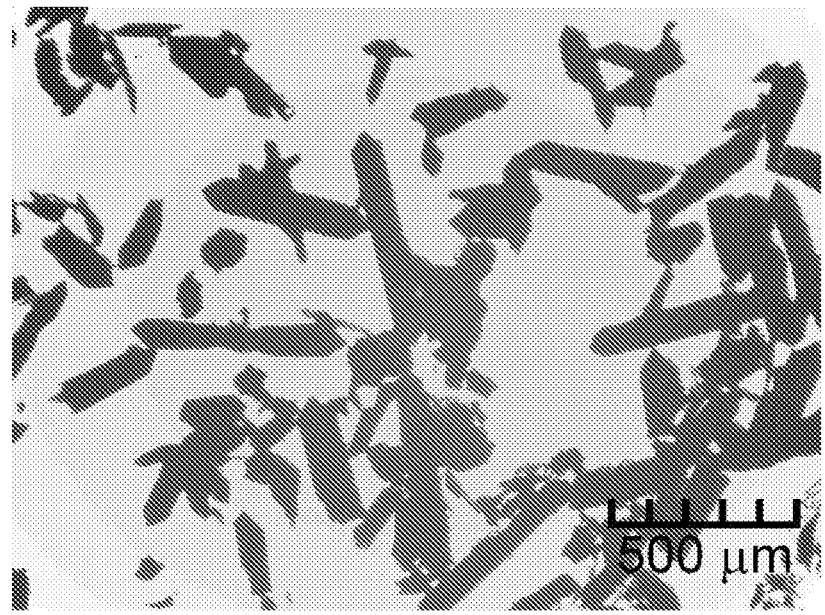
FIG. 8A shows an optical microscope image of PCN-240 (Example 7).
Figure 8B:
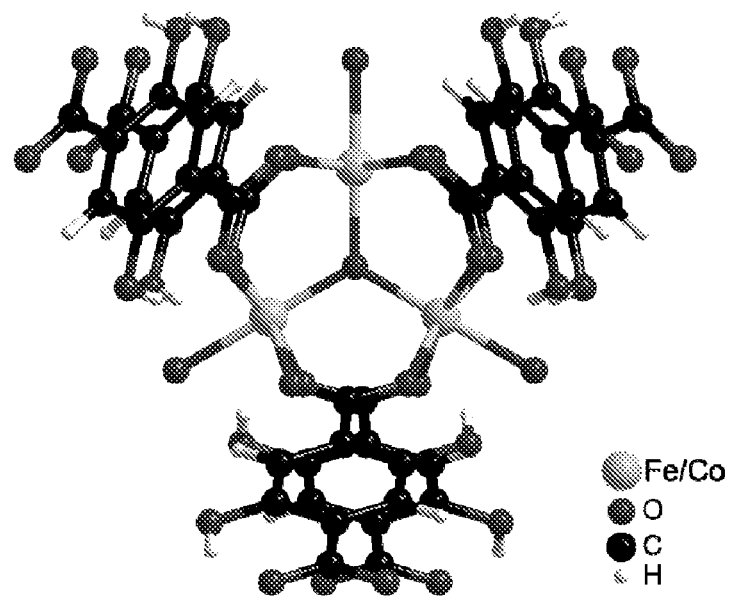
FIG. 8B illustrates a fragment structure of PCN-240 (Example 7).

An optical microscope image of PCN-240 is shown in FIG. 8a. FIG. 8b illustrates a fragment structure of PCN-240.

The crystal data and structure refinements for a single crystal of PCN-240 (CCDC 975777) are shown in Table 7.

TABLE 7

| Compound PCN-240 | | | |
|---|---|---|---|
| Formula | Fe$_2$CoC$_{24}$H$_{12}$O$_{22}$ | μ (mm$^{-1}$) | 0.767 |
| Fw | 822.97 | F(000) | 822 |
| Color/Shape | Brown Rod | θ$_{max}$ [deg] | 24.55 |
| Crystal system | Hexagonal | Completeness | 99.9% |
| Space group | P 6$_3$/mmc | Collected reflections | 28022 |
| a (Å) | 14.392(3) | Unique reflections | 1029 |
| b (Å) | 14.392(3) | Parameters | 52 |
| c (Å) | 17.416(5) | Restraints | 0 |
| α (°) | 90.00 | R$_{int}$ | 0.1240 |
| β (°) | 90.00 | R1 [I > 2σ(I)] | 0.0625 |
| γ (°) | 120.00 | wR2 [I > 2σ(I)] | 0.1447 |
| V (Å$^3$) | 3124.1(13) | R1 (all data) | 0.0865 |
| Z | 2 | wR2 (all data) | 0.1563 |
| T (K) | 110(2) | GOF on F$^2$ | 1.006 |
| d$_{calcd.}$ (g/cm$^3$) | 0.875 | Δρ$_{max}$/Δρ$_{min}$ [e · Å$^3$] | 1.025/−0.468 |

Example 8: Synthesis of PCN-241

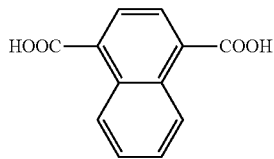 [SMILES: O=C(O)c1ccc(C(=O)O)c2ccccc12]

L4 (10 mg), Fe$_2$CoO(CH$_3$COO)$_6$ (15 mg) and acetic acid (0.8 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 9A:
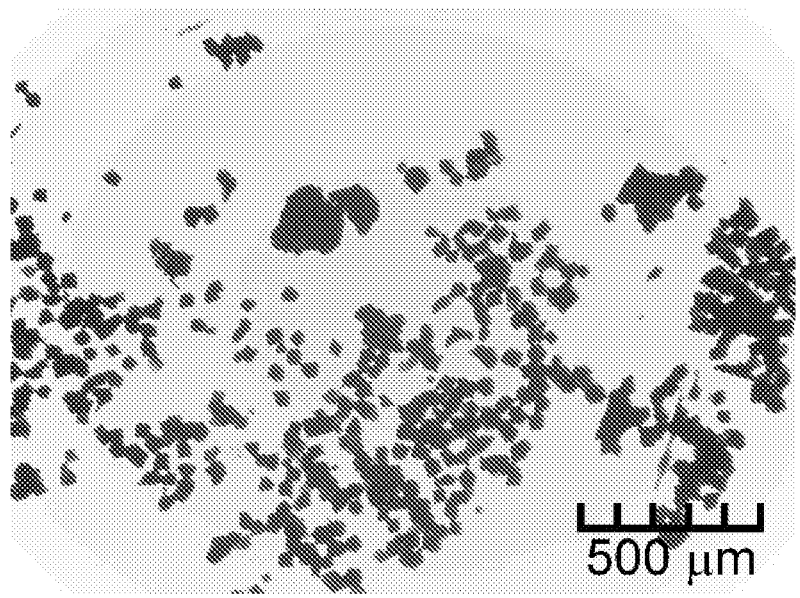
FIG. 9A shows an optical microscope image of PCN-241 (Example 8).
Figure 9B:
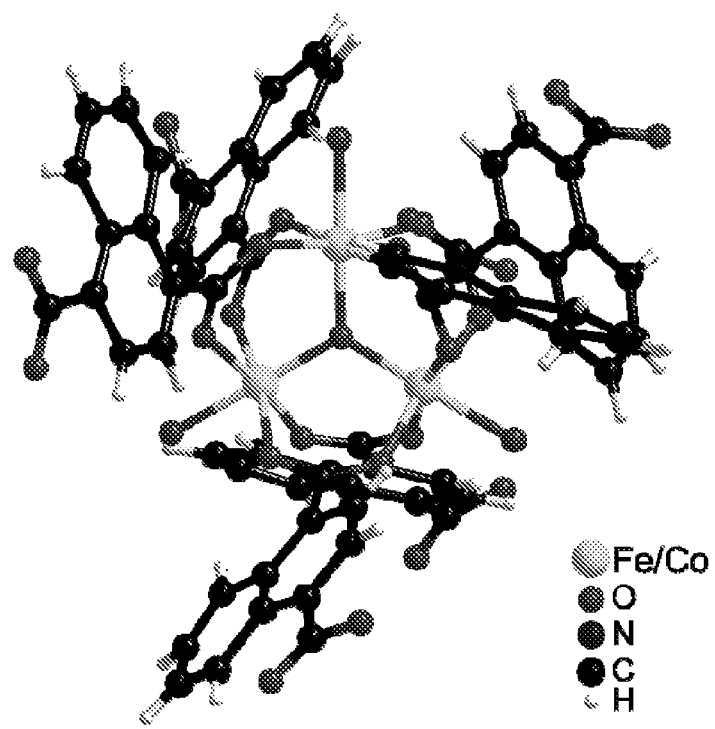
FIG. 9B illustrates a fragment structure of PCN-241 (Example 8).

An optical microscope image of PCN-241 is shown in FIG. 9a. FIG. 9b illustrates a fragment structure of PCN-241.

The crystal data and structure refinements for a single crystal of PCN-241 (CCDC 975778) are shown in Table 8.

TABLE 8

| Compound PCN-241 Absolute structure parameter: 0.09(5) | | | |
|---|---|---|---|
| Formula | Fe$_2$CoC$_{45}$H$_{39}$N$_3$O$_{16}$ | μ (mm$^{-1}$) | 0.967 |
| Fw | 1048.42 | F (000) | 1074 |
| Color/Shape | Brown Sheet | θ$_{max}$ [deg] | 24.8 |
| Crystal system | Hexagonal | Completeness | 99.9% |
| Space group | P31c | Collected reflections | 22992 |
| a (Å) | 12.493(2) | Unique reflections | 2886 |
| b (Å) | 12.493(2) | Parameters | 207 |
| c (Å) | 18.533(3) | Restraints | 1 |
| α (°) | 90.00 | R$_{int}$ | 0.0771 |
| β (°) | 90.00 | R1 [I > 2σ(I)] | 0.0690 |
| γ (°) | 120.00 | wR2 [I > 2σ(I)] | 0.1869 |
| V (Å$^3$) | 2504.9(7) | R1 (all data) | 0.0739 |
| Z | 2 | wR2 (all data) | 0.1912 |
| T (K) | 110(2) | GOF on F$^2$ | 1.006 |
| d$_{calcd.}$ (g/cm$^3$) | 1.390 | Δρ$_{max}$/Δρ$_{min}$ [e · Å$^3$] | 0.799/−0.618 |

Example 9: Synthesis of PCN-242

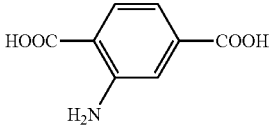

L2 (10 mg), Fe$_3$O(CH$_3$COO)$_6$OH (10 mg) and acetic acid (0.45 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 10:
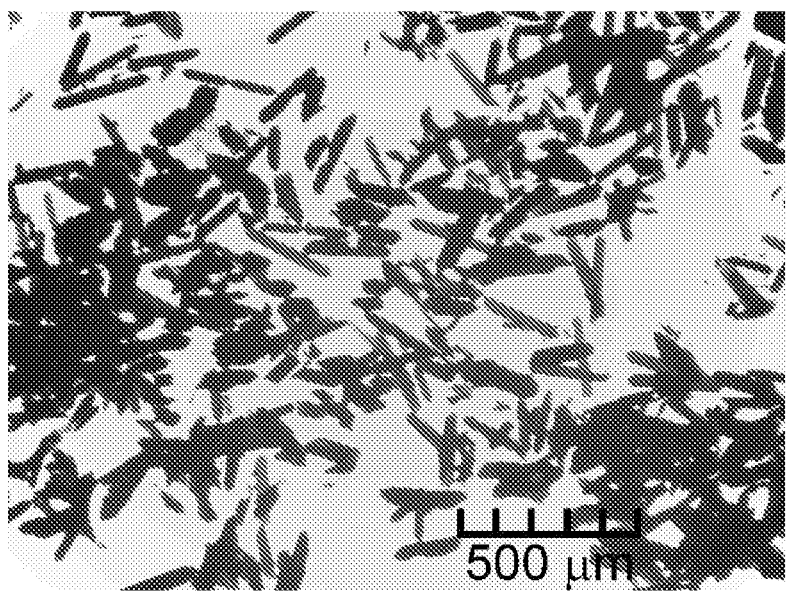
FIG. 10 shows an optical microscope image of PCN-242 (Example 9).

An optical microscope image of PCN-242 is shown in FIG. 10. A single crystal of PCN-242 is isostructural to PCN-240.

Example 10: Synthesis of PCN-243

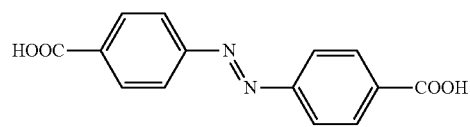

L8 (10 mg), Fe$_3$O(CH$_3$COO)$_6$OH (10 mg) and acetic acid (0.45 ml) in 2 mL of DMF were ultrasonically dissolved in a Pyrex vial. The mixture was heated in 150° C. oven for 48 h.

After cooling down to room temperature, dark brown crystals were harvested by filtration (Yield. 80%).

Figure 11A:
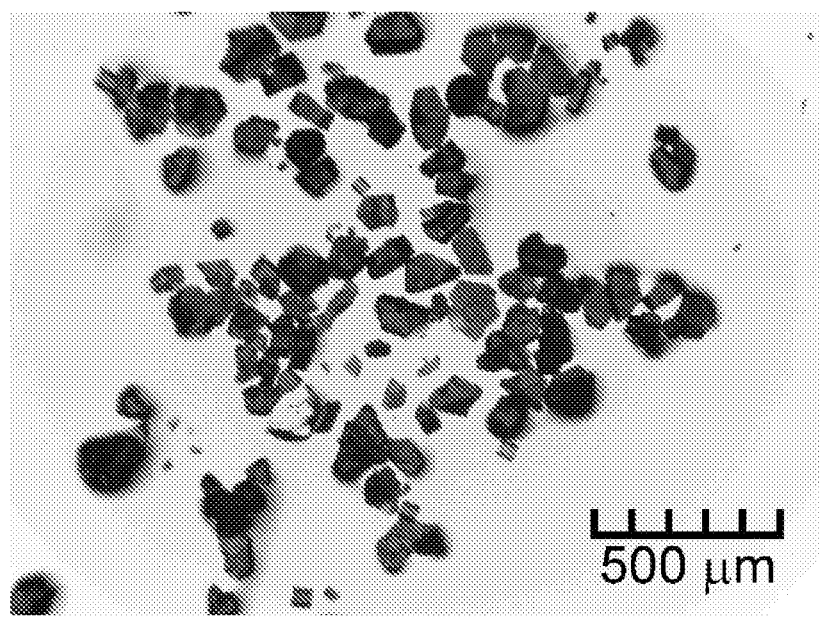
FIG. 11A shows an optical microscope image of PCN-243 (Example 10).
Figure 11B:
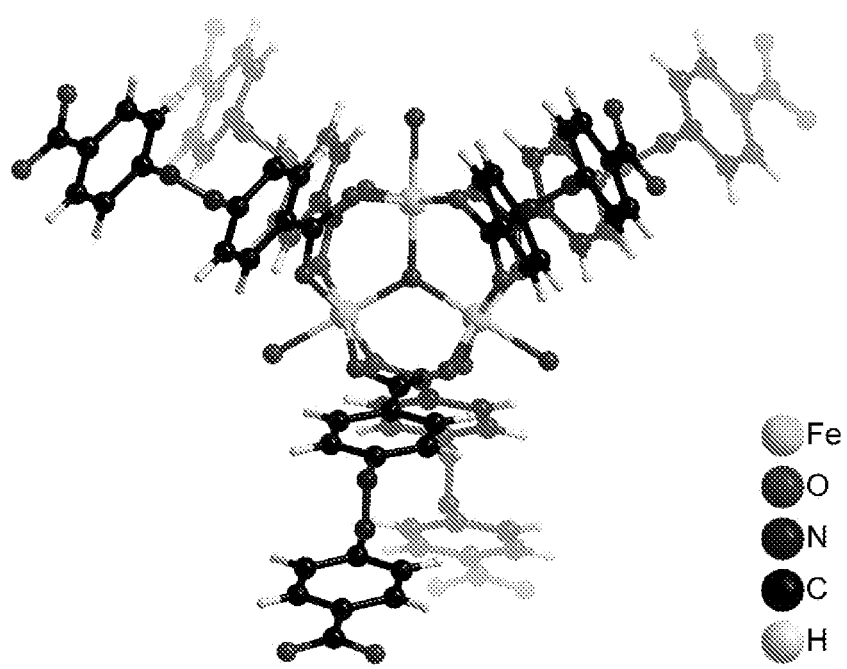
FIG. 11B illustrates a fragment structure of PCN-243 (Example 10).

An optical microscope image of PCN-243 is shown in FIG. 11a. FIG. 11b illustrates a fragment structure of PCN-243.

The crystal data and structure refinements for a single crystal of PCN-243 (CCDC 975779) are shown in Table 9.

TABLE 9

| Compound PCN-243 Absolute structure parameter: 0.47(15) | | | |
|---|---|---|---|
| Formula | Fe$_6$C$_{84}$H$_{48}$N$_{12}$O$_{32}$ | μ (mm$^{-1}$) | 0.797 |
| Fw | 2072.44 | F (000) | 3144 |
| Color/Shape | Red Hexagonal Prism | θ$_{max}$ [deg] | 23.29 |
| Crystal system | Hexagonal | Completeness | 99.9% |
| Space group | P6$_3$mc | Collected reflections | 71186 |
| a (Å) | 18.6996(8) | Unique reflections | 4662 |
| b (Å) | 18.6996(8) | Parameters | 153 |
| c (Å) | 28.8572(18) | Restraints | 84 |
| α (°) | 90.00 | R$_{int}$ | 0.0353 |
| β (°) | 90.00 | R1 [I > 2σ(I)] | 0.1487 |
| γ (°) | 120.00 | wR2 [I > 2σ(I)] | 0.2802 |
| V (Å$^3$) | 8738.8(8) | R1 (all data) | 0.1589 |
| Z | 3 | wR2 (all data) | 0.2849 |
| T (K) | 110(2) | GOF on F$^2$ | 0.842 |
| d$_{calcd.}$ (g/cm$^3$) | 1.181 | Δρ$_{max}$/Δρ$_{min}$ [e · Å$^3$] | 2.284/−1.561 |

Example 11: Synthesis of PCN-245

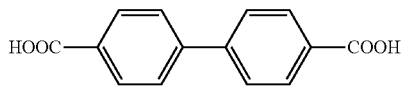 [SMILES: O=C(O)c1ccc(-c2ccc(C(=O)O)cc2)cc1]

L5 (10 mg), Fe$_3$O(CH$_3$COO)$_6$OH (10 mg) and acetic acid (0.15 ml) in 2 mL of DMF were ultrasonically dissolved in a Pyrex vial. The mixture was heated in 150° C. oven for 12 h. After cooling down to room temperature, dark brown crystals were harvested by w filtration (Yield. 80%).

Figure 12A:
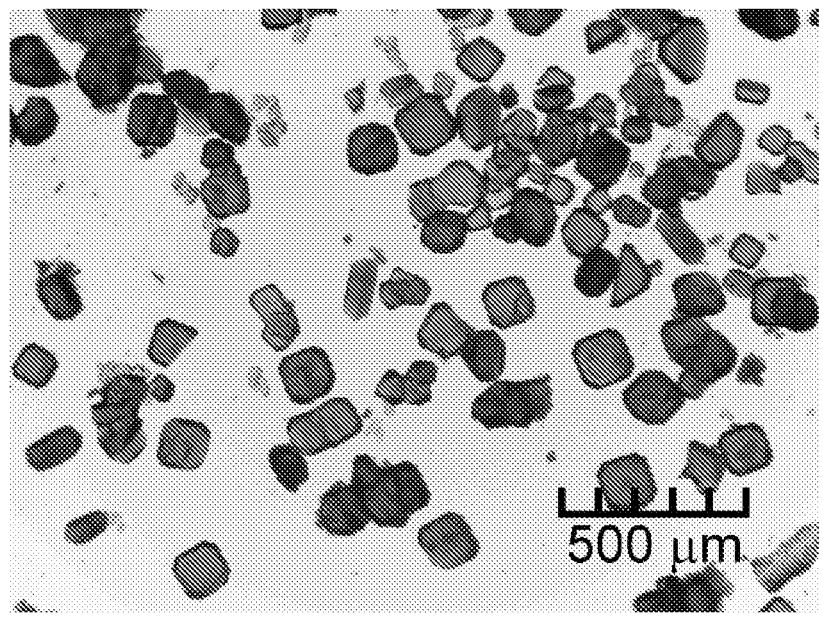
FIG. 12A shows an optical microscope image of PCN-245 (Example 11).
Figure 12B:
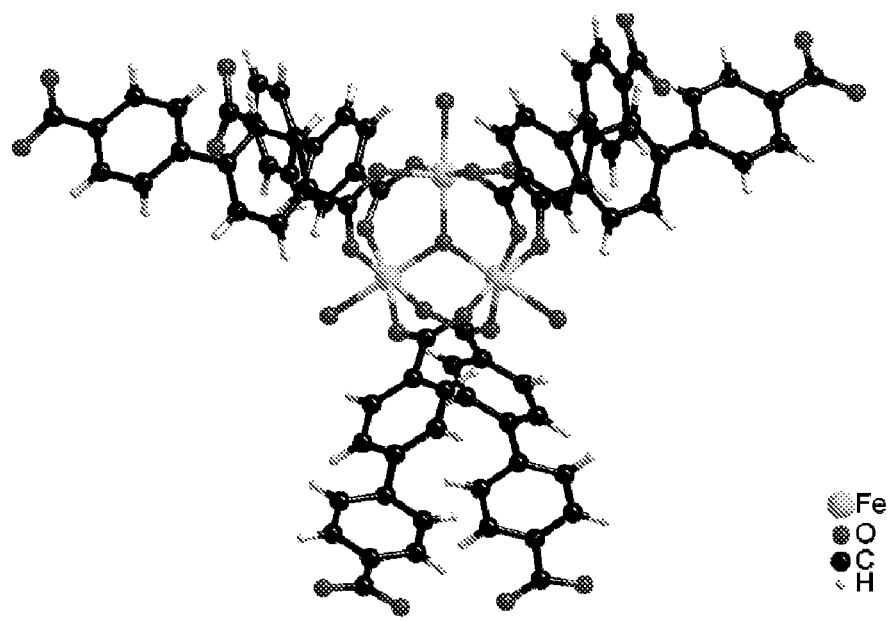
FIG. 12B illustrates a fragment structure of PCN-245 (Example 11).

An optical microscope image of PCN-245 is shown in FIG. 12a. FIG. 12b illustrates a fragment structure of PCN-245.

The crystal data and structure refinements for a single crystal of PCN-245 (CCDC 975780) are shown in Table 10.

TABLE 10

Compound PCN-245
Absolute structure parameter: 0.04(3)

| Formula | Fe$_3$C$_{42}$H$_{24}$O$_{16}$ | μ (mm$^{-1}$) | 0.550 |
|---|---|---|---|
| Fw | 952.16 | F (000) | 3856 |
| Color/Shape | Orange Square Bulk | θ$_{max}$ [deg] | 21.77 |
| Crystal system | Tetragonal | Completeness | 99.0% |
| Space group | P4$_2$2$_1$2 | Collected reflections | 60402 |
| a (Å) | 21.757(11) | Unique reflections | 9857 |
| b (Å) | 21.757(11) | Parameters | 245 |
| c (Å) | 35.299(18) | Restraints | 0 |
| α (°) | 90.00 | R$_{int}$ | 0.1889 |
| β (°) | 90.00 | R1 [I > 2σ(I)] | 0.0639 |
| γ (°) | 90.00 | wR2 [I > 2σ(I)] | 0.1337 |
| V (Å$^3$) | 16709(14) | R1 (all data) | 0.0961 |
| Z | 8 | wR2 (all data) | 0.1423 |
| T (K) | 110(2) | GOF on F$^2$ | 1.000 |
| d$_{calcd.}$ (g/cm$^3$) | 0.757 | Δρ$_{max}$/Δρ$_{min}$ [e · Å$^3$] | 0.583/−0.404 |

Example 12: Synthesis of PCN-246

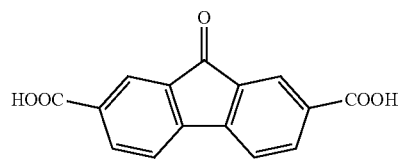 [SMILES: O=C(O)c1ccc2c(c1)C(=O)c1cc(C(=O)O)ccc1-2]

L7 (10 mg), Fe$_3$O(CH$_3$OO)$_6$OH (15 mg) and acetic acid (0.2 ml) in 2 mL of DMF were ultrasonically dissolved in a Pyrex vial. The mixture was heated in 120° C. oven for 12 h. After cooling down to room temperature, dark brown crystals were harvested by filtration (Yield. 80%).

Figure 13A:
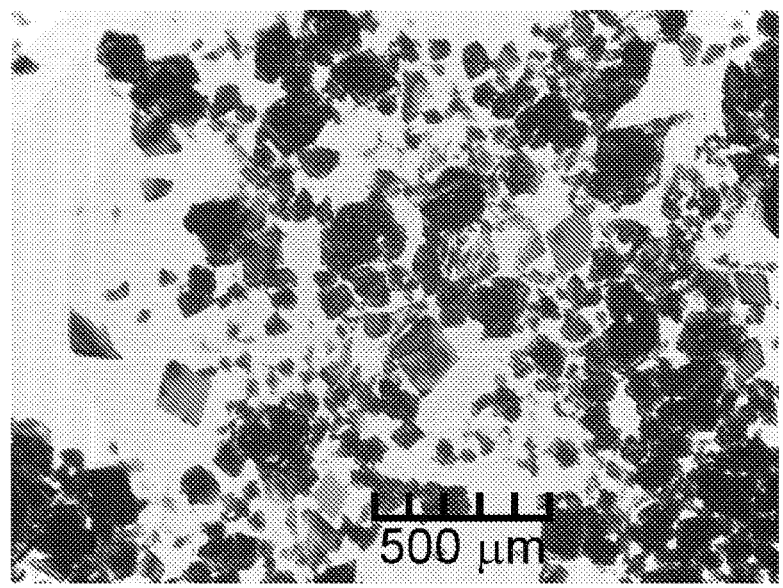
FIG. 13A shows an optical microscope image of PCN-246 (Example 12).
Figure 13B:
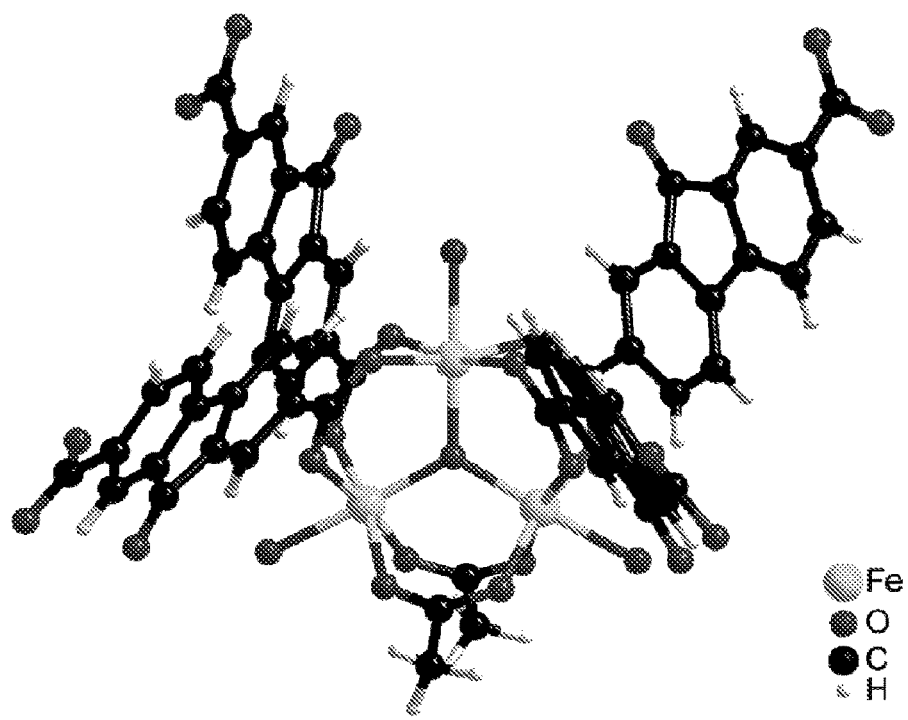
FIG. 13B illustrates a fragment structure of PCN-246 (Example 12).

An optical microscope image of PCN-246 is shown in FIG. 13a. FIG. 13b illustrates a fragment structure of PCN-246.

The crystal data and structure refinements for a single crystal of PCN-246 (CCDC 975781) are shown in Table 11.

TABLE 11

Compound PCN-246

| Formula | Fe$_3$C$_{34}$H$_{21}$O$_{18}$ | μ (mm$^{-1}$) | 0.618 |
|---|---|---|---|
| Fw | 885.06 | F (000) | 1788 |

TABLE 11-continued

Compound PCN-246

| Color/Shape | Orange Slice | θ$_{max}$ [deg] | 26.46 |
|---|---|---|---|
| Crystal system | Orthorhombic | Completeness | 99.7% |
| Space group | Pnma | Collected reflections | 78031 |
| a (Å) | 18.358(2) | Unique reflections | 7907 |
| b (Å) | 15.888(2) | Parameters | 266 |
| c (Å) | 25.435(3) | Restraints | 2 |
| α (°) | 90.00 | R$_{int}$ | 0.0807 |
| β (°) | 90.00 | R1 [I > 2σ(I)] | 0.0460 |
| γ (°) | 90.00 | wR2 [I > 2σ(I)] | 0.1069 |
| V (Å$^3$) | 7418.6(17) | R1 (all data) | 0.0721 |
| Z | 4 | wR2 (all data) | 0.1127 |
| T (K) | 110(2) | GOF on F$^2$ | 1.000 |
| d$_{calcd.}$ (g/cm$^3$) | 0.792 | Δρ$_{max}$/Δρ$_{min}$ [e · Å$^3$] | 0.997/−0.409 |

Example 13: Synthesis of PCN-247

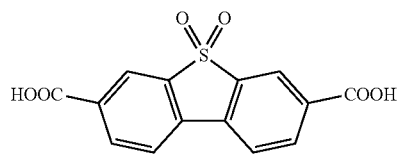 [SMILES: O=C(O)c1ccc2c(c1)S(=O)(=O)c1cc(C(=O)O)ccc1-2]

L6 (10 mg), Fe$_3$O(CH$_3$OO)$_6$OH (15 mg) and acetic acid (0.35 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 14A:
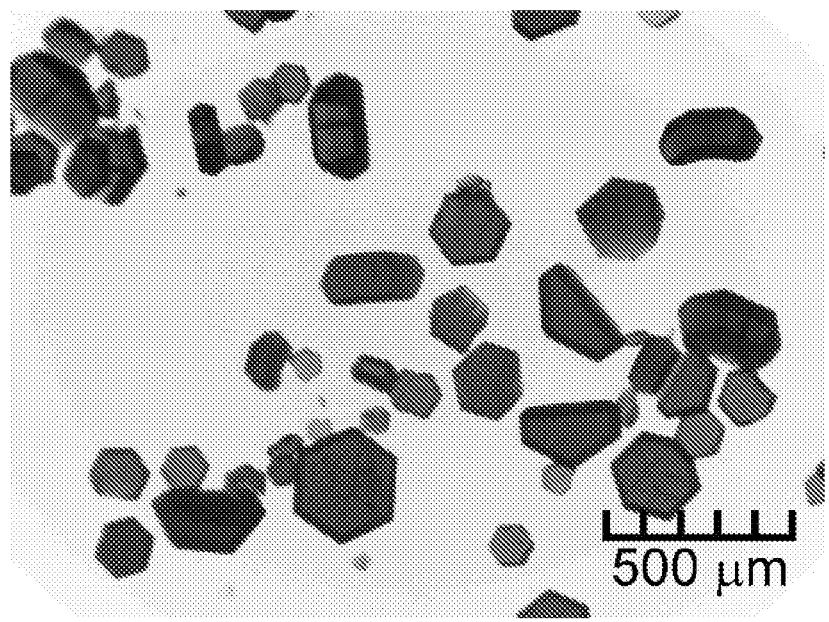
FIG. 14A shows an optical microscope image of PCN-247 (Example 13).
Figure 14B:
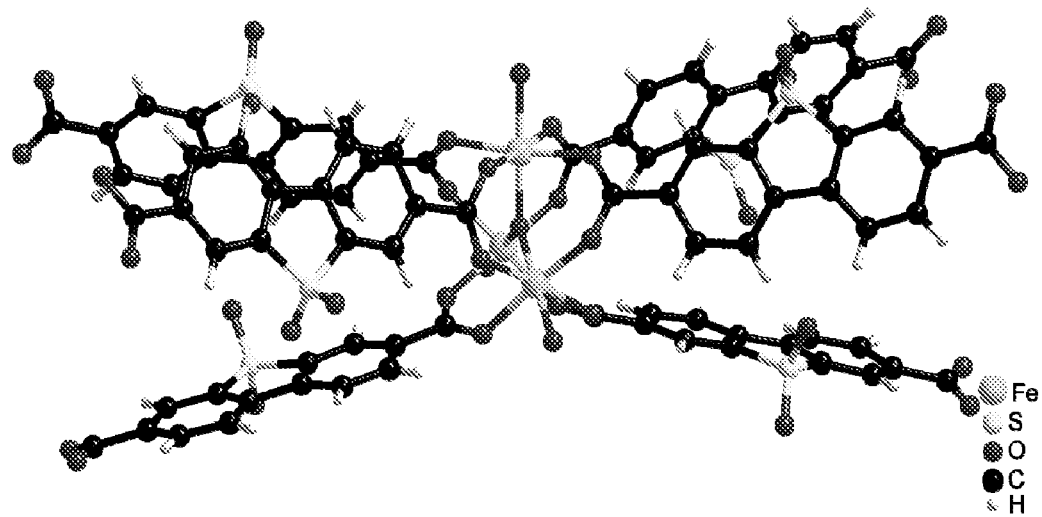
FIG. 14B illustrates a fragment structure of PCN-247 (Example 13).

An optical microscope image of PCN-247 is shown in FIG. 14a. FIG. 14b illustrates a fragment structure of PCN-247.

The crystal data and structure refinements for a single crystal of PCN-247 (CCDC 975782) are shown in Table 12.

TABLE 12

Compound PCN-247
Absolute structure parameter: 0.51(5)

| Formula | Fe$_3$C$_{42}$H$_{19}$O$_{22}$S$_3$ | μ (mm$^{-1}$) | 0.739 |
|---|---|---|---|
| Fw | 1139.30 | F (000) | 1146 |
| Color/Shape | Orange Hexagon | θ$_{max}$ [deg] | 26.44 |
| Crystal system | Hexagonal | Completeness | 99.7% |
| Space group | P6$_3$22 | Collected reflections | 29673 |
| a (Å) | 12.3081(8) | Unique reflections | 2494 |
| b (Å) | 12.3081(8) | Parameters | 102 |
| c (Å) | 27.375(4) | Restraints | 0 |
| α (°) | 90.00 | R$_{int}$ | 0.0556 |
| β (°) | 90.00 | R1 [I > 2σ(I)] | 0.0601 |
| γ (°) | 120.00 | wR2 [I > 2σ(I)] | 0.1320 |
| V (Å$^3$) | 3591.4(6) | R1 (all data) | 0.0691 |
| Z | 2 | wR2 (all data) | 0.1364 |
| T (K) | 110(2) | GOF on F$^2$ | 1.002 |
| d$_{calcd.}$ (g/cm$^3$) | 1.054 | Δρ$_{max}$/Δρ$_{min}$ [e · Å$^3$] | 0.598/−0.516 |

Example 14: Synthesis of PCN-248

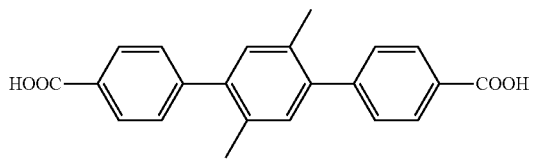

L9 (10 mg), Fe$_2$CoO(CH$_3$COO)$_6$ or Fe$_3$O(CH$_3$COO)$_6$ (10 mg) and acetic acid (0.25 ml) in 2 mL of NMP were ultrasonically dissolved in a Pyrex vial. The mixture was heated in 150° C. oven for 24 h. After cooling down to room temperature, dark brown crystals were harvested by filtration (Yield. 80%).

Figure 15A:
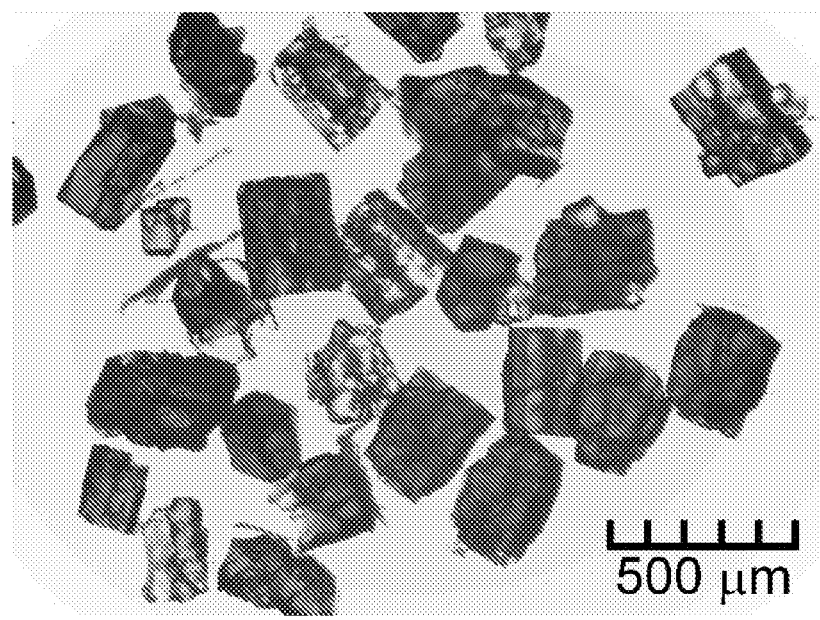
FIG. 15A shows an optical microscope image of PCN-248 (Example 14).
Figure 15B:
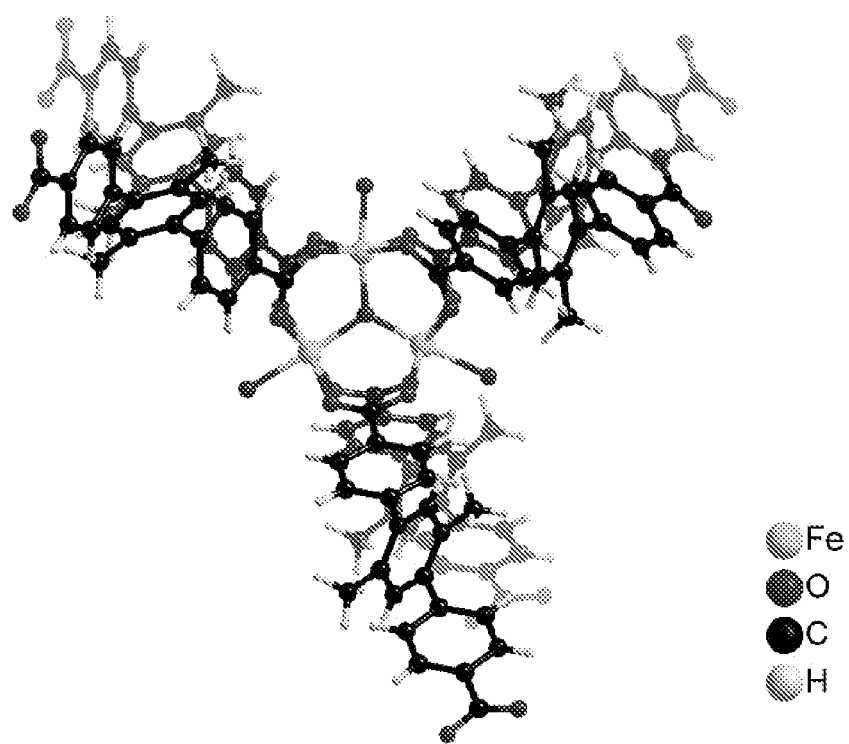
FIG. 15B illustrates a fragment structure of PCN-248 (Example 14).

An optical microscope image of PCN-248 is shown in FIG. 15a. FIG. 15b illustrates a fragment structure of PCN-248.

The crystal data and structure refinements for a single crystal of PCN-248 (CCDC 975783) are shown in Table 13.

TABLE 13

Compound PCN-248
Absolute structure parameter:

| Formula* | Fe$_3$C$_{66}$H$_{48}$O$_{16}$S | μ (mm$^{-1}$) | 0.535 |
|---|---|---|---|
| Fw | 1296.65 | F (000) | 2664 |
| Color/Shape | Red Bulk | θ$_{max}$ [deg] | 24.69 |
| Crystal system | Orthorhombic | Completeness | 98.2% |
| Space group | Pnma | Collected reflections | 81621 |
| a (Å) | 11.870(6) | Unique reflections | 7833 |
| b (Å) | 31.338(15) | Parameters | 266 |
| c (Å) | 24.763(12) | Restraints | 97 |
| α (°) | 90.00 | R$_{int}$ | 0.1452 |
| β (°) | 90.00 | R1 [I > 2σ(I)] | 0.1006 |
| γ (°) | 120.00 | wR2 [I > 2σ(I)] | 0.2197 |
| V (Å$^3$) | 9211(8) | R1 (all data) | 0.1398 |
| Z | 4 | wR2 (all data) | 0.2365 |
| T (K) | 110(2) | GOF on F$^2$ | 1.002 |
| d$_{calcd.}$ (g/cm$^3$) | 0.935 | Δρ$_{max}$/Δρ$_{min}$ [e · Å$^3$] | 2.668/−2.574 |

*Note: S atom in the formula is part of one DMSO solvent molecule, which does not affect structure model and charge balance. It is extremely hard to identify complete solvents in the structure due to its highly disorder and enormous thermal parameters. However, if we did not label this Sulfur atom, we would get an Alert A about large residual density (6.72 e · Å$^{-3}$).

Example 15(1): Synthesis of PCN-250

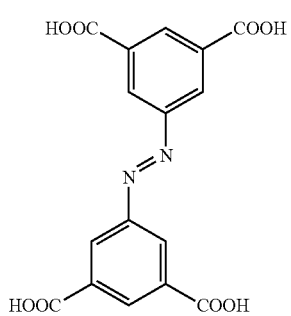 [SMILES: O=C(O)c1cc(/N=N/c2cc(C(=O)O)cc(C(=O)O)c2)cc(C(=O)O)c1]

L22 (10 mg), Fe$_2$M (Mg, Mn, Fe, Co, Ni, Cu, Zn, Ca)O(CH$_3$COO)$_6$ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Example 15(1)A: Synthesis of PCN-250 (Fe$_2$Co)

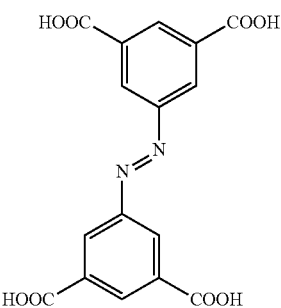 [SMILES: O=C(O)c1cc(/N=N/c2cc(C(=O)O)cc(C(=O)O)c2)cc(C(=O)O)c1]

L22 (10 mg), Fe$_2$CoO(CH$_3$COO)$_6$ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Figure 16:
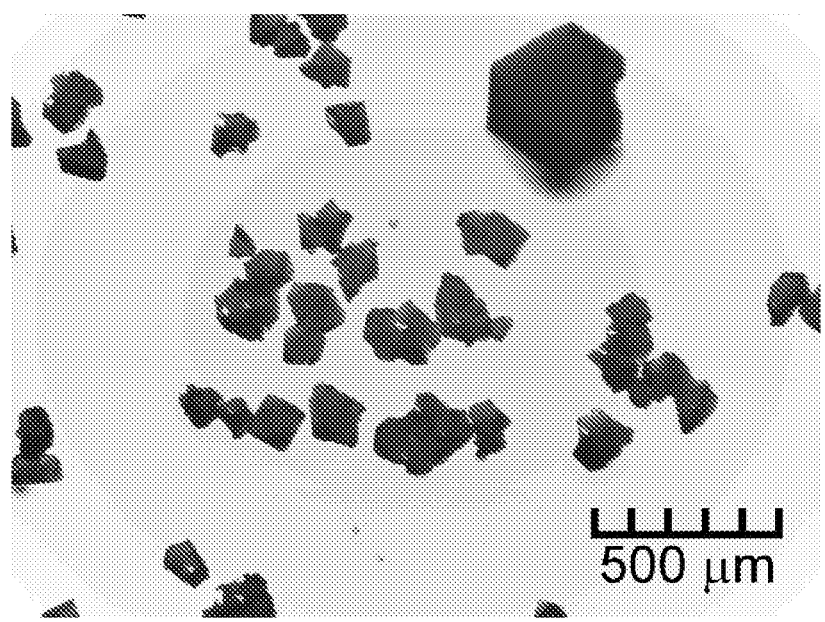
FIG. 16 shows an optical microscope image of PCN-250 ($Fe_2Co$), (Example 15(1)A).

An optical microscope image of PCN-250 (Fe$_2$Co) is shown in FIG. 16.

Example 15(1)B: Synthesis of PCN-250 (Fe$_3$)

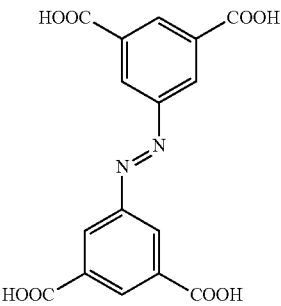

L22 (10 mg), Fe$_3$O(CH$_3$COO)$_6$ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Figure 17A:
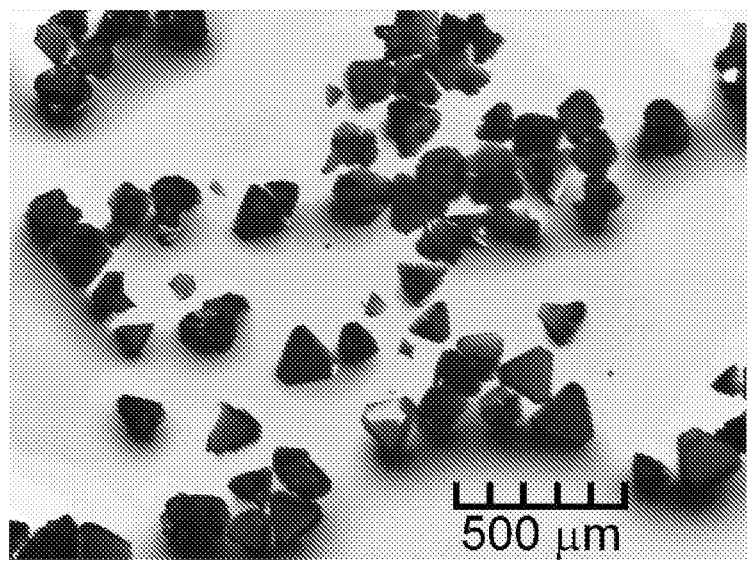
FIG. 17A shows an optical microscope image of PCN-250 ($Fe_3$), (Example 15(1)B).
Figure 17B:
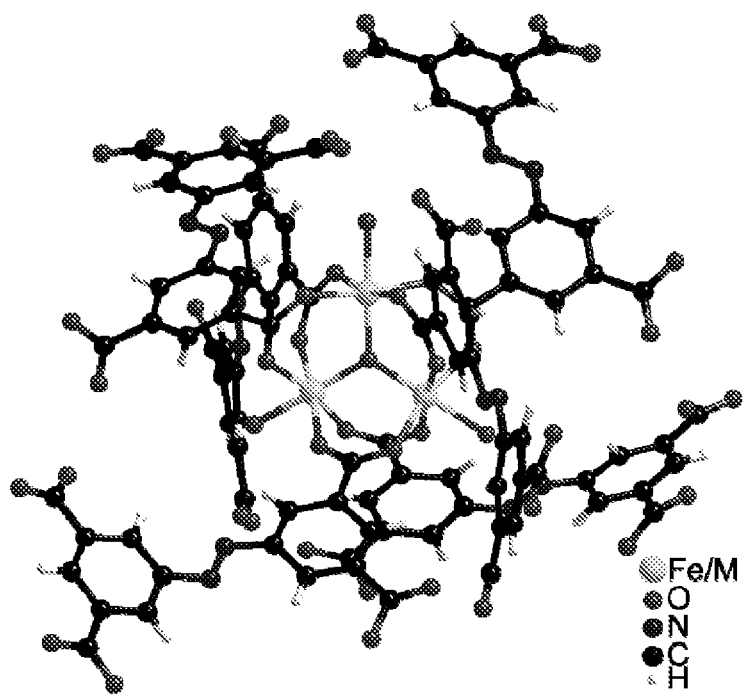
FIG. 17B illustrates a fragment structure of PCN-250 ($Fe_3$), (Example 15(1)B).

An optical microscope image of PCN-250 (Fe$_3$) is shown in FIG. 17a. FIG. 17b illustrates a fragment structure of PCN-250 (Fe$_3$).

The crystal data and structure refinements for a single crystal of PCN-250 (Fe$_3$) (CCDC 975784) are shown in Table 14.

TABLE 14

Compound PCN-250 (Fe$_3$)
Absolute structure parameter: 0.51(2)

| Formula | Fe$_6$C$_{48}$H$_{20}$N$_6$O$_{32}$ | μ (mm$^{-1}$) | 0.855 |
|---|---|---|---|
| Fw | 1527.80 | F (000) | 3048 |
| Color/Shape | Orange Triangle | θ$_{max}$ [deg] | 26.41 |
| Crystal system | Cubic | Completeness | 99.9% |
| Space group | P$\bar{4}$3n | Collected reflections | 109367 |
| a (Å) | 21.966(3) | Unique reflections | 3644 |
| b (Å) | 21.966(3) | Parameters | 143 |
| c (Å) | 21.966(3) | Restraints | 1 |
| α (°) | 90.00 | R$_{int}$ | 0.1061 |
| β (°) | 90.00 | R1 [I > 2σ(I)] | 0.0332 |
| γ (°) | 90.00 | wR2 [I > 2σ(I)] | 0.0837 |

TABLE 14-continued

| Compound PCN-250 (Fe₃) Absolute structure parameter: 0.51(2) | | | |
|---|---|---|---|
| V (Å$^3$) | 10599(2) | R1 (all data) | 0.0381 |
| Z | 4 | wR2 (all data) | 0.0856 |
| T (K) | 110(2) | GOF on F$^2$ | 1.000 |
| d$_{calcd.}$ (g/cm$^3$) | 0.957 | Δρ$_{max}$/Δρ$_{min}$ [e · Å$^3$] | 0.317/−0.214 |

Example 15(1)C: Synthesis of PCN-250 (Fe₂Mn)

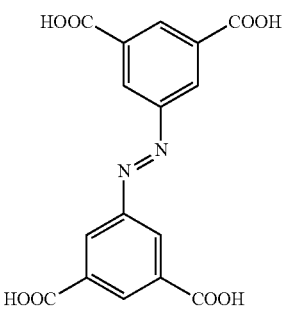 [SMILES: O=C(O)c1cc(/N=N/c2cc(C(=O)O)cc(C(=O)O)c2)cc(C(=O)O)c1]

L22 (10 mg), Fe₂MnO(CH₃COO)₆ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Figure 18:
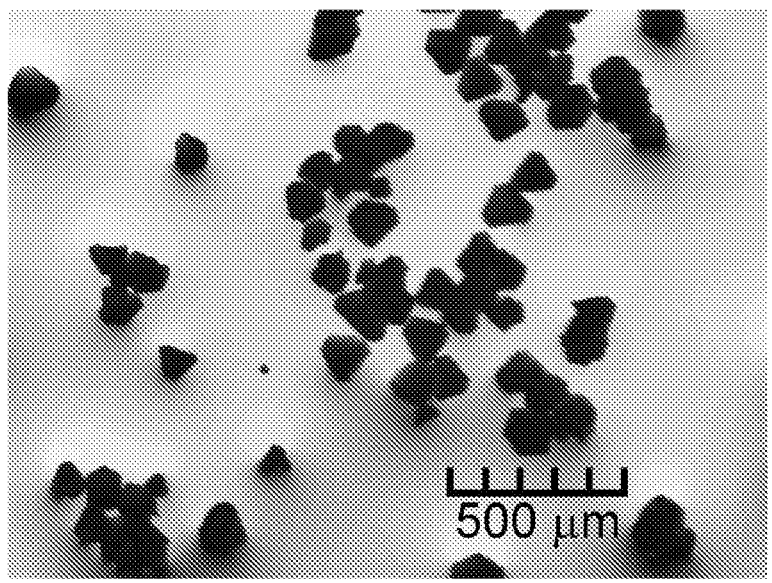
FIG. 18 shows an optical microscope image of PCN-250 ($Fe_2Mn$), (Example 15(1)C).

An optical microscope image of PCN-250 (Fe₂Mn) is shown in FIG. 18.

Example 15(1)D: Synthesis of PCN-250 (Fe₂Ni)

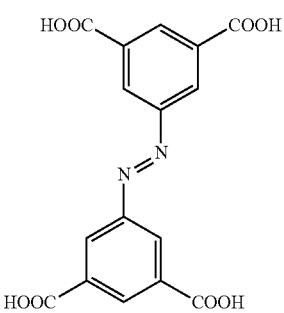

L22 (10 mg), Fe₂NiO(CH₃COO)₆ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Figure 19:
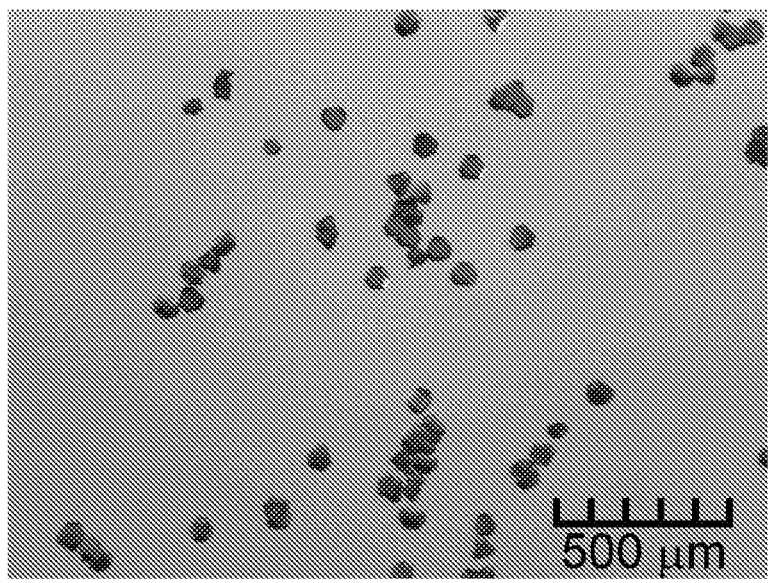
FIG. 19 shows an optical microscope image of PCN-250 ($Fe_2Ni$), (Example 15(1)D).

An optical microscope image of PCN-250 (Fe₂Ni) is shown in FIG. 19.

Example 15(1)E: Synthesis of PCN-250 (Fe₂Zn)

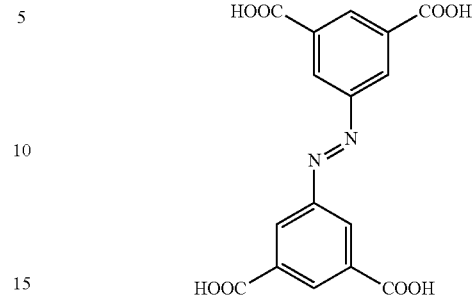

L22 (10 mg), Fe₂ZnO(CH₃COO)₆ (15 mg) and acetic acid (1 ml) in 2 mL of DMF were ultrasonically dissolved in a Pyrex vial. The mixture was heated in 140° C. oven for 12 h. After cooling down to room temperature, dark brown crystals were harvested by filtration (Yield. 80%).

Figure 20:
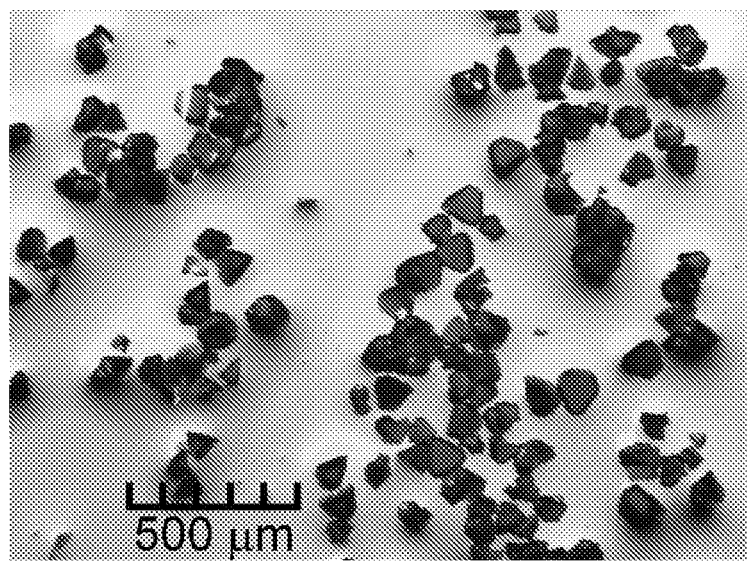
FIG. 20 shows an optical microscope image of PCN-250 ($Fe_2Zn$), (Example 15(1)E).

An optical microscope image of PCN-250 (Fe₂Zn) is shown in FIG. 20.

Example 15(2): Large-Scale Synthesis of PCN-250

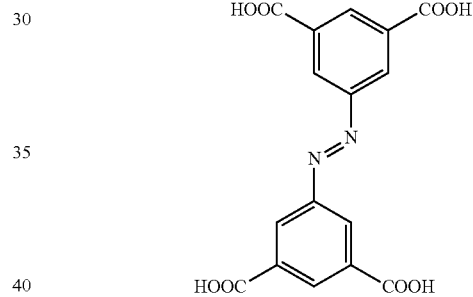

L22 (1 g), Fe₂M (Mn, Fe, Co, Ni, Cu, Zn)O(CH₃COO)₆ (1 g) and acetic acid (100 mL) in 200 mL of DMF were ultrasonically dissolved in a 500 mL Pyrex vial. The mixture was heated in 140° C. oven for 12 h. After cooling down to room temperature, dark brown crystals were harvested by filtration (Yield. 80%).

Example 16a: Synthesis of PCN-250'

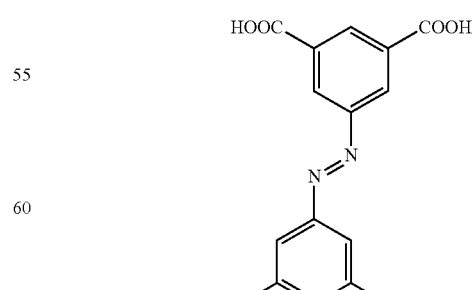

L22 (10 mg), Fe₂M(Mg, Mn, Fe, Co, Ni, Cu, Zn, Ca)O(CH₃COO)₆ (15 mg) and acetic acid (1 ml) in 2 mL of NMP were ultrasonically dissolved in a Pyrex vial. The mixture was heated in 140° C. oven for 12 h. After cooling down to room temperature, dark brown crystals were harvested by filtration (Yield. 80%).

Example 16b: Synthesis of PCN-250' (Fe₂Co)

L22 (10 mg), Fe₂CoO(CH₃COO)₆ (15 mg) and acetic acid (1 ml) in 2 mL of NMP were ultrasonically dissolved in a Pyrex vial. The mixture was heated in 140° C. oven for 12 h. After cooling down to room temperature, dark brown crystals were harvested by filtration (Yield. 80%).

Figure 21A:
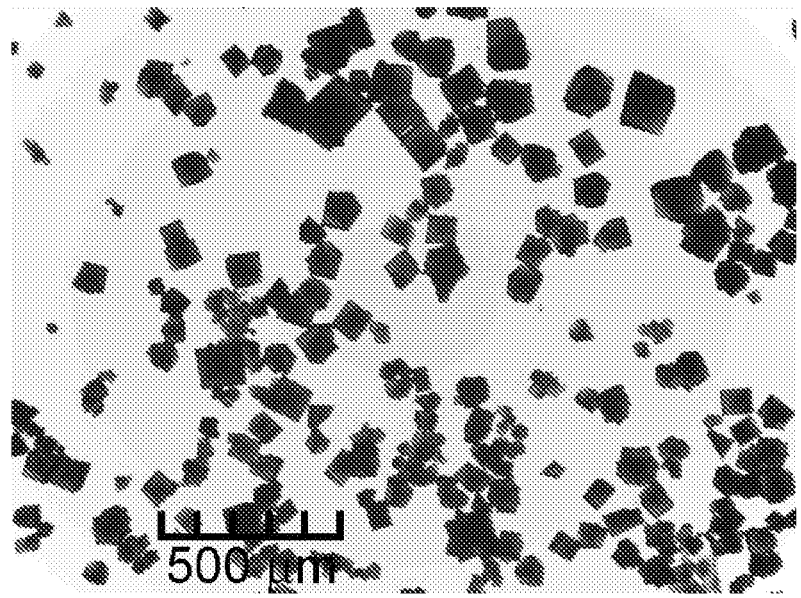
FIG. 21A shows an optical microscope image of PCN-250' ($Fe_2Co$), (Example 161)).
Figure 21B:
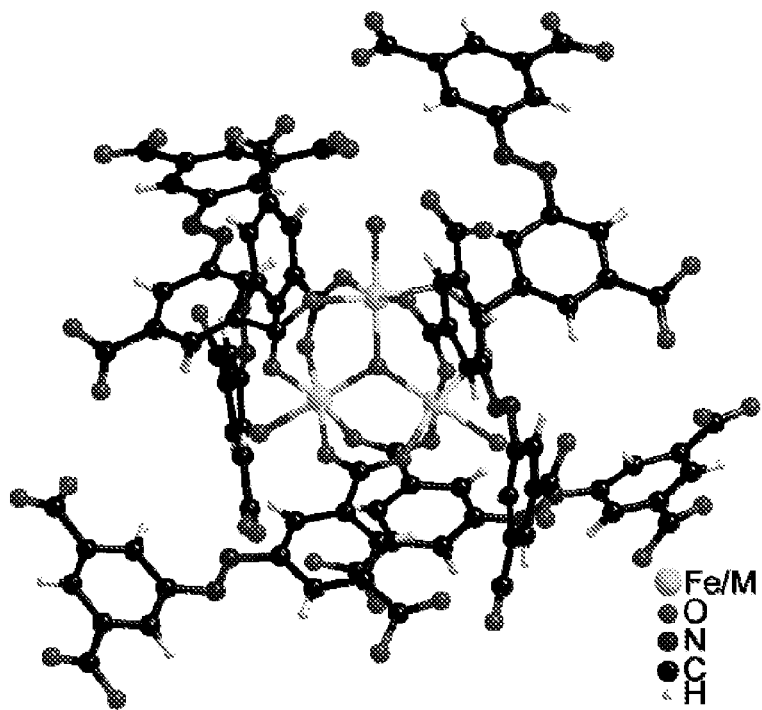
FIG. 21B illustrates a fragment structure of PCN-250' ($Fe_2Co$), (Example 161)).

An optical microscope image of PCN-250' (Example 16b) is shown in FIG. 21a. FIG. 21b illustrates a fragment structure of PCN-250' (Example 16b).

The crystal data and structure refinements for a single crystal of PCN-250' (Example 16b) are shown in Table 15.

TABLE 15

Compound PCN-250'

| Formula | Fe₄CO₂C₄₈H₁₈N₆O₃₂ | $\mu$ (mm$^{-1}$) | 0.888 |
|---|---|---|---|
| Fw | 1531.94 | F (000) | 24384 |
| Color/Shape | Red Triangle | $\theta_{max}$ [deg] | 24.77 |
| Crystal system | Cubic | Completeness | 99.6% |
| Space group | Ia$\bar{3}$ | Collected reflections | 246510 |
| a (Å) | 44.043(17) | Unique reflections | 12181 |
| b (Å) | 44.043(17) | Parameters | 233 |
| c (Å) | 44.043(17) | Restraints | 0 |
| α (°) | 90.00 | $R_{int}$ | 0.2013 |
| β (°) | 90.00 | R1 [I > 2σ(I)] | 0.1827 |
| γ (°) | 90.00 | wR2 [I > 2σ(I)] | 0.3782 |
| V (Å³) | 85433(56) | R1 (all data) | 0.2463 |
| Z | 32 | wR2 (all data) | 0.4110 |
| T (K) | 110(2) | GOF on F² | 1.080 |
| $d_{calcd.}$ (g/cm³) | 0.953 | $\Delta\rho_{max}/\Delta\rho_{min}$ [e · Å³] | 1.933/−1.185 |

Example 17: Synthesis of PCN-251

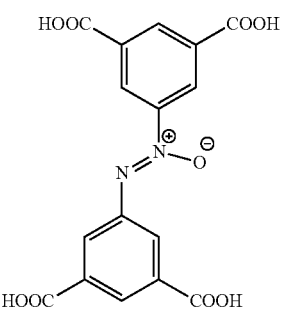 [SMILES: O=C(O)c1cc(/N=[N+](\[O-])c2cc(C(=O)O)cc(C(=O)O)c2)cc(C(=O)O)c1]

L22 (10 mg), Fe₂M (Mg, Mn, Fe, Co, Ni, Cu, Zn, Ca) O(CH₃COO)₆ (15 mg) and acetic acid (1 ml) in 2 mL of NMP were ultrasonically dissolved in a Pyrex vial. The mixture was heated in 140° C. oven for 12 h. After cooling down to room temperature, dark brown crystals were harvested by filtration (Yield. 80%).

Example 18a: Synthesis of PCN-252

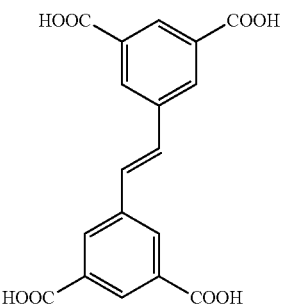

L23 (10 mg), Fe₂M (Mg, Mn, Fe, Co, Ni, Cu, Zn, Ca) O(CH₃COO)₆ (10 mg) and acetic acid (0.8 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Example 18b: Synthesis of PCN-252 (Fe₂Co)

L23 (10 mg), Fe₂CoO(CH₃COO)₆ (10 mg) and acetic acid (0.8 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 22A:
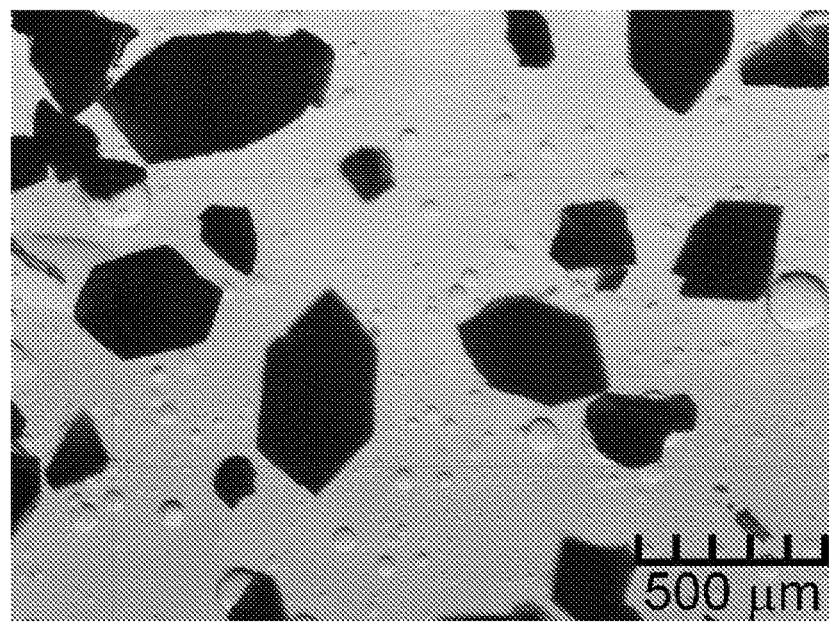
FIG. 22A shows an optical microscope image of PCN-252 ($Fe_2Co$), (Example 181)).
Figure 22B:
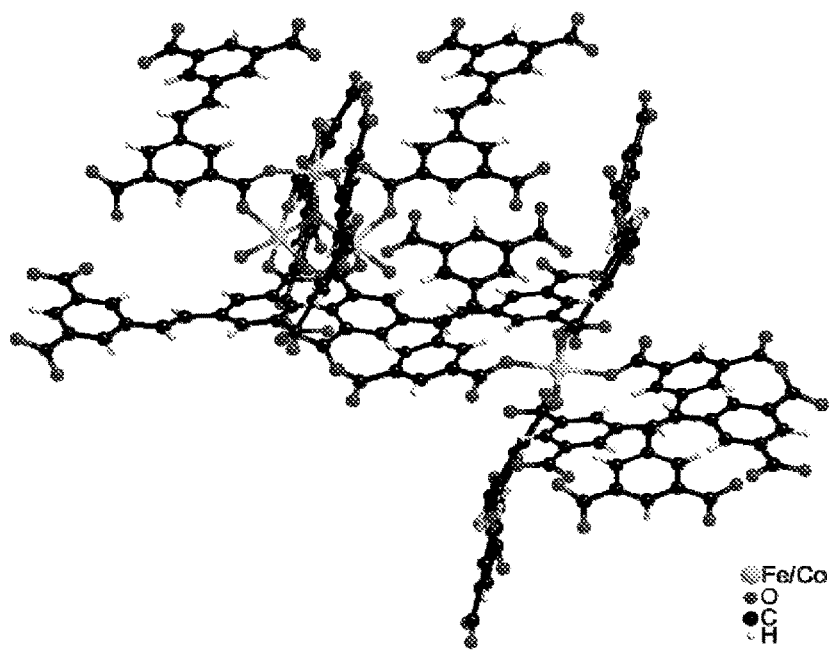
FIG. 22B illustrates a fragment structure of PCN-252 ($Fe_2Co$), (Example 181)).

An optical microscope image of PCN-252 (Example 18b) is shown in FIG. 22a. FIG. 22b illustrates a fragment structure of PCN-252 (Example 18b).

The crystal data and structure refinements for a single crystal of PCN-252 (Example 18b) are shown in Table 16.

TABLE 16

Compound PCN-252

| Formula | Fe₇Co₃C₁₀₈H₅₁O₆₀ | $\mu$ (mm$^{-1}$) | 0.834 |
|---|---|---|---|
| Fw | 2876.23 | F (000) | 8652 |
| Color/Shape | Brown Hexagon | $\theta_{max}$ [deg] | 26.40 |
| Crystal system | Hexagonal | Completeness | 99.9% |
| Space group | R$\bar{3}$c | Collected reflections | 100751 |
| a (Å) | 32.839(8) | Unique reflections | 6506 |
| b (Å) | 32.839(8) | Parameters | 262 |
| c (Å) | 30.571(7) | Restraints | 0 |
| α (°) | 90.00 | $R_{int}$ | 0.0539 |
| β (°) | 90.00 | R1 [I > 2σ(I)] | 0.0580 |
| γ (°) | 120.00 | wR2 [I > 2σ(I)] | 0.1410 |
| V (Å³) | 28551(12) | R1 (all data) | 0.0675 |
| Z | 6 | wR2 (all data) | 0.1454 |
| T (K) | 110(2) | GOF on F² | 1.007 |
| $d_{calcd.}$ (g/cm³) | 1.004 | $\Delta\rho_{max}/\Delta\rho_{min}$ [e · Å³] | 2.364/−1.752 |

Example 19a: Synthesis of PCN-253

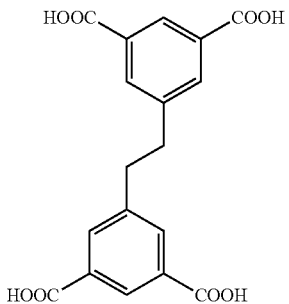

L24 (10 mg), Fe$_2$M (Mg, Mn, Fe, Co, Ni, Cu, Zn, Ca) O(CH$_3$COO)$_6$ (15 mg) and acetic acid (1 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Example 19b: Synthesis of PCN-253 (Fe$_2$Co)

L24 (10 mg), Fe$_2$CoO(CH$_3$COO)$_6$ (15 mg) and acetic acid (1 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 23A:
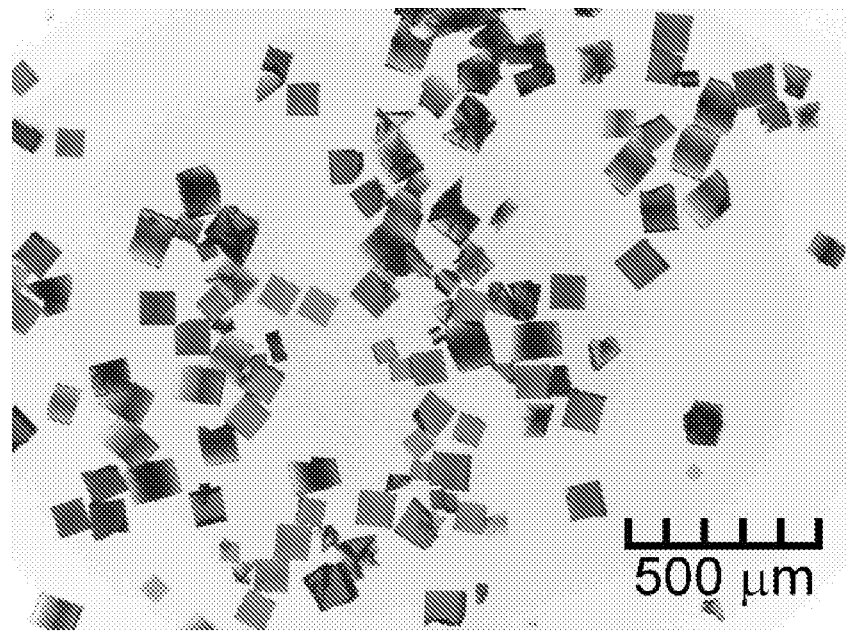
FIG. 23A shows an optical microscope image of PCN-253 ($Fe_2Co$), (Example 191)).
Figure 23B:
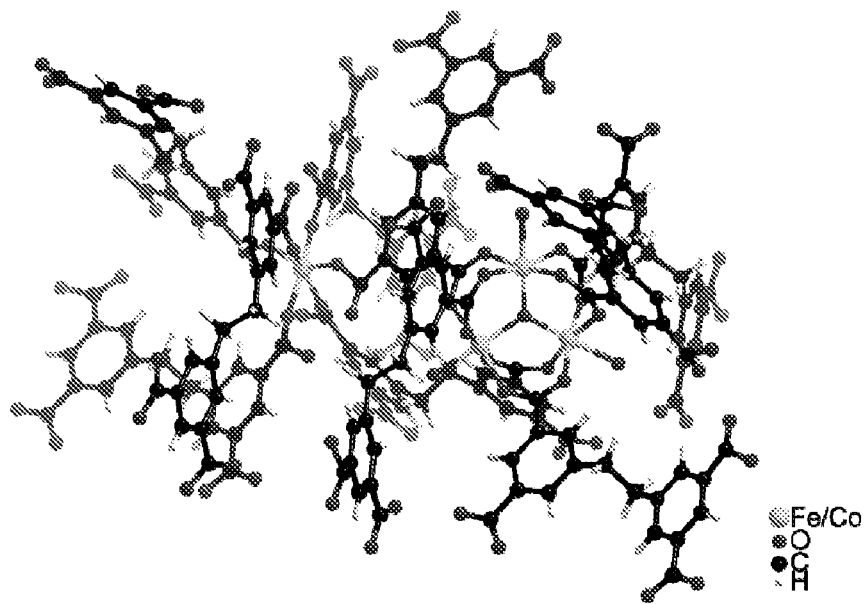
FIG. 23B illustrates a fragment structure of PCN-253 ($Fe_2Co$), (Example 191)).

An optical microscope image of PCN-253 (Example 19b) is shown in FIG. 23a. FIG. 23b illustrates a fragment structure of PCN-253 (Example 19b).

The crystal data and structure refinements for a single crystal of PCN-253 (Example 19b) are shown in Table 17.

TABLE 17

| Compound PCN-253 | | | |
|---|---|---|---|
| Formula | Fe$_7$Co$_3$C$_{108}$H$_{63}$O$_{60}$ | μ (mm$^{-1}$) | 0.813 |
| Fw | 2888.32 | F (000) | 8724 |
| Color/Shape | Orange Cube | θ$_{max}$ [deg] | 24.65 |
| Crystal system | Hexagonal | Completeness | 99.1% |
| Space group | R$\bar{3}$c | Collected reflections | 63421 |
| a (Å) | 32.00(6) | Unique reflections | 5474 |
| b (Å) | 32.00(6) | Parameters | 272 |
| c (Å) | 33.04(6) | Restraints | 60 |
| α (°) | 90.00 | R$_{int}$ | 0.2034 |
| β (°) | 90.00 | R1 [I > 2σ(I)] | 0.0690 |
| γ (°) | 120.00 | wR2 [I > 2σ(I)] | 0.1684 |
| V (Å$^3$) | 29303(89) | R1 (all data) | 0.1511 |
| Z | 6 | wR2 (all data) | 0.1896 |
| T (K) | 110(2) | GOF on F$^2$ | 1.008 |
| d$_{calcd.}$ (g/cm$^3$) | 0.982 | Δρ$_{max}$/Δρ$_{min}$ [e · Å$^3$] | 0.710/−0.543 |

Example 20a: Synthesis of PCN-254

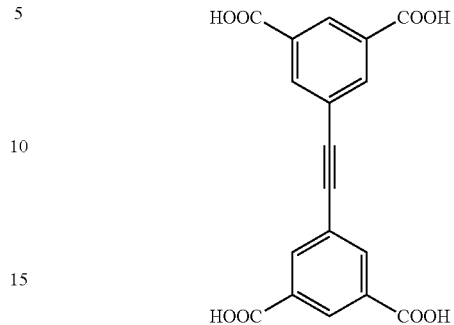

L25 (10 mg), Fe$_2$M (Mg, Mn, Fe, Co, Ni, Cu, Zn, Ca) O(CH$_3$COO)$_6$ (15 mg) and acetic acid (1 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Example 20b: Synthesis of PCN-254 (Fe$_2$Co)

L25 (10 mg), Fe$_2$CoO(CH$_3$COO)$_6$ (15 mg) and acetic acid (1 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 24A:
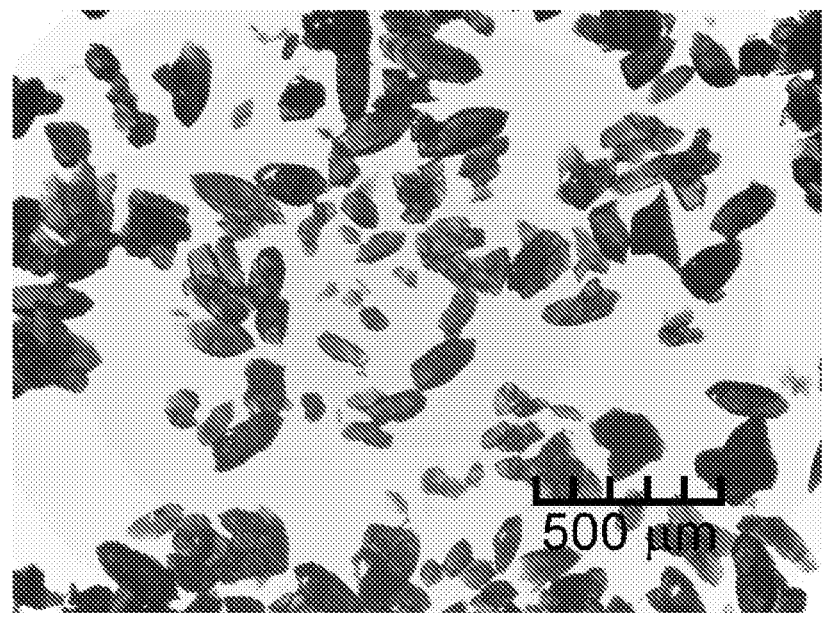
FIG. 24A shows an optical microscope image of PCN-254 ($Fe_2Co$), (Example 201)).
Figure 24B:
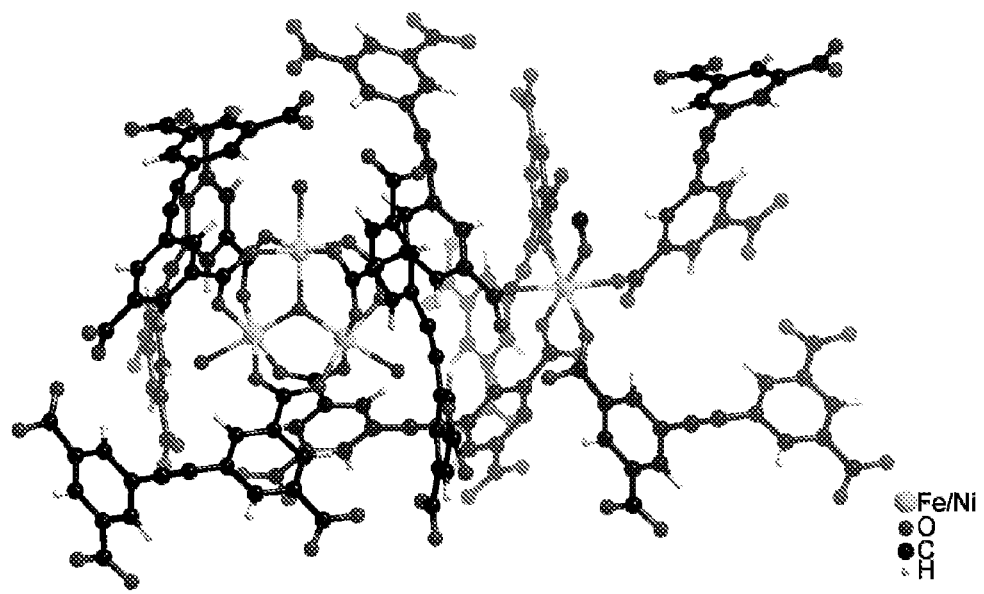
FIG. 24B illustrates a fragment structure of PCN-254 ($Fe_2Co$), (Example 201)).

An optical microscope image of PCN-254 (Example 20b) is shown in FIG. 24a. FIG. 24b illustrates a fragment structure of PCN-254 (Example 20b).

The crystal data and structure refinements for a single crystal of PCN-254 (Example 20b) are shown in Table 18.

TABLE 18

| Compound PCN-254 | | | |
|---|---|---|---|
| Formula | Fe$_7$Ni$_3$C$_{108}$H$_{39}$O$_{60}$ | μ (mm$^{-1}$) | 0.820 |
| Fw | 2863.47 | F (000) | 8598 |
| Color/Shape | Red Bulk | θ$_{max}$ [deg] | 24.43 |
| Crystal system | Hexagonal | Completeness | 99.8% |
| Space group | R$\bar{3}$c | Collected reflections | 67399 |
| a (Å) | 32.356(7) | Unique reflections | 5557 |
| b (Å) | 32.356(7) | Parameters | 268 |
| c (Å) | 33.363(7) | Restraints | 0 |
| α (°) | 90.00 | R$_{int}$ | 0.1530 |
| β (°) | 90.00 | R1 [I > 2σ(I)] | 0.0621 |
| γ (°) | 120.00 | wR2 [I > 2σ(I)] | 0.1559 |
| V (Å$^3$) | 30248(11) | R1 (all data) | 0.1000 |
| Z | 6 | wR2 (all data) | 0.1674 |
| T (K) | 110(2) | GOF on F$^2$ | 1.001 |
| d$_{calcd.}$ (g/cm$^3$) | 0.943 | Δρ$_{max}$/Δρ$_{min}$ [e · Å$^3$] | 1.905/−0.491 |

Example 21: Synthesis of PCN-255

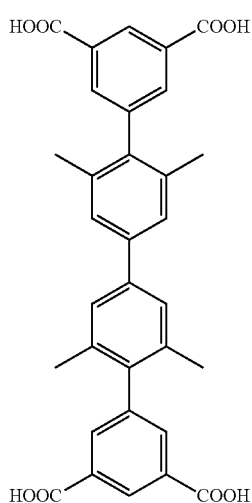

L26 (10 mg), Fe$_2$CoO(CH$_3$COO)$_6$ (15 mg) and acetic acid (0.5 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 25A:
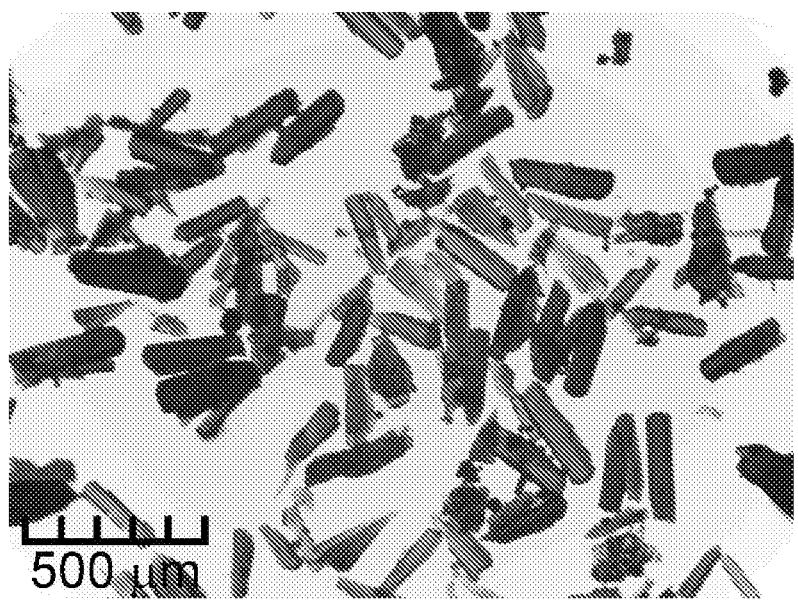
FIG. 25A shows an optical microscope image of PCN-255 (Example 21).
Figure 25B:
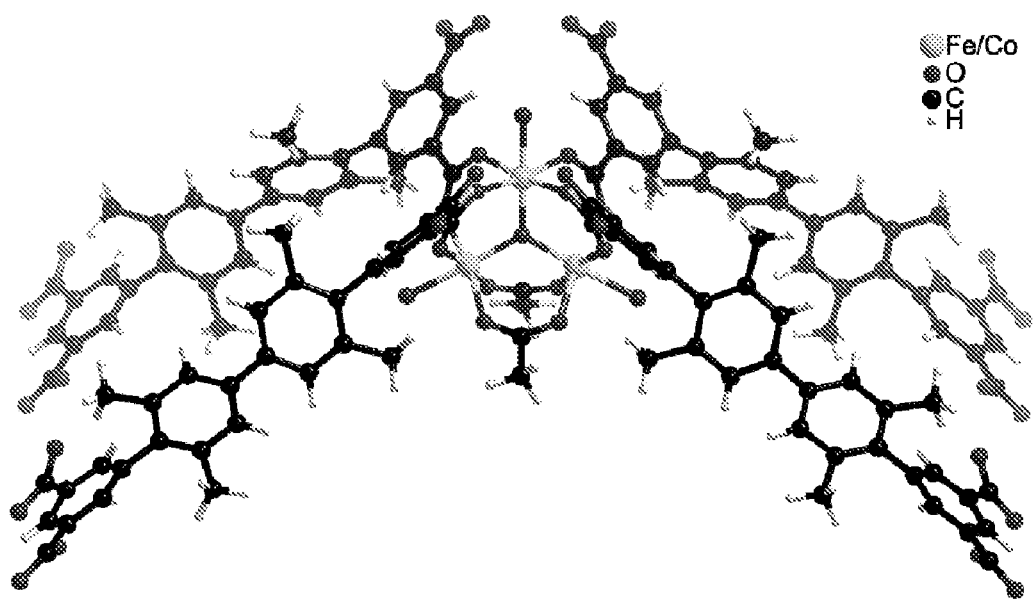
FIG. 25B illustrates a fragment structure of PCN-255 (Example 21).

An optical microscope image of PCN-255 is shown in FIG. 25a. FIG. 25b illustrates a fragment structure of PCN-255.

The crystal data and structure refinements for a single crystal of PCN-255 (CCDC 975789) are shown in Table 19.

TABLE 19

| Compound PCN-255 | | | |
|---|---|---|---|
| Formula | Fe$_2$CoC$_{36}$H$_{28}$O$_{16}$ | μ (mm$^{-1}$) | 0.748 |
| Fw | 887.21 | F (000) | 5412 |
| Color/Shape | Orange Rod | θ$_{max}$ [deg] | 24.64 |
| Crystal system | Hexagonal | Completeness | 99.3% |
| Space group | P6/mcc | Collected reflections | 167141 |
| a (Å) | 25.898(12) | Unique reflections | 5495 |
| b (Å) | 25.898(12) | Parameters | 236 |
| c (Å) | 32.995(19) | Restraints | 46 |
| α (°) | 90.00 | R$_{int}$ | 0.2159 |
| β (°) | 90.00 | R1 [I > 2σ(I)] | 0.1010 |
| γ (°) | 120.00 | wR2 [I > 2σ(I)] | 0.1890 |
| V (Å$^3$) | 19165(17) | R1 (all data) | 0.1795 |
| Z | 12 | wR2 (all data) | 0.2258 |
| T (K) | 110(2) | GOF on F$^2$ | 1.008 |
| d$_{calcd.}$ (g/cm$^3$) | 0.922 | Δρ$_{max}$/Δρ$_{min}$ [e · Å$^3$] | 1.503/-0.769 |

Example 22: Synthesis of PCN-256

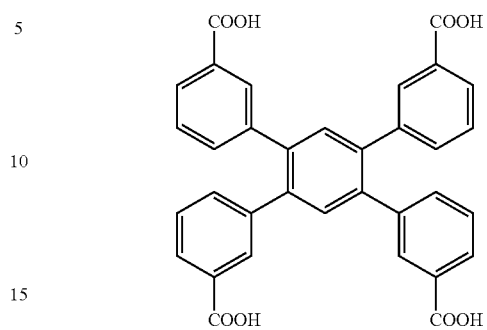

L27 (10 mg), Fe$_2$CoO(CH$_3$COO)$_6$ (15 mg) and acetic acid (0.4 ml) in 2 mL of NMP and 0.1 mL n-pentanol were ultrasonically dissolved in a Pyrex vial. The mixture was heated in 150° C. oven for 12 h. After cooling down to room temperature, dark brown crystals were harvested by filtration (Yield. 80%).

Figure 26A:
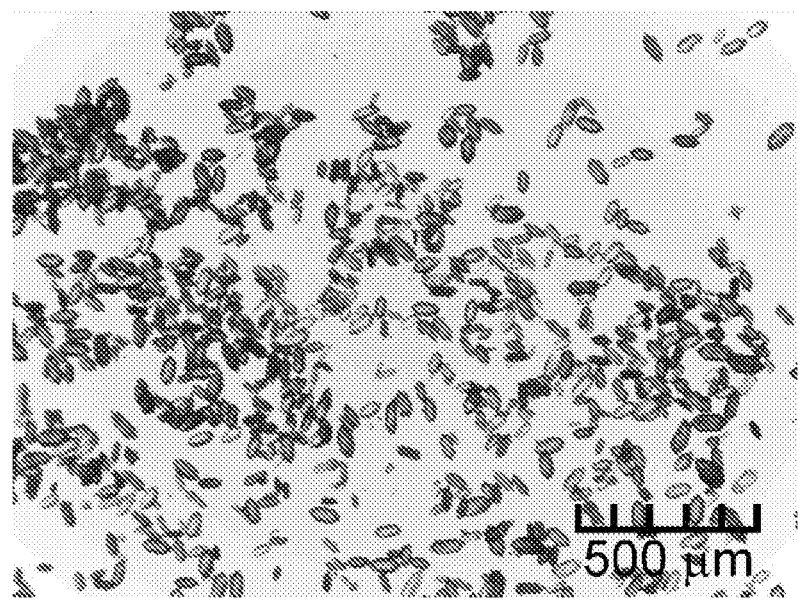
FIG. 26A shows an optical microscope image of PCN-256 (Example 22).
Figure 26B:
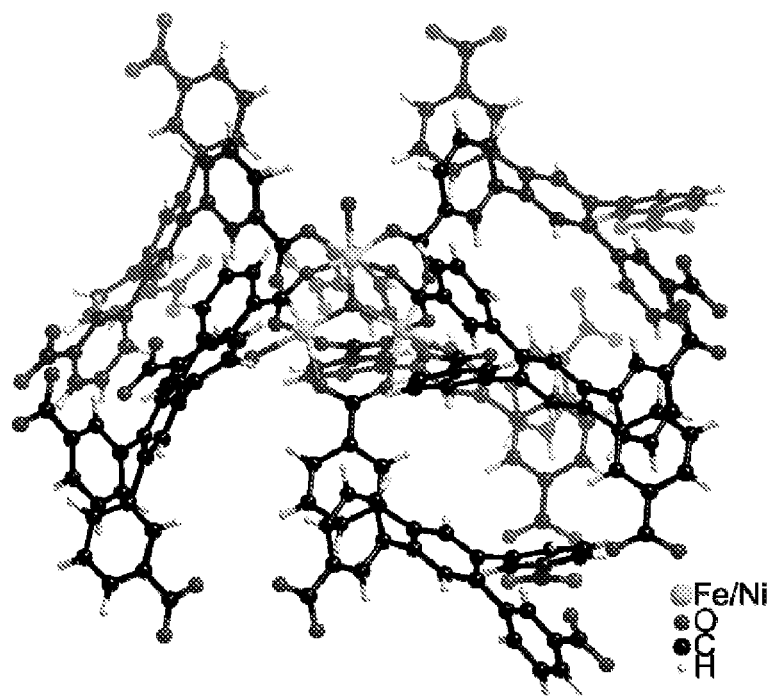
FIG. 26B illustrates a fragment structure of PCN-256 (Example 22).

An optical microscope image of PCN-256 is shown in FIG. 26a. FIG. 26b illustrates a fragment structure of PCN-256.

The crystal data and structure refinements for a single crystal of PCN-256 (CCDC 975790) are shown in Table 20.

TABLE 20

| Compound PCN-256 | | | |
|---|---|---|---|
| Formula | Fe$_6$C$_{102}$H$_{54}$O$_{32}$ | μ (mm$^{-1}$) | 0.569 |
| Fw | 2126.55 | F (000) | 2156 |
| Color/Shape | Orange Hexagon | θ$_{max}$ [deg] | 24.58 |
| Crystal system | Orthorhombic | Completeness | 99.6% |
| Space group | Cmma | Collected reflections | 36653 |
| a (Å) | 15.290(18) | Unique reflections | 3654 |
| b (Å) | 24.48(3) | Parameters | 169 |
| c (Å) | 21.79(3) | Restraints | 18 |
| α (°) | 90.00 | R$_{int}$ | 0.1400 |
| β (°) | 90.00 | R1 [I > 2σ(I)] | 0.0862 |
| γ (°) | 90.00 | wR2 [I > 2σ(I)] | 0.1925 |
| V (Å$^3$) | 8156(17) | R1 (all data) | 0.1606 |
| Z | 2 | wR2 (all data) | 0.2139 |
| T (K) | 110(2) | GOF on F$^2$ | 1.002 |
| d$_{calcd.}$ (g/cm$^3$) | 0.866 | Δρ$_{max}$/Δρ$_{min}$ [e · Å$^3$] | 0.550/-0.446 |

Example 23: Synthesis of PCN-257

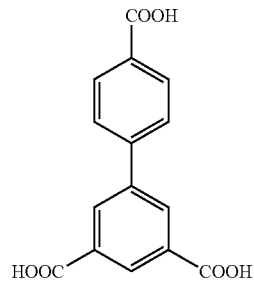 [SMILES: O=C(O)c1ccc(-c2cc(C(=O)O)cc(C(=O)O)c2)cc1]

L21 (10 mg), Fe$_3$O(CH$_3$COO)$_6$OH (15 mg) and acetic acid (0.4 ml) in 2 mL of NMP and 0.1 mL n-pentanol were ultrasonically dissolved in a Pyrex vial. The mixture was heated in 150° C. oven for 12 h. After cooling down to room temperature, dark brown crystals were harvested by filtration (Yield. 80%).

Figure 27A:
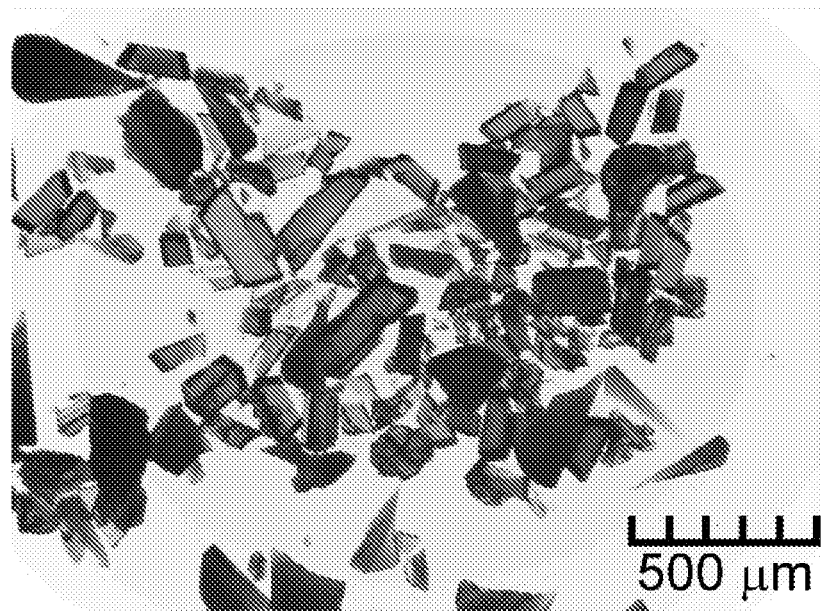
FIG. 27A shows an optical microscope image of PCN-257 (Example 23).
Figure 27B:
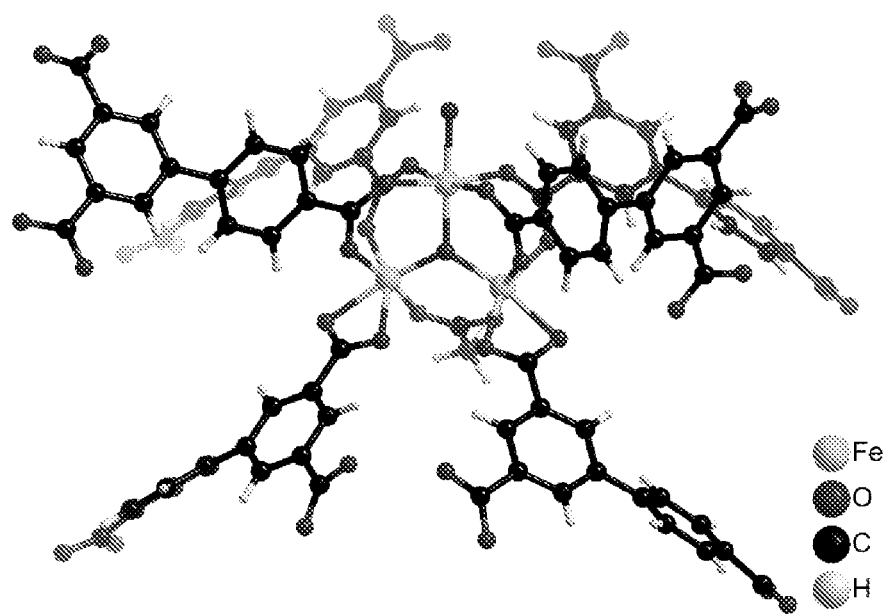
FIG. 27B illustrates a fragment structure of PCN-257 (Example 23).

An optical microscope image of PCN-257 is shown in FIG. 27a. FIG. 27b illustrates a fragment structure of PCN-257.

The crystal data and structure refinements for a single crystal of PCN-257 (CCDC 975791) are shown in Table 21.

TABLE 21

| Compound PCN-257 Absolute structure parameter: 0.036(14) | | | |
|---|---|---|---|
| Formula | $Fe_3C_{32}H_{17}O_{16}$ | μ (mm$^{-1}$) | 0.635 |
| Fw | 825.01 | F (000) | 830 |
| Color/Shape | Red Column | $\theta_{max}$ [deg] | 24.81 |
| Crystal system | Orthorhombic | Completeness | 99.7% |
| Space group | Pmn2$_1$ | Collected reflections | 33286 |
| a (Å) | 23.570(3) | Unique reflections | 6342 |
| b (Å) | 9.8918(11) | Parameters | 240 |
| c (Å) | 15.3668(18) | Restraints | 31 |
| α (°) | 90.00 | $R_{int}$ | 0.0636 |
| β (°) | 90.00 | R1 [I > 2σ(I)] | 0.0356 |
| γ (°) | 90.00 | wR2 [I > 2σ(I)] | 0.0715 |
| V (Å$^3$) | 3582.8(7) | R1 (all data) | 0.0422 |
| Z | 2 | wR2 (all data) | 0.0729 |
| T (K) | 110(2) | GOF on F$^2$ | 1.003 |
| $d_{calcd.}$ (g/cm$^3$) | 0.765 | $\Delta\rho_{max}/\Delta\rho_{min}$ [e · Å$^3$] | 0.350/-0.374 |

Example 24: Synthesis of PCN-260

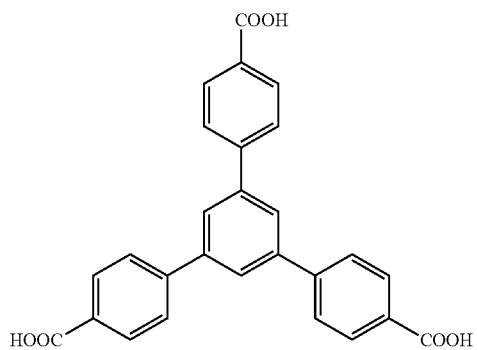 [SMILES: O=C(O)c1ccc(-c2cc(-c3ccc(C(=O)O)cc3)cc(-c3ccc(C(=O)O)cc3)c2)cc1]

L15 (15 mg), Fe$_2$CoO(CH$_3$COO)$_6$ (5 mg) and acetic acid (0.25 ml) in 2 mL of NMP were ultrasonically dissolved in a Pyrex vial. The mixture was heated in 150° C. oven for 24 h. After cooling down to room temperature, dark brown crystals were harvested by filtration (Yield. 80%).

Figure 28A:
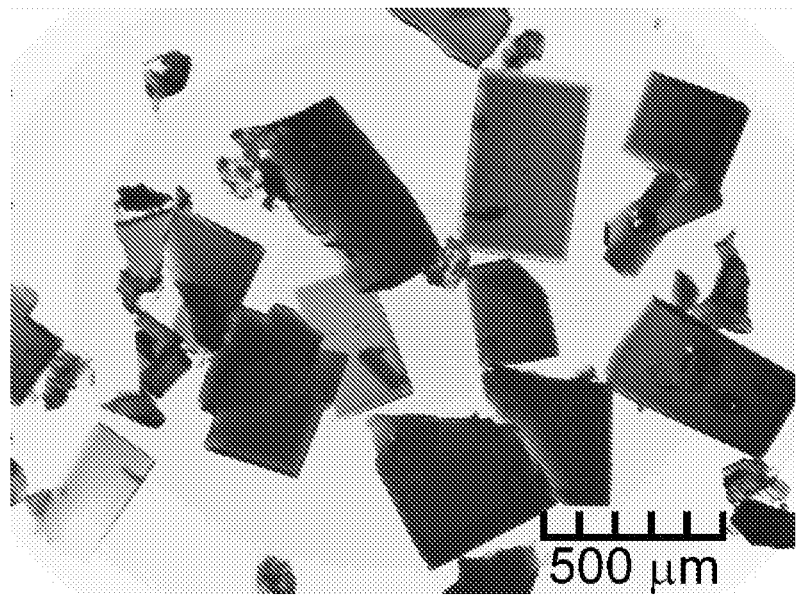
FIG. 28A shows an optical microscope image of PCN-260 (Example 24).
Figure 28B:
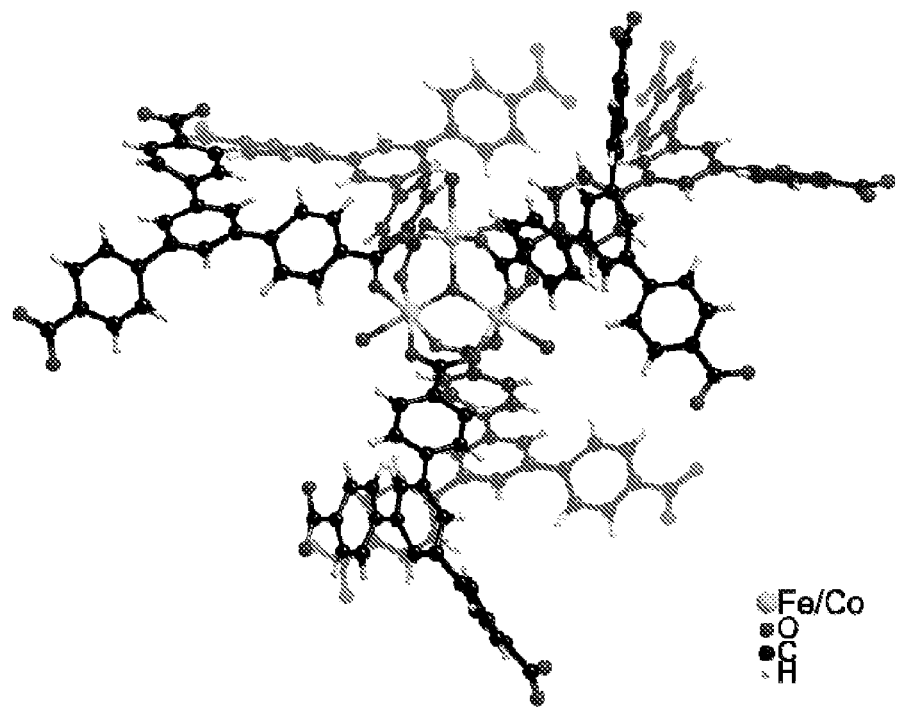
FIG. 28B illustrates a fragment structure of PCN-260 (Example 24).

An optical microscope image of PCN-260 is shown in FIG. 28a. FIG. 28b illustrates a fragment structure of PCN-260.

The crystal data and structure refinements for a single crystal of PCN-260 (CCDC 975820) are shown in Table 22.

TABLE 22

| Compound PCN-260 Absolute structure parameter: 0.453(11) | | | |
|---|---|---|---|
| Formula | $Fe_2CoC_{54}H_{30}O_{16}$ | μ (mm$^{-1}$) | 0.297 |
| Fw | 1105.41 | F (000) | 4488 |
| Color/Shape | Orange Rectangle | $\theta_{max}$ [deg] | 24.78 |
| Crystal system | Orthorhombic | Completeness | 99.8% |
| Space group | Pca2$_1$ | Collected reflections | 303240 |
| a (Å) | 36.155(4) | Unique reflections | 56026 |

TABLE 22-continued

| Compound PCN-260 Absolute structure parameter: 0.453(11) | | | |
|---|---|---|---|
| b (Å) | 18.566(2) | Parameters | 830 |
| c (Å) | 48.725(6) | Restraints | 1 |
| α (°) | 90.00 | $R_{int}$ | 0.0733 |
| β (°) | 90.00 | R1 [I > 2σ(I)] | 0.0630 |
| γ (°) | 90.00 | wR2 [I > 2σ(I)] | 0.1264 |
| V (Å$^3$) | 32707(6) | R1 (all data) | 0.0914 |
| Z | 8 | wR2 (all data) | 0.1339 |
| T (K) | 110(2) | GOF on F$^2$ | 1.000 |
| $d_{calcd.}$ (g/cm$^3$) | 0.449 | $\Delta\rho_{max}/\Delta\rho_{min}$ [e · Å$^3$] | 0.793/-0.688 |

Example 25: Synthesis of PCN-261-NH$_2$

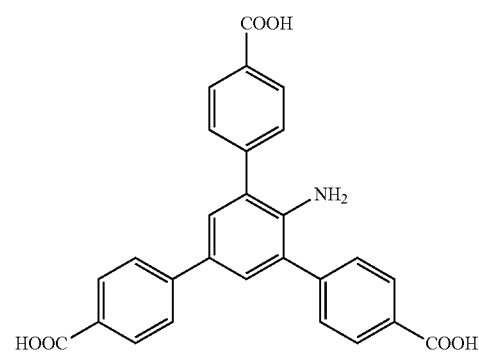 [SMILES: Nc1c(-c2ccc(C(=O)O)cc2)cc(-c2ccc(C(=O)O)cc2)cc1-c1ccc(C(=O)O)cc1]

L16 (15 mg), Fe$_2$CoO(CH$_3$COO)$_6$ (15 mg) and acetic acid (0.22 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 29A:
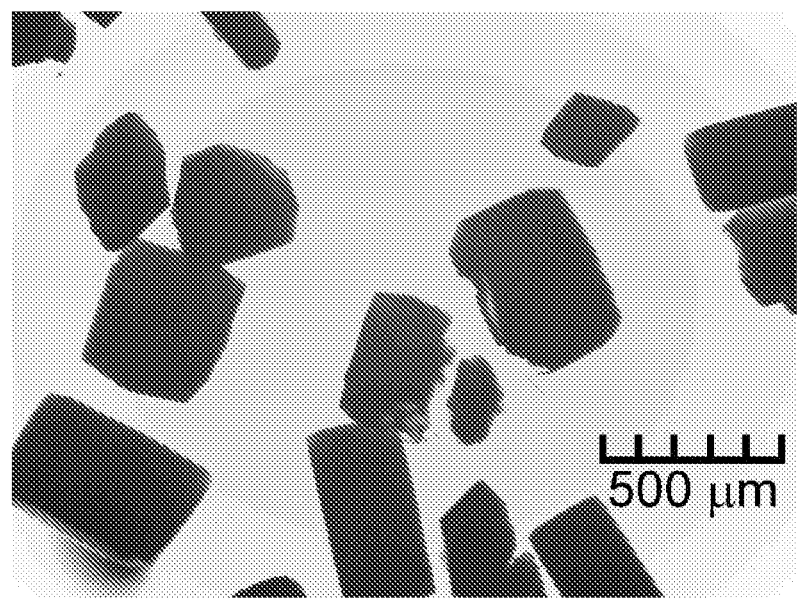
FIG. 29A shows an optical microscope image of PCN-261-$NH_2$ (Example 25).
Figure 29B:
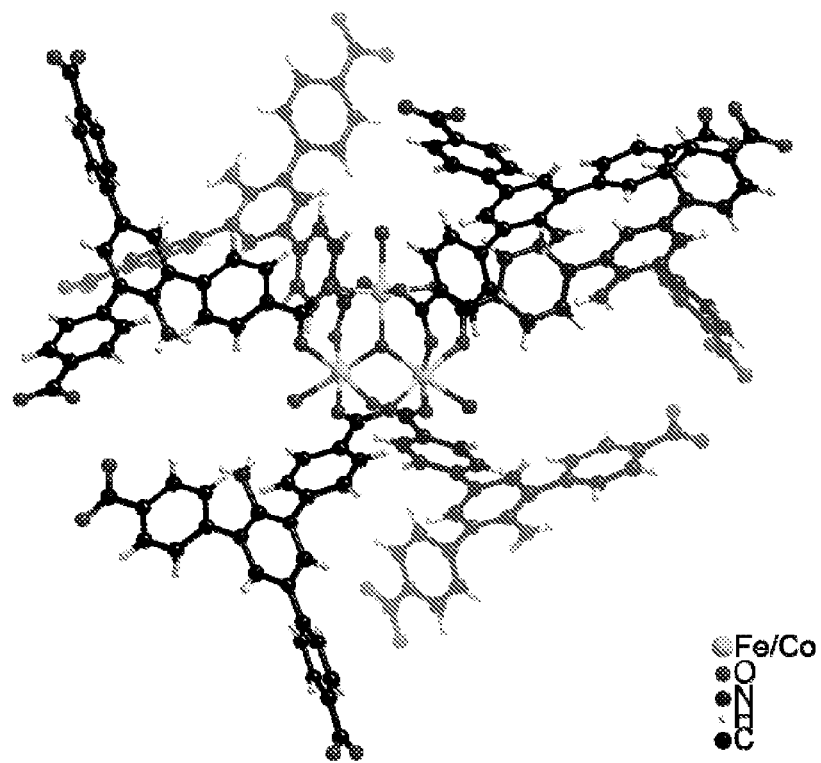
FIG. 29B illustrates a fragment structure of PCN-261-$NH_2$ (Example 25).

An optical microscope image of PCN-261-NH$_2$ is shown in FIG. 29a. FIG. 29b illustrates a fragment structure of PCN-261-NH$_2$.

The crystal data and structure refinements for a single crystal of PCN-261-NH$_2$ (CCDC 975821) are shown in Table 23.

TABLE 23

| Compound PCN-261 | | | |
|---|---|---|---|
| Formula | Fe$_2$ Co C$_{54}$ H$_{32}$ N$_2$ O$_{16}$ | μ(mm$^{-1}$) | 0.271 |
| Fw | 1135.45 | F(000) | 2308 |
| Color/Shape | Red Rectangle | $\theta_{max}$ [deg] | 26.00 |
| Crystal system | Monoclinic | Completeness | 99.8% |
| Space group | P2$_1$/c | Collected reflections | 141021 |
| a (Å) | 27.005 (4) | Unique reflections | 35362 |
| b (Å) | 18.564 (3) | Parameters | 553 |
| c (Å) | 36.389 (5) | Restraints | 0 |
| α (°) | 90.00 | $R_{int}$ | 0.0951 |
| β (°) | 98.848 (2) | R1 [I > 2σ(I)] | 0.0583 |
| γ (°) | 90.00 | wR2 [I > 2σ(I)] | 0.1172 |
| V (Å$^3$) | 18025 (5) | R1 (all data) | 0.1533 |
| Z | 4 | wR2 (all data) | 0.1259 |
| T (K) | 110 (2) | GOF on F$^2$ | 1.007 |
| $d_{calcd.}$ (g/cm$^3$) | 0.418 | $\Delta\rho_{max}/\Delta\rho_{min}$ [e · Å$^3$] | 0.494/-0.421 |

Example 26: Synthesis of PCN-261-CH₃

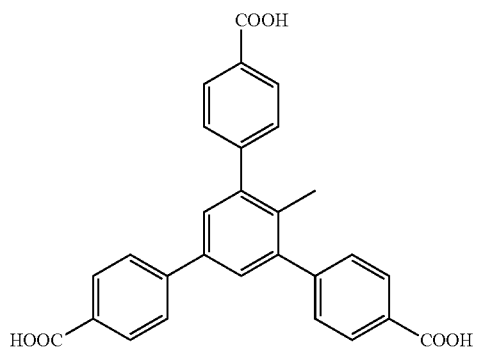 [SMILES: Cc1c(-c2ccc(C(=O)O)cc2)cc(-c2ccc(C(=O)O)cc2)cc1-c1ccc(C(=O)O)cc1]

L17 (15 mg), Fe₂CoO(CH₃COO)₆ (15 mg) and acetic acid (0.2 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 30:
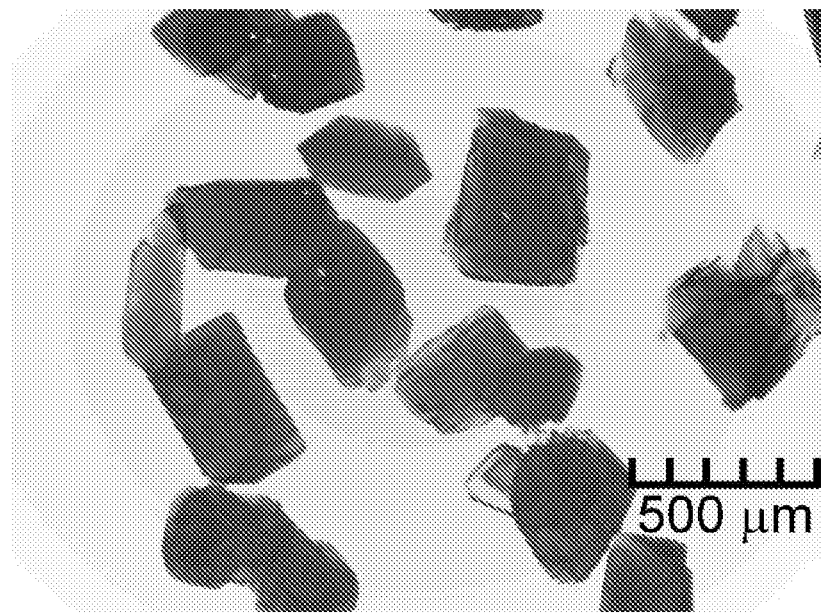

An optical microscope image of PCN-261-CH₃ is shown in FIG. 30. A single crystal of PCN-261-CH₃ is isostructural to PCN-261-NH₂.

Example 27: Synthesis of PCN-261-Chiral

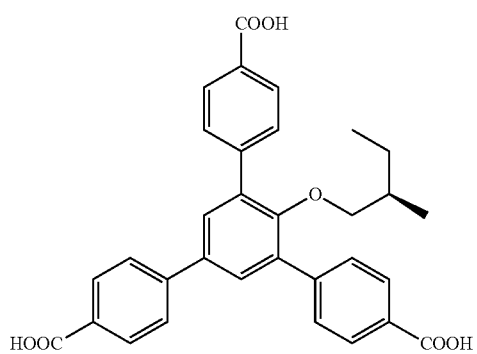 [SMILES: CC[C@@H](C)COc1c(-c2ccc(C(=O)O)cc2)cc(-c2ccc(C(=O)O)cc2)cc1-c1ccc(C(=O)O)cc1]

L19 (15 mg), Fe₂CoO(CH₃COO)₆ (15 mg) and acetic acid (0.2 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 31:
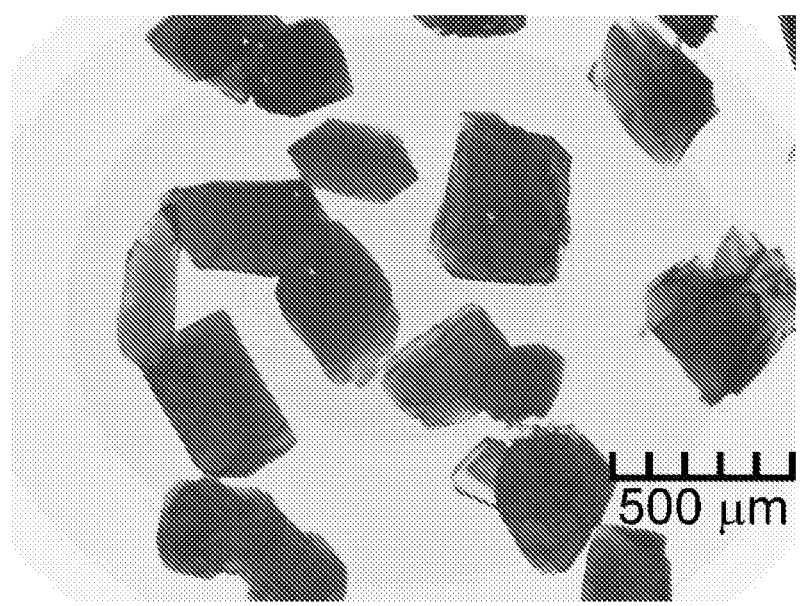
FIG. 31 shows an optical microscope image of PCN-261-Chiral (Example 27).

An optical microscope image of PCN-261-Chiral is shown in FIG. 31. A single crystal of PCN-261-Chiral is isostructural to PCN-261-NH₂.

Example 28: Synthesis of PCN-262

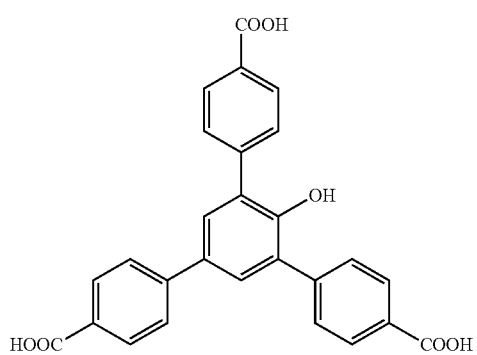 [SMILES: O=C(O)c1ccc(-c2cc(-c3ccc(C(=O)O)cc3)c(O)c(-c3ccc(C(=O)O)cc3)c2)cc1]

L18 (10 mg), Fe₂NiO(CH₃COO)₆ (10 mg) and acetic acid (0.25 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 32A:
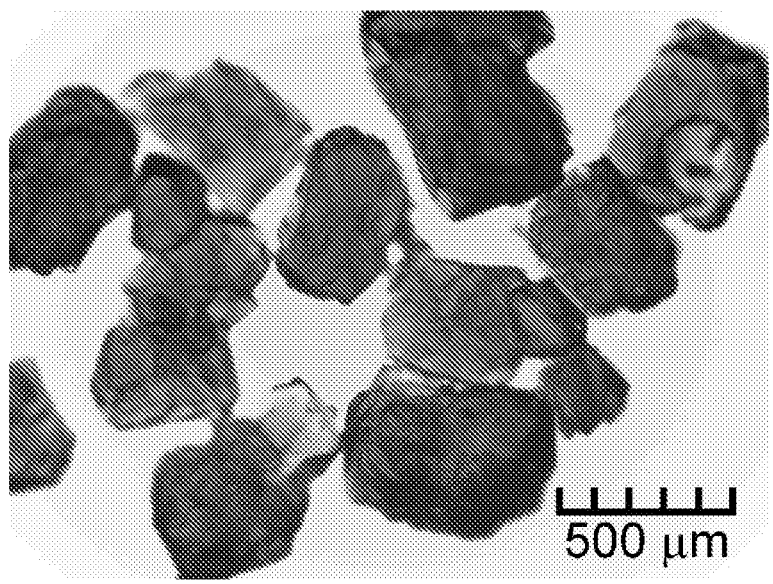
FIG. 32A shows an optical microscope image of PCN-262 (Example 28).
Figure 32B:
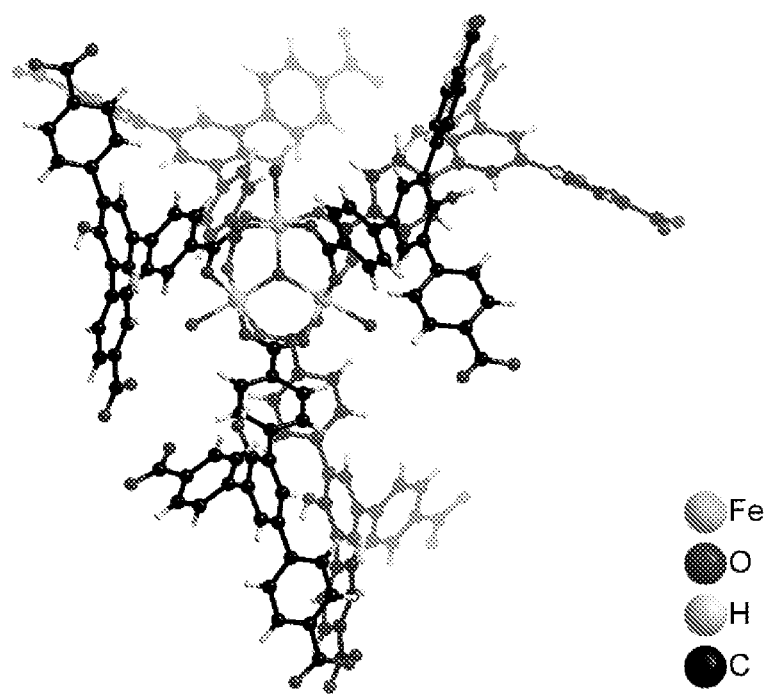
FIG. 32B illustrates a fragment structure of PCN-262 (Example 28).

An optical microscope image of PCN-262 is shown in FIG. 32a. FIG. 32b illustrates a fragment structure of PCN-262.

The crystal data and structure refinements for a single crystal of PCN-262 (CCDC 975822) are shown in Table 24.

TABLE 24

| Compound PCN-262 | | | |
|---|---|---|---|
| Formula | Fe₃ C₅₄ H₃₀ O₁₈ | $\mu(mm^{-1})$ | 0.292 |
| Fw | 1134.33 | F(000) | 2304 |
| Color/Shape | Orange Bulk | $\theta_{max}$ [deg] | 24.52 |
| Crystal system | Monoclinic, | Completeness | 99.5% |
| Space group | P2₁/c | Collected reflections | 143677 |
| a (Å) | 24.688 (4) | Unique reflections | 26567 |
| b (Å) | 18.375 (3) | Parameters | 438 |
| c (Å) | 35.257 (6) | Restraints | 144 |
| α (°) | 90.00 | $R_{int}$ | 0.0697 |
| β (°) | 90.345 (2) | R1 [I > 2σ(I)] | 0.0632 |
| γ (°) | 90.00 | wR2 [I > 2σ(I)] | 0.1321 |
| V (Å³) | 15994 (4) | R1 (all data) | 0.1117 |
| Z | 4 | wR2 (all data) | 0.1399 |
| T (K) | 110 (2) | GOF on F² | 1.000 |
| $d_{calcd.}$ (g/cm³) | 0.471 | $\Delta\rho_{max}/\Delta\rho_{min}$ [e · Å³] | 0.663/−0.341 |

Example 29a: Synthesis of PCN-263

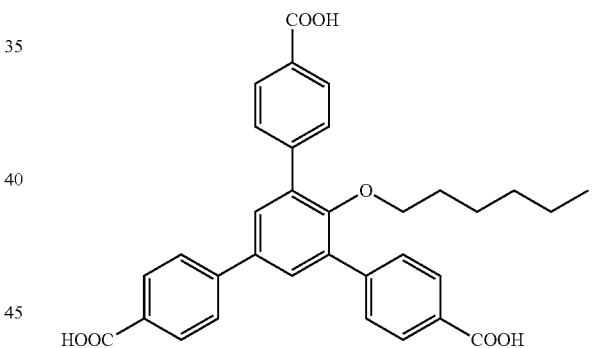

L20 (10 mg), Fe₂NiO(CH₃COO)₆ (10 mg) and acetic acid (0.3 ml) in 2 mL of DMF were ultrasonically dissolved in a Pyrex vial. The mixture was heated in 150° C. oven for 73 h. After cooling down to room temperature, dark brown crystals were harvested by filtration (Yield. 80%).

Figure 33A:
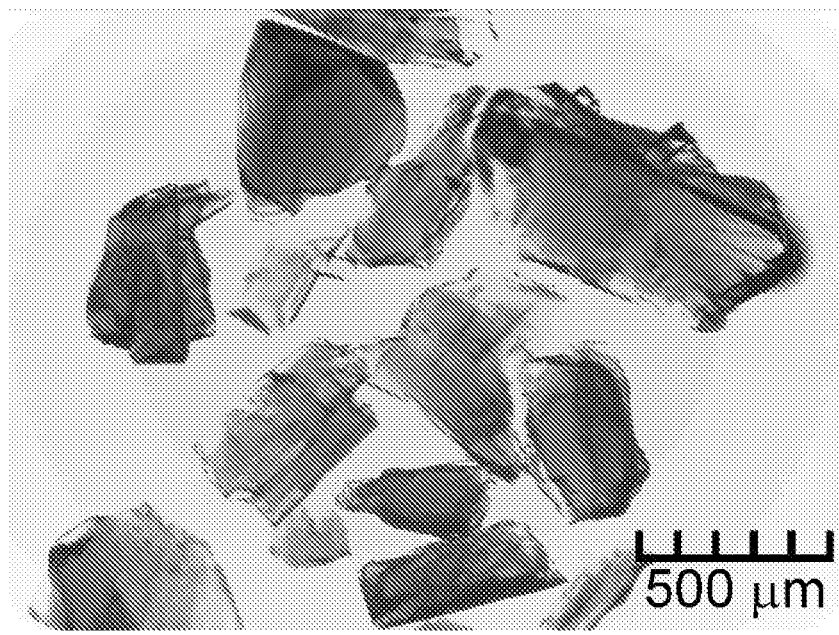
FIG. 33A shows an optical microscope image of PCN-263 (Example 29a).
Figure 33B:
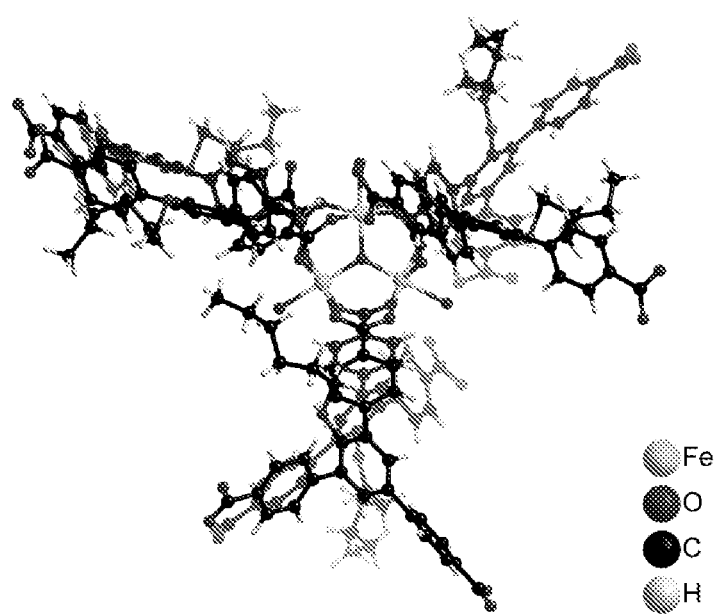
FIG. 33B illustrates a fragment structure of PCN-263 (Example 29a).

An optical microscope image of PCN-263 is shown in FIG. 33a. FIG. 33b illustrates a fragment structure of PCN-263.

The crystal data and structure refinements for a single crystal of PCN-263 (CCDC 975823) are shown in Table 25.

TABLE 25

| Compound PCN-263 | | | |
|---|---|---|---|
| Formula | Fe₃ C₆₆ H₅₄ O₁₈ | $\mu(mm^{-1})$ | 0.287 |
| Fw | 1302.64 | F(000) | 2688 |
| Color/Shape | Orange Bulk | $\theta_{max}$ [deg] | 26.00 |
| Crystal system | Monoclinic | Completeness | 99.9% |
| Space group | P2₁/c | Collected reflections | 130129 |

TABLE 25-continued

| Compound PCN-263 | | | |
|---|---|---|---|
| a (Å) | 25.085 (3) | Unique reflections | 32434 |
| b (Å) | 18.549 (3) | Parameters | 628 |
| c (Å) | 35.494 (5) | Restraints | 19 |
| α (°) | 90.00 | $R_{int}$ | 0.1060 |
| β (°) | 91.607 (2) | R1 [I > 2σ(I)] | 0.0575 |
| γ (°) | 90.00 | wR2 [I > 2σ(I)] | 0.1214 |
| V (Å³) | 16509 (4) | R1 (all data) | 0.1546 |
| Z | 4 | wR2 (all data) | 0.1253 |
| T (K) | 110 (2) | GOF on F² | 0.996 |
| $d_{calcd.}$ (g/cm³) | 0.524 | $\Delta\rho_{max}/\Delta\rho_{min}$ [e · Å⁻³] | 0.429/−0.327 |

Example 29b: Synthesis of PCN-264

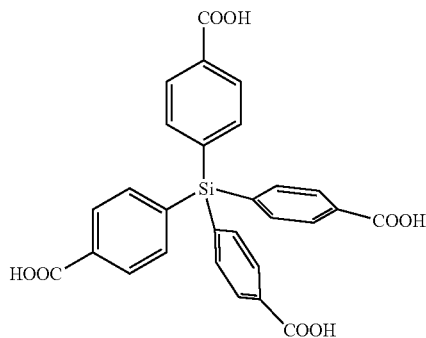 [SMILES: O=C(O)c1ccc([Si](c2ccc(C(=O)O)cc2)(c2ccc(C(=O)O)cc2)c2ccc(C(=O)O)cc2)cc1]

L28 (10 mg), Fe$_3$O(CH$_3$COO)$_6$OH (10 mg) and acetic acid (0.6 ml) in 2 mL of DMF were ultrasonically dissolved in a Pyrex vial. The mixture was heated in 150° C. oven for 24 h. After cooling down to room temperature, dark brown crystals were harvested by filtration (Yield. 80%).

Figure 34A:
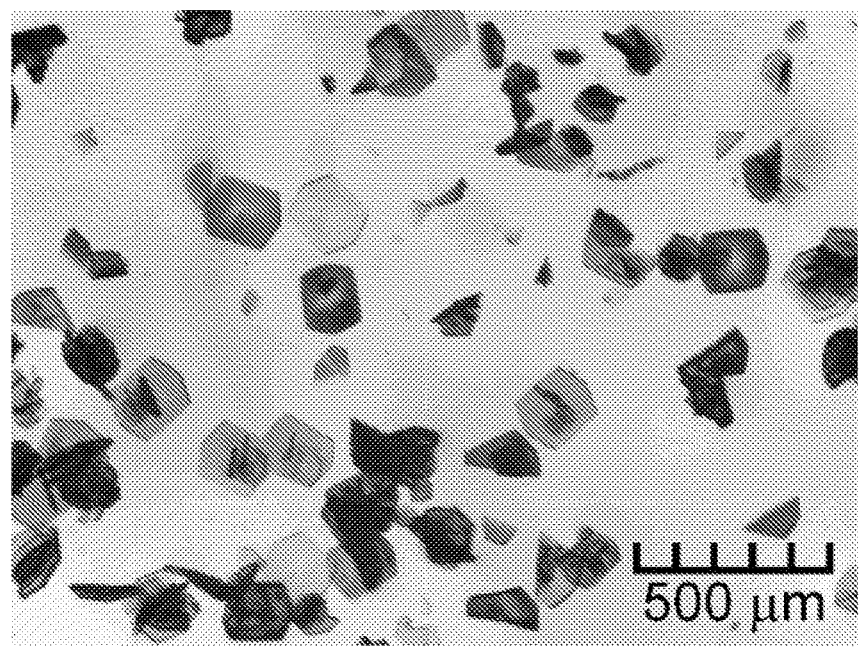
FIG. 34A shows an optical microscope image of PCN-264 (Example 29b).
Figure 34B:
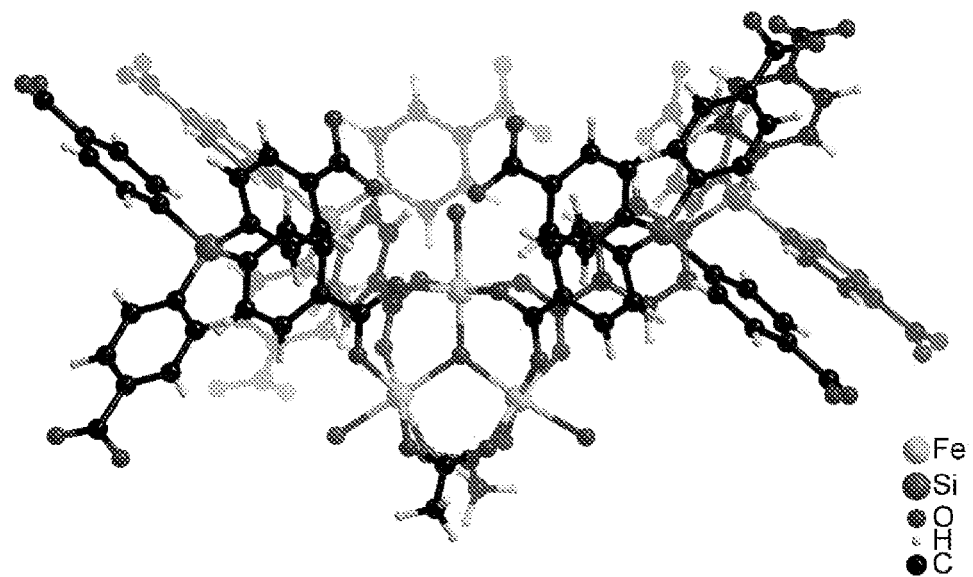
FIG. 34B illustrates a fragment structure of PCN-264 (Example 29b).

An optical microscope image of PCN-264 is shown in FIG. 34a. FIG. 34b illustrates a fragment structure of PCN-264.

The crystal data and structure refinements for a single crystal of PCN-264 (CCDC 975824) are shown in Table 26.

TABLE 26

| Compound PCN-264 | | | |
|---|---|---|---|
| Formula | Fe$_6$ C$_{64}$ H$_{46}$ O$_{32}$ Si$_2$ | μ(mm⁻¹) | 0.719 |
| Fw | 1718.29 | F(000) | 3480 |
| Color/Shape | Peach Plate | $\theta_{max}$ [deg] | 23.06 |
| Crystal system | Monoclinic | Completeness | 98.6% |
| Space group | P2$_1$/c | Collected reflections | 56104 |
| a (Å) | 24.24 (2) | Unique reflections | 13876 |
| b (Å) | 23.09 (2) | Parameters | 475 |
| c (Å) | 23.97 (2) | Restraints | 38 |
| α (°) | 90 | $R_{int}$ | 0.1466 |
| β (°) | 104.274 (8) | R$_1$ [I > 2σ(I)] | 0.1503 |
| γ (°) | 90 | wR2 [I > 2σ(I)] | 0.3554 |
| V (Å³) | 13002 (19) | R1 (all data) | 0.2459 |
| Z | 4 | wR2 (all data) | 0.3790 |
| T (K) | 150 (2) | GOF on F² | 1.003 |
| $d_{calcd.}$ (g/cm³) | 0.878 | $\Delta\rho_{max}/\Delta\rho_{min}$ [e · Å⁻³] | 1.459/−0.758 |

Example 30: Synthesis of PCN-265

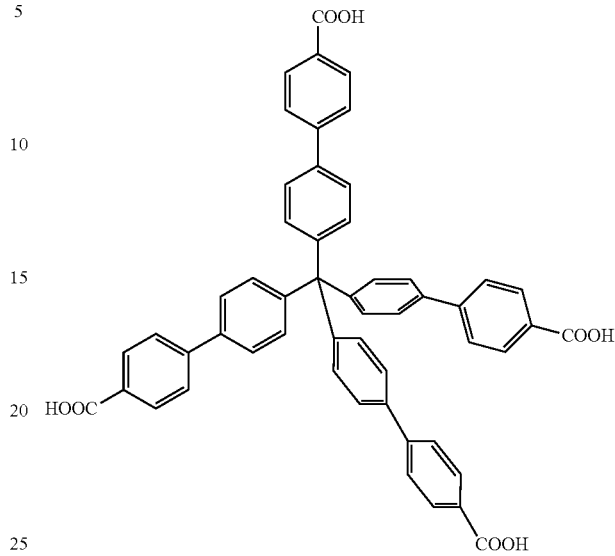

L29 (10 mg), Fe$_2$NiO(CH$_3$COO)$_6$ (15 mg) and acetic acid (0.43 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 35A:
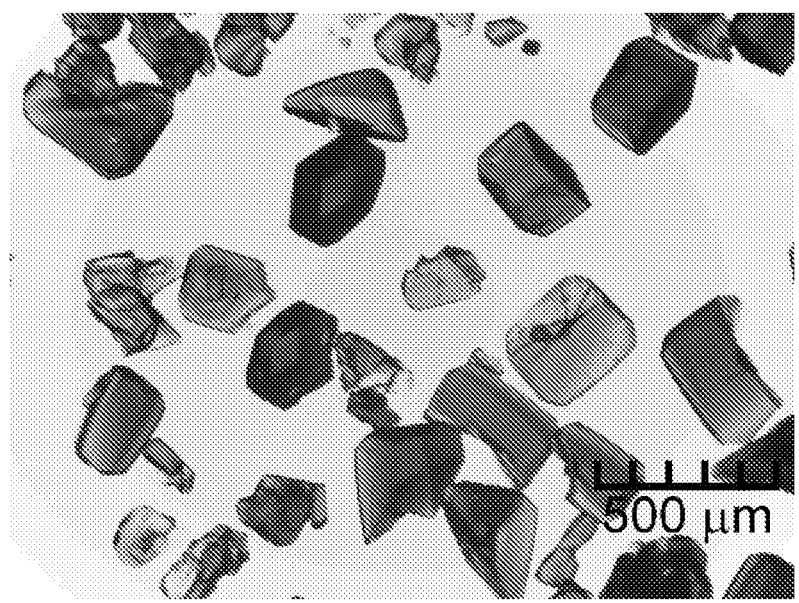
FIG. 35A shows an optical microscope image of PCN-265 (Example 30).
Figure 35B:
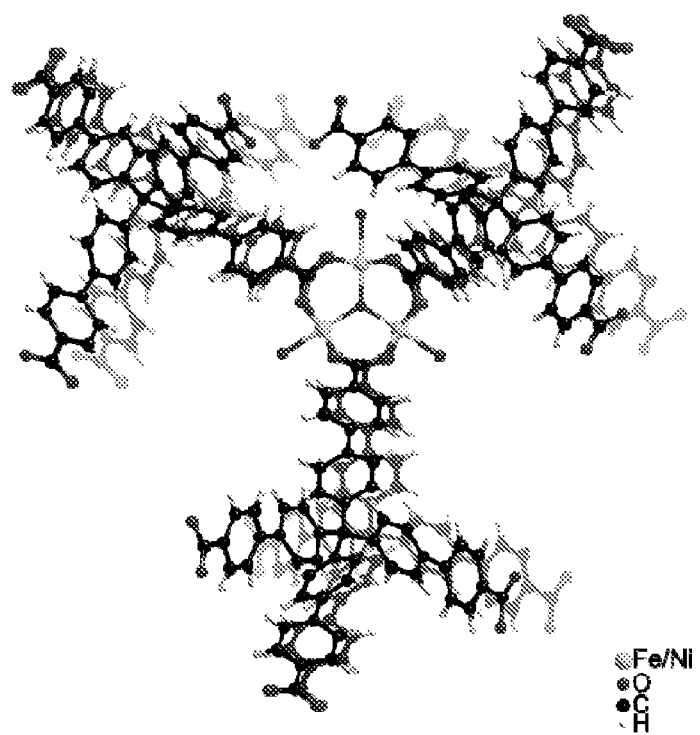
FIG. 35B illustrates a fragment structure of PCN-265 (Example 30).

An optical microscope image of PCN-265 is shown in FIG. 35a. FIG. 35b illustrates a fragment structure of PCN-265.

The crystal data and structure refinements for a single crystal of PCN-265 (CCDC 975825) are shown in Table 27.

TABLE 27

| Compound PCN-265 | | | |
|---|---|---|---|
| Formula | Fe$_2$ Ni C$_{106}$ H$_{64}$ O$_{20}$ | μ(mm⁻¹) | 0.362 |
| Fw | 1827.98 | F(000) | 3760 |
| Color/Shape | Orange Rectangle | $\theta_{max}$ [deg] | 26.51 |
| Crystal system | Orthorhombic | Completeness | 99.6% |
| Space group | Pbcm | Collected reflections | 145895 |
| a (Å) | 11.519 (4) | Unique reflections | 15639 |
| b (Å) | 33.385 (10) | Parameters | 512 |
| c (Å) | 38.702 (12) | Restraints | 0 |
| α (°) | 90.00 | $R_{int}$ | 0.0907 |
| β (°) | 90.00 | R1 [I > 2σ(I)] | 0.0726 |
| γ (°) | 90.00 | wR2 [I > 2σ(I)] | 0.2058 |
| V (Å³) | 14883 (8) | R1 (all data) | 0.1304 |
| Z | 4 | wR2 (all data) | 0.2265 |
| T (K) | 110 (2) | GOF on F² | 1.006 |
| $d_{calcd.}$ (g/cm³) | 0.816 | $\Delta\rho_{max}/\Delta\rho_{min}$ [e · Å⁻³] | 1.182/−0.503 |

Example 3: Synthesis of PCN-266

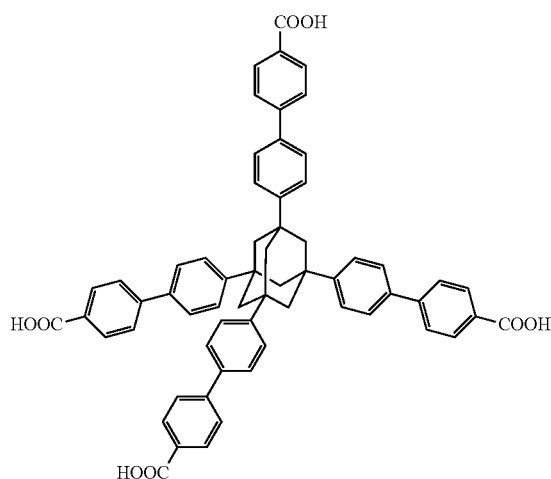 [SMILES: O=C(O)c1ccc(-c2ccc(C34CC5(c6ccc(-c7ccc(C(=O)O)cc7)cc6)CC(c6ccc(-c7ccc(C(=O)O)cc7)cc6)(C3)CC(c3ccc(-c6ccc(C(=O)O)cc6)cc3)(C4)C5)cc2)cc1]

L30 (10 mg), Fe$_3$O(CH$_3$COO)$_6$OH (15 mg) and acetic acid (0.3 ml) in 2 mL of DMF were ultrasonically dissolved in a Pyrex vial. The mixture was heated in 150° C. oven for 12 h. After cooling down to room temperature, dark brown crystals were harvested by filtration (Yield. 80%).

Figure 36A:
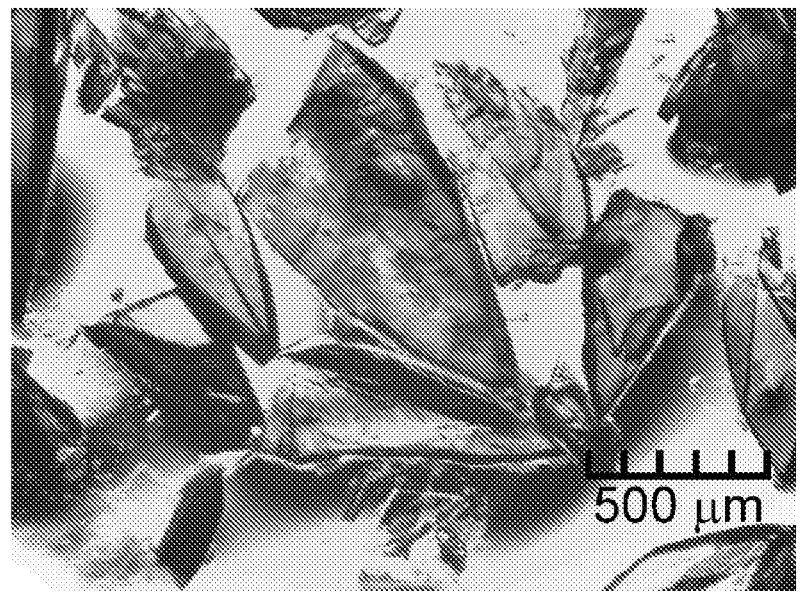
FIG. 36A shows an optical microscope image of PCN-266 (Example 31).
Figure 36B:
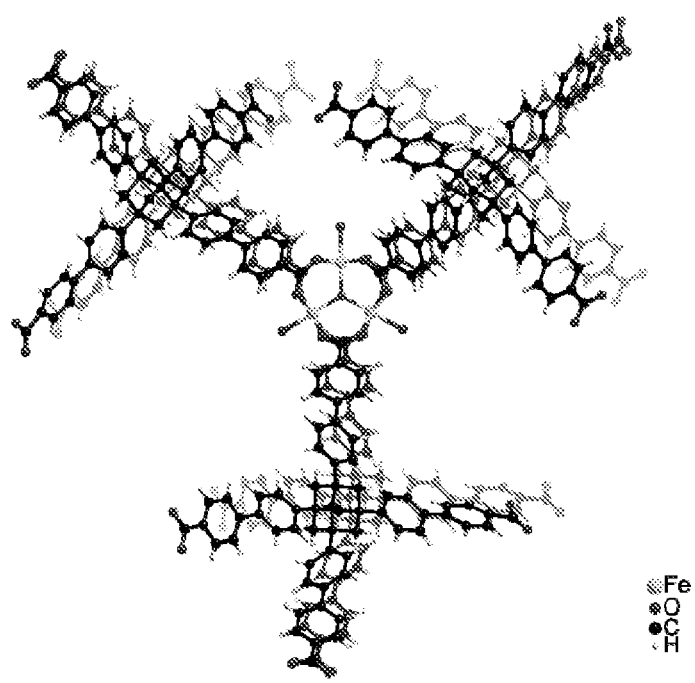
FIG. 36B illustrates a fragment structure of PCN-266 (Example 31).

An optical microscope image of PCN-266 is shown in FIG. 36a. FIG. 36b illustrates a fragment structure of PCN-266.

The crystal data and structure refinements for a single crystal of PCN-266 (CCDC 975826) are shown in Table 28.

TABLE 28

| Compound PCN-266 | | | |
|---|---|---|---|
| Formula | Fe$_3$ C$_{124}$ H$_{88}$ O$_{20}$ | μ(mm$^{-1}$) | 0.213 |
| Fw | 2065.49 | F(000) | 4280 |
| Color/Shape | Red Bulk | θ$_{max}$ [deg] | 24.21 |
| Crystal system | Orthorhombic | Completeness | 99.3% |
| Space group | Pbcm | Collected reflections | 207656 |
| a (Å) | 14.9208 (14) | Unique reflections | 19245 |
| b (Å) | 41.280 (4) | Parameters | 565 |
| c (Å) | 38.398 (3) | Restraints | 1 |
| α (°) | 90.00 | R$_{int}$ | 0.0772 |
| β (°) | 90.00 | R1 [I > 2σ(I)] | 0.0949 |
| γ (°) | 90.00 | wR2 [I > 2σ(I)] | 0.2025 |
| V (Å$^3$) | 23651 (4) | R1 (all data) | 0.1562 |
| Z | 4 | wR2 (all data) | 0.2255 |
| T (K) | 296 (2) | GOF on F$^2$ | 1.002 |
| d$_{calcd.}$ (g/cm$^3$) | 0.580 | Δρ$_{max}$/Δρ$_{min}$ [e · Å$^3$] | 0.906/−0.472 |

Example 32: Synthesis of PCN-280

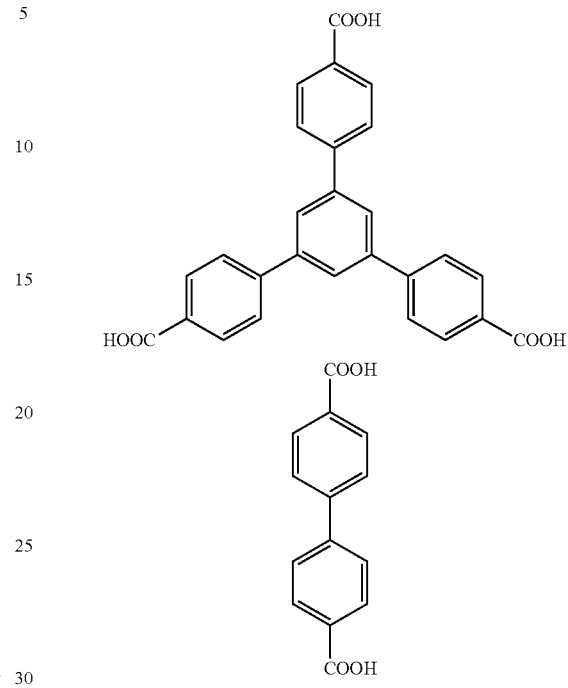

L5 (10 mg), L15 (10 mg), Fe$_3$O(CH$_3$COO)$_6$OH (10 mg) and acetic acid (0.2 ml) in 2 mL of NMP and 0.1 mL n-pentanol were ultrasonically dissolved in a Pyrex vial. The mixture was heated in 150° C. oven for 12 h. After cooling down to room temperature, dark brown crystals were harvested by filtration (Yield. 80%).

Figure 37A:
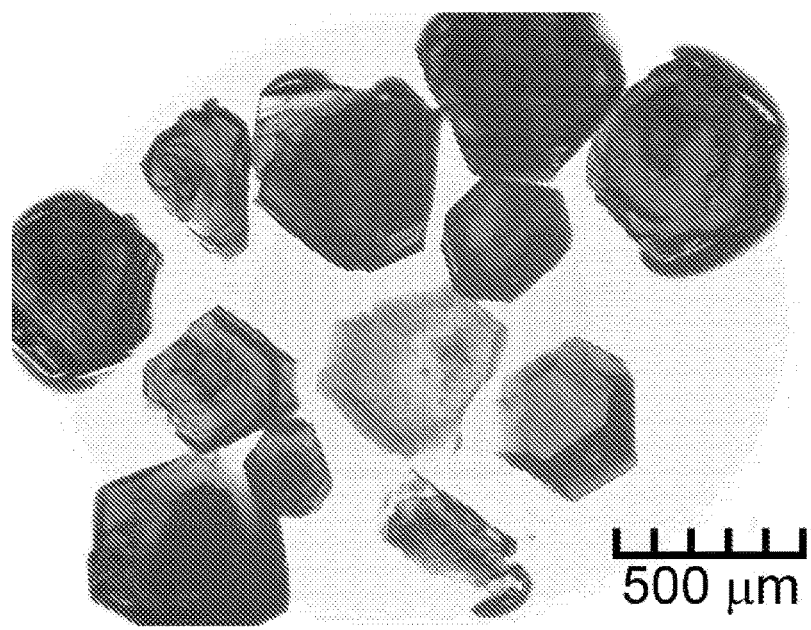
FIG. 37A shows an optical microscope image of PCN-280 (Example 32).
Figure 37B:
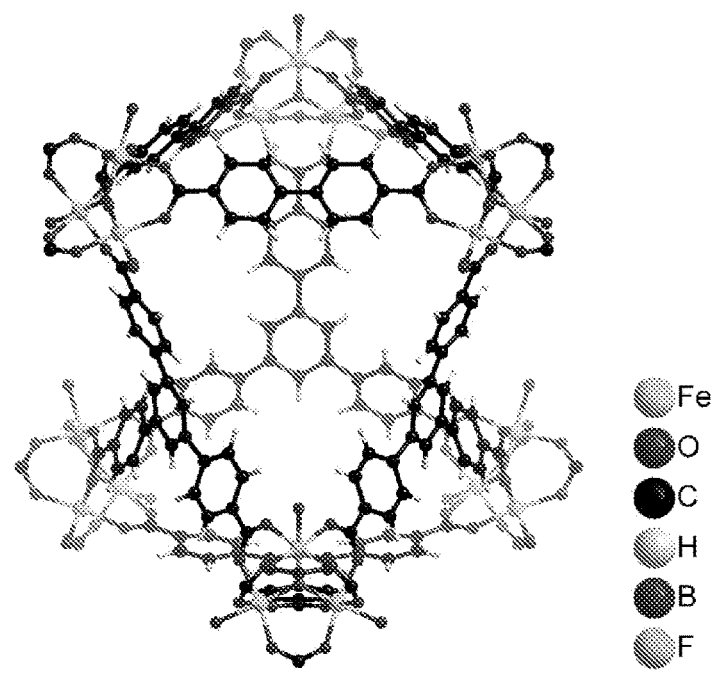
FIG. 37B illustrates a fragment structure of PCN-280 (Example 32).

An optical microscope image of PCN-280 is shown in FIG. 37a. FIG. 37b illustrates a fragment structure of PCN-280.

The crystal data and structure refinements for a single crystal of PCN-280 (CCDC 975827) are shown in Table 29.

TABLE 29

| Compound PCN-280 Absolute structure parameter: 0.11(2) | | | |
|---|---|---|---|
| Formula | Fe$_9$ C$_{150}$ H$_{84}$ O$_{48}$ | μ(mm$^{-1}$) | 0.484 |
| Fw | 3156.82 | F(000) | 4806 |
| Color/Shape | Red Truncated Triangle | θ$_{max}$ [deg] | 24.49 |
| Crystal system | Hexagonal | Completeness | 99.9% |
| Space group | R3m | Collected reflections | 46734 |
| a (Å) | 33.020 (16) | Unique reflections | 8359 |
| b (Å) | 33.020 (16) | Parameters | 214 |
| c (Å) | 22.796 (11) | Restraints | 107 |
| α (°) | 90.00 | R$_{int}$ | 0.1077 |
| β (°) | 90.00 | R1 [I > 2σ(I)] | 0.0552 |
| γ (°) | 120.00 | wR2 [I > 2σ(I)] | 0.1327 |
| V (Å$^3$) | 21525 (18) | R1 (all data) | 0.0856 |
| Z | 3 | wR2 (all data) | 0.1414 |
| T (K) | 110 (2) | GOF on F$^2$ | 1.000 |
| d$_{calcd.}$ (g/cm$^3$) | 0.731 | Δρ$_{max}$/Δρ$_{min}$ [e · Å$^3$] | 0.560/−0.394 |

Example 33: Synthesis of PCN-285

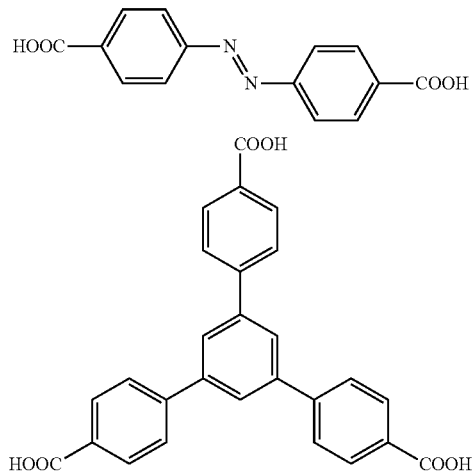

L8 (10 mg) and L15 (10 mg), Fe₃O(CH₃COO)₆OH (10 mg) and acetic acid (0.2 ml) in 2 mL of NMP and 0.1 mL n-pentanol were ultrasonically dissolved in a Pyrex vial. The mixture was heated in 150° C. oven for 12 h. After cooling down to room temperature, dark brown crystals were harvested by filtration (Yield. 80%).

Figure 38A:
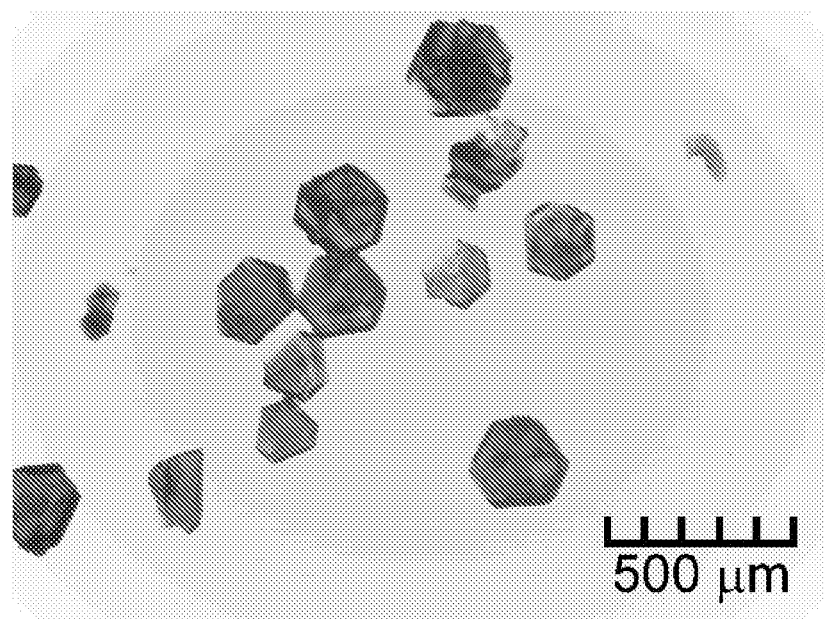
FIG. 38A shows an optical microscope image of PCN-285 (Example 33).
Figure 38B:
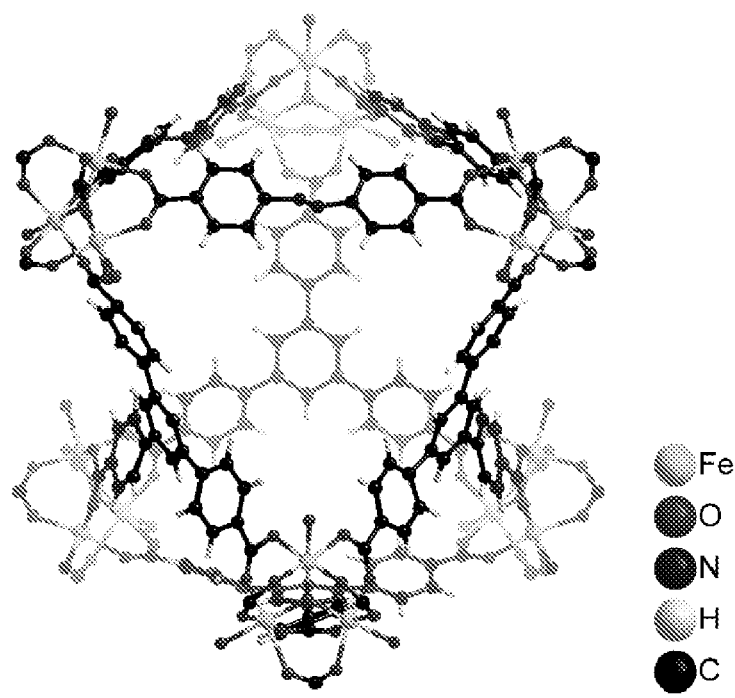
FIG. 38B illustrates a fragment structure of PCN-285 (Example 33).

An optical microscope image of PCN-285 is shown in FIG. 38a. FIG. 38b illustrates a fragment structure of PCN-285.

The crystal data and structure refinements for a single crystal of PCN-285 (CCDC 975828) are shown in Table 30.

TABLE 30

| Compound PCN-285 Absolute structure parameter: 0.267(16) | | | |
|---|---|---|---|
| Formula | Fe₉ C₁₅₀ H₈₄ N₆ O₄₈ | μ(mm⁻¹) | 0.225 |
| Fw | 3240.88 | F(000) | 4932 |
| Color/Shape | Red Truncated Triangle | $\theta_{max}$ [deg] | 24.34 |
| Crystal system | Hexagonal | Completeness | 98.4% |
| Space group* | R3 | Collected reflections | 132298 |
| a (Å) | 34.663 (15) | Unique reflections | 32920 |
| b (Å) | 34.663 (15) | Parameters | 329 |
| c (Å) | 44.712 (19) | Restraints | 133 |
| α (°) | 90.00 | $R_{int}$ | 0.1806 |
| β (°) | 90.00 | R1 [I > 2σ(I)] | 0.0733 |
| γ (°) | 120.00 | wR2 [I > 2σ(I)] | 0.1472 |
| V (Å³) | 46526 (34) | R1 (all data) | 0.1719 |
| Z | 3 | wR2 (all data) | 0.1813 |
| T (K) | 110 (2) | GOF on F² | 0.661 |
| $d_{calcd.}$ (g/cm³) | 0.347 | $\Delta\rho_{max}/\Delta\rho_{min}$ [e · Å³] | 0.349/−0.200 |

Note:
Platon suggests that the space group should be raised to R3m; however, the N—N double bond of the NBPDC ligand loses its normal bond angles. Therefore, we removed the mirror plane located at the N—N double bond, determining this structure with R3 space group.

Example 34: Synthesis of Al₃O(ABTC)₆—PCN-250 (Al₃)

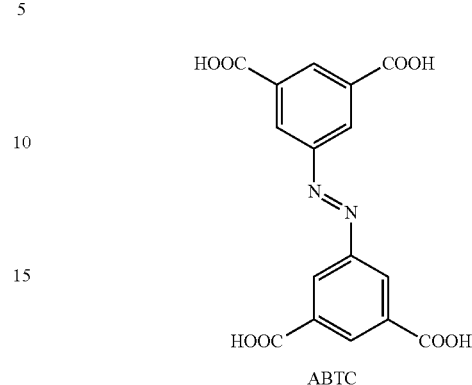

ABTC 10 mg of [Al₃O(OOCCH₃)₆·3CH₃CN][AlCl₄] and 10 mg of ABTC were dissolved in 2 ml of DMF, then 0.5 ml of acetic acid was added. The solution was sealed in a 4 ml vial and put into oven under 150 degree for 5 days.

Example 35: Synthesis of MIL-88

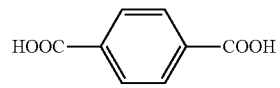

BDC (10 mg), Fe₂CoO(CH₃COO)₆ (10 mg) or Fe₃O(CH₃COO)₆OH (10 mg), and acetic acid (0.2 ml) in 2 mL of NMP were ultrasonically dissolved in a Pyrex vial. The mixture was heated in 150° C. oven for 12 h. After cooling down to room temperature, dark brown crystals were harvested by filtration (Yield. 80%).

Figure 39A:
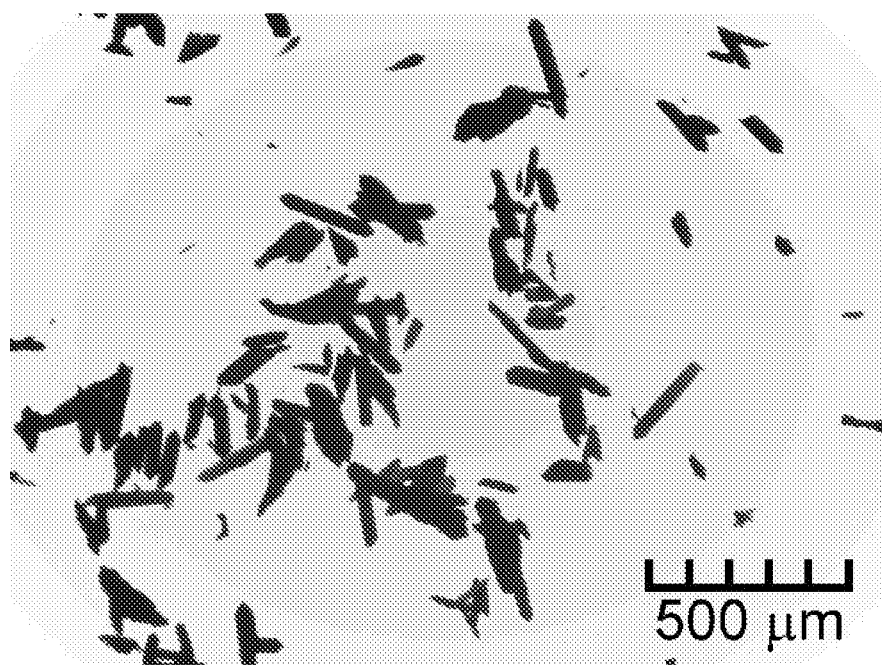
FIG. 39A shows an optical microscope image of MIL-88 (Example 35).
Figure 39B:
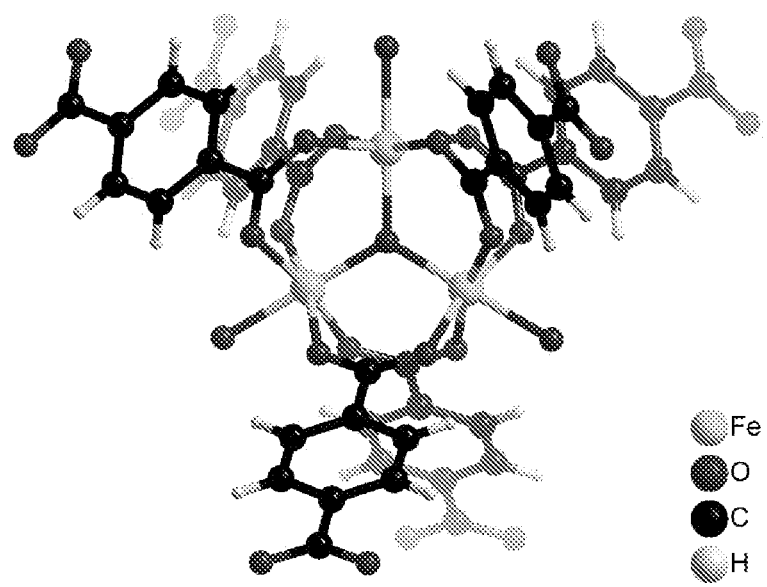
FIG. 39B illustrates a fragment structure of MIL-88 (Example 35).

An optical microscope image of MIL-88 is shown in FIG. 39a. FIG. 39b illustrates a fragment structure of MIL-88.

The crystal data and structure refinements for a single crystal of MIL-88 are shown in Table 31.

TABLE 31

| Compound MIL-88 | | | |
|---|---|---|---|
| Formula | Fe₃ C₂₄ H₁₂ O₁₆ | μ(mm⁻¹) | 0.693 |
| Fw | 723.89 | F(000) | 724 |
| Color/Shape | Red Rod | $\theta_{max}$ [deg] | 25.01 |
| Crystal system | Hexagonal | Completeness | 99.9% |
| Space group | P6₃/mmc | Collected reflections | 30162 |
| a (Å) | 14.8778 (10) | Unique reflections | 1123 |
| b (Å) | 14.8778 (10) | Parameters | 41 |
| c (Å) | 16.964 (2) | Restraints | 0 |
| α (°) | 90.00 | $R_{int}$ | 0.0965 |
| β (°) | 90.00 | R1 [I > 2σ(I)] | 0.0540 |
| γ (°) | 120.00 | wR2 [I > 2σ(I)] | 0.1295 |
| V (Å³) | 3251.9 (5) | R1 (all data) | 0.0754 |
| Z | 2 | wR2 (all data) | 0.1388 |

TABLE 31-continued

| Compound MIL-88 | | | |
|---|---|---|---|
| T (K) | 110 (2) | GOF on $F^2$ | 1.001 |
| $d_{calcd.}$ (g/cm$^3$) | 0.739 | $\Delta\rho_{max}/\Delta\rho_{min}$ [e · Å$^3$] | 0.413/−0.334 |

Example 36: Synthesis of PCN-666

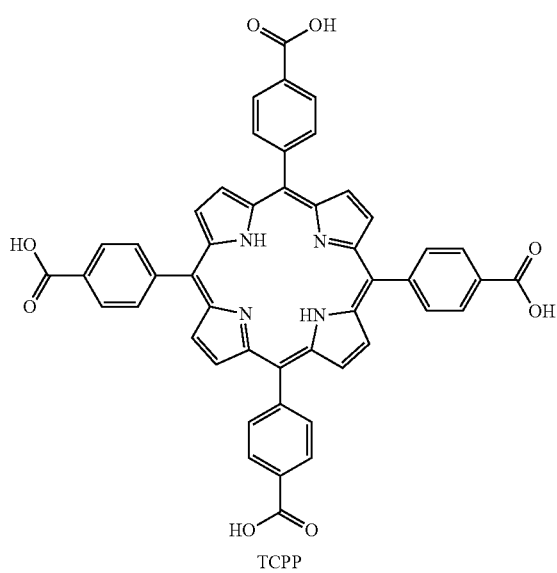

TCPP

TCPP (80 mg), Fe$_3$O(OOCCH$_3$)$_6$(OH)(80 mg), 16 ml DMF and 1.6 ml of CF$_3$COOH were added into a 20 ml Pyrex vial. The vial was heated to 150° C. for 12 h. After cooling down to room temperature, dark needle-shaped crystals were harvested by filtration (50 mg, 35% yield).

Figure 40:
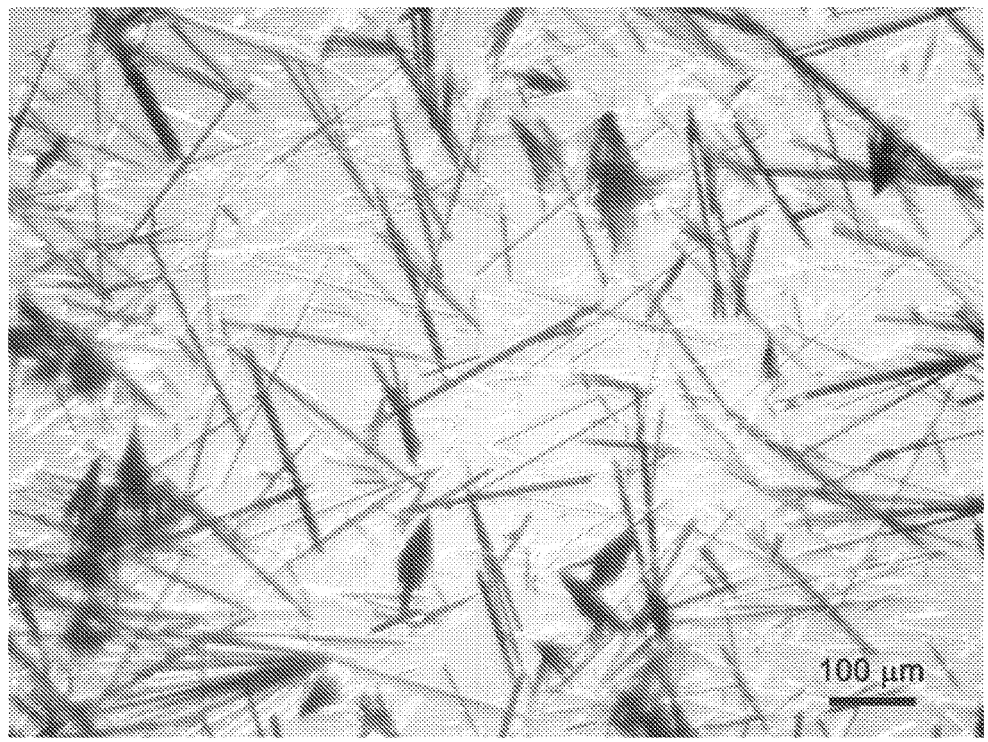
FIG. 40 shows an optical microscope image of PCN-266 (Example 36).

An optical microscope image of PCN-666 is shown in FIG. 40.

The crystal data and structure refinements for a single crystal of PCN-666 are shown in Table 32.

TABLE 32

| | PCN-666 |
|---|---|
| Crystal Color/Shape | Light Red needle |
| Crystal System | Hexagonal |
| Space Group | P6/mmm |
| a (Å) | 31.26941 |
| b (Å) | 31.26941 |
| c (Å) | 16.95362 |
| α (°) | 90 |
| β (°) | 90 |
| γ (°) | 120 |
| V (Å$^3$) | 14355.97 |
| Z | 24 |
| $d_{calcd.}$ (g/cm$^3$) | 0.3429 |

Example 37: Synthesis of PCN-22 (Ti)

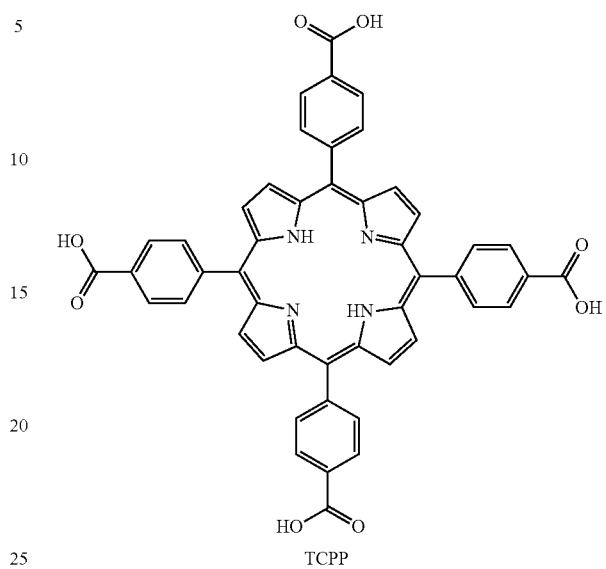

TCPP

TCPP (10 mg), Ti$_6$O$_6$(OPr)$_6$(OOCPh)$_6$ (3 mg) and benzoic acid (100 mg) in 2 mL of DEF were ultrasonically dissolved in a Pyrex vial. The mixture was heated in 150° C. oven for 24 h. After cooling down to room temperature, dark red crystal of PCN-22 were harvested by filtration (Yield. 80%).

Figure 41:
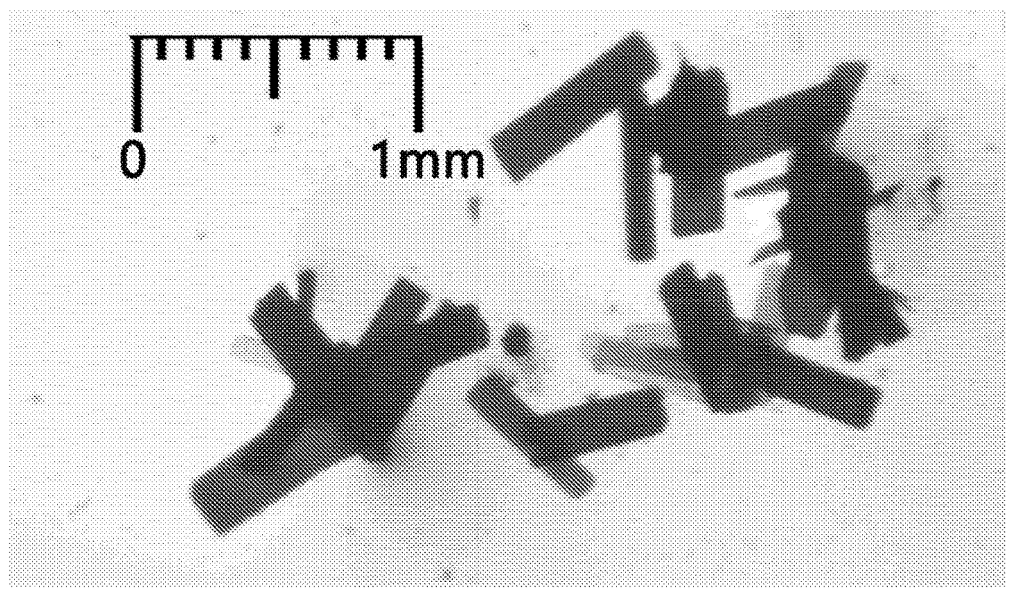
FIG. 41 shows an optical microscope image of PCN-22 (Ti), (Example 37).

An optical microscope image of PCN-22 (Ti) is shown in FIG. 41. The CE mean diameter was measured as 10.65 μm by a Malvern Mastersizer.

The crystal data and structure refinements for a single crystal of PCN-22 (Ti) are shown in Table 33.

TABLE 33

| | PCN-22-Ti |
|---|---|
| Formula | C100 H100 N10 Na0.25 O30 Ti7 |
| Formula weight | 2262.95 |
| Crystal Color/Shape | Red Block |
| Crystal System | Monoclinic |
| Space Group | P2/m |
| a (Å) | 17.6073 (6) |
| b (Å) | 17.0188 (7) |
| c (Å) | 25.0871 (10) |
| α (°) | 90 |
| β (°) | 101.722 (2) |
| γ (°) | 90 |
| V (Å$^3$) | 7360.7 (5) |
| Z | 4 |
| $d_{calcd.}$ (g/cm$^3$) | 2.042 |
| μ(mm$^{-1}$) | 0.839 |
| F(000) | 4667 |
| $\theta_{max}$ [deg] | 23.29 |
| Completeness | 99.7% |
| Collected reflections | 11005 |
| Unique reflections | 6514 |
| Parameters | 549 |
| Restraints | 0 |
| $R_{int}$ | 0.0724 |
| R1 [I > 2σ(I)] | 0.0966 |
| wR2 [I > 2σ(I)] | 0.2538 |
| R1 (all data) | 0.1270 |
| wR2 (all data) | 0.2777 |
| GOF on $F^2$ | 0.969 |
| $\Delta\rho_{max}/\Delta\rho_{min}$ [e · Å$^{-3}$] | 1.033/−1.117 |

Syntheses of Ti$_6$O$_6$(OPr)$_6$(OOCPh)$_6$ Cluster

A solution of titanium(IV) isopropoxide (0.6 g, 2.3 mmol) in toluene (20 ml) was added to a solution of benzoic acid (2.789 g, 13.08 mmol) in toluene (50 ml). After refluxing for 15 h, the solvent was removed under vacuum and crystals of Ti$_6$O$_6$(OPr)$_6$(OOCPh)$_6$ cluster was obtained at 0° C. from a CH$_2$Cl$_2$ solution.

Example 38: Synthesis of Al$_3$O(ABTC)$_6$—PCN 250 (Al)

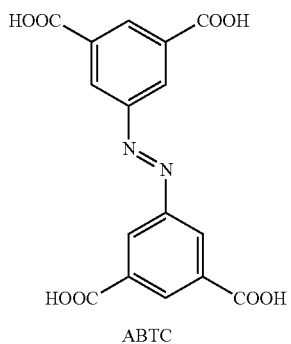 [SMILES: O=C(O)c1cc(/N=N/c2cc(C(=O)O)cc(C(=O)O)c2)cc(C(=O)O)c1]

ABTC 10 mg of [Al$_3$O(OOCCH$_3$)$_6$.3CH$_3$CN][AlCl$_4$] and 10 mg of ABTC were dissolved in 2 ml of DMF, then 0.5 ml of acetic acid was added. The solution was sealed in a 4 ml vial and put into oven at 150° C. for 5 days. After cooling down to room temperature, light yellow crystals were harvested.

Figure 42A:
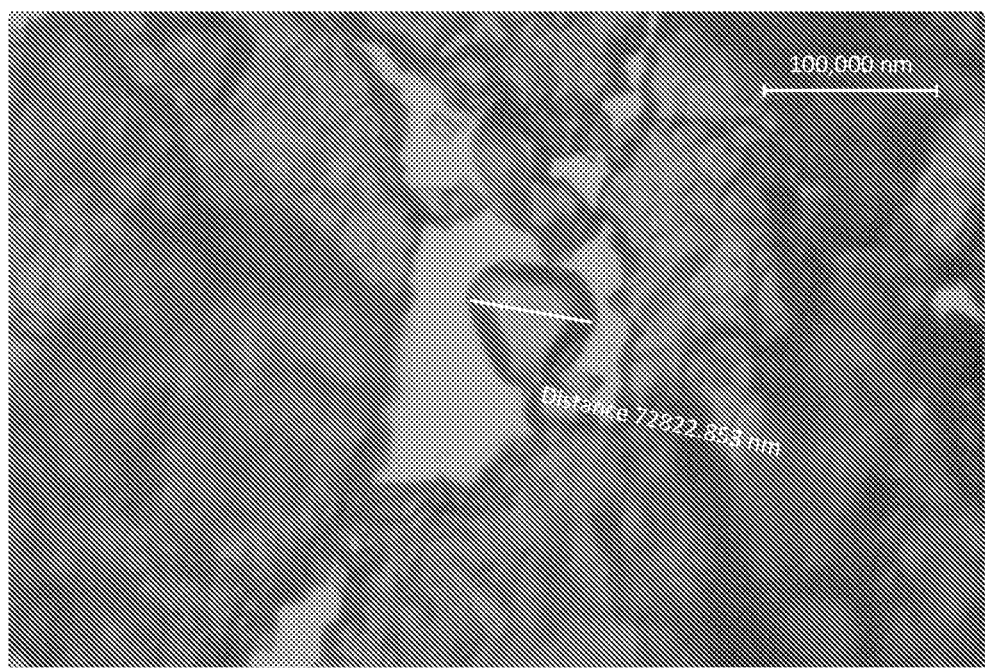
FIGS. 42A, 42B, and 42C show microscope images of PCN-250 (Al), (Example 38).
Figure 42B:
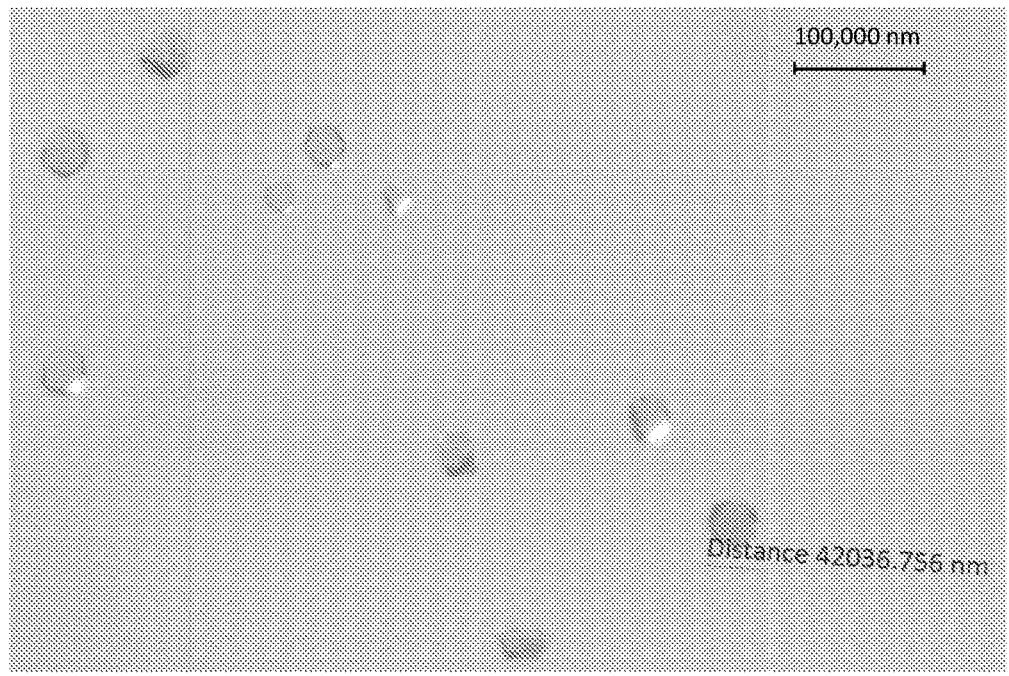
Figure 42C:
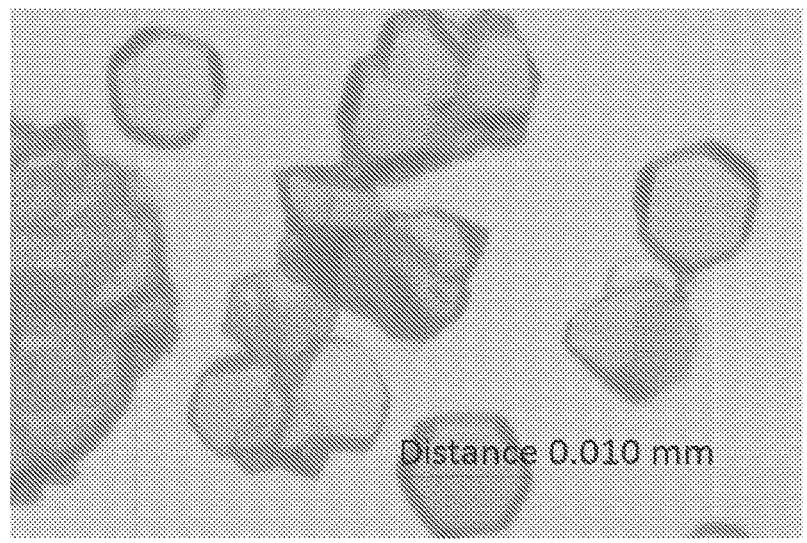

Optical microscope images of PCN-250 (Al) (Example 1) are shown in FIG. 42a, b, a& c. Crystal sizes of 42 μm, 10 μm, and 72 μm respectively were observed.

The crystal data and structure refinements for a single crystal of PCN-250 (Al) (Example 38) are shown in Table 34.

TABLE 34

| | PCN-250-Al |
|---|---|
| Formula | C$_9$ H$_6$ Al O$_{5.33}$ |
| Formula weight | 226.45 |
| Crystal Color/Shape | Light Yellow Block |
| Crystal System | Cubic |
| Space Group | P43n |
| a (Å) | 21.6035 (10) |
| V (Å$^3$) | 10082.60 (8) |
| Z | 24 |
| d$_{calcd.}$ (g/cm$^3$) | 0.895 |
| μ(mm$^{-1}$) | 0.121 |
| F(000) | 2776 |
| θ$_{max}$ [deg] | 26.37 |
| Completeness | 98.8% |
| Collected reflections | 3427 |
| Unique reflections | 3238 |
| Parameters | 145 |
| Restraints | 3 |
| R$_{int}$ | 0.0308 |
| R1 [I > 2σ(I)] | 0.0386 |
| wR2 [I > 2σ(I)] | 0.1241 |
| R1 (all data) | 0.0408 |
| wR2 (all data) | 0.1254 |
| GOF on F$^2$ | 1.136 |
| Δρ$_{max}$/Δρ$_{min}$ [e · Å$^{-3}$] | 0.371/−0.250 |

Results & Testing

Even though the ligands employed in the present invention may vary in symmetry, functionality, connectivity and size, the structure of the metal cluster, e.g. Fe$_2$MO, starting material is maintained in these frameworks. Partially substituted metal clusters, e.g. Fe$_2$MO clusters, have been discovered when complete substitution becomes incompatible with some of the ligands for symmetric or steric reasons. Moreover, even after the insertion of softer Lewis acidic species into some metal cluster species, e.g. Fe$_2$MO species, the whole building block does not suffer from decomposition under solvothermal conditions, which is confirmed by EDX and ICP.

To elucidate the universality of our strategy, several MOFs with different features have been compared in detail.

Usually, L3 tends to form a structure with two hydroxyl groups participating in the coordination. However, when starting from Fe$_2$MO(COOCH$_3$)$_6$, the in situ formation of the one dimensional chain can be avoided and only a simple substitution reaction happens between carboxylates, which leaves two hydroxyl groups free for other potential modifications. With elongated ligands L5 and L9, 2-fold perpendicular interpenetration and 3-fold parallel interpenetration are observed. Interestingly, the interpenetration restricts the flexibility in the single net and therefore generates permanent porosity. The mixed ligand strategy is always challenging due to the high probability of obtaining mixed phases, especially for MOFs whose structure determination rely on powder x-ray diffraction. When starting with pre-assembled inorganic building blocks (the starting material employed in the process of the present invention), the interference from impurities containing different inorganic building blocks is eliminated. The mixed ligand strategy can be more easily applied with the process of the present invention which allows us to grow single crystals in many more cases than were previously possible. Using the combinations of L15 and L5, and L15 and L8, we obtained large single crystals of PCN-280 and PCN-285.

In PCN-234, when the ligand is functionalized by bulky groups like —CN, the limited distance between each ligand prevents complete substitution on the Fe$_2$MO cluster and forces the formation of a 5-connected cluster with acetic acid as the remaining terminal ligand. Such connectivity reduction also happens on the tetrahedral ligands: in PCN-256, Ligand 29 slightly stretches from the ideal T$_d$ symmetry to D$_{2d}$ symmetry to form a 6-connected Fe$_2$M containing framework while the smaller tetrahedral ligand L28 is too rigid to bend and maintains the original T$_d$ symmetry. Complete substitution on the Fe$_2$MO core is unable to form a long range ordered structure with T$_d$ symmetric L28, so the connectivity of the Fe$_2$MO cluster reduces to four. Such reduced connectivity on the Fe$_2$MO cluster is first discovered in Fe-MOFs, which is also evidence of the substitution reaction on the preformed basic carboxylate.

Although all the Fe-MOFs are synthesized under similar conditions, the optimal concentration of acetic acid for each one varies greatly. According to our rationalization but without wishing to be bound by theory, extra acetic acid could slow down the substitution reaction rate, which is a kinetic factor. Whenever the concentration of acetic acid is much smaller than the best value, gels or amorphous products were obtained, which suggests an insufficient control of the substitution and dissociation balance. When the concentration of acetic acid is too large, solutions remain clear with no solid products. From the MOF formation equilibrium, this can be clearly attributed to the thermodynamic effect. Gibbs free energy of MOF formation, entropic, and enthalpic effects can be clearly observed from the synthetic conditions.

A series of Fe-MOFs (the PCN-250 series) consists of 6-connected Fe$_2$MO building blocks and rectangular tetratopic L22. Interestingly, PCN-250', another framework isomer of PCN-250, is found under different synthetic conditions. Along one axis, ligands constructing the same cube in PCN-250 adopt mirror configurations and are alternatively arranged. In PCN-250', ligands adopt the same configuration in the one cube and mirror configuration in the adjacent cubes along any axis. The isostructural indium MOF of PCN-250 was reported to have H$_2$ uptake of 2.6 wt % at low pressure. In comparison, PCN-250(Fe$_2$Co) has a lower density, larger void volume and 50% more open metal sites than the indium MOF. As a result, PCN-250 exhibits a higher H$_2$ uptake both gravimetrically and volumetrically. Experimental results show a record high H$_2$ uptake at 1.2 bar, 77K of PCN-250(Fe$_2$Co).

The gravimetric H$_2$ uptake, 3.07 wt % and volumetric uptake (32 g/L) of PCN-250(Fe$_2$Co) are both the highest among all the reported MOFs under the same conditions and even comparable with high pressure uptake of most MOFs. PCN-250(Fe$_2$Co) also possesses total CH$_4$ uptake of 215 V/V at 35 bar 298K, which is one of the highest among all the reported MOFs (28). Such high CH$_4$ uptake could be explained based on the structural features of PCN-250. The cubes constructing PCN-250 are faced by L22 and the channels between each cube are surrounded by open metal sites. Therefore, all the void space is provided with adsorption sites which could strongly interact with CH$_4$ molecules and result in an efficient space utilization to reach a high volumetric uptake.

Despite the insertion of the softer Lewis acid Co(II) in the $\mu_3$-oxo trimmer, the PCN-250 series still shows extraordinary chemical stability. The powder patterns of PCN-250 (Fe$_2$Co) remained unaltered upon immersion in glacial acetic acid and pH=1 to pH=12 aqueous solutions for 24 h. The framework of PCN-250(Fe$_2$Co) remained stable under H$_2$O after 6 months. Moreover, the N$_2$ adsorption isotherms of PCN-250(Fe$_2$Co) keep constant after all these treatments, which suggests no phase transition or framework decomposition during all treatments. Combination of high uptake and chemical stability is quite rare for MOFs, which can guarantee the reusability of the sorbent in terms of industrial applications.

Kinetic and Thermodynamic Effects in MOF Synthesis

Figure 62:
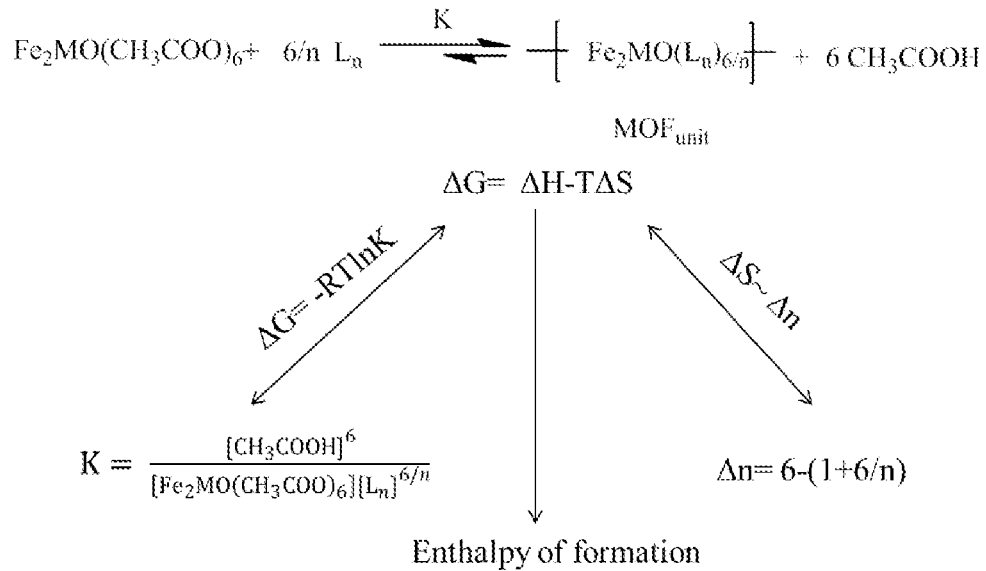
FIG. 62 shows the formation of certain MOFs as expressed as an equilibrium process with acetic acid.

Although all the MOFs (e.g. Fe-MOFs) are synthesized under similar conditions, the amount of acetic acid added for each one still varies a lot. For each ligand, when the amount of acetic acid is much smaller than the optimized value, gels are always obtained which shows an insufficient control of the ligand substitution rate. When the amount of acetic acid is much larger than the optimized value, clear solutions are always obtained (see Table 34 and Table 35 below). MOFs' formation can be expressed as an equilibrium process as shown in FIG. 62.

If the formation of clear solution is treated as the point of a positive Gibbs free energy, then the amount of acetic acid is actually an indication of relative values for MOFs' formation free energy. Also, the entropy effect could be clearly observed from the synthetic conditions. The relationship between the concentration of acetic acid used to generate a single crystal and the connectivity of the ligand is shown in Table 35. For ligands with similar size and connectivity, MOFs containing Fe$_2$MO clusters with lower connectivity always need lower concentration of acetic acid as the competing reagent. Meanwhile, for Fe$_2$MO cluster with the same connectivity, ligands with higher connecting numbers always need more acetic acid. Assuming these MOFs have similar enthalpy of formation, the concentration change of acetic acid is consistent with the entropy change. Moreover, even if the connectivity of clusters and ligands are the same, the amount of acetic acid for those MOFs still varies. This is shown in Table 36 below, and may be attributed to the enthalpy effect.

TABLE 35

| Ligand | Connectivity of ligand | CN on cluster | Acetic acid in 2 mL solvent | | |
|---|---|---|---|---|---|
| | | | Gel | Single crystal | Clear solution |
| L13 | 2 | 5 | << | ~0.10 mL | >> |
| L14 | 2 | 5 | << | ~0.10 mL | >> |
| L11 | 2 | 6 | << | ~0.20 mL | >> |
| L5 | 2 | 6 | << | ~0.15 mL | >> |
| L15 | 3 | 6 | << | ~0.25 mL | >> |
| L29 | 4 | 6 | << | ~0.40 mL | >> |

TABLE 36

| Ligand | Topics of Ligand | CN on cluster | Acetic acid in 2 mL solvent | | |
|---|---|---|---|---|---|
| | | | Gel | Single crystal | Clear solution |
| L22 | 4 | 6 | << | ~1.00 mL | >> |
| L26 | 4 | 6 | << | ~0.50 mL | >> |
| L29 | 4 | 6 | << | ~0.40 mL | >> |

$\Delta G = \Delta G° + RT\ln K$. When $\Delta G=0$ (we can take the critical point where there is no MOF coming out), then $\Delta G° = -RT\ln K$. In that case, $\Delta G°$ of the MOF could be evaluated by the acetic acid added into the system to make a clear solution.

Gas Adsorption Measurement and Stability Test of PCN-250(Fe$_2$Co)

The adsorption and desorption characteristics of PCN-250(Fe$_2$Co) were measured.

Before measurements were carried out, as-synthesized PCN-250(Fe$_2$Co) samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry CH$_2$Cl$_2$ several times, and CH$_2$Cl$_2$ solvent exchange was conducted under a well-sealed vial at 60° C. for 3 days. After that, the solvent was removed on a vacuum line and the sample was transported in a glove box to prevent the re-adsorption of H$_2$O from the air. The sample was then activated again using the 'outgas' function of the adsorption instrument for 12 h at 190° C. Gas adsorption/desorption was then measured.

For the stability test, samples from the same batch were treated with different aqueous solutions for the listed period. After that, the activation process was repeated as described above and N$_2$ adsorption was measured at 77K.

Figure 43:
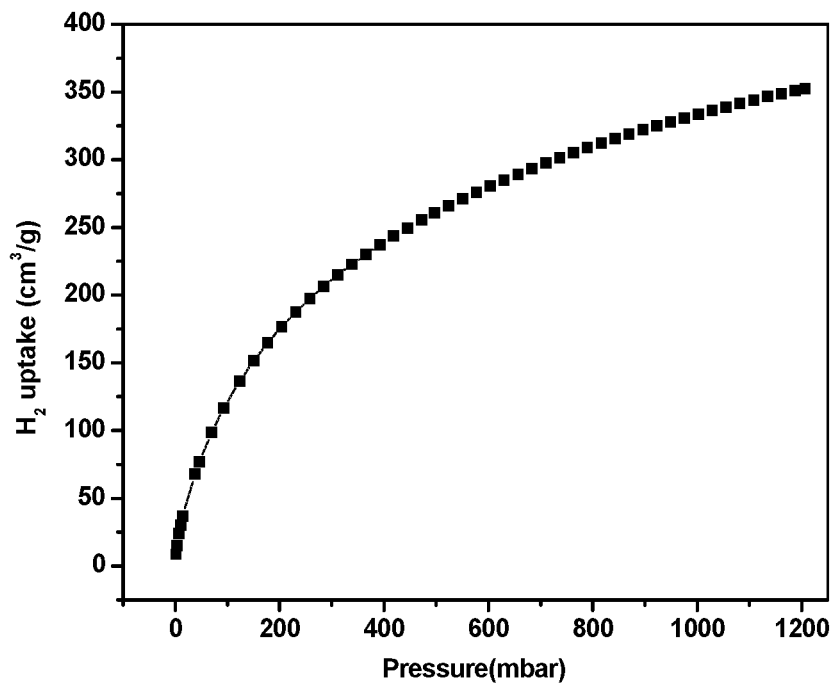
FIG. 43 shows the low-pressure $H_2$ adsorption isotherm measured for PCN-250($Fe_2Co$) at 77 K.

FIG. 43 shows the low-pressure H$_2$ adsorption isotherm measured for PCN-250(Fe$_2$Co) at 77 K.

Figure 44:
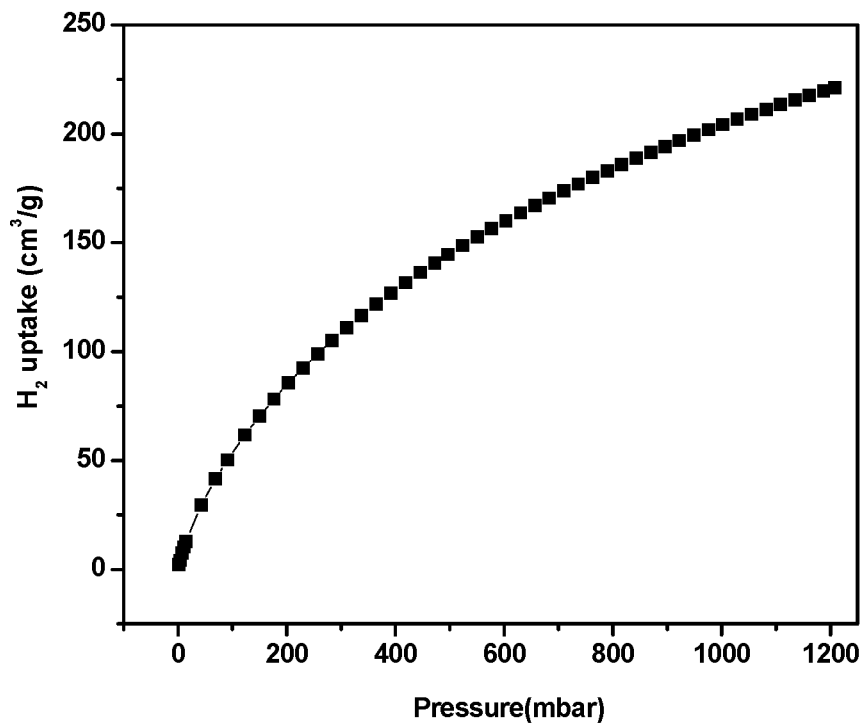
FIG. 44 shows the low-pressure $H_2$ adsorption isotherm measured for PCN-250($Fe_2Co$) at 87 K.

FIG. 44 shows the low-pressure H$_2$ adsorption isotherm measured for PCN-250(Fe$_2$Co) at 87 K.

Figure 45:
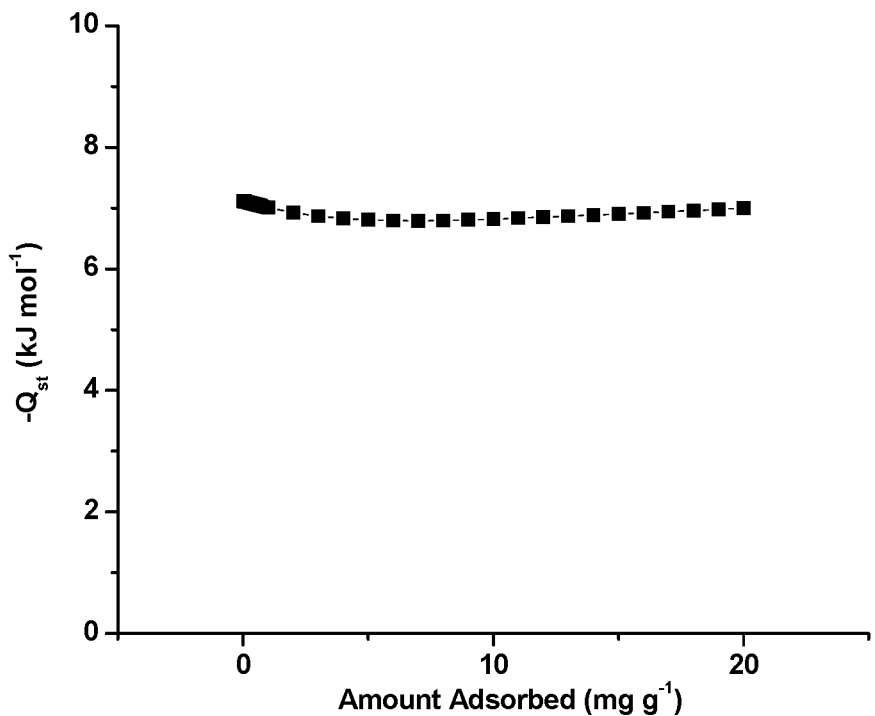
FIG. 45 shows the heat of adsorption measured during $H_2$ adsorption for PCN-250($Fe_2Co$).

FIG. 45 shows the heat of adsorption measured during H$_2$ adsorption for PCN-250(Fe$_2$Co).

Figure 46:
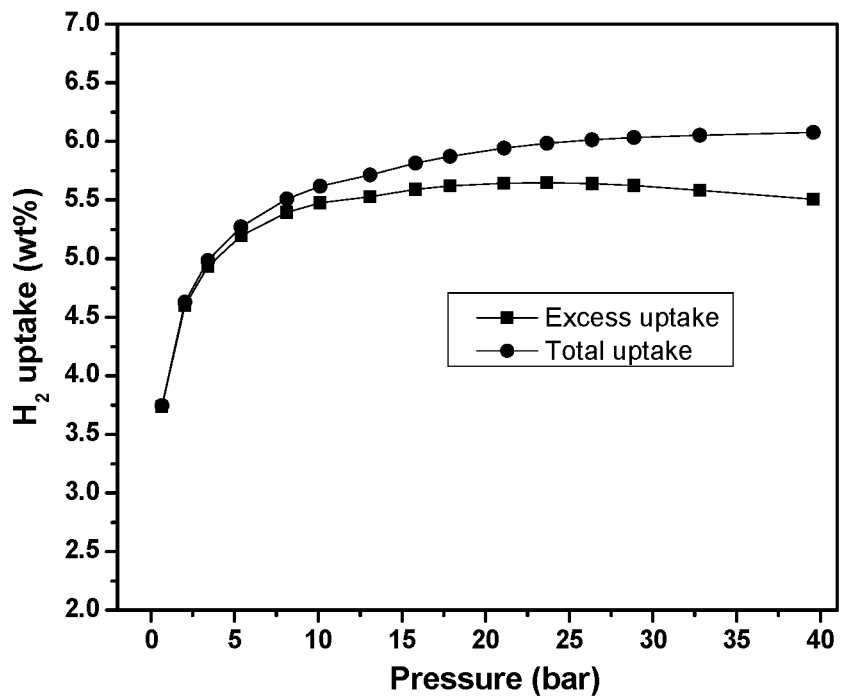
FIG. 46 shows the high-pressure $H_2$ adsorption isotherm measured for PCN-250($Fe_2Co$).

FIG. 46 shows the high-pressure H$_2$ adsorption isotherm measured for PCN-250(Fe$_2$Co).

Simulation and Computation Results and Methods

Methane uptake for both experimental and hypothetical Fe-MOFs was predicted.

Hypothetical metal-organic frameworks were enumerated based on the $Fe_2Co$ secondary building unit (SBU) with trigonal prismatic coordination (i.e., six-connected). This SBU was combined separately with each linker from a set of 120 linear dicarboxylic acids from the eMolecules.com commercial database, which had been previously utilized in the assembly of MOF-5 analogues (i.e., structures exhibiting the pcu net, and based on a $Zn_4O$ SBU). The combination of linear linkers and the trigonal prismatic $Fe_2Co$ SBU yields the acs net, and as such these hypothetical materials are isostructural to MIL-88. In total, 105 structure models were produced; 15 linkers produced no valid structure due to collision between the building blocks. The structure models were not relaxed.

Figure 47:
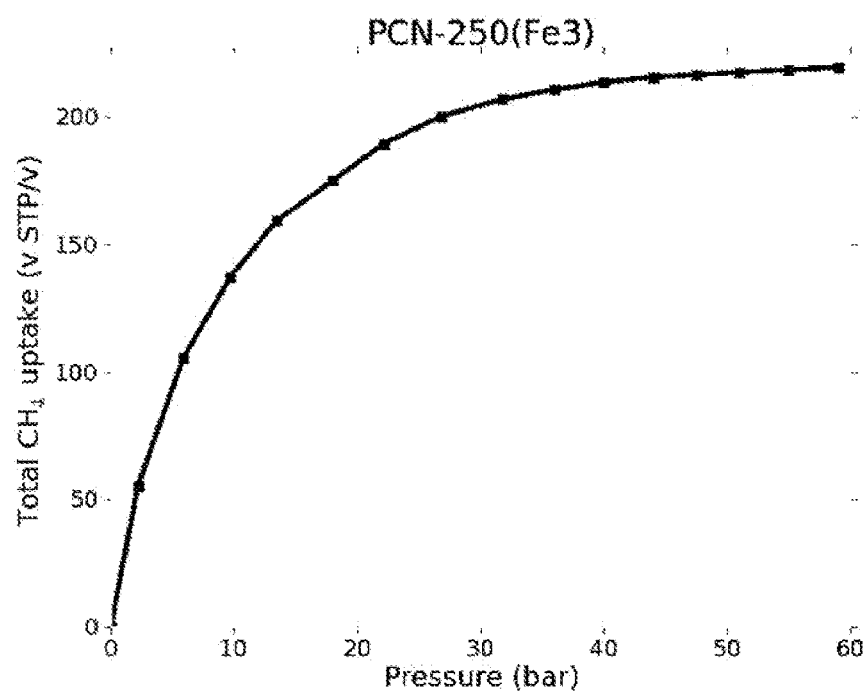
FIG. 47 shows the methane adsorption isotherm measured and the methane adsorption isotherm predicted for PCN-250($Fe_3$).

FIG. 47 shows the methane adsorption isotherm measured and the methane adsorption isotherm predicted for PCN-250($Fe_3$). The figure shows that the predicted isotherm provided a good approximation of the measured isotherm.

Potential energy surfaces were calculated for PCN-250 structures.

The energetic interactions of a gas (hydrogen or methane) molecule were modelled between the solid and another gas molecule with Lennard-Jones potentials. Both methane and hydrogen were modeled as uncharged, united atoms (i.e. a single sphere with a Lennard-Jones potential). The Lennard-Jones parameters for the solid atoms were taken from the Universal Force Field, for methane were taken from TraPPE, and for hydrogen are taken from Ref. (S9). Ref (S9) implicitly includes the partial charges of hydrogen by fitting the Lennard-Jones parameters to the virial coefficients obtained experimentally. TraPPE parameters for methane reproduce its critical properties and vapor-liquid coexistence curve. Lorentz-Berthelot mixing rules yield the Lennard-Jones parameters for interactions between two atoms of different identities. This force field for methane and hydrogen is generally good for modelling adsorption in MOFs. The Lennard-Jones potential was approximated to be zero beyond a critical radius of 12.5 Å. This allowed periodic boundary conditions to be applied to mimic an infinite crystal. The crystal was considered rigid in the calculations.

To predict the equilibrium adsorption isotherms for both hydrogen and methane, Monte Carlo simulations of the grand canonical ensemble were performed. The Peng-Robinson equation of state was used to relate the pressure in experiment to the fugacity (chemical potential). The simulated isotherms were the total adsorption (not excess).

Potential energy contours were calculated for PCN-250 and PCN-250' materials. The space of the crystal unit cell was divided into a three-dimensional regular grid with a unit step size of about 0.1 Å. At each point in the grid, the interaction energy of a gas molecule at that position with the solid material was computed; a highly parallel graphics processing unit (GPU) implementation of this algorithm was utilized to accelerate computation of high-resolution potential energy grids. The same force-field described above was used to model the potential energy of the gas molecule with the solid framework. The contours in FIGS. 48-51 illustrate potential energy values of −6.25 kJ/mol (dark blue) and −5 (light blue) kJ/mol for hydrogen (global minimum is −7.20 kJ/mol in PCN-250($Fe_2Co$) and −7.45 kJ/mol in PCN-250' ($Fe_2Co$)); and −16.5 kJ/mol (dark green) and −14 (light green) kJ/mol for methane (global minimum is −19.08 kJ/mol in PCN-250($Fe_2Co$) and −19.59 kJ/mol in PCN-250' ($Fe_2Co$)).

Figure 48:
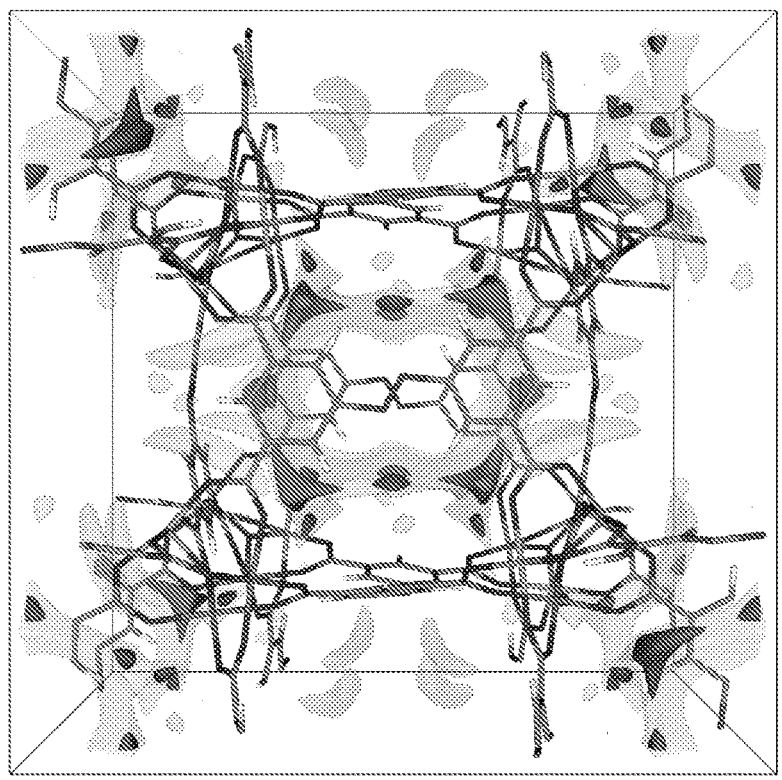
FIG. 48 shows the potential energy contours of adsorbed $H_2$ gas in PCN-250 ($Fe_2Co$).

FIG. 48 shows the potential energy contours of adsorbed $H_2$ gas in PCN-250 ($Fe_2Co$).

Figure 49:
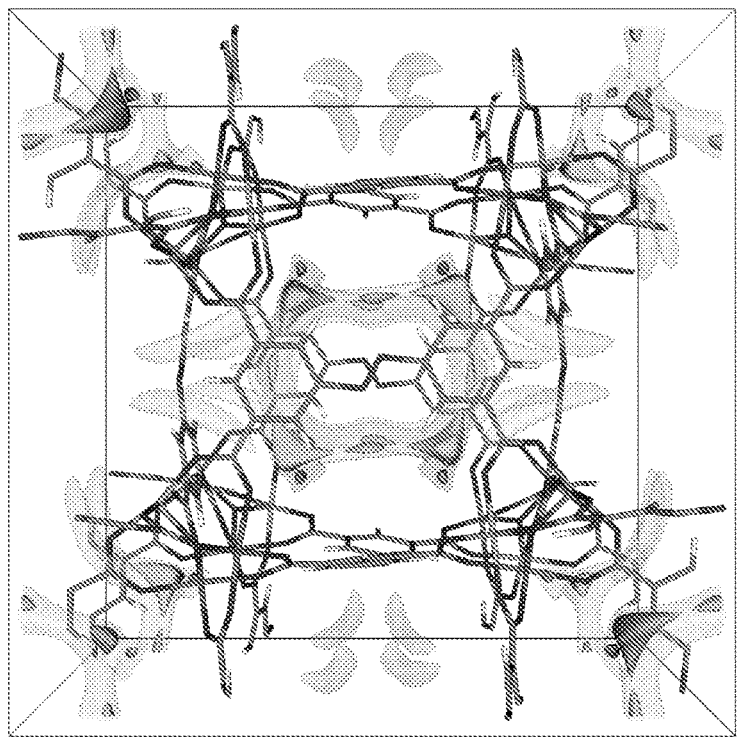
FIG. 49 shows the potential energy contours of adsorbed $CH_4$ gas in PCN-250 ($Fe_2Co$).

FIG. 49 shows the potential energy contours of adsorbed $CH_4$ gas in PCN-250 ($Fe_2Co$).

Figure 50:
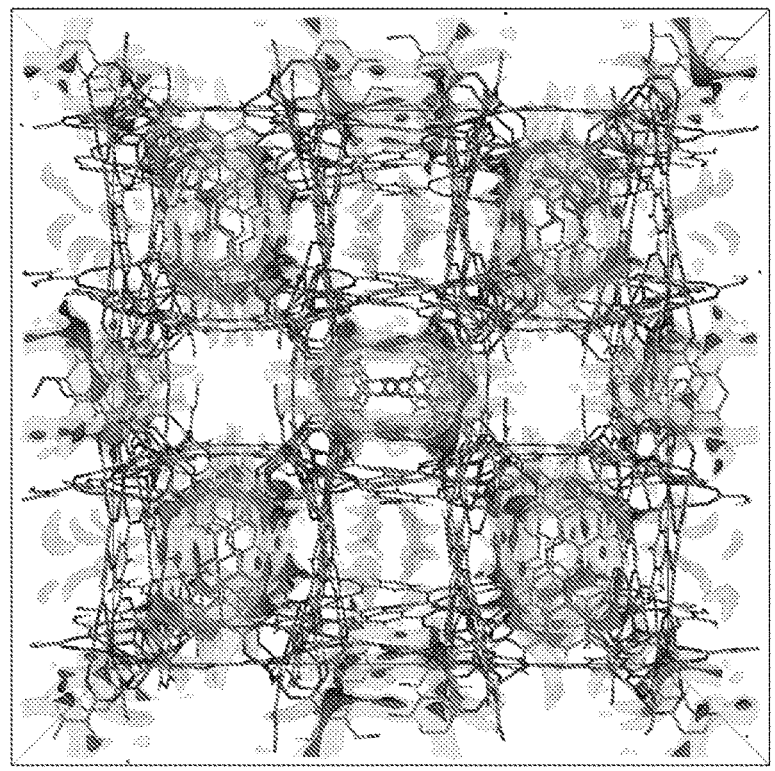
FIG. 50 shows the potential energy contours of adsorbed $H_2$ gas in PCN-250' ($Fe_2Co$).

FIG. 50 shows the potential energy contours of adsorbed $H_2$ gas in PCN-250' ($Fe_2Co$).

Figure 51:
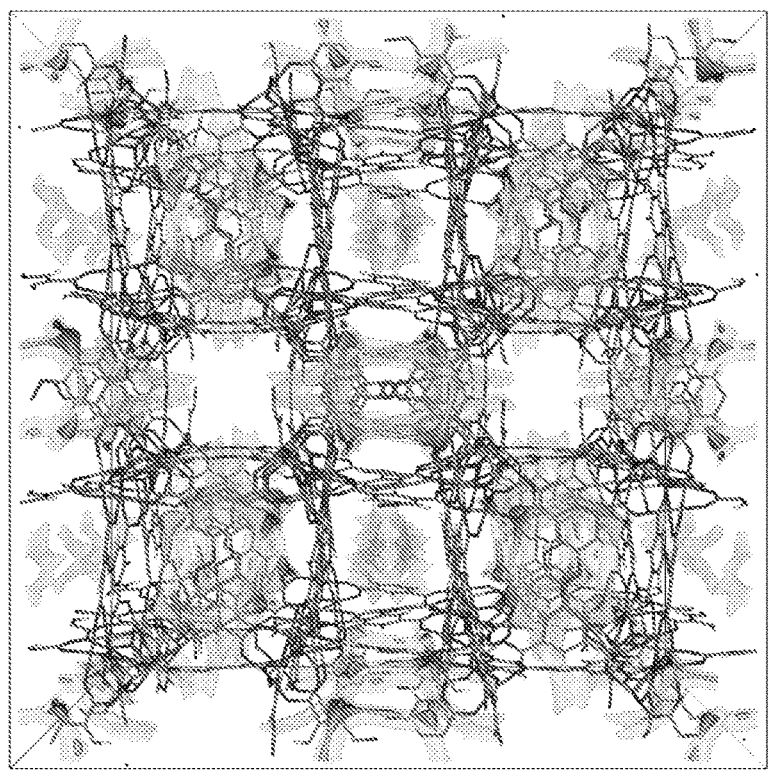
FIG. 51 shows the potential energy contours of adsorbed $CH_4$ gas in PCN-250' ($Fe_2Co$).

FIG. 51 shows the potential energy contours of adsorbed $CH_4$ gas in PCN-250' ($Fe_2Co$).

Thermogravimetric Analysis of PCN-250 and PCN-250'

About 15 mg samples of PCN-250($Fe_2Co$) and PCN-250' ($Fe_2Co$) were heated on a TGA-50 (Shimadzu) thermogravimetric analyzer from room temperature to 650° C. at a rate of 5° C. $min^{-1}$ under $N_2$ flow of 15 mL $min^{-1}$.

Figure 52:
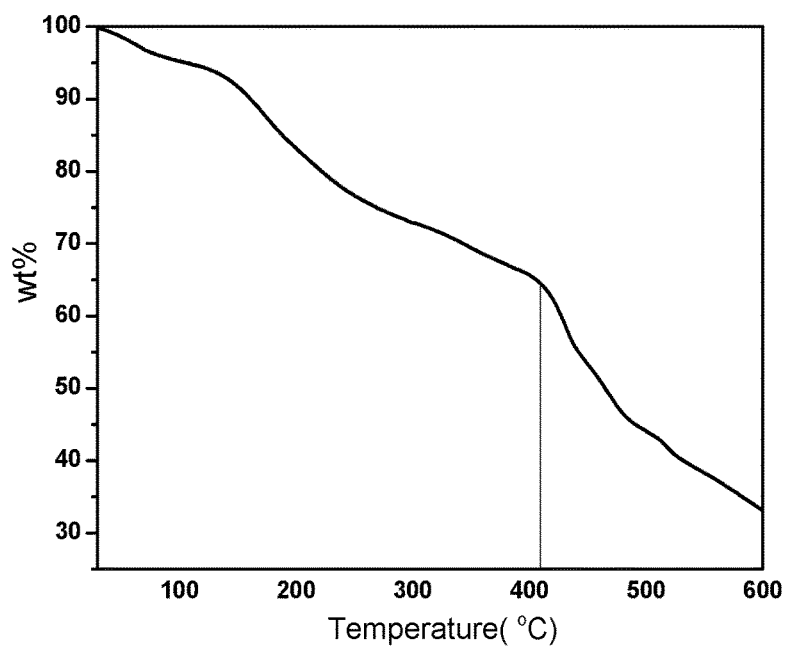
FIG. 52 shows a thermogravimetric analysis trace for a fresh sample of PCN-250($Fe_2Co$).

FIG. 52 shows the thermogravimetric analysis trace for a fresh sample of PCN-250($Fe_2Co$) and confirms solvent content. Based upon the calculated composition, 35% weight loss is expected for DMF within the pores and the coordinating $H_2O$ (30-400° C.) for the fresh sample.

Figure 53:
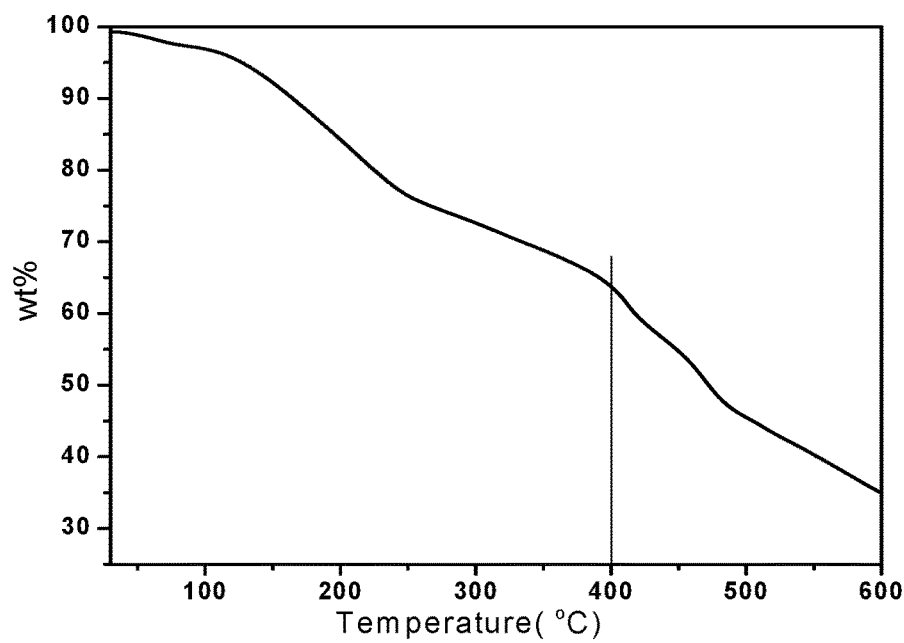
FIG. 53 shows a thermogravimetric analysis trace for a fresh sample of PCN-250 ($Fe_2Co$).

FIG. 53 shows the thermogravimetric analysis trace for a fresh sample of PCN-250 ($Fe_2Co$) fresh sample and confirms solvent content. Based upon the calculated composition, 35% weight loss is expected for NMP within the pores and the coordinating $H_2O$ (30-400° C.) for the fresh sample.

The Atomic ratio of Fe and Co in PCN-250 ($Fe_2Co$) was measured and the results are shown in Table 37.

TABLE 37

| Element | Weight % Trial 1 | Atomic % Trial 1 | Weight % Trial 2 | Atomic % Trial 2 | Weight % Trial 3 | Atomic % Trial 3 |
|---|---|---|---|---|---|---|
| Fe | 18.19 | 5.48 | 20.40 | 6.32 | 17.79 | 5.33 |
| Co | 9.23 | 2.64 | 9.77 | 2.87 | 9.17 | 2.60 |
| | | | Average Fe:Co ratio = 2:1 | | | |

ICP analysis was carried out for $Fe_2CoO(CH_3COO)_6$ precursor and PCN-250($Fe_2Co$).

Samples of $Fe_2CoO(CH_3COO)_6$ precursor and PCN-250 ($Fe_2Co$) were prepared in triplicate with weights of 1-4 mg per sample. Each sample was dissolved in J.T. Baker Ultrex® II Ultrapure 70% nitric acid at 70° C. for 12 hours. Samples were then diluted to 150× in 1% nitric acid and 18.2 MΩ water from Millipore Milli-Q® water purification system. Calibration standards were prepared from certified reference standards from RICCA Chemical Company. Samples were further analyzed with a Perkin Elmer NexION® 300D ICP-MS. Resulting calibration curves had minimum $R^2$=0.9999. Additionally, in order to maintain accuracy, quality control samples from certified reference standards and internal standards were utilized. The individual results of the triplicate samples were averaged to determine the metal ratios.

ICP analysis results of $Fe_2CoO(CH_3COO)_6$ precursor and PCN-250($Fe_2Co$) are shown in Table 38.

TABLE 38

| | Fe:Co ratio | | |
|---|---|---|---|
| Compounds | Trial 1 | Trial 2 | Trial 3 |
| $Fe_2CoO(CH_3COO)_6$ | 2.05:1 | 2.02:1 | 2.07:1 |
| PCN-250($Fe_2Co$) | 2.10:1 | 2.05:1 | 2.03:1 |

Gas Adsorption Measurement for PCN-250 (Al):

The adsorption characteristics of PCN-250(Al) were measured.

Before measurements were carried out, as-synthesized PCN-250(Al) samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

Figure 54:
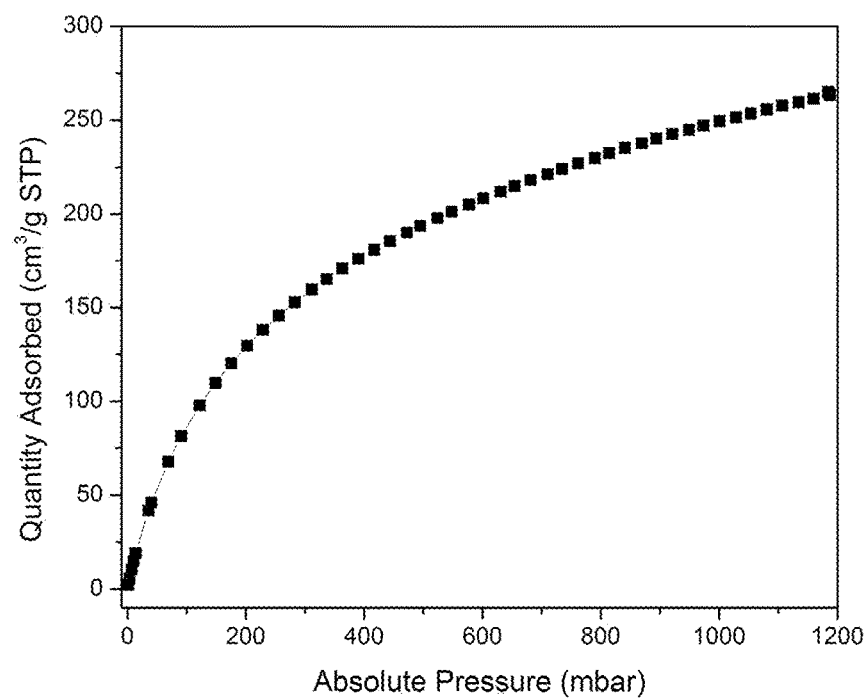
FIG. 54 shows the $H_2$ uptake (adsorption) measured for PCN-250(Al).

FIG. 54 shows the $H_2$ uptake (adsorption) measured for PCN-250(Al).

Figure 55:
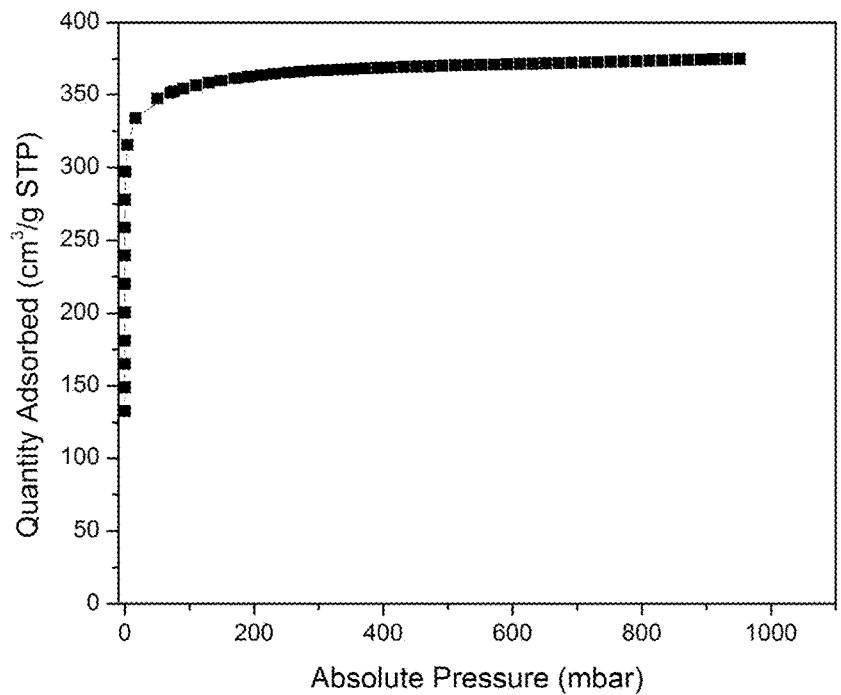
FIG. 55 shows the $N_2$ uptake (adsorption) measured for PCN-250(Al).

FIG. 55 shows the $N_2$ uptake (adsorption) measured for PCN-250(Al).

Figure 56:
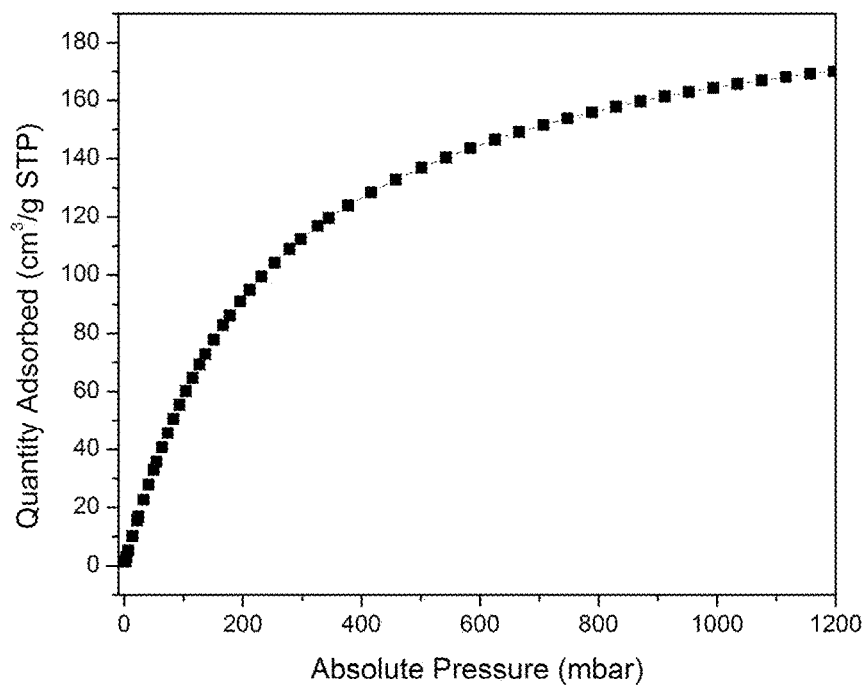
FIG. 56 shows the $CH_4$ uptake (adsorption) measured for PCN-250(Al).

FIG. 56 shows the $CH_4$ uptake (adsorption) measured for PCN-250(Al).

Figure 57:
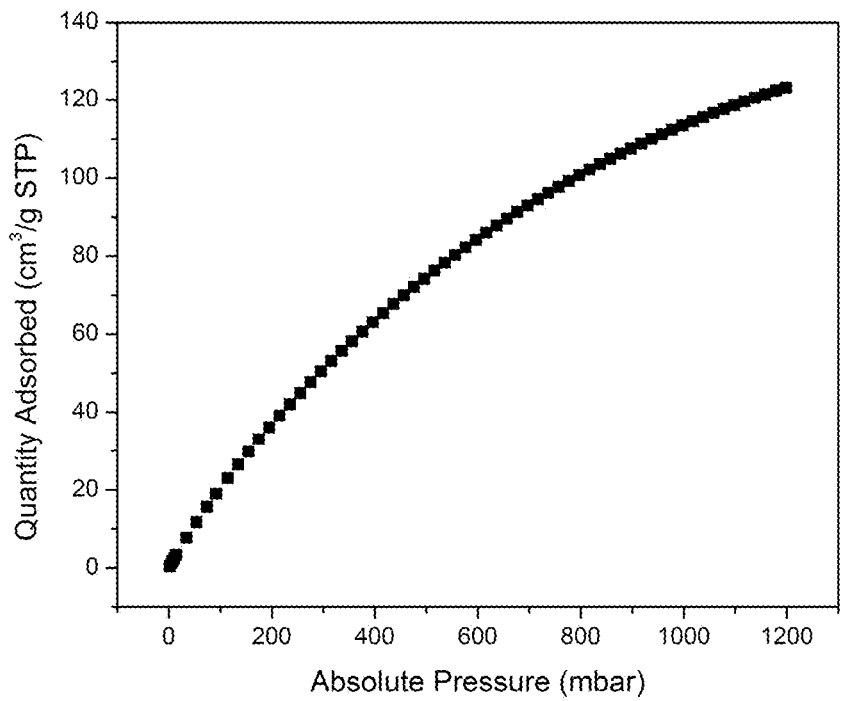
FIG. 57 shows the $CO_2$ uptake (adsorption) measured for PCN-250(Al).

FIG. 57 shows the $CO_2$ uptake (adsorption) measured for PCN-250(Al).

Thermogravimetric Analysis of PCN-250(Al)

About 15 mg samples of PCN-250(Al) was heated on a TGA-50 (Shimadzu) thermogravimetric analyzer from room temperature to 650° C. at a rate of 5° C. $min^{-1}$ under $N_2$ flow of 15 mL $min^{-1}$.

Figure 60:
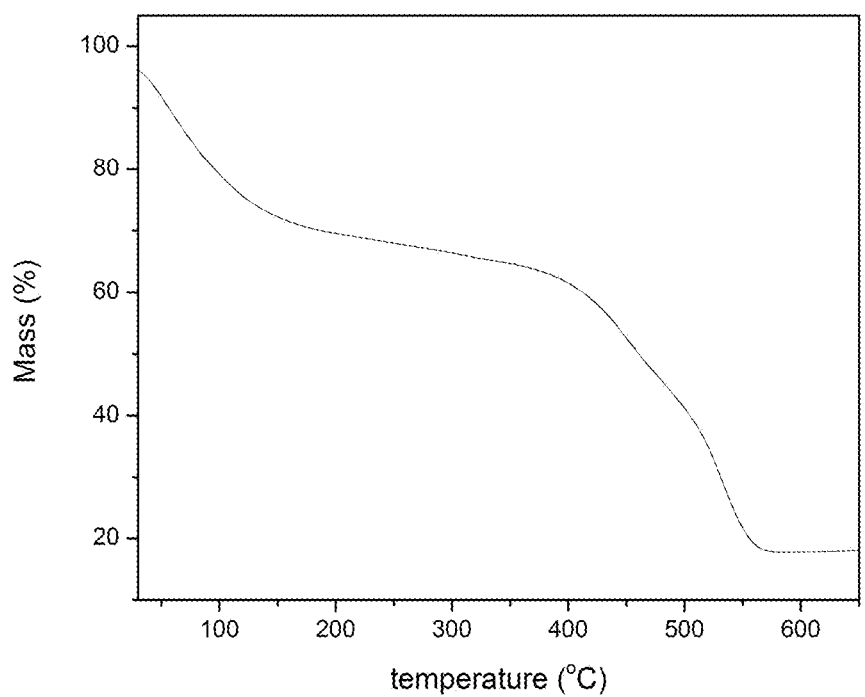
FIG. 60 shows a thermogravimetric analysis trace for a fresh sample of PCN-250(Al).
Figure 61A:
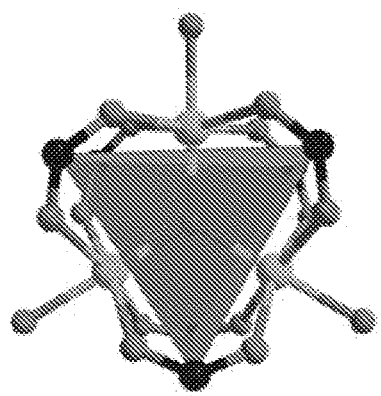
FIGS. 61A, 61B, and 61C show the crystallographic structure of the material obtained (PCN-250) represented schematically.
Figure 61B:
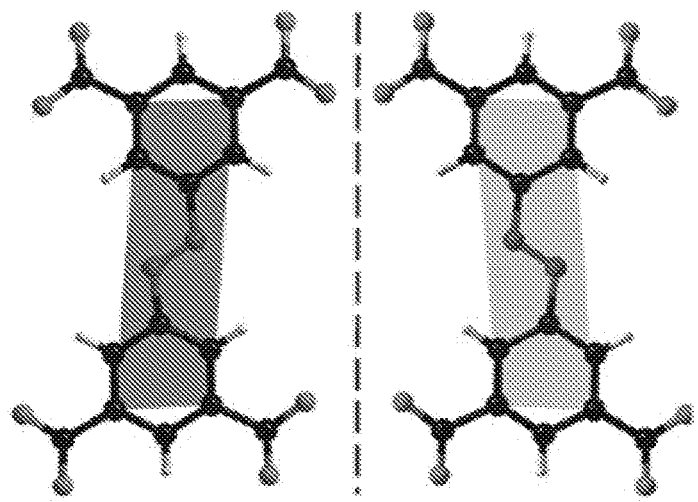
Figure 61C:
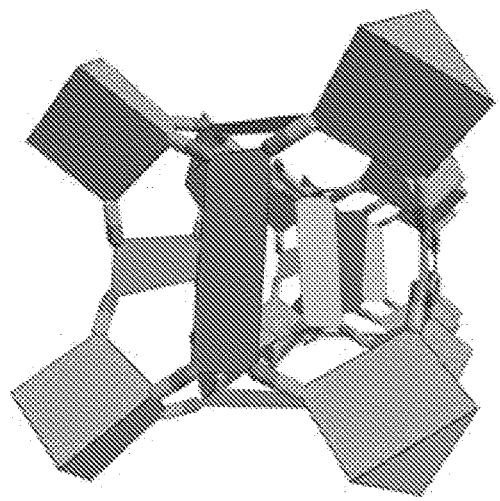

FIG. 60 shows the thermogravimetric analysis trace for a fresh sample of PCN-250(Al).

Titanium MOFs

Metal organic (framework) powder material has been prepared by various methods but prior to the present invention large single crystals of metal organic frameworks containing a number of different metal ions has not been prepared. In particular, monocrystalline titanium metal organic frameworks had not been prepared prior to the present invention. An object of the invention, therefore, is to provide a titanium based metal organic framework having a large crystal size. Another object is to provide a method of preparing monocrystalline titanium metal organic frameworks having a larger crystal size than previously achieved.

In Dan-Hardi, M.; Serre, C.; Frot, T.; Rozes, L.; Maurin, G.; Sanchez, C.; Férey, G. *J. Am. Chem. Soc.* 2009, 131, 10857-10859 is described a titanium(IV)-MOF (MIL-125). MIL-125 uses metal nodes as an important functional moiety. First of all, the $Ti^{4+}$ ion has a high Z/r value which forms a strong electrostatic interaction with the carboxylate, resulting in an ultra-stable framework. Second, the titanium(IV) oxo cluster in the structure can be viewed as an extremely small $TiO_2$ nanoparticle of precisely controlled size, which not only acts as a connecting node, but also endows excellent photocatalytic activity to the framework through a pure electron transfer process. The exceptional stability and photocatalytic properties make titanium-MOFs suitable platforms for photoinduced catalysis.

As an extensively used photocatalyst, $TiO_2$ has several drawbacks, such as low surface area and charge recombination inside the semiconductor after photoactivation. However, when acting as nodes in a MOF, titanium oxo clusters are periodically arranged and separated by organic linkers, which leads to a highly accessible surface. Meanwhile, the size of the titanium oxo cluster is much smaller which can significantly diminish the charge transportation distance and therefore charge recombination. Another disadvantage of $TiO_2$ lies in its large band-gap (3.0 eV for rutile) which limits the photosensitivity to the ultraviolet region. Effort has been made to extend the optical response of $TiO_2$ into visible light through the modification of $TiO_2$ with dyes to realize visible light utilization through a dye sensitized scheme. The organic unit in MOFs offers an opportunity to fully mimic dye sensitized $TiO_2$. Unfortunately, the BDC ligand in MIL-125 has no visible light adsorption (BDC=Benzenedicarboxylate). Although approaches have been attempted to enhance the optical absorption, such as using $NH_2$-BDC or other modified linkers, their potential is still limited due to the low dye efficiency and incompatible energy levels.

Porphyrin derivatives are the most frequently used dyes in dye sensitized $TiO_2$ systems due to their high efficiency and chemical stability. Coincidently, porphyrinic linkers have also been applied in many MOFs due to their multiple functionalities. Herein, using TCPP (TCPP=tetrakis(4-carboxyphenyl)porphyrin) as the organic linker and a preformed Ti(IV) oxo carboxylate cluster, the inventors have successfully obtained single crystalline Ti-MOF based on a titanium oxo cluster and a carboxylate containing linker, designated as PCN-22 (PCN=porous coordination network). PCN-22 is composed of unprecedented $Ti_7O_6$ clusters and porphyrinic TCPP ligands. It shows high porosity, excellent stability in strong Lewis acidic species and photocatalytic activity. Among the limited cases of titanium(IV)-MOFs, the vast majority of such MOFs were obtained in a polycrystalline form. This is partially because the crystallization processes are poorly controlled. The inventors have prepared single crystalline PCN-22 by the solvothermal reaction of the preformed $Ti_6O_6(OPr)_6(OOCPh)_6$ cluster, TCPP ligand and benzoic acid in DEF at 150° C. for 2 days. The inventors reasoned that several solvothermal reaction parameters, including using a preformed titanium cluster as a precursor, benzoic acid as a competing reagent and DEF as solvent, are crucial for the formation of single crystalline PCN-22. An optical microscope image of single crystals of PCN-22 is shown in FIG. 41. The preformed $Ti_6O_6(OPr)_6(OOCPh)_6$ cluster is adopted as a starting material instead of the titanium salt, which not only slows down the crystallization process but also effectively diminishes the hydrolysis of $Ti^{4+}$, avoiding the formation of $TiO_2$. The air stable titanium(IV)-oxo-carboxylate clusters are also easier to handle compared to titanium containing salts. When reactions were attempted with $Ti(OPr)_4$ or $TiCl_4$, no crystals or crystalline powders were obtained. An excess amount of benzoic acid was added as a competing reagent which could slow down the forward reaction of the MOF growth process and facilitate the backward dissociation process to assist the formation of crystalline product. Replacement of DEF with DMF gives rise to an amorphous gel instead of crystals. This is the first single crystalline Ti(IV)-MOF based on pure carboxylate containing linkers.

Single-crystal X-ray diffraction studies have revealed that PCN-22 crystallizes in the space group P 2/m. The asymmetric unit of PCN-22 contains seven $Ti^{4+}$ ions, three TCPP ligands, six $O^{2-}$ ions and two disordered DEF molecules. There are three symmetrically independent $Ti^{4+}$ ions. The titanium ions are jointed into $Ti_3O_3$ clusters by $\mu_3$-$O^{2-}$ ions and carboxylates which are further bridged by one Ti atom, two DEF molecules and four carboxylates into an unprecedented $Ti_7O_6$ cluster. The $Ti_7O_6$ cluster is a twelve-connected titanium(IV)-oxo cluster composed of seven $Ti^{4+}$ ions, two $\mu_3$-$O^{2-}$ ions, four terminal $O^{2-}$ ions and two bridging DEF molecules.

Each $Ti_3O_3$ subunit is six-connected by tetratopic TCPP ligands, forming a 2D layer which is composed of a 1D tetragonal channel. The 2D layers are further linked by bridging Ti atoms into a 3D structure. Topologically, each $Ti_3O_3$ can be regarded as a six connected node and TCPP ligand can be seen as a four connected node. The overall structure is simplified into a novel (4, 6) connected net with vertx symbol of $\{4^4.6^2\}_3\{4^9.6^{12}\}_2$. Further examination of the structure reveals that PCN-22 has two types of channels, a small orthorhombic channel and large tetragonal channel respectively, with diameters of ~0.3 and ~1.7 nm. Without wishing to be bound by theory, the large tetragonal channel accounts for the gas adsorption properties of PCN-22 while the small channel is not accessible by gas molecules. The $Ti_7O_6$ cluster and the $\{4^4.6^2\}_3\{4^9.6^{12}\}_2$ topology have never been reported before.

The phase purity of PCN-22 is verified by the powder X-ray diffraction pattern, which is consistent with the simulated one from the single-crystal X-ray diffraction data. Attempts to directly use metalloporphyrinic ligands in the synthesis of metalloporphyrinic PCN-22 result in amorphous precipitation. Hence, the inventors adopted the post-synthetic metal insertion to obtain metalloporphyrinic PCN-22.

Figure 58:
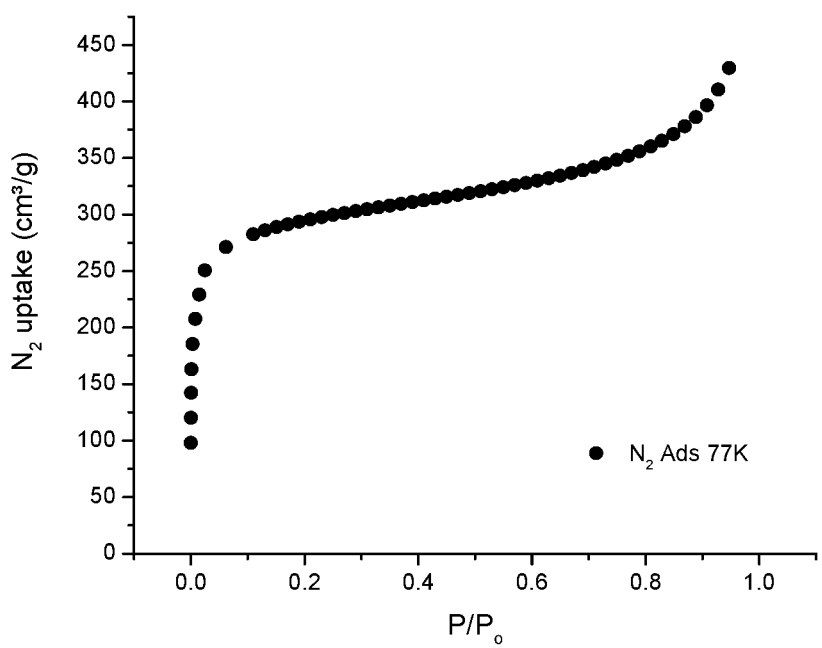
FIG. 58 shows the $N_2$ uptake (adsorption) results for PCN-22 (Ti).

The activation of PCN-22 was optimized by using supercritical carbon dioxide, after applying a diluted $TiCl_4$/DEF solution for pre-activation treatments. The porosity of PCN-22 has been examined by nitrogen adsorption experiments at 77 K. FIG. 58 shows nitrogen adsorption isotherms for PCN-22 at 77 K, 1 atm. A $N_2$ uptake of 430 $cm^3\ g^{-1}$ (STP) and a Brunauer-Emmett-Teller (BET) surface area of 1284 $m^2\ g^{-1}$ has been observed for PCN-22 (no metal). The experimental total pore volume of 0.64 $cm^3\ g^{-1}$ is close to the calculated pore volume of 0.86 $cm^3\ g^{-1}$. Evaluation of a density functional theory (DFT) simulation from the $N_2$ sorption curve indicates that there is one type of pore with a diameter of 1.7 nm assigned to the solvent accessible tetragonal channel, which is consistent with the crystallographic data when van der Waals contact is considered.

Figure 59:
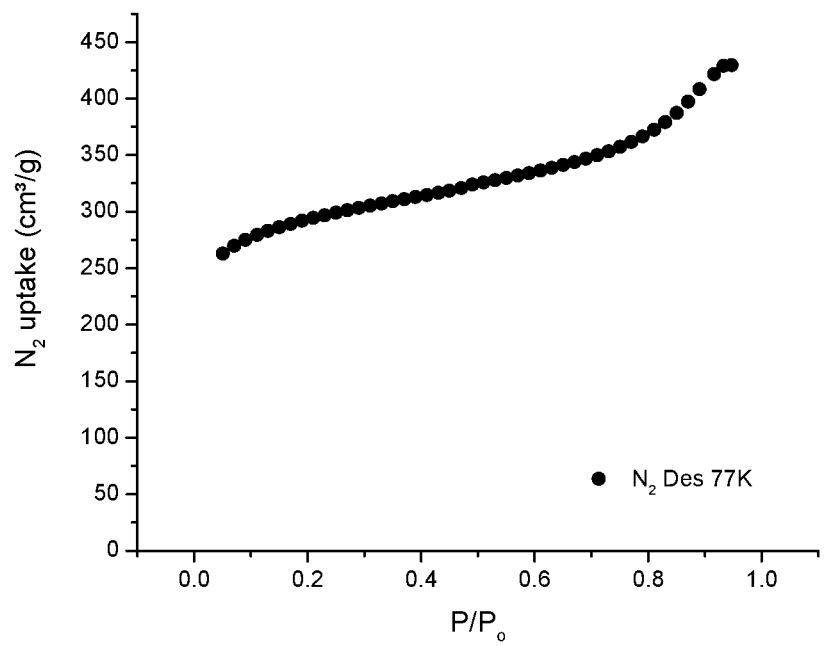
FIG. 59 shows the $N_2$ desorption results for PCN-22 (Ti).

FIG. 59 shows the $N_2$ desorption results for PCN-22.

Most hard Lewis acidic metal species based MOFs exhibit excellent stability under acidic conditions because those cations bond strongly to carboxylates and thus could be more competitive compared to protons. As an extremely strong Lewis acidic species, $Ti^{4+}$ in solution can competitively bond to carboxylates more strongly, and therefore destroy the MOF structure, which makes a solution containing it an even harsher conditions for examination of MOF stability. The inventors tested the stability of PCN-22 using $TiCl_4$ solution, under which most MOFs could be destroyed immediately. PCN-22 was treated in $TiCl_4$ DEF solution (0.1 M) at 100° C. overnight. The P-XRD pattern of PCN-22 is almost unaltered after $TiCl_4$ treatment. As a comparison, two well-known stable Zr MOFs, PCN-224 and UiO-66 respectively, were also tested, both of which lost crystallinity after the same treatment. PCN-22 also shows high thermostability. The thermogravimetric (TG) curves were measured in a $N_2$ atmosphere which shows no decomposition before 350° C.

PCN-22, with large channels, small titanium(IV)-oxo clusters as catalytic centers and porphyrinic ligands as photosensitizers, is a suitable candidate for light harvesting and photoinduced catalysis. In order to test the catalytic activity of PCN-22, the inventors designed a PCN-22/TEMPO system for a photocatalyzed alcohol oxidation reaction (TEMPO=2,2,6,6-tetramethylpiperidinyloxyl). According to a relevant research on a dye/$TiO_2$/TEMPO system reported by Jincai Zhao et al., the inventors proposed a similar mechanism for the PCN-22/TEMPO system. Without wishing to be bound by theory, the mechanism shown in FIG. 63 is proposed.

Figure 63:
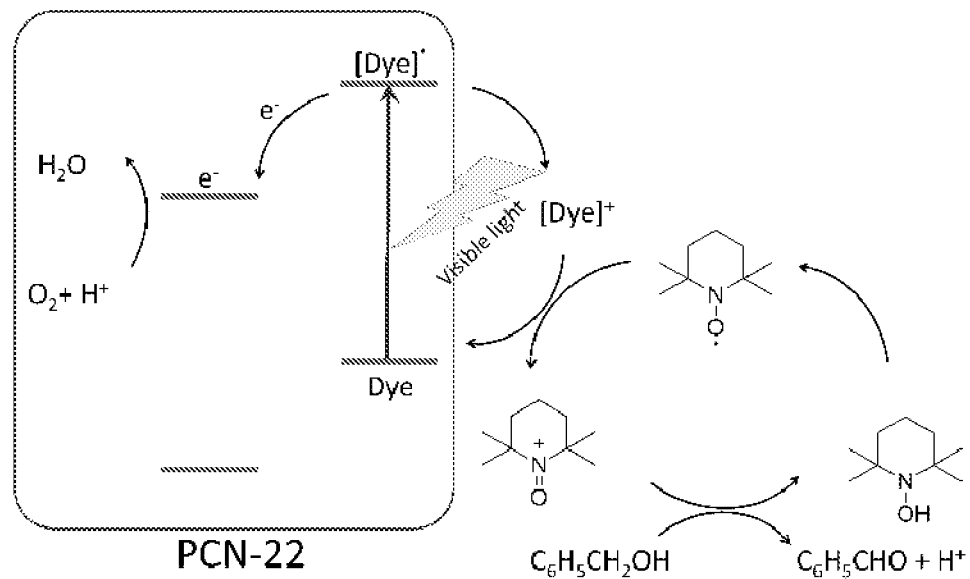
FIG. 63 shows a proposed mechanism for the PCN-22/TEMPO system and the reaction catalysed by PCN-22.

The mechanism shown in FIG. 63 for the PCN-22/TEMPO system and the reaction catalysed by PCN-22. The TCPP ligands are excited by visible light to inject electrons into $Ti_7O_6$ clusters, yielding $[TCPP]^+$. Meanwhile, TEMPO is oxidized to $TEMPO^+$ by [TCPP]+, which then selectively oxidizes alcohol into aldehyde by a two-electron-transfer mechanism. The conversion of benzylic alcohol to a benzaldehyde reaches 28% under visible-light irradiation for two hours and the selectivity is almost 100%, showing that the PCN-22/TEMPO system exhibited high reactivity and selectivity. The turnover number (TON) is over 100, indicating a catalytic process. To evaluate the recyclability of PCN-22, it was recovered after the completion of each reaction by simple centrifugation and reused for the next reaction. There was no obvious decrease in activity or selectivity after three successive runs demonstrating a good recyclability of PCN-22 as a recyclable heterogeneous catalyst.

In summary, the inventors report the first single crystalline Ti(IV)-MOF based on a pure carboxylate containing linker, PCN-22, built from a novel $Ti_7O_6$ cluster and a porphyrinic ligand. PCN-22 shows high porosity as well as photocatalytic activity. With large surface area, small catalytic centers and strong visible light absorption, PCN-22 represents an important step towards mimicking dye sensitized $TiO_2$ in MOFs, which will extend the potential applications of using MOFs for clean energy generation.

The invention claimed is:

1. A single crystal iron metal-organic framework, the metal organic framework comprising at least one metal-ligand cluster comprising a metal cluster and one or more ligands having two or more carboxylate groups;
wherein the metal cluster has the formula $Fe_2XO$, where X is a metal ion selected from the group consisting of Fe, Co, Mn, Zn, Ni, Mg, Cu, and Ca;
wherein the single crystal has a size greater than or equal to 10 μm; the metal organic framework comprises cavities having a free diameter of about 4 to about 40 Å; and the metal organic framework comprises pores having a pore volume of from about 0.1 $cm^3$/g to about 4 $cm^3$/g.

2. The single crystal iron metal-organic framework of claim 1, wherein the crystal is monocrystalline or polycrystalline.

3. The single crystal metal-organic framework according to claim 1, having a Brunauer-Emmett-Teller (BET) specific surface area of at least 200 $m^2$/g.

4. The single crystal metal-organic framework according to claim 1, having a surface area of less than or equal to 8000 $m^2$/g.

5. The single crystal metal-organic framework according to claim 1, the metal-organic framework comprising cavities having a free diameter of from about 5 Å to about 25 Å.

6. The single crystal metal-organic framework according to claim 1, the metal-organic framework comprising pores having a pore volume from about 0.2 $cm^3$/g to about 3 $cm^3$/g.

7. The single crystal metal-organic framework according to claim 1, having a size greater than or equal to 20 μm.

8. The single crystal metal-organic framework according to claim 1, having a crystal size from 10 μm to about 2000 μm.

9. The single crystal metal-organic framework according to claim 1, wherein the one or more ligands are derived from a dicarboxylic acid, a tricarboxylic acid, a tetracarboxylic acid, a hexacarboxylic acid, or a octacarboxylic acid.

10. The single crystal metal-organic framework according to claim 1, wherein each metal cluster is coordinated with 4, 5, or 6 ligands.

11. The single crystal of a metal-organic framework according to claim 1, wherein the at least one metal ion is Fe(II) or Fe(III).

12. The single crystal of a metal-organic framework according to claim 1, wherein the metal cluster has a formula $Fe_3O$.

13. A process for preparing the single crystal iron metal-organic framework of claim 1, the process comprising:
reacting a starting compound of formula $M_3O(CH_3COO)_6$ with a ligand precursor having at least two carboxylic acid groups in the presence of acetic acid to provide a metal-organic framework comprising a $M_3O$ cluster where at least one $(CH_3COO)$ ligand is replaced by at least one ligand having at least two carboxylate groups; wherein $M_3$ has the formula $Fe_2X$, where X is a metal ion selected from the group consisting of Fe, Co, Mn, Zn, Ni, Mg, Cu, and Ca.

14. The process according to claim 13, wherein the starting compound has a formula $Fe_2MO(CH_3COO)_6$ or $Fe_3O(CH_3COO)_6$, where M is Co, Mn, Zn, or Ni.

* * * * *

UNITED STATES PATENT AND TRADEMARK OFFICE
CERTIFICATE OF CORRECTION

PATENT NO. : 9,724,668 B2
APPLICATION NO. : 15/165247
DATED : August 8, 2017
INVENTOR(S) : Hong-Cai Zhou, Dawei Feng and Kecheng Wang Page 1 of 1

It is certified that error appears in the above-identified patent and that said Letters Patent is hereby corrected as shown below:

In the Specification

Column 1, Line 17 insert:
--STATEMENT REGARDING FEDERALLY SPONSORED RESEARCH
This invention was made with government support under contract number DE-AR0000249 awarded by the Department of Energy. The government has certain rights in the invention.--

Signed and Sealed this
Tenth Day of July, 2018

Andrei Iancu
*Director of the United States Patent and Trademark Office*